United States Patent
Soula et al.

(10) Patent No.: US 10,449,256 B2
(45) Date of Patent: Oct. 22, 2019

(54) INJECTABLE SOLUTION AT PH 7 COMPRISING AT LEAST ONE BASAL INSULIN THE ISOELECTRIC POINT OF WHICH IS BETWEEN 5.8 AND 8.5 AND A HYDROPHOBIZED ANIONIC POLYMER

(71) Applicant: ADOCIA, Lyons (FR)

(72) Inventors: Olivier Soula, Meyzieu (FR); Richard Charvet, Rillieux La-Pape (FR)

(73) Assignee: ADOCIA, Lyons (FR)

( * ) Notice: Subject to any disclaimer, the term of this patent is extended or adjusted under 35 U.S.C. 154(b) by 0 days.

(21) Appl. No.: 15/899,795

(22) Filed: Feb. 20, 2018

(65) Prior Publication Data

US 2018/0169249 A1    Jun. 21, 2018

Related U.S. Application Data

(63) Continuation of application No. 14/179,042, filed on Feb. 12, 2014.

(60) Provisional application No. 61/763,769, filed on Feb. 12, 2013.

(30) Foreign Application Priority Data

Feb. 12, 2013   (FR) .................................... 13 51200

(51) Int. Cl.
| | | |
|---|---|---|
| A61K 47/34 | (2017.01) | |
| A61K 38/28 | (2006.01) | |
| A61K 47/36 | (2006.01) | |
| A61K 9/00 | (2006.01) | |
| A61K 9/08 | (2006.01) | |

(52) U.S. Cl.
CPC ............ *A61K 47/34* (2013.01); *A61K 9/0019* (2013.01); *A61K 9/08* (2013.01); *A61K 38/28* (2013.01); *A61K 47/36* (2013.01)

(58) Field of Classification Search
CPC ........ A61K 47/34; A61K 9/08; A61K 9/0019; A61K 47/36; A61K 38/28
See application file for complete search history.

(56) References Cited

U.S. PATENT DOCUMENTS

| | | | |
|---|---|---|---|
| 2,387,201 A | 10/1945 | Weiner | |
| 4,826,818 A | 5/1989 | Mori et al. | |
| 5,656,722 A | 8/1997 | Dorschug | |
| 6,100,376 A | 8/2000 | Dorschug | |
| 6,384,016 B1 | 5/2002 | Kaarsholm | |
| 7,226,618 B1 | 6/2007 | Touraud et al. | |
| 7,718,609 B2 | 5/2010 | Steiner et al. | |
| 8,426,382 B2 | 4/2013 | Soula et al. | |
| 2003/0225033 A1 | 12/2003 | Groman et al. | |
| 2004/0048783 A1 | 3/2004 | Brunner-Schwarz et al. | |
| 2006/0099264 A1 | 5/2006 | Chan et al. | |
| 2006/0188555 A1 | 8/2006 | Cormier et al. | |
| 2007/0196497 A1 | 8/2007 | Pouliquen et al. | |
| 2008/0014250 A1 | 1/2008 | Soula et al. | |
| 2008/0026120 A1 | 1/2008 | Bonnet-Gonnet | |
| 2008/0039368 A1 | 2/2008 | Steiner et al. | |
| 2009/0011028 A1 | 1/2009 | Checot et al. | |
| 2009/0048412 A1 | 2/2009 | Soula et al. | |
| 2009/0110742 A1 | 4/2009 | Constancis et al. | |
| 2009/0304665 A1 | 12/2009 | Frost et al. | |
| 2010/0069292 A1 | 3/2010 | Pohl et al. | |
| 2010/0167984 A1 | 7/2010 | Soula et al. | |
| 2010/0167991 A1 | 7/2010 | Soula et al. | |
| 2010/0249020 A1 | 9/2010 | Soula et al. | |
| 2011/0097386 A1 | 4/2011 | Steiner et al. | |
| 2011/0172166 A1 | 7/2011 | Charvet et al. | |
| 2011/0178011 A1 | 7/2011 | Soula et al. | |
| 2011/0179011 A1 | 7/2011 | Cardno et al. | |
| 2011/0195913 A1 | 8/2011 | Charvet et al. | |
| 2011/0212901 A1 | 9/2011 | Akiyoshi et al. | |
| 2012/0295833 A1 | 11/2012 | Charvet et al. | |
| 2012/0298533 A1 | 11/2012 | Sahlstrom | |
| 2012/0309680 A1 | 12/2012 | Charvet et al. | |
| 2013/0065826 A1 | 3/2013 | Soula et al. | |
| 2013/0178415 A1 | 7/2013 | Soula | |
| 2014/0187499 A1 | 7/2014 | Soula et al. | |
| 2014/0378373 A2 | 12/2014 | Soula et al. | |
| 2015/0025005 A1 | 1/2015 | Langer et al. | |
| 2015/0250858 A1 | 9/2015 | Soula et al. | |
| 2015/0291680 A1 | 10/2015 | Ward et al. | |

FOREIGN PATENT DOCUMENTS

| | | | |
|---|---|---|---|
| AU | 2007/255367 A1 | 12/2007 | |
| EP | 1 222 926 A1 | 7/2002 | |
| EP | 2 360 188 A1 | 8/2011 | |
| EP | 2 387 989 A2 | 11/2011 | |
| FR | 2 801 226 A1 | 5/2001 | |
| FR | 2 840 614 A1 | 12/2003 | |
| FR | 2 862 536 A1 | 5/2005 | |

(Continued)

OTHER PUBLICATIONS

ICI Americas Inc., "The HLB System, a time-saving guide to emulsifier selection," 1980, pp. 1-22.
Package insert for Neut® Sodium Bicarbonate Additive Solution, Publication EN-0545, Hospira Corporation, revised Nov. 2014, pp. 1-4.
Apr. 20, 2015 Office Action issued in U.S. Appl. No. 14/179,212.
Nov. 19, 2015 Office Action issued in U.S. Appl. No. 14/179,212.
Aug. 25, 2016 Office Action issued in U.S. Appl. No. 14/721,889.
Mar. 10, 2017 Office Action issued in U.S. Appl. No. 14/179,212.
Sep. 16, 2016 Office Action issued in U.S. Appl. No. 14/179,212.
Yamaguchi, Shigehiko et al., "O/w Emuslion as Formed by Cholesterol-Bearing Pullulan," Bull. Chem. Soc., Japan, 1992 vol. 2, pp. 186-190.
Mar. 21, 2017 Office Action issued in Chinese Patent Application No. 201380009297.1.

(Continued)

*Primary Examiner* — Sudhakar Katakam
(74) *Attorney, Agent, or Firm* — Oliff PLC

(57) ABSTRACT

The invention relates to a composition in the form of an injectable aqueous solution, the pH of which is between 6.6 and 7.8, including at least: a) a basal insulin, the isoelectric point pI of which is between 5.8 and 8.5; and b) a hydrophobized anionic polymer. In one embodiment, the compositions according to the invention also include a prandial insulin.

10 Claims, 7 Drawing Sheets

(56) References Cited

FOREIGN PATENT DOCUMENTS

| | | | |
|---|---|---|---|
| FR | 2 985 428 A1 | 7/2013 | |
| FR | 2 985 429 A1 | 7/2013 | |
| GB | 1202607 A | 8/1970 | |
| RU | 2313362 C2 | 12/2007 | |
| WO | 03/053339 A2 | 7/2003 | |
| WO | 2004/060968 A1 | 7/2004 | |
| WO | 2004/096454 A1 | 11/2004 | |
| WO | 2004/096854 A2 | 11/2004 | |
| WO | 2006/051103 A2 | 5/2006 | |
| WO | 2007/116143 A1 | 10/2007 | |
| WO | 2007/121256 A2 | 10/2007 | |
| WO | 2007/141344 A2 | 12/2007 | |
| WO | 2008/030119 A1 | 3/2008 | |
| WO | 2009/021955 A1 | 2/2009 | |
| WO | 2009/063072 A2 | 5/2009 | |
| WO | 2010/028055 A1 | 3/2010 | |
| WO | 2010/041138 A2 | 4/2010 | |
| WO | 2010/053140 A1 | 5/2010 | |
| WO | 2010/056403 A1 | 5/2010 | |
| WO | 2010/122385 A1 | 10/2010 | |
| WO | 2011/077405 A1 | 6/2011 | |
| WO | 2011/098962 A2 | 8/2011 | |
| WO | 2011/138802 A1 | 11/2011 | |
| WO | 2011/144673 A2 | 11/2011 | |
| WO | 2011/144676 A1 | 11/2011 | |
| WO | 2011/147980 A1 | 12/2011 | |
| WO | 2012/153070 A1 | 11/2012 | |
| WO | 2013/021143 A1 | 2/2013 | |
| WO | 2013/101749 A1 | 7/2013 | |
| WO | 2013/104861 A1 | 7/2013 | |
| WO | 2014/096440 A2 | 6/2014 | |
| WO | 2014/124993 A1 | 8/2014 | |
| WO | 2014/124994 A1 | 8/2014 | |
| WO | 2015/095389 A1 | 6/2015 | |

OTHER PUBLICATIONS

May 31, 2017 Office Action issued in U.S. Appl. No. 14/721,889.
"Improved Outcomes for Patients Treated With Lantus and Apidra Regimen Compared With Sliding Scale Insulin". Sanofi-Aventis Press Release, 2010.
Mckeage et al., "Insulin Glargine—A Review of its Therapeutic Use as a Long-Acting Agent for the Management of Type 1 and 2 Diabetes Mellitus". Drugs, Adis International Limited, vol. 61, No. 11, pp. 1599-1624, 2001.
Oct. 23, 2014 Office Action issued in U.S. Appl. No. 13/737,353.
Draft Prescribing Information Concerning Lantus, pp. 1-14, 2000.
Deming "Polypeptide and Polypetide Hybrid Copolymer Synthesis via NCA Polymerization" Adv Polm Sci, vol. 202, pp. 1-18, 2006.
Deming "Facile Synthesis of Block Copolypeptides of Defined Architecture". Nature, vol. 390, pp. 386-389, 1997.
Lu et al., "Hexamethydisilazane-Mediated Controlled Polymerization of a-Amino Acide N-Carboxyanhydrides". J. Am. Chem. Soc., vol. 129, pp. 14114-14115, 2007.
Huile et al., "Controlled Release of Insulin From Nanoparticles of Amphiphilic Block Copolyamino Acid". Journal of Controlled Release, vol. 64, pp. 319-321, 2000.
"Byetta Approved for Use With Insulin Glargine in the U.S: Patients in Pivotal Study Achieved Better Glycemic Control Without Weight Gain or Increased Hypoglycemia Risk Versus Insulin Glargine". Lilly, XP-00268281, 2011.
"Highlights of Prescribing Information and Full Prescribing Information" Lantus, Sanofi-Aventis US LLC., 2009.
Dubowchik et al.,"Improved Cytotoxicity of Antitumor Compounds Deliverable by the LDL Pathway". Bioconjugate Chem, vol. 6, pp. 427-439, 1995.
Smoot et al., "Oligosaccharide Synthesis: From Conventional Methods of Modern Expeditious Strategies". Advances in Carbohydrate Chemistry and Biochemistry, vol. 62, pp. 161-250, 2009.
Lindhorst, "Essentials of Carbohydrate Chemistry and Biochemistry", pp. 157-208, 2007.

U.S. Appl. No. 13/571,026, filed Aug. 9, 2012.
U.S. Appl. No. 13/737,353, filed Jan. 9, 2013.
U.S. Appl. No. 14/179,212, filed Feb. 12, 2014.
May 9, 2013, Office Action issued in U.S. Appl. No. 13/571,023.
Dec. 20, 2013 Office Action issued in U.S. Appl. No. 13/737,353.
Nov. 21, 2013 Office Action issued in U.S. Appl. No. 13/571,026.
Cengiz et al., "Early Pharmacokinetic and Pharmacodynamic Effects of Mixing Lispro and Glargine Insulin". Diabetes Care, vol. 33, No. 5, pp. 1009-1012, 2010.
Cengiz et al., "Should We Mix Lispro With Glargine? Removing the Guesswork by Euglycemic Clamp Studies". 69th Annual Scientific Sessions of the American Diabetes Association (ADA), No. 19-OR, 2009.
Testa et al., "Patient Satisfaction, Quality of Life and Glycemic Variability in Type 1 and 2 Diabetes: A Cross-Over Trial of Insulin Glargine + Gluisine vs Premix Analog Insulin". 70th Scientific Sessions of the American Diabetes Assosciation (ADA), No. 0001-LB, 2010.
Uehata et al., "Effect of Sulfobutyl Ether-B-Cyclodextrin on Bioavailability of Insulin Glargine and Blood Glucose Level After Subcutaneous Injection to Rats". International Journal of Pharmaceutics, vol. 419, pp. 71-76, 2011.
Full Prescribing Information for Lantus, Sanofi-Aventis U.S. LLC., pp. 1-24, 2009.
Magnani et al., "Novel Polysaccharide Hydrogels: Characterization and Properties". Polymers for Advanced Technologies, vol. 11, pp. 488-495, 2000.
Papisov et al., "Semisynthetic Hydrophilic Polyals". Biomacromolecules, vol. 6, pp. 2659-2670, 2005.
Yurkovetskiy et al., "Fully Degradable Hydrophilic Polyals for Protein Modification" Biomacromolecules, vol. 6, pp. 2648-2658, 2005.
Yurkovetskiy et al., "Synthesis of a Macromolecular Camptothecin Conjugate With Dual Phase Drug Release". Molecular Pharmaceutics, vol. 1, No. 5, pp. 375-382, 2004.
Baudys et al., "Extending Insulin Action In Vivo by Conjugation to Carboxymethl Dextran". Bioconjugate Chem, vol. 9, pp. 176-183, 1998.
Ishak and Painter, "Kinetic Evidence for Hemiacetal Formation During the Oxidation of Detrac in Aqueous Periodate". Carbohydrate Research, vol. 64, pp. 189-197, 1978.
Takata et al., "Prodrugs of Vitamin E. 1. Preparation and Enzymatic Hydrolysis of Aminoalkanecarboxlyic Acid Esters of d-a-Tocopherol". Journal of Pharmaceutical Sciences, vol. 84, No. 1, pp. 96-100, 1995.
Sanchez-Chavez et al., "Poly (Vinyl Alcohol) Funcationalized by Monosuccinate Groups. Cupling of Bioactive Amino Compounds". Polymer, vol. 39. No. 13, pp. 2751-2757, 1998.
Mar. 23, 2012 French Search Report issued in French Application No. 1157291.
Dec. 3, 2012 International Search Report issued in International Application No. PCT/FR2012/051880.
"The HLB System, A Time-Saving Guide to Emulsifier Selection". ICI Americas Inc, pp. 1-22, 1980.
Package Insert for Neut Sodium Bicrbonate Additive Solution, Pulication EN-0545, Hospira Coporation, revised Nov. 2014, pp. 1-4.
U.S. Appl. No. 14/179,042, filed Feb. 12, 2014 in the name of Soula et al.
May 11, 2016 Office Action issued in U.S. Appl. No. 14/179,042.
Mar. 29, 2017 Office Action issued in Korean Patent Application No. 10-2014-7005655.
Lu et al., "N-Trimethylsilyl Amines for Controlled Ring-Opening Polymerization of Amino Acid N-Carboxyanhydrides and Facile End Group Functionalization of Polypeptides," J. Am. Chem. Soc., vol. 130, pp. 12562-12563, 2008. (with supporting Information pp. S1-S8).
Papisov et al.; "Acyclic Polyacetals from Polysaccharides: Biomimetic Biomedical "Stealth" Polymers." Biopolymers from Polysaccharides and Agroproteins, Chapter 19, p. 301-314, 2001.
Dec. 8, 2016 Office Action issued in Canadian Patent Application No. 2,843,586.

(56) References Cited

OTHER PUBLICATIONS

Jan. 12, 2015 Office Action issued in Chinese Patent Application No. 201280038926.9.
Sep. 29, 2015 Office Action issued in Chinese Patent Application No. 201280038926.9.
Apr. 19, 2016 Office Action issued in Chinese Patent Application No. 201280038926.9.
Jun. 30, 2016 Office Action issued in Korean Patent Application No. 10-2014-7005655.
May 31, 2016 Search Report issued in European Patent Application No. 16162474.
Jul. 7, 2015 Office Action issued in Russian Patent Application No. 2014108829.
Sep. 12, 2013 Office Action issued in U.S. Appl. No. 13/571,026.
Sep. 14, 2015 Office Action issued in Chinese Patent Application No. 201380009297.1.
Jun. 7, 2016 Office Action issued in Chinese Patent Application No. 201380009297.1.
Mar. 6, 2013 Search Report issued in International Application No. PCT/FR2013/080043.
Mar. 19, 2014 Search Report issued in Intenational Application No. PCT/EP2014/052763.
Apr. 11, 2014 Search Report issued in International Application No. PCT/EP2014/052762.
Aug. 9, 2017 Search Report issued in International Application No. PCT/EP2017/063886.
Aug. 9, 2017 Search Report issued in International Application No. PCT/EP2017/063865.
Aug. 9, 2017 Search Report issued in International Application No. PCT/EP2017/063888.
Aug. 9, 2017 Search Report issued in International Application No. PCT/EP2017/063887.
Onoue et al.; Mishandling of the Therapeutic Peptide Glucagon Generates Cytotoxic Amyloidogenic Fibrils; Pharmaceutical Research; Jul. 2003; pp. 1274-1283; vol. 21, No. 7.
Kirsch et al.; "The degradation pathways of glucagon in acidic solutions;" International Journal of Pharmaceutics; 2000; pp. 115-125; vol. 203.
Jackson et al.; "Stable Liquid Glucagon Formulations for Rescue Treatment and Bi-Hormonal Closed-Loop Pancreas;" Curr Diab Rep; 2012; pp. 705-710; vol. 12.
Matilainen et al; "The stability and dissolution properties of solid glucagon/g-cyclodextrin powder;" Europoean Journal of Pharmaceutical Sciences; 2009; pp. 412-420; vol. 36.
Garay et al.; "Antibodies against polyethylene glycol in healthy subjects and in patients treated with PEG-conjugated agents;" Expert Opin. Drug Deliv.; 2012; pp. 1319-1323; vol. 9.
Ganson et al.; "Pre-existing anti-polyethylene glycol antibody linked to first-exposure allergic reactions to pegnivacogin, a PEGylated RNA aptamer;" J Allergy Clin Immunol; May 2015.
Tan et al.; Coadministration of Glucagon-Like Peptide-1 During Glucagon Infusion in Humans Results in Increased Energy Expenditure and Amelioration of Hyperglycemia; Diabetes; Apr. 2013; pp. 1131-1138; vol. 62.
Subramanian et al.; "Structure of Complexes of Cationic Lipids and Poly(Glutamic Acid) Polypeptides: A Pinched Lamellar Phase;" J. Am. Chem. Soc.; 2000; pp. 26-34; vol. 122.
Naiki et al.; "Fluorometric Determination of Amyloid Fibrils in Vitro Using the Fluorescent Dye, Thioflavine T1;" Analytical Biochemistry; 1989; pp. 244-249; vol. 177.
Levine, III; "Quantification of β-Sheet Amyloid Fibril Structures with Thioflavin T;" Methods in Enzymology; 1999; pp. 274-284; vol. 309.
Apr. 19, 2018 Office Action issued in U.S. Appl. No. 14/922,633.
Dec. 19, 2017 Office Action issued in Chinese Patent Application No. 201380009297.1.
U.S. Appl. No. 13/737,353, filed Jan. 9, 2013 in the name of Soula et al.
Jul. 8, 2015 Office Action issued in U.S. Appl. No. 14/179,042.
May 9, 2013 Office Action issued in U.S. Appl. No. 13/571,026.
Jan. 19, 2017 Office Action issued in U.S. Appl. No. 14/179,042.

INJECTABLE SOLUTION AT PH 7 COMPRISING AT LEAST ONE BASAL INSULIN THE ISOELECTRIC POINT OF WHICH IS BETWEEN 5.8 AND 8.5 AND A HYDROPHOBIZED ANIONIC POLYMER

The present application is a continuation of Ser. No. 14/179,042 filed Feb. 17, 2014, which claims the benefit of Provisional Application No. 61/763,769 filed Feb. 12, 2013. The disclosures of the prior applications are incorporated herein by reference in their entireties.

The invention relates to therapies by injection of insulin(s) for treating diabetes.

Insulin therapy, or therapy for diabetes by injection of insulin, has experienced remarkable progress over the past few years by virtue in particular of the development of new insulins which offer better correction of blood glucose level in patients in comparison with human insulin and which make it possible to simulate more closely the physiological activity of the pancreas.

When type II diabetes is diagnosed in a patient, a gradual treatment is put in place. The patient firstly takes oral antidiabetics (OADs) such as metformin. When OADs alone are no longer sufficient to regulate the glucose level in the blood, a change in the treatment must be made and, depending on the patient's specificities, various treatment combinations can be put in place. The patient can, for example, have a treatment based on a basal insulin of glargine or detemir type as a supplement to the OADs, then subsequently, depending on the progression of the disease, a treatment based on basal insulin and prandial insulin.

Moreover, today, in order to ensure the transition from treatments with OADs, when the latter are no longer able to control the glucose level in the blood, to a basal insulin/prandial insulin treatment, the injection of GLP-1 analogs is recommended.

GLPs-1, for Glucagon-Like Peptides-1, are insulinotropic peptides or incretins, and belong to the family of gut hormones which stimulate insulin secretion when the blood glucose level is too high, for example after a meal.

Gut hormones are also called satiating hormones. They comprise in particular GLP-1 (Glucagon like peptide-1) and GIP (Glucose-dependent insulinotropic peptide), oxyntomodulin (a proglucagon derivative), peptide YY, amylin, cholecystokinin, pancreatic polypeptide (PP), ghrelin and enterostatin which have peptide or protein structures. They also stimulate insulin secretion, in response to glucose and fatty acids, and are therefore in this respect potential candidates for the treatment of diabetes.

Among these gut hormones, GLPs-1 are those which have to date provided the best results in the development of medicaments. They have enabled patients suffering from type II diabetes to lose weight while at the same time having a better control of their blood glucose level.

GLP-1 analogs or derivatives have thus been developed, in particular for improving their stability.

Furthermore, to cover his daily insulin needs, a diabetic patient currently has, schematically, two types of insulins that have complementary actions: prandial insulins (or "fast-acting" insulins) and basal insulins (or "slow-acting" insulins).

The prandial insulins allow a rapid management (metabolization and/or storage) of the glucose taken in during meals and snacks. The patient must inject himself with a prandial insulin before each food intake, i.e. approximately 2 to 3 injections per day. The prandial insulins most widely used are: recombinant human insulin, NovoLog® (insulin aspart from NOVO NORDISK), Humalog® (insulin lispro from ELI LILLY) and Apidra® (insulin glulisine from SANOFI-AVENTIS).

The basal insulins maintain the glycemic homeostasis of the patient, outside periods of food intake. They act essentially to block the endogenous production of glucose (hepatic glucose). The daily dose of basal insulin generally corresponds to 40-50% of the total daily insulin needs. Depending on the basal insulin used, this dose is dispensed in 1 or 2 injections, spread out regularly over the course of the day. The basal insulins most widely used are Levemir® (insulin detemir from NOVO NORDISK) and Lantus® (insulin glargine from SANOFI-AVENTIS).

It will be noted, in the interests of being thorough, that NPH (insulin NPH for Neutral Protamine Hagedorn; Humuline NPH®, Insulatard®) is the oldest basal insulin. This formulation is the result of a precipitation of human insulin (anionic at neutral pH) using a cationic protein, protamine. The microcrystals thus formed are dispersed in an aqueous suspension and dissolve slowly after subcutaneous injection. This slow dissolution provides a prolonged release of the insulin. However, this release does not provide a constant concentration of insulin over time. The release profile is bell-shaped and only lasts between 12 and 16 hours. It is therefore injected twice a day. This NPH basal insulin is much less effective than the modern basal insulins, Levemir® and Lantus®. NPH is an intermediate-action basal insulin.

The principle of NPH has evolved with the appearance of the fast-acting insulin analogs to give products called "Premix" that offer both a fast action and an intermediate action. NovoLog Mix® (NOVO NORDISK) and Humalog Mix® (ELI LILLY) are formulations comprising a fast-acting insulin analog, Novolog® and Humalog®, partially complexed with protamine. These formulations thus contain insulin analog microcrystals, the action of which is termed intermediate, and an insulin component that has remained soluble, the action of which is fast. These formulations clearly offer the advantage of a fast-acting insulin, but they also have the defect of NPH, i.e. a limited duration of action of between 12 and 16 hours and an insulin with a "bell-shaped" release profile. However, these products allow patients to give themselves, in one go, an injection of an intermediate-action basal insulin with a fast-acting prandial insulin. As it happens, there are many patients who are anxious to reduce their number of injections.

The basal insulins currently marketed and currently in clinical development can be classified according to the technical solution which makes it possible to obtain the prolonged action, and, to date, two approaches are used.

The first approach, which is that of insulin detemir, is binding to albumin in vivo. Insulin detemir is an analog, which is soluble at pH 7, and which comprises a fatty acid (tetradecanoyl) side chain attached in position B29 which, in vivo, enables this insulin to associate with albumin. Its prolonged action is mainly due to this affinity for albumin after subcutaneous injection.

However, its pharmacokinetic profile does not make it possible to cover a day, which means that it is most commonly used as two injections per day.

Other basal insulins which are soluble at pH 7, such as Degludec®, are currently in development. Degludec® also comprises a fatty acid side chain attached to the insulin (hexadecanedioyl-γ-L-Glu).

The second approach, which is that of insulin glargine, is precipitation at physiological pH. Insulin glargine is a human insulin analog obtained by elongation of the C-terminal part of the B chain of human insulin with two arginine residues, and by substitution of asparagine residue A21 with a glycine residue (U.S. Pat. No. 5,656,722). The addition of two arginine residues was considered in order to adjust the pI (isoelectric point) of insulin glargine at physiological pH, and thus to render this human insulin analog insoluble in physiological medium.

Also, the substitution of A21 was considered in order to render insulin glargine stable at acid pH and thus to be able to formulate it in the form of an injectable solution at add pH. During subcutaneous injection, the passing of insulin glargine from an acid pH (pH 4-4.5) to a physiological pH (neutral pH) causes it to precipitate under the skin. The slow redissolution of the insulin glargine microparticles provides a slow and prolonged action.

The hypoglycemic effect of insulin glargine is virtually constant over a period of 24 hours, which enables most patients to limit themselves to a single injection per day.

Insulin glargine is today considered to be the best basal insulin on the market.

However, the necessarily acid pH of the formulations of basal insulins, the isoelectric point of which is between 5.8 and 8.5, of insulin glargine type, can be a real drawback since this acid pH of the insulin glargine formulation sometimes causes pain on injection in patients and especially prevents any formulation with other proteins and in particular with prandial insulins, since the latter are not stable at acid pH. The impossibility of formulating a prandial insulin at acid pH comes from the fact that a prandial insulin undergoes, under these conditions, a side reaction consisting of deamidation in position A21, which does not make it possible to meet the requirement of the US Pharmacopeia, namely less than 5% of by-products after 4 weeks at 30° C.

Thus, no one has to date sought to solubilize these basal insulins, of insulin glargine type, the isoelectric point of which is between 5.8 and 8.5, at neutral pH while at the same time maintaining a difference in solubility between the in vitro medium (the container) and the in vivo medium (under the skin), independently of the pH.

From the analysis of the compositions described in the literature and the patents, it appears that the insolubility at pH 7 of the basal insulins, of the insulin glargine type, is a prerequisite for having a slow action.

Indeed, the principle of how basal insulins, of insulin glargine type, the isoelectric point of which is between 5.8 and 8.5, function is that they are soluble at acid pH and precipitate at physiological pH. This diverts those skilled in the art from any solution in which the insulin of insulin glargine type would be solubilized at pH 6-8 while keeping its essential property which is that of precipitating in subcutaneous medium.

Furthermore, this acid pH of the formulations of basal insulins, the isoelectric point of which is between 5.8 and 8.5, of insulin glargine type, even prevents any extemporaneous combination with prandial insulins at neutral pH.

Indeed, a recent clinical study, presented at the 69th Scientific Sessions of the American Diabetes Association, New Orleans, La., Jun. 5-9, 2009, 0019-OR made it possible to verify this limitation of the use of insulin glargine. A dose of insulin glargine and a dose of prandial insulin (in the case in point, insulin lispro) were mixed just before injection (E. Cengiz et al., 2010; Diabetes care—33(5): 1009-12). This experiment made it possible to demonstrate a significant delay in the pharmacokinetic and the pharmacodynamic profiles of the prandial insulin, possibly giving rise to postprandial hyperglycemia and to nocturnal hypoglycemia. This study clearly confirms the incompatibility of insulin glargine with the fast-acting insulins currently on the market.

Moreover, the instruction leaflet for Lantus®, the commercial product based on insulin glargine from the company SANOFI-AVENTIS, explicitly informs users not to mix with a solution of prandial insulin, whatever it may be, owing to the serious risk of modifying the pharmacokinetics and the pharmacodynamics of the insulin glargine and/or of the prandial insulin mixed together.

However, from a therapeutic point of view, it has been demonstrated, as illustrated hereinafter, that treatments combining either an insulin glargine and a prandial insulin, or an insulin glargine and a GLP-1 analog, are of real interest.

As regards the combination of an insulin glargine and a prandial insulin, clinical studies made public during the 70th annual scientific sessions of the *American Diabetes Association* (ADA) of 2010, abstract 2163-PO and abstract number 0001-LB, in particular those carried out by the company SANOFI-AVENTIS, showed that treatments which combine Lantus®, insulin glargine and a prandial insulin are much more effective than treatments based on products of the "Premix" type, Novolog Mix® or Humalog Mix®.

As regards the combination of an insulin glargine and a GLP-1 analog, the FDA (US Food and Drug Administration) approved, in October 2011, the injection of exenatide (Byetta®, Amylin Pharmaceuticals, Inc and Eli Lilly and Company) as therapy supplementing insulin glargine for patients suffering from type II diabetes who are not able to achieve control of their blood glucose level with the basal insulin analog alone.

It so happens, owing to the fact that the very principle, set out above, of basal insulins, the isoelectric point of which is between 5.8 and 8.5, is that they are soluble at acid pH and precipitate at physiological pH, all the solutions proposed for combining them with other products, such as prandial insulins or GLP-1 analogs or derivatives, are based on tests for solubilization of the prandial insulins or GLP-1 analogs or derivatives at acid pH, see, for example, WO2007/121256, WO2009/021955, WO2011/144673, WO2011/147980 or else WO2009/063072.

For example, as regards the combinations of insulin glargine and fast-acting insulin, the company Biodel has described, in particular in U.S. Pat. No. 7,718,609, compositions comprising a basal insulin and a prandial insulin at a pH of between 3.0 and 4.2 in the presence of a chelating agent and of polyacids. This patent teaches how to make a prandial insulin at acid pH compatible in the presence of insulin glargine. It does not teach how to prepare a combination of insulin of insulin glargine type and of a prandial insulin at neutral pH.

Likewise by way of example, as regards the solubilization of insulin glargine at neutral pH and combinations with a GLP-1 analog, mention will be made of patent application WO2011/144676 published on Nov. 24, 2011, in the name of SANOFI-AVENTIS, which describes formulations, at pH 9.5, of insulin glargine with the cyclodextrin SVE4-β-CYD in which the solubility of the insulin glargine is improved from 0.75 mM to 1.25 mM. This application also mentions compositions additionally comprising a GLP-1, although they are not exemplified. The solubilizing effect at pH 7.4 in a phosphate buffer is mentioned. These results of solubilization at pH 7.4 are described in the publication entitled "Effect of sulfobutyl ether-β-cyclodextrin on bioavailability of insulin glargine and blood glucose level after subcutaneous injection to rats" (*International Journal of Pharmaceu-*

*tics*, 419 (2011), 71-76) in FIG. 3A. The sulfobutyl ether-β-cyclodextrin improves the solubility of the insulin glargine at pH 7.4 from 5 µM to 8 µM, which is of no therapeutic interest, since the commercial concentration of insulin glargine is 600 µM (100 IU/ml). The problem has thus not been satisfactorily solved by the invention described in this patent application.

To our knowledge, a formulation which is stable at physiological pH, comprising a basal insulin, the isoelectric point of which is between 5.8 and 8.5, alone or in combination with a prandial insulin and/or a gut hormone, in which the solubility of the insulin is sufficient for a therapeutic treatment, has therefore never been described.

The present invention, by solving this problem of solubility at a pH between 6.6 and 7.8, makes it possible:
- to propose an injectable composition, intended for the treatment of diabetes, comprising a basal insulin, the isoelectric point of which is between 5.8 and 8.5, in the form of a homogeneous solution at a pH of between 6.6 and 7.8, while at the same time retaining its biological activity and its slow action profile,
- to propose an injectable composition in the form of a homogeneous solution at a pH of between 6.6 and 7.8, also comprising a combination of a basal insulin, the isoelectric point of which is between 5.8 and 8.5, and of a prandial insulin without modification of the activity profile of the prandial insulin which is soluble at pH 6-8 and unstable at acid pH, while at the same time maintaining the slow action profile specific to the basal insulin,
- to propose an injectable composition in the form of a homogeneous solution at a pH of between 6.6 and 7.8, also comprising a combination of a basal insulin, the isoelectric point of which is between 5.8 and 8.5, and of a gut hormone derivative or analog, such as GLP-1 or glucagon like peptide-1,
- to reduce the number of injections in the context of the treatment of diabetes,
- for said compositions to comply with the requirements of the US and European Pharmacopeias.

Surprisingly, the compositions according to the invention make it possible to solubilize, at a pH between 6.6 and 7.8, a basal insulin, the isoelectric point of which is between 5.8 and 8.5.

Surprisingly, the compositions according to the invention make it possible to maintain the duration of the hypoglycemic activity of the basal insulin, the isoelectric point of which is between 5.8 and 8.5, despite its solubilization at a pH of between 6.6 and 7.8 before injection. This notable property comes from the fact that the insulin of insulin glargine type solubilized at a pH of between 6.6 and 7.8 in the composition of the invention precipitates in subcutaneous medium through a change in composition of the medium. The element which triggers the precipitation of the insulin of insulin glargine type is no longer the pH modification, but a modification of the composition of the environment when the pharmaceutical composition passes from the container to the physiological medium. Surprisingly, in the combinations of insulin of insulin glargine type with a prandial insulin, which are subjects of the invention, the fast action of the prandial insulin is preserved despite the precipitation of the insulin of insulin glargine type in subcutaneous medium.

The solution according to the invention which makes it possible to solubilize the basal insulin, the isoelectric point of which is between 5.8 and 8.5, at a pH of between 6.6 and 7.8, preserves its biological activity.

In the combinations of the insulin of insulin glargine type with a prandial insulin which are subjects of the invention, the fast action of the prandial insulin is preserved despite the precipitation of the insulin of insulin glargine type in subcutaneous medium. Furthermore, the presence of the prandial insulin does not modify the solubility of the basal insulin at a pH of between 6.6 and 7.8 and likewise does not modify the precipitation properties of the basal insulin.

The invention relates to a composition in the form of an injectable aqueous solution, the pH of which is between 6.0 and 8.0, comprising at least:
a) a basal insulin, the isoelectric point pH of which is between 5.8 and 8.5;
b) a dextran substituted with radicals bearing carboxylate charges and hydrophobic radicals of formula I or of formula II:

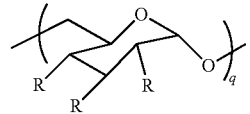

Formula I in which,
R is —OH or chosen from the group consisting of the radicals:
-(f-[A]-COOH)$_n$;
-(g-[B]-k-[D])$_m$, D comprising at least one alkyl chain comprising at least 8 carbon atoms;
n represents the degree of substitution of the glucoside units with -f-[A]-COOH and $0.1 \leq n \leq 2$;
m represents the degree of substitution of the glucoside units with -g-[B]-k-[D] and $0 < m \leq 0.5$;
q represents the degree of polymerization of glucoside units, i.e. the average number of glucoside units per polysaccharide chain and $3 \leq q \leq 50$;
-(f-[A]-COOH)$_n$;
-A- is a linear or branched radical comprising 1 to 4 carbon atoms; said radical -A-:
being bonded to a glucoside unit via a function f chosen from the group consisting of ether, ester and carbamate functions;
-(g-[B]-k-[D])$_m$;
-B- is a linear or branched, at least divalent radical comprising 1 to 4 carbon atoms; said radical -B-:
being bonded to a glucoside unit via a function g chosen from the group consisting of ether, ester and carbamate functions;
being bonded to a radical -D via a function k; k chosen from the group consisting of ester, amide and carbamate functions; said radical -D:
being a radical -X(-l-Y)$_p$, X being an at least divalent radical comprising from 1 to 12 atoms chosen from the group consisting of C, N or O atoms, optionally bearing carboxyl or amine functions and/or derived from an amino acid, from a dialcohol, from a diamine or from a mono- or polyethylene glycol mono- or diamine; Y being a linear or cyclic $C_8$ to $C_{30}$ alkyl group, a $C_8$ to $C_{30}$ alkylaryl or arylalkyl, optionally substituted with one or more $C_1$ to $C_3$ alkyl groups; $p \geq 1$ and l a function chosen from the group consisting of ester, amide and carbamate functions;

f, g and k being identical or different;
the free acid functions being in the form of salts of alkali metal cations chosen from the group consisting of $Na^+$ and $K^+$;
and when p=1, if Y is a $C_8$ to $C_{14}$ alkyl, then $q^*m \geq 2$, if Y is a $C_{15}$ alkyl, then $q^*m \geq 2$; and if Y is a $C_{16}$ to $C_{20}$ alkyl, then $q^*m \geq 1$;
and when p≥2, if Y is a $C_8$ to $C_9$ alkyl, then $q^*m \geq 2$ and, if Y is $C_{10}$ to $C_{16}$ alkyl, then $q^*m \geq 0.2$.

Formula II in which,
R is —OH or a radical -(f-[A]-COOH)$_n$:
- -A- is a linear or branched radical comprising 1 to 4 carbon atoms; said radical -A-:
  being bonded to a glucoside unit via a function f chosen from the group consisting of ether, ester or carbamate functions;
- n represents the degree of substitution of the glucoside units with -f-[A]-COOH and $0.1 \leq n \leq 2$;
R' is chosen from the group consisting of the radicals:
—C(O)NH-[E]-(o-[F])$_t$;
—CH$_2$N(L)$_z$-[E]-(o-[F])$_t$;
in which,
z is a positive integer equal to 1 or 2,
L is chosen from the group consisting of:
—H and z is equal to 1, and/or
-[A]-COOH and z is equal to 1 or 2, if f is an ether function,
—CO-[A]-COOH and z is equal to 1, if f is an ester function, and
—CO—NH-[A]-COOH and z is equal to 1 if f is a carbamate function;
-[E]-(o-[F])$_t$:
- -E- is a linear or branched, at least divalent radical comprising 1 to 8 carbon atoms and optionally comprising heteroatoms such as O, N or S;
- -F- being a $C_{12}$ to $C_{30}$ linear or cyclic alkyl group or a $C_{12}$ to $C_{30}$ alkylaryl or arylalkyl, optionally substituted with one or more $C_1$ to $C_3$ alkyl groups;
- o is a function chosen from the group consisting of ether, ester, amide or carbamate functions;
- t is a positive integer equal to 1 or 2;
q represents the degree of polymerization of glucoside units, i.e. the average number of glucoside units per polysaccharide chain and $3 \leq q \leq 50$;
the free acid functions being in the form of salts of alkali metal cations chosen from the group consisting of $Na^+$ and K+;
when z=2, the nitrogen atom is in the form of a quaternary ammonium.
In one embodiment, when p=1, if Y is a $C_{21}$ to $C_{30}$ group, then $q^*m \geq 1$.
In one embodiment, when p=1, if Y is a $C_{21}$ to $C_{30}$ group, then $q^*m \geq 0.1$.
In one embodiment, the radical -(f-[A]-COOH)$_n$ is such that:
-A- is a radical comprising 1 carbon atom; said radical -A- being bonded to a glucoside unit via an ether function f.
In one embodiment, the radical -(g-[B]-k-[D])$_m$ is such that:
-B- is a radical comprising 1 carbon atom; said radical -B- being bonded to a glucoside unit via an ether function g, and
X is a radical derived from an amino acid.
In one embodiment, the radical -(f-[A]-COOH)$_n$ is such that:
-A- is a radical comprising 1 carbon atom; said radical -A- being bonded to a glucoside unit via an ether function f, and
the radical -(g-[B]-k-[D])$_m$ is such that:
-B- is a radical comprising 1 carbon atom; said radical -B- being bonded to a glucoside unit via an ether function g, and
X is a radical derived from an amino acid, and
k is an amide function.
In one embodiment, the dextran substituted with radicals bearing carboxylate charges and hydrophobic radicals is of formula III:

Formula III in which,
R is —OH or chosen from the group consisting of the radicals:
-(f-[A]-COOH)$_n$;
-(g-[B]-k-[D])$_m$, D comprising at least one alkyl chain comprising at least 8 carbon atoms;
n represents the degree of substitution of the glucoside units with -f-[A]-COOH and $0.1 \leq n \leq 2$;
m represents the degree of substitution of the glucoside units with -g-[B]-k-[D] and $0 < m \leq 0.5$;
q represents the degree of polymerization of glucoside units, i.e. the average number of glucoside units per polysaccharide chain and $3 \leq q \leq 50$;
-(f-[A]-COOH)$_n$:
-A- is a linear or branched radical comprising 1 to 4 carbon atoms; said radical -A-:
being bonded to a glucoside unit via a function f chosen from the group consisting of ether, ester and carbamate functions;
-(g-[B]-k-[D])$_m$:
-B- is a linear or branched, at least divalent radical comprising 1 to 4 carbon atoms; said radical -B-:
being bonded to a glucoside unit via a function g chosen from the group consisting of ether, ester and carbamate functions;
being bonded to a radical -D via a function k; k chosen from the group consisting of ester, amide and carbamate functions; said radical -D:
being a radical -X(-l-Y)$_p$, X being an at least divalent radical comprising from 1 to 12 atoms chosen from the group consisting of C, N or O atoms, optionally bearing carboxyl or amine functions and/or derived from an amino acid, from a dialcohol, from a diamine or from a mono- or polyethylene glycol mono- or diamine; Y being a linear or cyclic $C_8$ to $C_{20}$ alkyl group, a $C_8$ to $C_{20}$ alkylaryl or arylalkyl, optionally substituted with one or more $C_1$ to $C_3$ alkyl groups; p≥1 and l a function chosen from the group consisting of ester, amide and carbamate functions;

f, g and k being identical or different;

the free acid functions being in the form of salts of alkali metal cations chosen from the group consisting of Na$^+$ and K$^+$;

and when p=1, if Y is a $C_8$ to $C_{14}$ alkyl, then q*m≥2, if Y is a $C_{15}$ alkyl, then q*m≥2; and if Y is a $C_{16}$ to $C_{20}$ alkyl, then q*m≥1;

and when p≥2, if Y is a $C_8$ to $C_{11}$ alkyl, then q*m≥2 and, if Y is $C_{12}$ to $C_{16}$ alkyl, then q*m≥0.3.

In one embodiment, the dextran substituted with radicals bearing carboxylate charges and hydrophobic radicals of for formula IV:

Formula IV

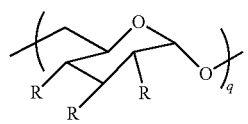

in which,

R is —OH or chosen from the group consisting of the radicals:

-(f-[A]-COOH)$_n$;

-(g-[B]-k-[D])$_m$; D comprising at least one alkyl chain comprising at least 8 carbon atoms;

n represents the degree of substitution of the hydroxyl —OH functions with -f-[A]-COOH per glucoside unit; and 0.1≤n≤2;

m represents the degree of substitution of the hydroxyl —OH functions with -g-[B]-k-[D] per glucoside unit; and 0≤m≤0.5;

q represents the degree of polymerization of glucoside units, i.e. the average number of glucoside units per polysaccharide chain and 3≤q≤50;

-(f-[A]-COOH)$_n$;

-A- is a linear or branched radical comprising 1 to 4 carbon atoms; said radical -A-:

being bonded to a glucoside unit via a function f chosen from the group consisting of ether, ester and carbamate functions;

-(g-[B]-k-[D])$_m$;

-B- is a linear or branched, at least divalent radical comprising 1 to 4 carbon atoms; said radical -B-:

being bonded to a glucoside unit via a function g chosen from the group consisting of ether, ester and carbamate functions;

being bonded to a radical -D via a function k; k chosen from the group consisting of ester, amide and carbamate functions; said radical -D:

being a radical -X(-l-Y)$_p$, X being an at least divalent radical comprising from 1 to 12 atoms chosen from the group consisting of C, N or O atoms, optionally bearing carboxyl or amine functions and/or derived from an amino acid, from a dialcohol, from a diamine or from a mono- or polyethylene glycol mono- or diamine; Y being a linear or cyclic $C_8$ to $C_{30}$ alkyl group, a $C_8$ to $C_{30}$ alkylaryl or arylalkyl, optionally substituted with one or more $C_1$ to $C_3$ alkyl groups; p≥1 and l a function chosen from the group consisting of ester, amide and carbamate functions;

f, g and k being identical or different;

the free acid functions being in the form of salts of alkali metal cations chosen from the group consisting of Na$^+$ and K$^+$;

and when p=1, if Y is a $C_8$ to $C_{14}$ alkyl, then q*m≥2, if Y is a $C_{15}$ alkyl, then q*m≥2; and if Y is a $C_{16}$ to $C_{30}$ alkyl, then q*m≥1;

and when p≥2, if Y is a $C_8$ to $C_9$ alkyl, then q*m≥2 and, if Y is $C_{10}$ to $C_{16}$ alkyl, then q*m≥0.2.

The structure drawn corresponds to the representation commonly used to represent dextran, which is a polysaccharide consisting in the majority of (1,6) sequences between glucoside units, which is the representation adopted. Dextran also contains (1,3) sequences generally at approximately 5%, which are intentionally not represented, but which are of course included in the scope of the invention.

In one embodiment, 0.3≤n≤1.7.
In one embodiment, 0.7≤n≤1.5.
In one embodiment, 0.9≤n≤1.2.
In one embodiment, 0.01≤m≤0.5.
In one embodiment, 0.02≤m≤0.4.
In one embodiment, 0.03≤m≤0.3.
In one embodiment, 0.05≤m≤0.2.
In one embodiment, 3≤q≤50.
In one embodiment, 3≤q≤40.
In one embodiment, 3≤q≤30.
In one embodiment, 3≤q≤20.
In one embodiment, 3≤q≤10.

In one embodiment, the radical -(f-[(A)-COOH)$_n$ is chosen from the group consisting of the following sequences, f having the meaning given above:

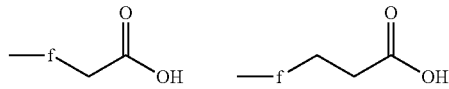

In one embodiment, the radical -(g-[B]-k-[D])$_m$ is chosen from the group consisting of the following sequences; g, k and D having the meanings given above:

In one embodiment, D is such that the radical X is an at least divalent radical derived from an amino acid.

In one embodiment, D is such that the radical X is an at least divalent radical derived from an amino add chosen from the group consisting of glycine, leucine, phenylalanine, lysine, isoleucine, alanine, valine, aspartic acid and glutamic acid.

The radicals derived from amino acids can be either levorotatory or dextrorotatory.

In one embodiment, D is such that the radical X is an at least divalent radical derived from a mono- or polyethylene glycol.

In one embodiment, D is such that the radical X is an at least divalent radical derived from ethylene glycol.

In one embodiment, D is such that the radical X is an at least divalent radical derived from a polyethylene glycol chosen from the group consisting of diethylene glycol and triethylene glycol.

In one embodiment, D is such that the radical X is an at least divalent radical derived from a mono- or polyethylene glycol amine.

In one embodiment, D is such that the radical X is an at least divalent radical derived from a mono- or polyethylene glycol amine chosen from the group consisting of ethanolamine, diethylene glycol amine and triethylene glycol amine.

In one embodiment, D is such that the radical X is an at least divalent radical derived from a mono- or polyethylene glycol diamine.

In one embodiment, D is such that the radical X is an at least divalent radical derived from ethylenediamine.

In one embodiment, D is such that the radical X is an at least divalent radical derived from a mono- or polyethylene glycol diamine chosen from the group consisting of diethylene glycol diamine and triethylene glycol diamine.

In one embodiment, D is such that the Y group is an alkyl group derived from a hydrophobic alcohol.

In one embodiment, D is such that the Y group is an alkyl group derived from a hydrophobic alcohol, chosen from the group consisting of octanol (capryl alcohol), 3,7-dimethyloctan-1-ol, decanol (decyl alcohol), dodecanol (lauryl alcohol), tetradecanol (myristyl alcohol) and hexadecanol (cetyl alcohol).

In one embodiment, D is such that the Y group is an alkyl group derived from a hydrophobic acid.

In one embodiment, D is such that the Y group is an alkyl group derived from a hydrophobic acid, chosen from the group consisting of decanoic acid, dodecanoic acid, tetradecanoic acid and hexadecanoic acid.

In one embodiment, D is such that the Y group is a group derived from a sterol.

In one embodiment, D is such that the Y group is a group derived from a sterol, chosen from the group consisting of cholesterol and derivatives thereof.

In one embodiment, D is such that the Y group is a group derived from a tocopherol.

In one embodiment, D is such that the Y group is a group derived from a tocopherol derivative, chosen from the racemate, the L isomer or the D isomer of α-tocopherol.

In one embodiment, D is such that the radical X is derived from glycine, p=1, the Y group is derived from octanol and the function l is an ester function.

In one embodiment, D is such that the radical X is derived from glycine, p=1, the Y group is derived from dodecanol and the function l is an ester function.

In one embodiment, D is such that the radical X is derived from glycine, p=1, the Y group is derived from hexadecanol and the function l is an ester function.

In one embodiment, D is such that the radical X is derived from phenylalanine, p=1, the Y group is derived from octanol and the function l is an ester function.

In one embodiment, D is such that the radical X is derived from phenylalanine, p=1, the Y group is derived from 3,7-dimethyloctan-1-ol and the function l is an ester function.

In one embodiment, D is such that the radical X is derived from aspartic acid, p=2, the Y groups are derived from octanol and the functions l are ester functions.

In one embodiment, D is such that the radical X is derived from aspartic acid, p=2, the Y groups are derived from decanol and the functions l are ester functions.

In one embodiment, D is such that the radical X is derived from aspartic acid, p=2, the Y groups are derived from dodecanol and the functions l are ester functions.

In one embodiment, D is such that the radical X is derived from ethylenediamine, the Y group is derived from dodecanoic acid and the function l is an amide function.

In one embodiment, D is such that the radical X is derived from diethylene glycol amine, p=1, the Y group is derived from dodecanoic acid and the function l is an ester function.

In one embodiment, D is such that the radical X is derived from triethylene glycol diamine, p=1, the Y group is derived from dodecanoic acid and the function l is an amide function.

In one embodiment, D is such that the radical X is derived from triethylene glycol diamine, p=1, the Y group is derived from hexadecanoic acid and the function l is an amide function.

In one embodiment, D is such that the radical X is derived from leucine, p=1, the Y group is derived from cholesterol and the function l is an ester function.

In one embodiment, D is such that X is derived from ethylenediamine, p=1, the Y group is derived from cholesterol and the function l is a carbamate function.

In one embodiment, the radical E is an at least divalent radical derived from an amino acid chosen from the group consisting of glycine, leucine, phenylalanine, lysine, isoleucine, alanine, valine, serine, threonine, aspartic acid and glutamic acid.

The radicals derived from amino acids can be either levorotatory or dextrorotatory.

In one embodiment, the radical E is an at least divalent radical derived from a mono- or polyethylene glycol amine.

In one embodiment, the radical E is an at least divalent radical derived from a mono- or polyethylene glycol amine chosen from the group consisting of ethanolamine, diethylene glycol amine and triethylene glycol amine.

In one embodiment, the radical E is an at least divalent radical derived from a mono- or polyethylene glycol diamine.

In one embodiment, the radical E is an at least divalent radical derived from ethylenediamine.

In one embodiment, the radical E is an at least divalent radical derived from a mono- or polyethylene glycol diamine chosen from the group consisting of diethylene glycol diamine and triethylene glycol diamine.

In one embodiment, the F group is an alkyl group derived from a hydrophobic alcohol.

In one embodiment, the F group is a group derived from a hydrophobic alcohol, chosen from the group consisting of dodecanol (lauryl alcohol), tetradecanol (myristyl alcohol) and hexadecanol (cetyl alcohol).

In one embodiment, the F group is a group derived from a hydrophobic acid.

In one embodiment, the F group is a group derived from a hydrophobic acid, chosen from the group consisting of dodecanoic acid, tetradecanoic acid and hexadecanoic acid.

In one embodiment, the F group is a group derived from a sterol.

In one embodiment, the F group is a group derived from a sterol, chosen from the group consisting of cholesterol and derivatives thereof.

In one embodiment, the F group is a group derived from a tocopherol.

In one embodiment, the F group is a group derived from a tocopherol derivative, chosen from the racemate, the L isomer or the D isomer of α-tocopherol.

In one embodiment, the radical E is derived from ethylenediamine, t=1, o is a carbamate function, and the F group is derived from cholesterol.

In one embodiment:
- -(f-[A]-COOH)$_n$ is such that A is the radical —CH$_2$— and f is an ether function;
- -(g-[B]-k-[D])$_m$ is such that g is an ether function, B is the radical —CH$_2$—, k is an amide function and D is such that X is derived from glycine, l is an ester function and Y is derived from octanol;
- q=38, n=0.9 and m=0.2.

In one embodiment:
- -(f-[A]-COOH)$_n$ is such that A is the radical —CH$_2$— and f is an ether function;
- -(g-[B]-k-[D])$_m$ is such that g is an ether function, B is the radical —CH$_2$—, k is an amide function and D is such that X is derived from glycine, p=1, l is an ester function and Y is derived from hexadecanol;
- q=19, n=1.0 and m=0.1.

In one embodiment:
- -(f-[A]-COOH)$_n$ is such that A is the radical —CH$_2$— and f is an ether function;
- -(g-[B]-k-[D])$_m$ is such that g is an ether function, B is the radical —CH$_2$—, k is an amide function and D is such that X is derived from phenylalanine, p=1, l is an ester function and Y is derived from octanol;
- q=38, n=1.0 and m=0.1.

In one embodiment:
- -(f-[A]-COOH)$_n$ is such that A is the radical —CH$_2$— and f is an ether function;
- -(g-[B]-k-[D])$_m$ is such that g is an ether function, B is the radical —CH$_2$—, k is an amide function and D is such that X is derived from phenylalanine, p=1 l is an ester function and Y is derived from octanol;
- q=19, n=1.0 and m=0.2.

In one embodiment:
- -(f-[A]-COOH)$_n$ is such that A is the radical —CH$_2$— and f is an ether function;
- -(g-[B]-k-[D])$_m$ is such that g is an ether function, B is the radical —CH$_2$—, k is an amide function and D is such that X is derived from phenylalanine, p=1, l is an ester function and Y is derived from 3,7-dimethyloctan-1-ol;
- q=38, n=1.0 and m=0.1.

In one embodiment:
- -(f-[A]-COOH)$_n$ is such that A is the radical —CH$_2$— and f is an ether function;
- -(g-[B]-k-[D])$_m$ is such that g is an ether function, B is the radical —CH$_2$—, k is an amide function and D is such that X is derived from aspartic acid, p=2, l are ester functions and Y are derived from octanol;
- q=38, n=1.05 and m=0.05.

In one embodiment:
- -(f-[A]-COOH)$_n$ is such that A is the radical —CH$_2$— and f is an ether function;
- -(g-[B]-k-[D])$_m$ is such that g is an ether function, B is the radical —CH$_2$—, k is an amide function and D is such that X is derived from aspartic acid, p=2, l are ester functions and Y are derived from decanol;
- q=38, n=1.05 and m=0.05.

In one embodiment:
- -(f-[A]-COOH)$_n$ is such that A is the radical —CH$_2$— and f is an ether function;
- -(g-[B]-k-[D])$_m$ is such that g is an ether function, B is the radical —CH$_2$—, k is an amide function and D is such that X is derived from aspartic acid, p=2, l are ester functions and Y are derived from dodecanol;
- q=19, n=1.05 and m=0.05.

In one embodiment:
- -(f-[A]-COOH)$_n$ is such that A is the radical —CH$_2$— and f is an ether function;
- -(g-[B]-k-[D])$_m$ is such that g is an ether function, B is the radical —CH$_2$—, k is an amide function and D is such that X is derived from ethylenediamine, p=1, l is an amide function and Y is derived from dodecanoic acid;
- q=38, n=1.0 and m=0.1.

In one embodiment:
- -(f-[A]-COOH)$_n$ is such that A is the radical —CH$_2$—CH$_2$— and f is an ester function;
- -(g-[B]-k-[D])$_m$ is such that g is an ester function, B is the radical —CH$_2$—CH$_2$—, k is an amide function and D is such that X is derived from glycine, p=1, l is an ester function and Y is derived from dodecanol;
- q=38, n=1.3 and m=0.1.

In one embodiment:
- -(f-[A]-COOH)$_n$ is such that A is the radical —CH$_2$— and f is a carbamate function;
- -(g-[B]-k-[D])$_m$ is such that g is a carbamate function, B is the radical —CH$_2$—, k is an amide function and D is such that X is derived from aspartic acid, p=2, l are ester functions and Y are derived from octanol;
- q=38, n=1.3 and m=0.1.

In one embodiment:
- -(f-[A]-COOH)$_n$ is such that A is the radical —CH$_2$— and f is an ether function;
- -(g-[B]-k-[D])$_m$ is such that g is an ether function, B is the radical —CH$_2$—, k is an amide function and D is such that X is derived from aspartic acid, p=2, l are ester functions and Y are derived from dodecanol;
- q=4, n=0.96 and m=0.07.

In one embodiment:
- -(f-[A]-COOH)$_n$ is such that A is the radical —CH$_2$— and f is an ether function;
- -(g-[B]-k-[D])$_m$ is such that g is an ether function, B is the radical —CH$_2$—, k is an amide function and D is such that X is derived from diethylene glycol amine, p=1, l is an ester function and Y is derived from dodecanoic add; q=38, n=1.0 and m=0.1.

In one embodiment:
- -(f-[A]-COOH)$_n$ is such that A is the radical —CH$_2$— and f is an ether function;
- -(g-[B]-k-[D])$_m$ is such that g is an ether function, B is the radical —CH$_2$—, k is an amide function and D is such that X is derived from triethylene glycol diamine, p=1, l is an amide function and Y is derived from dodecanoic acid;
- q=38, n=1.0 and m=0.1.

In one embodiment:
- -(f-[A]-COOH)$_n$ is such that A is the radical —CH$_2$— and f is an ether function;
- -(g-[B]-k-[D])$_m$ is such that g is an ether function, B is the radical —CH$_2$—, k is an amide function and D is such that X is derived from triethylene glycol diamine, p=1, l is an amide function and Y is derived from hexadecanoic add;
- q=38, n=1.05 and m=0.05.

In one embodiment:
- -(f-[A]-COOH)$_n$ is such that A is the radical —CH$_2$— and f is an ether function;
- -(g-[B]-k-[D])$_m$ is such that g is an ether function, B is the radical —CH$_2$—, k is an amide function and D is such that X is derived from glycine, p=1, l is an ester function and Y is derived from hexadecanol;
- q=19, n=1.05 and m=0.05.

In one embodiment:
- -(f-[A]-COOH)$_n$ is such that A is the radical —CH$_2$— and f is an ether function;

-(g-[B]-k-[D])$_m$ is such that g is an ether function, B is the radical —CH$_2$—, k is an amide function and D is such that X is derived from glycine, p=1, l is an ester function and Y is derived from hexadecanol;
q=38, n=0.37 and m=0.05.

In one embodiment:
-(f-[A]-COOH)$_n$ is such that A is the radical —CH$_2$— and f is an ether function;
-(g-[B]-k-[D])$_m$ is such that g is an ether function, B is the radical —CH$_2$—, k is an amide function and D is such that X is derived from leucine, p=1, l is an ester function and Y is derived from cholesterol;
q=19, n=1.61 and m=0.04.

In one embodiment:
-(f-[A]-COOH)$_n$ is such that A is the radical —CH$_2$— and f is an ether function;
-(g-[B]-k-[D])$_m$ is such that g is an ether function, B is the radical —CH$_2$—, k is an amide function and D is such that X is derived from leucine, p=1, l is an ester function and Y is derived from cholesterol;
q=19, n=1.06 and m=0.04.

In one embodiment:
-(f-[A]-COOH)$_n$ is such that A is the radical —CH$_2$— and f is an ether function;
-(g-[B]-k-[D])$_m$ is such that g is an ether function, B is the radical —CH$_2$—, k is an amide function and D is such that X is derived from leucine, p=1, l is an ester function and Y is derived from cholesterol;
q=19, n=0.66 and m=0.04.

In one embodiment:
-(f-[A]-COOH)$_n$ is such that A is the radical —CH$_2$— and f is an ether function;
-(g-[B]-k-[D])$_m$ is such that g is an ether function, B is the radical —CH$_2$—, k is an amide function and D is such that X is derived from leucine, p=1, l is an ester function and Y is derived from cholesterol;
q=19, n=0.46 and m=0.04.

In one embodiment:
-(f-[A]-COOH)$_n$ is such that A is the radical —CH$_2$— and f is an ether function;
-(g-[B]-k-[D])$_m$ is such that g is an ether function, B is the radical —CH$_2$—, k is an amide function and D is such that X is derived from leucine, p=1, l is an ester function and Y is derived from cholesterol;
q=4, n=1.61 and m=0.05.

In one embodiment:
-(f-[A]-COOH)$_n$ is such that A is the radical —CH$_2$— and f is an ether function;
-(g-[B]-k-[D])$_m$ is such that g is an ether function, B is the radical —CH$_2$—, k is an amide function and D is such that X is derived from ethylenediamine, p=1, l is a carbamate function and Y is derived from cholesterol;
q=19, n=1.61 and m=0.04.

In one embodiment:
-(f-[A]-COOH)$_n$ is such that A is the radical —CH$_2$— and f is a carbamate function;
-(g-[B]-k-[D])$_m$ is such that g is a carbamate function, B is the radical —CH$_2$—, k is an amide function and D is such that X is derived from leucine, p=1, l is an ester function and Y is derived from cholesterol; q=19, n=1.96 and m=0.04.

In one embodiment:
-(f-[A]-COOH)$_n$ is such that A is the radical —CH$_2$— and f is an ether function;
-[E]-(o-[F])$_t$ is such that E is derived from ethylenediamine, o is a carbamate function and F is derived from cholesterol;
q=19 and n=1.65.

In one embodiment:
-(f-[A]-COOH)$_n$ is such that A is the radical —CH$_2$— and f is an ether function;
-(g-[B]-k-[D])$_m$ is such that g is an ether function, B is the radical —CH$_2$—, k is an amide function and D is such that X is derived from leucine, p=1, l is an ester function and Y is derived from cholesterol;
q=38, n=0.99 and m=0.05.

In one embodiment:
-(f-[A]-COOH)$_n$ is such that A is the radical —CH$_2$— and f is an ether function;
-(g-[B]-k-[D])$_m$ is such that g is an ether function, B is the radical —CH$_2$—, k is an amide function and D is such that X is derived from aspartic acid, p=2, l are ester functions and Y are derived from dodecanol;
q=4, n=1.41 and m=0.16.

In one embodiment:
-(f-[A]-COOH)$_n$ is such that A is the radical —CH$_2$— and f is an ether function;
-(g-[B]-k-[D])$_m$ is such that g is an ether function, B is the radical —CH$_2$—, k is an amide function and D is such that X is derived from aspartic add, p=2, l are ester functions and Y are derived from dodecanol;
q=4, n=1.50 and m=0.07.

In one embodiment:
-(f-[A]-COOH)$_n$ is such that A is the radical —CH$_2$— and f is an ether function;
-(g-[B]-k-[D])$_m$ is such that g is an ether function, B is the radical —CH$_2$—, k is an amide function and D is such that X is derived from aspartic acid, p=2, l are ester functions and Y are derived from decanol;
q=4, n=1.05 and m=0.05.

In one embodiment, the compositions according to the invention comprise a dextran chosen from the group consisting of the following dextrans of formula I, III or IV:
  sodium dextranmethylcarboxylate modified with octyl glycinate,
  sodium dextranmethylcarboxylate modified with cetyl glycinate,
  sodium dextranmethylcarboxylate modified with octyl phenylalaninate,
  sodium dextranmethylcarboxylate modified with 3,7-dimethyl-1-octyl phenylalaninate,
  sodium dextranmethylcarboxylate modified with dioctyl aspartate,
  sodium dextranmethylcarboxylate modified with didecyl aspartate,
  sodium dextranmethylcarboxylate modified with N-(2-aminoethyl)dodecanamide,
  sodium dextransuccinate modified with lauryl glycinate,
  N-(sodium methylcarboxylate) dextran carbamate modified with dioctyl aspartate,
  sodium dextranmethylcarboxylate modified with dilauryl aspartate,
  sodium dextranmethylcarboxylate modified with 2-(2-aminoethoxy)ethyl dodecanoate,
  sodium dextranmethylcarboxylate modified with 2-(2-{2-[dodecanoylamino]ethoxy}ethoxy)ethylamine,
  sodium dextranmethylcarboxylate modified with 2-(2-{2-[hexadecanoylamino]ethoxy}ethoxy)ethylamine,
  sodium dextranmethylcarboxylate modified with cholesteryl leucinate,
  sodium dextranmethylcarboxylate modified with cholesteryl 1-ethylenediaminecarboxylate,
  N-(sodium methylcarboxylate) dextran carbamate modified with cholesteryl leucinate.

In one embodiment, the compositions according to the invention comprise a dextran chosen from the group consisting of the following dextran of formula II:

sodium dextranmethylcarboxylate modified with cholesteryl 1-ethylenediaminecarboxylate grafted by reductive amination onto the reducing chain end.

The invention also relates to a composition in the form of an injectable aqueous solution, the pH of which is between 6.6 and 7.8, comprising at least:
a) a basal insulin, the isoelectric point pI of which is between 5.8 and 8.5;
b) a hydrophobized anionic polymer of formula II-I:

Formula II-I in which,
l=0 or 1,
m=0, 1 or 2,
a=0 or 1,
n being the degree of polymerization, of between 3 and 1000, and
—$R_1$ is a hydrogen —H,
—$R_2$, —$R_3$, —$R_4$ and —$R_6$ are radicals —$CH_2R'$,
—$R_5$ is either a —COOH group, or a radical —$CH_2R'$, or a radical -k-[D], in which:
-[D] is a radical -[Hy] or -[E]-($\alpha$-[Hy])$_t$;
-[E]- is an at least divalent radical comprising from 1 to 15 carbon atoms comprising at least one heteroatom chosen from O, N and S, optionally bearing carboxyl or amine functions and/or -k-[E]-(o)$_t$, comprising from 2 to 16 carbon atoms, is derived from an amino acid, from a dialcohol, from a diamine or from an amine alcohol;
-[Hy] is a $C_8$ to $C_{30}$ linear or cyclic alkyl group or a $C_8$ to $C_{30}$ alkylaryl or arylalkyl, optionally substituted with one or more $C_1$ to $C_3$ alkyl groups, which is derived from a hydrophobic compound;
k resulting from the reaction between a carboxyl, amine or alcohol function of the precursor of -k-[E]-(o)$_t$ and an alcohol, carboxyl or amine function of the polymer and is a function chosen from the group consisting of ester, amide, carbonate and carbamate functions;
resulting from the reaction between a carboxyl, amine or alcohol function of the precursor of -k-[E]-(o)$_t$ and an alcohol or acid function of the precursor of -[Hy] is a function chosen from the group consisting of ester, amide, urea (carbamide), carbonate and carbamate functions;
t is a positive integer equal to 1 or 2;
and/or
—$R_1$ and —$R_3$ form a six-membered ring —$R_1$-$R_3$—=—CH(NHCOCH$_3$)— and —$R_2$ is a radical —$CH_2R'$,
and/or
—$R_2$ and —$R_3$ form a six-membered ring and —$R_2$-$R_3$—=—(CH(R'))$_3$— and —$R_1$ is a hydrogen,
and/or
—$R_4$ and —$R_6$ form a six-membered ring and —$R_4$-$R_6$—=—(CH(R'))$_2$—, and —R' is chosen from the group consisting of the radicals:
—OH
—O-Alk, Alk being a $C_1$ to $C_3$ alkyl chain,
-(f-[A]-COOH), in which:
-[A]- is an at least divalent radical comprising from 1 to 15 carbon atoms comprising at least one heteroatom chosen from O, N and S, optionally bearing carboxyl or amine functions and/or -f-[A]-COOH, comprising from 2 to 16 carbon atoms, is derived from an amino acid, from a diacid or from an alcohol acid and is bonded to the backbone of the molecule via a function f,
f resulting from the reaction between a carboxyl or alcohol or amine function of the precursor of -f-[A]-COOH and a hydroxyl function of the backbone is chosen from the group consisting of ether, ester, carbamate or carbonate functions;
-g-[B]-(k-[D])$_p$, in which:
-[B]- is an at least divalent radical comprising from 1 to 15 carbon atoms comprising at least one heteroatom chosen from O, N and S, optionally bearing carboxyl or amine functions and/or -g-[B]-(k-)$_p$, comprising from 2 to 16 carbon atoms, is derived from an amino acid, from a diacid, from a dialcohol, from an alcohol acid, from a diamine or from an amine alcohol and is bonded to the backbone of the molecule via a function g and is bonded to at least one radical -[D] via a function k,
g resulting from the reaction between a carboxyl or alcohol or amine function of the precursor of -g-[B]-(k-)$_p$ and a function of the backbone is chosen from the group consisting of ether, amine, ester, carbamate or carbonate functions,
k resulting from the reaction between a carboxyl or alcohol or amine function of the precursor of -g-[B]-(k-)$_p$ and an alcohol or acid function of the precursor of -[D] is chosen from the group consisting of ester, amide or carbamate functions;
p is a positive integer equal to 1 or 2;
and -[A]-, -[B]- and -[E]- are identical or different,
and k and o are identical or different;
and, if -[B]- is a trivalent radical, then -[D] is a radical -[Hy],
and, if m and a=0 then —$R_2$=—$CH_2R'$,
and the degree of substitution with carboxylate charges is the average number of carboxylate charges per monomer divided by (l+m) and is greater than or equal to 0.4,
and the degree of substitution with hydrophobic radicals is the average number of hydrophobic radicals per monomer divided by (l+m) and is less than or equal to 0.5, and, if the hydrophobized anionic polymer is a polysaccharide, then the identical or different glycosidic linkages may be of a type and/or of β type.

The hydrophobized anionic polymers are chosen from the polymers of formula II-I, in which the asymmetric carbon atoms are of absolute configuration R or S.

They are also chosen from the polymers of which the free acid functions are in the form of salts of alkali metal cations chosen from the group consisting of Na$^+$ and K$^+$.

The term "hydrophobized polymer" is intended to mean a polymer bearing a hydrophobic radical or group.

The term "hydrophobic" radical or group is intended to mean a radical or a group derived from a hydrophobic compound.

The term "hydrophobic compound" is intended to mean a compound having a Log P greater than or equal to 2. The Log P or Log Kow or partition coefficient is a measure of the distribution of a compound in an n-octanol immiscible solvent/water mixture. The Log P can be measured according to the shake flask method, or when this is not possible, by the HPLC method (OECD Guideline for the testing of chemicals, 117, 30.03.89, Partition coefficient (n-octanol/water): HPLC method and 107, 27.07.95, Partition coefficient (n-octanol/water): Shake Flask Method). Said Log P of a compound been defined by the equation:

$$\log P = \log(c_{oct}/c_{water})$$

in which $c_{oct}$ is the concentration of said compound in the n-octanol and $c_{water}$ is the concentration of said compound in water.

In one embodiment, the composition according to the invention is characterized in that the hydrophobized anionic polymer is chosen from the hydrophobized anionic polymers of formula II-I in which, when —$R_1$ and —$R_3$ form a six-membered ring —$R_1$-$R_3$—=—CH(NHCOCH$_3$)— and —$R_2$ is a radical —CH$_2$R', then —$R_4$ and —$R_6$ do not form a six-membered ring.

In one embodiment, the composition according to the invention is characterized in that the hydrophobized anionic polymer is chosen from the hydrophobized anionic polymers of formula II-I in which —$R_1$ and —$R_3$ do not form a six-membered ring with —$R_1$-$R_3$—=—CH(NHCOCH$_3$)— and —$R_2$ is a radical —CH$_2$R'.

In one embodiment, the composition according to the invention is characterized in that the hydrophobized anionic polymer is chosen from the compounds of formula II-I in which the radical -f-[A]-COOH, comprising from 2 to 8 carbon atoms, is derived from an amino acid, from a dialcohol, from a diamine, from a diacid or from an amine alcohol.

In one embodiment, the composition according to the invention is characterized in that the hydrophobized anionic polymer is chosen from the compounds of formula II-I in which the radical -f-[A]-COOH, comprising from 2 to 6 carbon atoms, is derived from an amino acid, from a dialcohol, from a diamine, from a diacid or from an amine alcohol.

In one embodiment, the composition according to the invention is characterized in that the hydrophobized anionic polymer is chosen from the hydrophobized anionic polymers of formula II-I in which the radical -f-[A]-COOH is chosen from the radicals of formula II-II below:

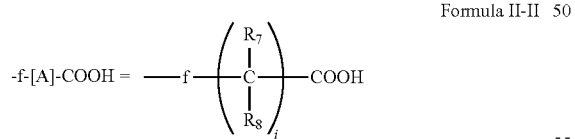

Formula II-II in which:
i is greater than or equal to 1 and less than or equal to 12, and
—$R_7$ and —$R_8$, which may be identical or different, are chosen from the group consisting of a hydrogen atom, a saturated or unsaturated, linear, branched or cyclic $C_1$ to $C_6$ alkyl, a benzyl, an alkylaryl, optionally comprising heteroatoms chosen from the group consisting of O, N and/or S, or functions chosen from the group consisting of carboxylic acid, amine, alcohol and thiol functions.

In one embodiment, the composition according to the invention is characterized in that the hydrophobized anionic polymer is chosen from the hydrophobized anionic polymers of formula II-I in which the radical -f-[A]-COOH is chosen from the group consisting of the following radicals, f having the meaning given above:

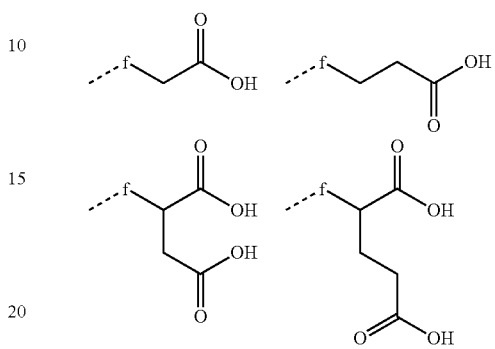

or the salts thereof with alkali metal cations chosen from the group consisting of Na$^+$ and K$^-$.

In one embodiment, the composition according to the invention is characterized in that the hydrophobized anionic polymer is chosen from the hydrophobized anionic polymers of formula II-I in which the radical -[A]- is a radical —CH$_2$—.

In one embodiment, the composition according to the invention is characterized in that the hydrophobized anionic polymer is chosen from the hydrophobized anionic polymers of formula II-I in which the radical -f-[A]-COOH is derived from an amino acid.

In one embodiment, the composition according to the invention is characterized in that the hydrophobized anionic polymer is chosen from the hydrophobized anionic polymers of formula II-I in which the radical -f-[A]-COOH is derived from glycine.

In one embodiment, the composition according to the invention is characterized in that the hydrophobized anionic polymer is chosen from the hydrophobized anionic polymers of formula II-I in which the radical -f-[A]-COOH is derived from aspartic acid.

In one embodiment, the composition according to the invention is characterized in that the hydrophobized anionic polymer is chosen from the hydrophobized anionic polymers of formula II-I in which the radical -f-[A]-COOH is derived from glutamic acid.

In one embodiment, the composition according to the invention is characterized in that the hydrophobized anionic polymer is chosen from the hydrophobized anionic polymers of formula II-I in which the radical -f-[A]-COOH is derived from succinic acid.

In one embodiment, the composition according to the invention is characterized in that the hydrophobized anionic polymer is chosen from the hydrophobized anionic polymers of formula II-I in which the function f is an ether function.

In one embodiment, the composition according to the invention is characterized in that the hydrophobized anionic polymer is chosen from the hydrophobized anionic polymers of formula II-I in which the function f is a carbamate function.

In one embodiment, the composition according to the invention is characterized in that the hydrophobized anionic polymer is chosen from the hydrophobized anionic polymers of formula II-I in which the function f is an ester function.

In one embodiment, the composition according to the invention is characterized in that the hydrophobized anionic polymer is chosen from the hydrophobized anionic polymers of formula II-I in which the function f is a carbonate function.

In one embodiment, the composition according to the invention is characterized in that the hydrophobized anionic polymer is chosen from the hydrophobized anionic polymers of formula II-I in which the function f is an amide function.

In one embodiment, the composition according to the invention is characterized in that the hydrophobized anionic polymer is chosen from the hydrophobized anionic polymers of formula II-I in which the radical -g-[B]- is chosen from the radicals of formula II-III below:

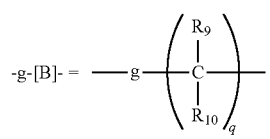

Formula II-III in which:
q is greater than or equal to 1 and less than or equal to 12, and
—$R_9$ and —$R_{10}$, which may be identical or different, are chosen from the group consisting of a hydrogen atom, a saturated or unsaturated, linear, branched or cyclic $C_1$ to $C_6$ alkyl, a benzyl, an alkylaryl, optionally comprising heteroatoms chosen from the group consisting of O, N and/or S, or functions chosen from the group consisting of carboxylic acid, amine, alcohol and thiol functions.

In one embodiment, the composition according to the invention is characterized in that the hydrophobized anionic polymer is chosen from the hydrophobized anionic polymers of formula II-I in which the radical -g-[B]-k-[D] is chosen from the group consisting of the following radicals:

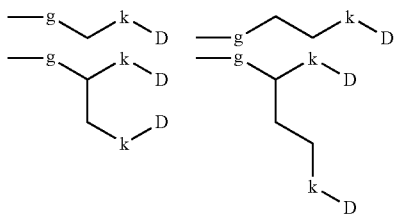

g, k and -[D] having the meanings given above.

In one embodiment, the composition according to the invention is characterized in that the hydrophobized anionic polymer is chosen from the hydrophobized anionic polymers of formula II-I in which the radical -[B]- is a radical —$CH_2$—.

In one embodiment, the composition according to the invention is characterized in that the hydrophobized anionic polymer is chosen from the hydrophobized anionic polymers of formula II-I in which the radical -g-[B]-(k-[D])$_p$ is such that -g-[B]-k- is derived from an amino acid.

In one embodiment, the composition according to the invention is characterized in that the hydrophobized anionic polymer is chosen from the hydrophobized anionic polymers of formula II-I in which the radical -g-[B]-(k-[D])$_p$ is such that -g-[B]-k- is derived from glycine.

In one embodiment, the composition according to the invention is characterized in that the hydrophobized anionic polymer is chosen from the hydrophobized anionic polymers of formula II-I in which the radical -g-[B]-(k-[D])$_p$ is such that -g-[B]-k- is derived from aspartic acid.

In one embodiment, the composition according to the invention is characterized in that the hydrophobized anionic polymer is chosen from the hydrophobized anionic polymers of formula II-I in which the radical -g-[B]-(k-[D])$_p$ is such that -g-[B]-k- is derived from glutamic acid.

In one embodiment, the composition according to the invention is characterized in that the hydrophobized anionic polymer is chosen from the hydrophobized anionic polymers of formula II-I in which the radical -g-[B]-(k-[D])$_p$ is such that -g-[B]-k- is derived from succinic acid.

In one embodiment, the composition according to the invention is characterized in that the hydrophobized anionic polymer is chosen from the hydrophobized anionic polymers of formula II-I in which the function g is an ether function.

In one embodiment, the composition according to the invention is characterized in that the hydrophobized anionic polymer is chosen from the hydrophobized anionic polymers of formula II-I in which the function g is a carbamate function.

In one embodiment, the composition according to the invention is characterized in that the hydrophobized anionic polymer is chosen from the hydrophobized anionic polymers of formula II-I in which the function g is an ester function.

In one embodiment, the composition according to the invention is characterized in that the hydrophobized anionic polymer is chosen from the hydrophobized anionic polymers of formula II-I in which the function g is an amine function.

In one embodiment, the composition according to the invention is characterized in that the hydrophobized anionic polymer is chosen from the hydrophobized anionic polymers of formula II-I in which the function g is a carbonate function.

In one embodiment, the composition according to the invention is characterized in that the hydrophobized anionic polymer is chosen from the hydrophobized anionic polymers of formula II-I in which the function k is an amide function.

In one embodiment, the composition according to the invention is characterized in that the hydrophobized anionic polymer is chosen from the hydrophobized anionic polymers of formula II-I in which the function k is a carbamate function.

In one embodiment, the composition according to the invention is characterized in that the hydrophobized anionic polymer is chosen from the hydrophobized anionic polymers of formula II-I in which the function k is an ester function.

In one embodiment, the composition according to the invention is characterized in that the hydrophobized anionic polymer is chosen from the hydrophobized anionic polymers of formula II-I in which the radical -k-[E]-(o)$_t$ is an at least divalent radical derived from an amino acid.

In one embodiment, the composition according to the invention is characterized in that the hydrophobized anionic polymer is chosen from the hydrophobized anionic polymers of formula II-I in which the radical -k-[E]-(o)$_t$ is an at least divalent radical derived from an alpha amino acid.

In one embodiment, the composition according to the invention is characterized in that the hydrophobized anionic polymer is chosen from the hydrophobized anionic polymers of formula II-I in which the radical -k-[E]-(o)$_t$ is an at least divalent radical derived from a natural alpha amino add chosen from the group consisting of glycine, leucine, phenylalanine, lysine, isoleucine, alanine, valine, aspartic acid and glutamic acid, in their L, D or racemic forms.

In one embodiment, the composition according to the invention is characterized in that the hydrophobized anionic polymer is chosen from the hydrophobized anionic polymers of formula II-I in which the radical -k-[E]-(o)$_t$ is an at least divalent radical derived from a mono- or polyethylene glycol.

In one embodiment, the composition according to the invention is characterized in that the hydrophobized anionic polymer is chosen from the hydrophobized anionic polymers of formula II-I in which the radical -k-[E]-(o)$_t$ is an at least divalent radical derived from ethylene glycol.

In one embodiment, the composition according to the invention is characterized in that the hydrophobized anionic polymer is chosen from the hydrophobized anionic polymers of formula II-I in which the radical -k-[E]-(o)$_t$ is an at least divalent radical derived from a polyethylene glycol chosen from the group consisting of diethylene glycol, triethylene glycol and tetraethylene glycol.

In one embodiment, the composition according to the invention is characterized in that the hydrophobized anionic polymer is chosen from the hydrophobized anionic polymers of formula II-I in which the radical -k-[E]-(o)$_t$ is an at least divalent radical derived from a mono- or polyethylene glycol amine.

In one embodiment, the composition according to the invention is characterized in that the hydrophobized anionic polymer is chosen from the hydrophobized anionic polymers of formula II-I in which the radical -k-[E]-(o)$_t$ is an at least divalent radical derived from a mono- or polyethylene glycol amine chosen from the group consisting of ethanolamine, diethylene glycol amine and triethylene glycol amine.

In one embodiment, the composition according to the invention is characterized in that the hydrophobized anionic polymer is chosen from the hydrophobized anionic polymers of formula II-I in which the radical -k-[E]-(o)$_t$ is an at least divalent radical derived from a mono- or polyethylene glycol diamine.

In one embodiment, the composition according to the invention is characterized in that the hydrophobized anionic polymer is chosen from the hydrophobized anionic polymers of formula II-I in which the radical -k-[E]-(o)$_t$ is an at least divalent radical derived from a mono- or polyethylene glycol diamine chosen from the group consisting of diethylene glycol diamine and triethylene glycol diamine.

In one embodiment, the composition according to the invention is characterized in that the hydrophobized anionic polymer is chosen from the hydrophobized anionic polymers of formula II-I in which the radical -k-[E]-(o)$_t$ is an at least divalent radical derived from ethylenediamine.

In one embodiment, the composition according to the invention is characterized in that the hydrophobized anionic polymer is chosen from the hydrophobized anionic polymers of formula II-I in which the function o is an ester function.

In one embodiment, the composition according to the invention is characterized in that the hydrophobized anionic polymer is chosen from the hydrophobized anionic polymers of formula II-I in which the function o is an amide function.

In one embodiment, the composition according to the invention is characterized in that the hydrophobized anionic polymer is chosen from the hydrophobized anionic polymers of formula II-I in which the function o is a carbamate function.

In one embodiment, the composition according to the invention is characterized in that the hydrophobized anionic polymer is chosen from the hydrophobized anionic polymers of formula II-I in which the function o is a carbonate function.

In one embodiment, the composition according to the invention is characterized in that the hydrophobized anionic polymer is chosen from the hydrophobized anionic polymers of formula II-I in which the function o is a carbamide function.

In one embodiment, the composition according to the invention is characterized in that the hydrophobized anionic polymer is chosen from the hydrophobized anionic polymers of formula II-I in which the -[Hy] group is an alkyl group derived from a branched or unbranched, unsaturated and/or saturated, hydrophobic alcohol comprising from 8 to 30 carbon atoms.

In one embodiment, the composition according to the invention is characterized in that the hydrophobized anionic polymer is chosen from the hydrophobized anionic polymers of formula II-I in which the -[Hy] group is an alkyl group derived from a hydrophobic alcohol chosen from the group consisting of octanol, decanol, dodecanol (lauryl alcohol), tetradecanol (myristyl alcohol), hexadecanol (cetyl alcohol), stearyl alcohol, cetearyl alcohol and oleyl alcohol.

In one embodiment, the composition according to the invention is characterized in that the hydrophobized anionic polymer is chosen from the hydrophobized anionic polymers of formula II-I in which the -[Hy] group is a group derived from a sterol.

In one embodiment, the composition according to the invention is characterized in that the hydrophobized anionic polymer is chosen from the hydrophobized anionic polymers of formula II-I in which the -[Hy] group is a group derived from a sterol, chosen from the group consisting of cholesterol and derivatives thereof.

In one embodiment, the composition according to the invention is characterized in that the hydrophobized anionic polymer is chosen from the hydrophobized anionic polymers of formula II-I in which the -[Hy] group is a group derived from cholesterol.

In one embodiment, the composition according to the invention is characterized in that the hydrophobized anionic polymer is chosen from the hydrophobized anionic polymers of formula II-I in which the -[Hy] group is a group derived from a tocopherol.

In one embodiment, the composition according to the invention is characterized in that the hydrophobized anionic polymer is chosen from the hydrophobized anionic polymers of formula II-I in which the -[Hy] group is a group derived from a tocopherol derivative, chosen from the racemate, the L isomer or the D isomer of α-tocopherol.

In one embodiment, the composition according to the invention is characterized in that the hydrophobized anionic polymer is chosen from the hydrophobized anionic polymers of formula II-I in which the -[Hy] group is a group derived from DL-α-tocopherol.

In one embodiment, the composition according to the invention is characterized in that the hydrophobized anionic polymer is chosen from the hydrophobized anionic polymers of formula II-I in which the -[Hy] group is a group derived from menthol.

In one embodiment, the composition according to the invention is characterized in that the hydrophobized anionic polymer is chosen from the hydrophobized anionic polymers of formula II-I in which the -[Hy] group is a group derived from menthol or derivatives thereof, chosen from the racemate, the L isomer or the D isomer of menthol.

In one embodiment, the composition according to the invention is characterized in that the hydrophobized anionic polymer is chosen from the hydrophobized anionic polymers of formula II-I in which the -[Hy] group is an alkyl group derived from a hydrophobic acid.

In one embodiment, the composition according to the invention is characterized in that the hydrophobized anionic polymer is chosen from the hydrophobized anionic polymers of formula II-I in which the -[Hy] group is an alkyl group derived from a linear hydrophobic acid, chosen from the group consisting of dodecanoic acid, tetradecanoic acid and hexadecanoic acid.

In one embodiment, the composition according to the invention is characterized in that the hydrophobized anionic polymer is chosen from the hydrophobized anionic polymers of formula II-I in which the -[Hy] group is an alkyl group derived from a fatty acid.

In one embodiment, the composition according to the invention is characterized in that the hydrophobized anionic polymer is chosen from the hydrophobized anionic polymers of formula II-I in which the -[Hy] group is an alkyl group derived from a fatty acid chosen from the group consisting of the acids consisting of a branched or unbranched, unsaturated or saturated, alkyl chain comprising from 8 to 30 carbons.

In one embodiment, the composition according to the invention is characterized in that the hydrophobized anionic polymer is chosen from the hydrophobized anionic polymers of formula II-I in which the -[Hy] group is an alkyl group derived from a fatty acid chosen from the group consisting of linear fatty acids.

In one embodiment, the composition according to the invention is characterized in that the hydrophobized anionic polymer is chosen from the hydrophobized anionic polymers of formula II-I in which the -[Hy] group is an alkyl group derived from a saturated linear fatty acid chosen from the group consisting of caprylic acid (octanoic acid), nonanoic acid, capric acid (decanoic acid), undecanoic acid, lauric acid (dodecanoic acid), myristic (tetradecanoic) acid, palmitic (hexadecanoic) acid, stearic (octadecanoic) acid, arachidic (eicosanoic) acid, behenic (docosanoic) acid, tricosanoic acid, lignoceric (tetracosanoic) acid, heptacosanoic acid, octacosanoic acid and melissic (triacontanoic) acid.

In one embodiment, the composition according to the invention is characterized in that the hydrophobized anionic polymer is chosen from the hydrophobized anionic polymers of formula II-I in which the -[Hy] group is an alkyl group derived from an unsaturated fatty acid.

In one embodiment, the composition according to the invention is characterized in that the hydrophobized anionic polymer is chosen from the hydrophobized anionic polymers of formula II-I in which the -[Hy] group is an alkyl group derived from an unsaturated fatty acid chosen from the group consisting of myristoleic ((Z)-tetradec-9-enoic) acid, palmitoleic ((Z)-hexadec-9-enoic) add, oleic ((Z)-octadec-9-enoic) acid, elaidic ((E)-octadec-9-enoic) acid, linoleic ((9Z,12Z)-octadeca-9,12-dienoic) acid, alpha-linoleic ((9Z,12Z,15Z)-octadeca-9,12,15-trienoic) acid, arachidonic ((5Z,8Z,11Z,14Z)-octadeca-5,8,11,14-tetraenoic) acid, eicosapentaenoic ((5Z,8Z,11Z,14Z,17Z)-eicosa-5,8,11,14,17-pentaenoic) acid, erucic (13-docoenoic) acid and docosahexaenoic ((4Z,7Z,10Z,13Z,16Z,19Z)-docosa-4,7,10,13,16,19-hexaenoic) acid.

In one embodiment, the composition according to the invention is characterized in that the hydrophobized anionic polymer is chosen from the hydrophobized anionic polymers of formula II-I in which the -[Hy] group is an alkyl group derived from a bile acid and derivatives thereof.

In one embodiment, the composition according to the invention is characterized in that the hydrophobized anionic polymer is chosen from the hydrophobized anionic polymers of formula II-I in which the -[Hy] group is an alkyl group derived from a bile acid and derivatives thereof, chosen from the group consisting of cholic acid, dehydrocholic acid, deoxycholic acid and chenodeoxycholic acid.

In one embodiment, the composition according to the invention is characterized in that the hydrophobized anionic polymer is chosen from the hydrophobized anionic polymers of formula II-I having a weight-average molar mass ranging from 2 to 40 kg/mol.

In one embodiment, the composition according to the invention is characterized in that the hydrophobized anionic polymer is chosen from the hydrophobized anionic polymers of formula II-I having a weight-average molar mass ranging from 2 to 20 kg/mol.

In one embodiment, the composition according to the invention is characterized in that the hydrophobized anionic polymer is chosen from the hydrophobized anionic polymers of formula II-I having a weight-average molar mass ranging from 2 to 12 kg/mol.

In one embodiment, the composition according to the invention is characterized in that the hydrophobized anionic polymer is chosen from the hydrophobized anionic polymers of formula II-I in which —$R_2$, —$R_4$ and —$R_6$ are radicals —$CH_2R'$.

In one embodiment, the composition according to the invention is characterized in that the hydrophobized anionic polymer of formula II-I in which —$R_2$, —$R_4$ and —$R_6$ are radicals —$CH_2R'$ is chosen from the hydrophobized anionic polymers of formula II-XII:

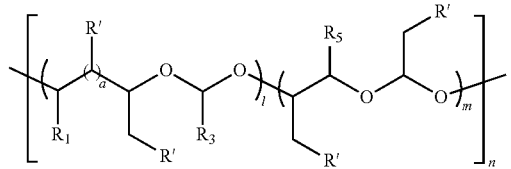

Formula II-XII in which,
l=0 or 1,
m=0, 1 or 2,
a=0 or 1,
n is the degree of polymerization, of between 3 and 1000, and
—$R_1$ is a hydrogen —H,
—$R_3$ is a radical —$CH_2R'$,
—$R_5$ is either a —COOH group, or a radical —$CH_2R'$, or a radical -k-[D],
or
—$R_1$ and —$R_3$ form a six-membered ring —$R_1$-$R_3$—=—CH(NHCOCH$_3$)—,
and
—R', n and -k-[D] being as defined above,
and the degree of substitution with carboxylate charges is the average number of carboxylate charges per monomer divided by (l+m) and is greater than or equal to 0.4,
and the degree of substitution with hydrophobic radicals is the average number of hydrophobic radicals per monomer divided by (l+m) and is less than or equal to 0.5.

In one embodiment, the composition according to the invention is characterized in that the hydrophobized anionic polymer is chosen from the hydrophobized anionic polymers of formula II-XII in which l=0 and m=1, in other words it is chosen from the hydrophobized anionic polymers of formula II-IV,

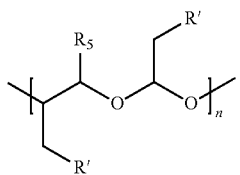
Formula II-IV in which —$R_5$ is either a —COOH group, or a radical —$CH_2R'$, or a radical -k-[D], —R' and n being as defined above.

In one embodiment, the composition according to the invention is characterized in that the hydrophobized anionic polymer is chosen from the hydrophobized anionic polymers of formula II-IV:

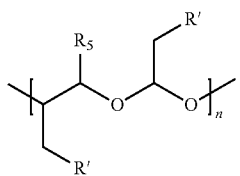
Formula II-IV in which —$R_5$ is either a —COOH group, or a radical -k-[D], —R' and n being as defined above.

In one embodiment, the composition according to the invention is characterized in that the hydrophobized anionic polymer is chosen from the hydrophobized anionic polymers of formula II-IV:

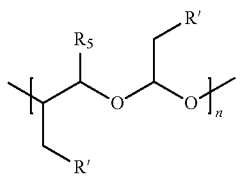
Formula II-IV in which —$R_5$ is a radical —$CH_2R'$, —R' and n being as defined above.

In one embodiment, the composition according to the invention is characterized in that the hydrophobized anionic polymer is chosen from the hydrophobized anionic polymers of formula II-XII in which m=0, l=1 and a=0, in other words it is chosen from the hydrophobized anionic polymers of formula II-V:

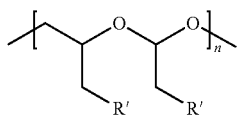
Formula II-V

—R' and n being as defined above.

In one embodiment, the composition according to the invention is characterized in that the hydrophobized anionic polymer is chosen from the hydrophobized anionic polymers of formula II-XII in which l=1, m=2 and a=0, in other words it is chosen from the hydrophobized anionic polymers of formula II-VI:

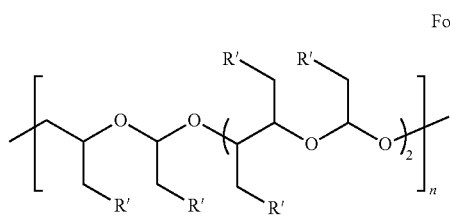
Formula II-VI

—R' and n being as defined above.

In one embodiment, the composition according to the invention is characterized in that the hydrophobized anionic polymer is chosen from the hydrophobized anionic polymers of formula II-XII in which m=1, l=1, a=1, —$R_1$-$R_3$=—CH(NHCOCH$_3$)—, —$R_2$=—$CH_2R'$, —$R_4$=—$CH_2R'$, —$R_5$ is either a —COOH group, or a radical -k-[D], —$R_6$=—$CH_2R'$, in other words it is chosen from the hydrophobized anionic polymers of formula II-VII:

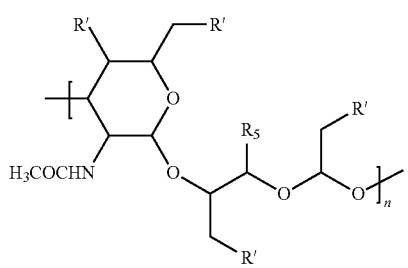
Formula II-VII

R' and n being as defined above.

In one embodiment, the composition according to the invention is characterized in that the hydrophobized anionic polymer is chosen from the hydrophobized anionic polymers of formulae II-IV to II-VII and II-XII, in which the radical -f-[A]-COOH is chosen from the radicals of formula II-II below:

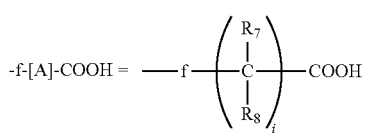
Formula II-II in which:
i is greater than or equal to 1 and less than or equal to 12, and
—$R_7$ and —$R_8$, which may be identical or different, are chosen from the group consisting of a hydrogen atom, a saturated or unsaturated, linear, branched or cyclic $C_1$ to $C_6$ alkyl, a benzyl, an alkylaryl, optionally comprising heteroatoms chosen from the group consisting of O, N and/or S, or functions chosen from the group consisting of carboxylic acid, amine, alcohol and thiol functions.

In one embodiment, the composition according to the invention is characterized in that the hydrophobized anionic polymer is chosen from the compounds of formulae II-IV to II-VII and II-XII, in which the radical -f-[A]-COOH, comprising from 2 to 8 carbon atoms, is derived from an amino acid, from a dialcohol, from a diamine, from a diacid or from an amine alcohol.

In one embodiment, the composition according to the invention is characterized in that the hydrophobized anionic polymer is chosen from the compounds of formulae II-IV to II-VII and II-XII, in which the radical -f-[A]-COOH, comprising from 2 to 6 carbon atoms, is derived from an amino acid, from a dialcohol, from a diamine, from a diacid or from an amine alcohol.

In one particular embodiment, the composition according to the invention is characterized in that the hydrophobized anionic polymer is chosen from the hydrophobized anionic polymers of formulae II-IV to II-VII and II-XII corresponding to the following conditions:
  when g-[B]-(k-[D])$_p$ comprises one Hy chain and Hy is a $C_8$ to $C_{15}$ alkyl, then the product of the degree of substitution with hydrophobic radicals and the average degree of polymerization (n) is greater than or equal to 2,
  when g-[B]-(k-[D])$_p$ comprises one Hy chain and Hy is a $C_{16}$ to $C_{20}$ alkyl, then the product of the degree of substitution with hydrophobic radicals and the average degree of polymerization (n) is greater than or equal to 1,
  when g-[B]-(k-[D])$_p$ comprises two Hy chains and Hy is a $C_8$ to $C_9$ alkyl, then the product of the degree of substitution with hydrophobic radicals and the average degree of polymerization (n) is greater than or equal to 2,
  when g-[B]-(k-[D])$_p$ comprises two Hy chains and Hy is a $C_{10}$ to $C_{16}$ alkyl, then the product of the degree of substitution with hydrophobic radicals and the average degree of polymerization (n) is greater than or equal to 0.2.

In one embodiment, the composition according to the invention is characterized in that the hydrophobized anionic polymer is chosen from the hydrophobized anionic polymers of formulae II-IV to II-VII and II-XII, in which the radical -f-[A]-COOH is chosen from the group consisting of the following radicals, f having the meaning given above:

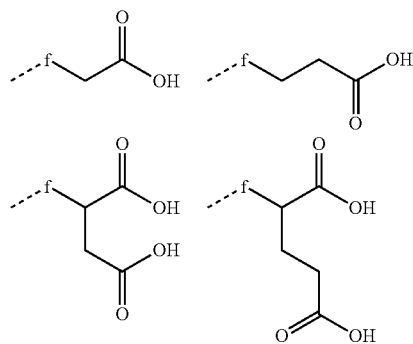

or the salts thereof with alkali metal cations chosen from the group consisting of Na$^+$ and K$^+$.

In one embodiment, the composition according to the invention is characterized in that the hydrophobized anionic polymer is chosen from the hydrophobized anionic polymers of formulae II-IV to II-VII and II-XII, in which the radical -[A]- is a radical —CH$_2$—.

In one embodiment, the composition according to the invention is characterized in that the hydrophobized anionic polymer is chosen from the hydrophobized anionic polymers of formulae II-IV to II-VII and II-XII, in which the radical -f-[A]-COOH is derived from an amino acid.

In one embodiment, the composition according to the invention is characterized in that the hydrophobized anionic polymer is chosen from the hydrophobized anionic polymers of formulae II-IV to II-VII and II-XII, in which the radical -f-[A]-COOH is derived from glycine.

In one embodiment, the composition according to the invention is characterized in that the hydrophobized anionic polymer is chosen from the hydrophobized anionic polymers of formulae II-IV to II-VII and II-XII, in which the radical -f-[A]-COOH is derived from aspartic acid.

In one embodiment, the composition according to the invention is characterized in that the hydrophobized anionic polymer is chosen from the hydrophobized anionic polymers of formulae II-IV to II-VII and II-XII, in which the radical -f-[A]-COOH is derived from glutamic acid.

In one embodiment, the composition according to the invention is characterized in that the hydrophobized anionic polymer is chosen from the hydrophobized anionic polymers of formulae II-IV to II-VII and II-XII, in which the radical -f-[A]-COOH is derived from succinic acid.

In one embodiment, the composition according to the invention is characterized in that the hydrophobized anionic polymer is chosen from the hydrophobized anionic polymers of formulae II-IV to II-VII and II-XII, in which the function f is an ether function.

In one embodiment, the composition according to the invention is characterized in that the hydrophobized anionic polymer is chosen from the hydrophobized anionic polymers of formulae II-IV to II-VII and II-XII, in which the function f is a carbamate function.

In one embodiment, the composition according to the invention is characterized in that the hydrophobized anionic polymer is chosen from the hydrophobized anionic polymers of formulae II-IV to II-VII and II-XII, in which the function f is an ester function.

In one embodiment, the composition according to the invention is characterized in that the hydrophobized anionic polymer is chosen from the hydrophobized anionic polymers of formulae II-IV to II-VII and II-XII, in which the function f is a carbonate function.

In one embodiment, the composition according to the invention is characterized in that the hydrophobized anionic polymer is chosen from the hydrophobized anionic polymers of formulae II-IV to II-VII and II-XII, in which the function f is an amide function.

In one embodiment, the composition according to the invention is characterized in that the hydrophobized anionic polymer is chosen from the hydrophobized anionic polymers of formulae II-IV to II-VII and II-XII, in which the radical -g-[B]- is chosen from the radicals of formula II-III below:

Formula II-III

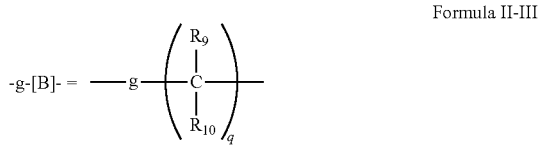

in which:
q is greater than or equal to 1 and less than or equal to 12, and
—R₉, and —R₁₀, which may be identical or different, are chosen from the group consisting of a hydrogen atom, a saturated or unsaturated, linear, branched or cyclic $C_1$ to $C_6$ alkyl, a benzyl, an alkylaryl, optionally comprising heteroatoms chosen from the group consisting of O, N and/or S, or functions chosen from the group consisting of carboxylic acid, amine, alcohol and thiol functions.

In one embodiment, the composition according to the invention is characterized in that the hydrophobized anionic polymer is chosen from the hydrophobized anionic polymers of formulae II-IV to II-VII, in which the radical -g-[B]-k-[D] is chosen from the group consisting of the following radicals; g, k and -[D] having the meanings given above:

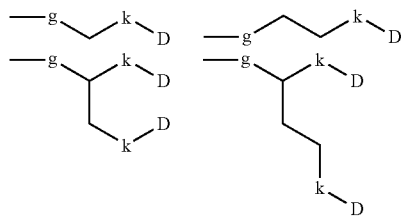

In one embodiment, the composition according to the invention is characterized in that the hydrophobized anionic polymer is chosen from the hydrophobized anionic polymers of formulae II-IV to II-VII and II-XII, in which the radical -[B]- is a radical —CH₂—.

In one embodiment, the composition according to the invention is characterized in that the hydrophobized anionic polymer is chosen from the hydrophobized anionic polymers of formulae II-IV to II-VII and II-XII, in which the radical -g-[B]-(k-[D])ₚ is such that -g-[B]-k- is derived from an amino acid.

In one embodiment, the composition according to the invention is characterized in that the hydrophobized anionic polymer is chosen from the hydrophobized anionic polymers of formulae II-IV to II-VII and II-XII, in which the radical -g-[B]-(k-[D])ₚ is such that -g-[B]-k- is derived from glycine.

In one embodiment, the composition according to the invention is characterized in that the hydrophobized anionic polymer is chosen from the hydrophobized anionic polymers of formulae II-IV to II-VII and II-XII, in which the radical -g-[B]-(k-[D])ₚ is such that -g-[B]-k- is derived from aspartic acid.

In one embodiment, the composition according to the invention is characterized in that the hydrophobized anionic polymer is chosen from the hydrophobized anionic polymers of formulae II-IV to II-VII and II-XII, in which the radical -g-[B]-(k-[D])ₚ is such that -g-[B]-k- is derived from glutamic acid.

In one embodiment, the composition according to the invention is characterized in that the hydrophobized anionic polymer is chosen from the hydrophobized anionic polymers of formulae II-IV to II-VII and II-XII, in which the radical -g-[B]-(k-[D])ₚ is such that -g-[B]-k- is derived from succinic acid.

In one embodiment, the composition according to the invention is characterized in that the hydrophobized anionic polymer is chosen from the hydrophobized anionic polymers of formulae II-IV to II-VII and II-XII, in which the function g is an ether function.

In one embodiment, the composition according to the invention is characterized in that the hydrophobized anionic polymer is chosen from the hydrophobized anionic polymers of formulae II-IV to II-VII and II-XII, in which the function g is a carbamate function.

In one embodiment, the composition according to the invention is characterized in that the hydrophobized anionic polymer is chosen from the hydrophobized anionic polymers of formulae II-IV to II-VII and II-XII, in which the function g is an ester function.

In one embodiment, the composition according to the invention is characterized in that the hydrophobized anionic polymer is chosen from the hydrophobized anionic polymers of formulae II-IV to II-VII and II-XII, in which the function g is an amine function.

In one embodiment, the composition according to the invention is characterized in that the hydrophobized anionic polymer is chosen from the hydrophobized anionic polymers of formulae II-IV to II-VII and II-XII, in which the function g is a carbonate function.

In one embodiment, the composition according to the invention is characterized in that the hydrophobized anionic polymer is chosen from the hydrophobized anionic polymers of formulae II-IV to II-VII and II-XII, in which the function k is an amide function.

In one embodiment, the composition according to the invention is characterized in that the hydrophobized anionic polymer is chosen from the hydrophobized anionic polymers of formulae II-IV to II-VII and II-XII, in which the function k is a carbamate function.

In one embodiment, the composition according to the invention is characterized in that the hydrophobized anionic polymer is chosen from the hydrophobized anionic polymers of formulae II-IV to II-VII and II-XII, in which the function k is an ester function.

In one embodiment, the composition according to the invention is characterized in that the hydrophobized anionic polymer is chosen from the hydrophobized anionic polymers of formulae II-IV to II-VII and II-XII, in which the radical -k-[E]-(o)ₜ is an at least divalent radical derived from an amino acid.

In one embodiment, the composition according to the invention is characterized in that the hydrophobized anionic polymer is chosen from the hydrophobized anionic polymers of formulae II-IV to II-VII and II-XII, in which the radical -k-[E]-(o)ₜ is an at least divalent radical derived from an alpha amino acid.

In one embodiment, the composition according to the invention is characterized in that the hydrophobized anionic polymer is chosen from the hydrophobized anionic polymers of formulae II-IV to II-VII and II-XII, in which the radical -k-[E]-(o)ₜ is an at least divalent radical derived from a natural alpha amino acid chosen from the group consisting of glycine, leucine, phenylalanine, lysine, isoleucine, alanine, valine, aspartic acid and glutamic acid, in their L, D or racemic forms.

In one embodiment, the composition according to the invention is characterized in that the hydrophobized anionic polymer is chosen from the hydrophobized anionic polymers of formulae II-IV to II-VII and II-XII, in which the radical -k-[E]-(o)ₜ is an at least divalent radical derived from a mono- or polyethylene glycol.

In one embodiment, the composition according to the invention is characterized in that the hydrophobized anionic polymer is chosen from the hydrophobized anionic polymers of formulae II-IV to II-VII and II-XII, in which the radical -k-[E]-(o)$_t$ is an at least divalent radical derived from ethylene glycol.

In one embodiment, the composition according to the invention is characterized in that the hydrophobized anionic polymer is chosen from the hydrophobized anionic polymers of formulae II-IV to II-VII and II-XII, in which the radical -k-[E]-(o)$_t$ is an at least divalent radical derived from a polyethylene glycol chosen from the group consisting of diethylene glycol, triethylene glycol and tetraethylene glycol.

In one embodiment, the composition according to the invention is characterized in that the hydrophobized anionic polymer is chosen from the hydrophobized anionic polymers of formulae II-IV to II-VII and II-XII, in which the radical -k-[E]-(o)$_t$ is an at least divalent radical derived from a mono- or polyethylene glycol amine.

In one embodiment, the composition according to the invention is characterized in that the hydrophobized anionic polymer is chosen from the hydrophobized anionic polymers of formulae II-IV to II-VII and II-XII, in which the radical -k-[E]-(o)$_t$ is an at least divalent radical derived from a mono- or polyethylene glycol amine chosen from the group consisting of ethanolamine, diethylene glycol amine and triethylene glycol amine.

In one embodiment, the composition according to the invention is characterized in that the hydrophobized anionic polymer is chosen from the hydrophobized anionic polymers of formulae II-IV to II-VII and II-XII, in which the radical -k-[E]-(o)$_t$ is an at least divalent radical derived from a mono- or polyethylene glycol diamine.

In one embodiment, the composition according to the invention is characterized in that the hydrophobized anionic polymer is chosen from the hydrophobized anionic polymers of formulae II-IV to II-VII and II-XII, in which the radical -k-[E]-(o)$_t$ is an at least divalent radical derived from a mono- or polyethylene glycol diamine chosen from the group consisting of diethylene glycol diamine and triethylene glycol diamine.

In one embodiment, the composition according to the invention is characterized in that the hydrophobized anionic polymer is chosen from the hydrophobized anionic polymers of formulae II-IV to II-VII and II-XII, in which the radical -k-[E]-(o)$_t$ is an at least divalent radical derived from ethylenediamine.

In one embodiment, the composition according to the invention is characterized in that the hydrophobized anionic polymer is chosen from the hydrophobized anionic polymers of formulae II-IV to II-VII and II-XII, in which the function o is an ester function.

In one embodiment, the composition according to the invention is characterized in that the hydrophobized anionic polymer is chosen from the hydrophobized anionic polymers of formulae II-IV to II-VII and II-XII, in which the function o is an amide function.

In one embodiment, the composition according to the invention is characterized in that the hydrophobized anionic polymer is chosen from the hydrophobized anionic polymers of formulae II-IV to II-VII and II-XII, in which the function o is a carbamate function.

In one embodiment, the composition according to the invention is characterized in that the hydrophobized anionic polymer is chosen from the hydrophobized anionic polymers of formulae II-IV to II-VII and II-XII, in which the function o is a carbonate function.

In one embodiment, the composition according to the invention is characterized in that the hydrophobized anionic polymer is chosen from the hydrophobized anionic polymers of formulae II-IV to II-VII and II-XII, in which the -[Hy] group is an alkyl group derived from a branched or unbranched, unsaturated and/or saturated, hydrophobic alcohol comprising from 8 to 30 carbons.

In one embodiment, the composition according to the invention is characterized in that the hydrophobized anionic polymer is chosen from the hydrophobized anionic polymers of formulae II-IV to II-VII and II-XII, in which the -[Hy] group is an alkyl group derived from a hydrophobic alcohol chosen from the group consisting of octanol, decanol, dodecanol (lauryl alcohol), tetradecanol (myristyl alcohol), hexadecanol (cetyl alcohol), stearyl alcohol, cetearyl alcohol and oleyl alcohol.

In one embodiment, the composition according to the invention is characterized in that the hydrophobized anionic polymer is chosen from the hydrophobized anionic polymers of formulae II-IV to II-VII and II-XII, in which the -[Hy] group is a group derived from a sterol.

In one embodiment, the composition according to the invention is characterized in that the hydrophobized anionic polymer is chosen from the hydrophobized anionic polymers of formulae II-IV to II-VII and II-XII, in which the -[Hy] group is a group derived from a sterol, chosen from the group consisting of cholesterol and derivatives thereof.

In one embodiment, the composition according to the invention is characterized in that the hydrophobized anionic polymer is chosen from the hydrophobized anionic polymers of formulae II-IV to II-VII and II-XII, in which the -[Hy] group is a group derived from cholesterol.

In one embodiment, the composition according to the invention is characterized in that the hydrophobized anionic polymer is chosen from the hydrophobized anionic polymers of formulae II-IV to II-VII and II-XII, in which the -[Hy] group is a group derived from a tocopherol.

In one embodiment, the composition according to the invention is characterized in that the hydrophobized anionic polymer is chosen from the hydrophobized anionic polymers of formulae II-IV to II-VII and II-XII, in which the -[Hy] group is a group derived from a tocopherol derivative, chosen from the racemate, the L isomer or the D isomer of α-tocopherol.

In one embodiment, the composition according to the invention is characterized in that the hydrophobized anionic polymer is chosen from the hydrophobized anionic polymers of formulae II-IV to II-VII and II-XII, in which the -[Hy] group is a group derived from DL-α-tocopherol.

In one embodiment, the composition according to the invention is characterized in that the hydrophobized anionic polymer is chosen from the hydrophobized anionic polymers of formulae II-IV to II-VII and II-XII, in which the -[Hy] group is a group derived from menthol.

In one embodiment, the composition according to the invention is characterized in that the hydrophobized anionic polymer is chosen from the hydrophobized anionic polymers of formulae II-IV to II-VII and II-XII, in which the -[Hy] group is a group derived from menthol or derivatives thereof, chosen from the racemate, the L isomer or the D isomer of menthol.

In one embodiment, the composition according to the invention is characterized in that the hydrophobized anionic polymer is chosen from the hydrophobized anionic polymers of formulae II-IV to II-VII and II-XII, in which the -[Hy] group is an alkyl group derived from a hydrophobic acid.

In one embodiment, the composition according to the invention is characterized in that the hydrophobized anionic polymer is chosen from the hydrophobized anionic polymers of formulae II-IV to II-VII and II-XII, in which the -[Hy] group is an alkyl group derived from a linear hydrophobic acid, chosen from the group consisting of dodecanoic acid, tetradecanoic acid and hexadecanoic acid.

In one embodiment, the composition according to the invention is characterized in that the hydrophobized anionic polymer is chosen from the hydrophobized anionic polymers of formulae II-IV to II-VII and II-XII, in which the -[Hy] group is an alkyl group derived from a fatty acid.

In one embodiment, the composition according to the invention is characterized in that the hydrophobized anionic polymer is chosen from the hydrophobized anionic polymers of formulae II-IV to II-VII and II-XII, in which the -[Hy] group is an alkyl group derived from a fatty acid chosen from the group consisting of the acids consisting of a branched or unbranched, unsaturated or saturated, alkyl chain comprising from 8 to 30 carbons.

In one embodiment, the composition according to the invention is characterized in that the hydrophobized anionic polymer is chosen from the hydrophobized anionic polymers of formulae II-IV to II-VII and II-XII, in which the -[Hy] group is an alkyl group derived from a fatty acid chosen from the group consisting of linear fatty acids.

In one embodiment, the composition according to the invention is characterized in that the hydrophobized anionic polymer is chosen from the hydrophobized anionic polymers of formulae II-IV to II-VII and II-XII, in which the -[Hy] group is an alkyl group derived from a saturated linear fatty acid chosen from the group consisting of caprylic acid (octanoic acid), nonanoic acid, capric acid (decanoic acid), undecanoic add, lauric acid (dodecanoic acid), myristic (tetradecanoic) acid, palmitic (hexadecanoic) acid, stearic (octadecanoic) acid, arachidic (eicosanoic) acid, behenic (docosanoic) acid, tricosanoic acid, lignoceric (tetracosanoic) acid, heptacosanoic acid, octacosanoic acid and melissic (tricontanoic) acid.

In one embodiment, the composition according to the invention is characterized in that the hydrophobized anionic polymer is chosen from the hydrophobized anionic polymers of formulae II-IV to II-VII and II-XII, in which the -[Hy] group is an alkyl group derived from an unsaturated fatty add.

In one embodiment, the composition according to the invention is characterized in that the hydrophobized anionic polymer is chosen from the hydrophobized anionic polymers of formulae II-IV to II-VII and II-XII, in which the -[Hy] group is an alkyl group derived from an unsaturated fatty acid chosen from the group consisting of myristoleic ((Z)-tetradec-9-enoic) acid, palmitoleic ((Z)-hexadec-9-enoic) acid, oleic ((Z)-octadec-9-enoic) acid, elaidic ((E)-octadec-9-enoic) acid, linoleic ((9Z,12Z)-octadeca-9,12-dienoic) acid, alpha-linoleic ((9Z,12Z,15Z)-octadeca-9,12,15-trienoic) acid, arachidonic ((5Z,8Z,11Z,14Z)-octadeca-5,8,11,14-tetraenoic) acid, eicosapentaenoic ((5Z,8Z,11Z,14Z,17Z)-eicosa-5,8,11,14,17-pentaenoic) acid, erucic (13-docoenoic) acid and docosahexaenoic ((4Z,7Z,10Z,13Z,16Z,19Z)-docosa-4,7,10,13,16,19-hexaenoic) acid.

In one embodiment, the composition according to the invention is characterized in that the hydrophobized anionic polymer is chosen from the hydrophobized anionic polymers of formulae II-IV to II-VII and II-XII, in which the -[Hy] group is an alkyl group derived from a bile acid and derivatives thereof.

In one embodiment, the composition according to the invention is characterized in that the hydrophobized anionic polymer is chosen from the hydrophobized anionic polymers of formulae II-IV to II-VII and II-XII, in which the -[Hy] group is an alkyl group derived from a bile acid and derivatives thereof, chosen from the group consisting of cholic add, dehydrocholic acid, deoxycholic acid and chenodeoxycholic add.

According to one embodiment, the composition according to the invention is characterized in that the hydrophobized anionic polymer according to the invention is chosen from the hydrophobized anionic polymers of formula II-V having a weight-average molar mass ranging from 2 to 40 kg/mol.

According to one embodiment, the hydrophobized anionic polymer according to the invention is chosen from the hydrophobized anionic polymers of formula II-V having a weight-average molar mass ranging from 2 to 20 kg/mol.

According to one embodiment, the hydrophobized anionic polymer according to the invention is chosen from the hydrophobized anionic polymers of formula II-V having a weight-average molar mass ranging from 2 to 12 kg/mol.

In one particular embodiment, the composition according to the invention is characterized in that the hydrophobized anionic polymer according to the invention is chosen from the hydrophobized anionic polymers of formula II-V corresponding to the following conditions:

when g-B-(k-D)p comprises one Hy chain and Hy is a $C_8$ to $C_{15}$ alkyl, then the product of the degree of substitution with hydrophobic radicals and the average degree of polymerization (n) is greater than or equal to 2, when g-B-(k-D)p comprises a Hy chain and Hy is a $C_{16}$ to $C_{20}$ alkyl, then the product of the degree of substitution with hydrophobic radicals and the average degree of polymerization (n) is greater than or equal to 1, when g-B-(k-D)p comprises two Hy chains and Hy is a $C_8$ to $C_9$ alkyl, then the product of the degree of substitution with hydrophobic radicals and the average degree of polymerization (n) is greater than or equal to 2, when g-B-(k-D)p comprises two Hy chains and Hy is a $C_{10}$ to $C_{16}$ alkyl, then the product of the degree of substitution with hydrophobic radicals and the average degree of polymerization (n) is greater than or equal to 0.2.

According to one embodiment, the composition according to the invention is characterized in that the hydrophobized anionic polymer according to the invention is chosen from the hydrophobized anionic polymers of formula II-V in which the radical -f-[A]-COOH is chosen from the group consisting of the following radicals, f having the meaning given above:

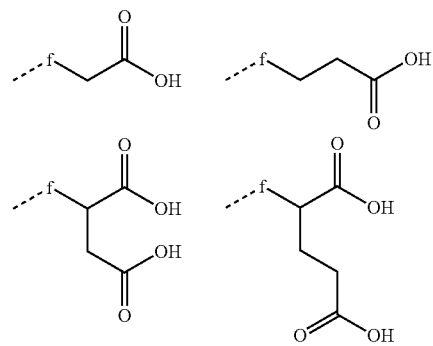

or the salts thereof with alkali metal cations chosen from the group consisting of Na$^+$ and K$^+$.

In one embodiment, the composition according to the invention is characterized in that the hydrophobized anionic polymer according to the invention is chosen from the hydrophobized anionic polymers of formula II-V in which the radical -[A]- is a radical —CH$_2$—.

In one embodiment, the composition according to the invention is characterized in that the hydrophobized anionic polymer according to the invention is chosen from the hydrophobized anionic polymers of formula II-V in which the function f is an ether function.

In one embodiment, the composition according to the invention is characterized in that the hydrophobized anionic polymer according to the invention is chosen from the hydrophobized anionic polymers of formula II-V in which the radical -g-[B]-k-[D] is chosen from the group consisting of the following radicals; g, k and -[D] having the meanings given above:

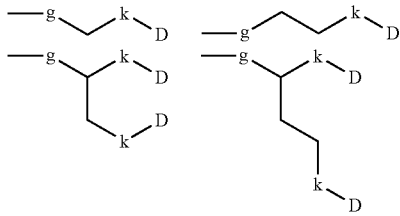

In one embodiment, the composition according to the invention is characterized in that the hydrophobized anionic polymer according to the invention is chosen from the hydrophobized anionic polymers of formula II-V in which the radical -[B]- is a radical —CH$_2$—.

In one embodiment, the composition according to the invention is characterized in that the hydrophobized anionic polymer according to the invention is chosen from the hydrophobized anionic polymers of formula II-V in which the function g is an ether function.

In one embodiment, the composition according to the invention is characterized in that the hydrophobized anionic polymer according to the invention is chosen from the hydrophobized anionic polymers of formula II-V in which the function k is an amide function.

In one embodiment, the composition according to the invention is characterized in that the hydrophobized anionic polymer according to the invention is chosen from the hydrophobized anionic polymers of formula II-V in which the radical -k-[E]-(o)$_t$ is an at least divalent radical derived from an amino acid.

In one embodiment, the composition according to the invention is characterized in that the hydrophobized anionic polymer according to the invention is chosen from the hydrophobized anionic polymers of formula II-V in which the radical -k-[E]-(o)$_t$ is an at least divalent radical derived from an alpha amino acid.

In one embodiment, the composition according to the invention is characterized in that the hydrophobized anionic polymer according to the invention is chosen from the hydrophobized anionic polymers of formula II-V in which the radical -k-[E]-(o)$_t$ is an at least divalent radical derived from a natural alpha amino acid chosen from the group consisting of glycine, leucine, phenylalanine, lysine, isoleucine, alanine, valine, aspartic acid and glutamic acid, in their L, D or racemic forms.

In one embodiment, the composition according to the invention is characterized in that the hydrophobized anionic polymer according to the invention is chosen from the hydrophobized anionic polymers of formula II-V in which the radical -k-[E]-(o)$_t$ is an at least divalent radical derived from a mono- or polyethylene glycol amine chosen from the group consisting of ethanolamine, diethylene glycol amine and triethylene glycol amine.

In one embodiment, the composition according to the invention is characterized in that the hydrophobized anionic polymer according to the invention is chosen from the hydrophobized anionic polymers of formula II-V in which the radical -k-[E]-(o)$_t$ is an at least divalent radical derived from ethylenediamine.

In one embodiment, the composition according to the invention is characterized in that the hydrophobized anionic polymer according to the invention is chosen from the hydrophobized anionic polymers of formula II-V in which the function o is an ester function.

In one embodiment, the composition according to the invention is characterized in that the hydrophobized anionic polymer according to the invention is chosen from the hydrophobized anionic polymers of formula II-V in which the function o is an amide function.

In one embodiment, the composition according to the invention is characterized in that the hydrophobized anionic polymer according to the invention is chosen from the hydrophobized anionic polymers of formula II-V in which the function o is a carbamate function.

In one embodiment, the composition according to the invention is characterized in that the hydrophobized anionic polymer according to the invention is chosen from the hydrophobized anionic polymers of formula II-V in which the -[Hy] group is an alkyl group derived from a hydrophobic alcohol having a Log P greater than or equal to 2.

In one embodiment, the composition according to the invention is characterized in that the hydrophobized anionic polymer according to the invention is chosen from the hydrophobized anionic polymers of formula II-V in which the -[Hy] group is an alkyl group derived from a branched or unbranched, unsaturated and/or saturated, hydrophobic alcohol comprising from 8 to 30 carbons.

In one embodiment, the composition according to the invention is characterized in that the hydrophobized anionic polymer according to the invention is chosen from the hydrophobized anionic polymers of formula II-V in which the -[Hy] group is an alkyl group derived from a hydrophobic alcohol chosen from the group consisting of octanol, decanol, dodecanol (lauryl alcohol), tetradecanol (myristyl alcohol), hexadecanol (cetyl alcohol), stearyl alcohol, cetearyl alcohol and oleyl alcohol.

In one embodiment, the composition according to the invention is characterized in that the hydrophobized anionic polymer according to the invention is chosen from the hydrophobized anionic polymers of formula II-V in which the -[Hy] group is a group derived from a sterol.

In one embodiment, the composition according to the invention is characterized in that the hydrophobized anionic polymer according to the invention is chosen from the hydrophobized anionic polymers of formula II-V in which the -[Hy] group is a group derived from a sterol, chosen from the group consisting of cholesterol and derivatives thereof.

In one embodiment, the composition according to the invention is characterized in that the hydrophobized anionic polymer according to the invention is chosen from the hydrophobized anionic polymers of formula II-V in which the -[Hy] group is a group derived from cholesterol.

In one embodiment, the composition according to the invention is characterized in that the hydrophobized anionic polymer according to the invention is chosen from the hydrophobized anionic polymers of formula II-V in which the -[Hy] group is a group derived from a tocopherol.

In one embodiment, the composition according to the invention is characterized in that the hydrophobized anionic polymer according to the invention is chosen from the hydrophobized anionic polymers of formula II-V in which the -[Hy] group is a group derived from a tocopherol derivative, chosen from the racemate, the L isomer or the D isomer of α-tocopherol.

In one embodiment, the composition according to the invention is characterized in that the hydrophobized anionic polymer according to the invention is chosen from the hydrophobized anionic polymers of formula II-V in which the -[Hy] group is a group derived from DL-α-tocopherol.

In one embodiment, the composition according to the invention is characterized in that the hydrophobized anionic polymer according to the invention is chosen from the hydrophobized anionic polymers of formula II-V in which the -[Hy] group is a group derived from menthol.

In one embodiment, the composition according to the invention is characterized in that the hydrophobized anionic polymer according to the invention is chosen from the hydrophobized anionic polymers of formula II-V in which the -[Hy] group is a group derived from menthol or derivatives thereof, chosen from the racemate, the L isomer or the D isomer of menthol.

In one embodiment, the composition according to the invention is characterized in that the hydrophobized anionic polymer according to the invention is chosen from the hydrophobized anionic polymers of formula II-V in which the -[Hy] group is an alkyl group derived from a hydrophobic acid.

In one embodiment, the composition according to the invention is characterized in that the hydrophobized anionic polymer according to the invention is chosen from the hydrophobized anionic polymers of formula II-V in which the -[Hy] group is an alkyl group derived from a hydrophobic acid having a Log P greater than or equal to 2.

In one embodiment, the composition according to the invention is characterized in that the hydrophobized anionic polymer according to the invention is chosen from the hydrophobized anionic polymers of formula II-V in which the -[Hy] group is an alkyl group derived from a linear hydrophobic acid, chosen from the group consisting of dodecanoic acid, tetradecanoic acid and hexadecanoic acid.

In one embodiment, the composition according to the invention is characterized in that the hydrophobized anionic polymer according to the invention is chosen from the hydrophobized anionic polymers of formula II-V in which the -[Hy] group is an alkyl group derived from a fatty acid.

In one embodiment, the composition according to the invention is characterized in that the hydrophobized anionic polymer according to the invention is chosen from the hydrophobized anionic polymers of formula II-V in which the -[Hy] group is an alkyl group derived from a fatty acid chosen from the group consisting of the acids consisting of a branched or unbranched, unsaturated or saturated, alkyl chain comprising from 8 to 30 carbons.

In one embodiment, the composition according to the invention is characterized in that the hydrophobized anionic polymer according to the invention is chosen from the hydrophobized anionic polymers of formula II-V in which the -[Hy] group is an alkyl group derived from a fatty acid chosen from the group consisting of linear fatty adds.

In one embodiment, the composition according to the invention is characterized in that the hydrophobized anionic polymer according to the invention is chosen from the hydrophobized anionic polymers of formula II-V in which the -[Hy] group is an alkyl group derived from a saturated linear fatty acid chosen from the group consisting of caprylic add (octanoic acid), nonanoic acid, capric add (decanoic acid), undecanoic acid, lauric add (dodecanoic acid), myristic (tetradecanoic) acid, palmitic (hexadecanoic) acid, stearic (octadecanoic) acid, arachidic (eicosanoic) acid, behenic (docosanoic) add, tricosanoic add, lignoceric (tetracosanoic) acid, heptacosanoic acid, octacosanoic acid and melissic (tricontanoic) acid.

In one embodiment, the composition according to the invention is characterized in that the hydrophobized anionic polymer according to the invention is chosen from the hydrophobized anionic polymers of formula II-V in which the -[Hy] group is an alkyl group derived from an unsaturated fatty acid.

In one embodiment, the composition according to the invention is characterized in that the hydrophobized anionic polymer according to the invention is chosen from the hydrophobized anionic polymers of formula II-V in which the -[Hy] group is an alkyl group derived from an unsaturated fatty acid chosen from the group consisting of myristoleic ((Z)-tetradec-9-enoic) acid, palmitoleic ((Z)-hexadec-9-enoic) acid, oleic ((Z)-octadec-9-enoic) add, elaidic ((E)-octadec-9-enoic) add, linoleic ((9Z,12Z)-octadeca-9,12-dienoic) acid, alpha-linoleic ((9Z,12Z,15Z)-octadeca-9,12,15-trienoic) acid, arachidonic ((5Z,8Z,11Z,14Z)-octadeca-5,8,11,14-tetraenoic) acid, eicosapentaenoic ((5Z,8Z,11Z,14Z,17Z)-eicosa-5,8,11,14,17-pentaenoic) acid, erucic (13-docoenoic) acid and docosahexaenoic ((4Z,7Z,10Z,13Z,16Z,19Z)-docosa-4,7,10,13,16,19-hexaenoic) acid.

In one embodiment, the composition according to the invention is characterized in that the hydrophobized anionic polymer according to the invention is chosen from the hydrophobized anionic polymers of formula II-V in which the -[Hy] group is an alkyl group derived from a bile acid and derivatives thereof.

In one embodiment, the composition according to the invention is characterized in that the hydrophobized anionic polymer according to the invention is chosen from the hydrophobized anionic polymers of formula II-V in which the -[Hy] group is an alkyl group derived from a bile acid and derivatives thereof, chosen from the group consisting of cholic acid, dehydrocholic add, deoxycholic add and chenodeoxycholic acid.

In one embodiment, the composition according to the invention is characterized in that the hydrophobized anionic polymer according to the invention is chosen from the hydrophobized anionic polymers of formula II-V in which —R' is either an —OH group, or a radical -f-[A]-COOH, or a radical -g-[B]-k-[D], f being an ether function, the radical -[A]- being a radical —$CH_2$—, g being an ether function, the radical -[B]- being a radical —$CH_2$—, k being an amide function, -[D] being a radical -[E]-o-Hy, p and t=1, the radical -k-[E]-(o)$_t$ being derived from an amino acid, o being an ester function and Hy being derived from a sterol or from a fatty alcohol, in particular:

the radical -k-[E]-(o)$_t$ being derived from leucine and Hy being derived from cholesterol, the radical -k-[E]-(o)$_t$ being derived from glycine and Hy being derived from dodecanol, the radical -k-[E]-(o)$_t$ being derived from leucine and Hy being derived from tocopherol, and the radical -k-[E]-(o)$_t$ being derived from phenylalanine and Hy being derived from octanol, and the radical -k-[E]-(o)$_t$ being derived from phenylalanine and Hy being derived from 3,7-dimethyloctan-1-ol.

In one embodiment, the composition according to the invention is characterized in that the hydrophobized anionic polymer according to the invention is chosen from the hydrophobized anionic polymers of formula II-V in which —R' is either an —OH group, or a radical -f-[A]-COOH, or a radical -g-[B]-k-[D], f being an ether function, the radical -[A]- being a radical —CH$_2$—, g being an ether function, the radical -[B]- being a radical —CH$_2$—, k being an amide function, -[D] being a radical -[E]-(o-Hy)$_2$, p=1 and t=2, the radical -k-[E]-(o)$_t$ being derived from an amino acid, o being an ester function and Hy being derived from a fatty alcohol, in particular the radical -k-[E]-(o)$_t$ being derived from aspartic acid and Hy being derived from dodecanol or decanol.

In one embodiment, the composition according to the invention is characterized in that the hydrophobized anionic polymer according to the invention is chosen from the hydrophobized anionic polymers of formula II-V in which —R' is either an —OH group, or a radical -f-[A]-COOH, or a radical -g-[B]-k-[D], f being an ether function, the radical -[A]- being a radical —CH$_2$—, g being an ether function, the radical -[B]- being a radical —CH$_2$—, k being an amide function, -[D] being a radical -[E]-o-Hy, p and t=1, the radical -k-[E]-(o)$_t$ being derived from a diamine, o being an amide function and Hy being derived from a fatty acid, in particular the radical -k-[E]-(o)$_t$ being derived from ethylenediamine and Hy being derived from dodecanoic acid.

In one embodiment, the composition according to the invention is characterized in that the hydrophobized anionic polymer according to the invention is chosen from the hydrophobized anionic polymers of formula II-V in which —R' is either an —OH group, or a radical -f-[A]-COOH, or a radical -g-[B]-k-[D], f being an ether function, the radical -[A]- being a radical —CH$_2$—, g being an ether function, the radical -[B]- being a radical —CH$_2$—, k being an amide function, -[D] being a radical -[E]-o-Hy, p and t=1, the radical -[E]- being derived from a diamine, o being a carbamate function and Hy being derived from a sterol, in particular the radical -k-[E]-(o)$_t$ being derived from ethylenediamine and Hy being derived from cholesterol.

In one embodiment, the composition according to the invention is characterized in that the hydrophobized anionic polymer according to the invention is chosen from the hydrophobized anionic polymers of formula II-V in which —R' is either an —OH group, or a radical -f-[A]-COOH, or a radical -g-[B]-k-[D], f being an ether function, the radical -[A]- being a radical —CH$_2$—, g being an ether function, the radical -[B]- being a radical —CH$_2$—, k being an amide function, -[D] being a radical -[E]-o-Hy, p and t=1, the radical -k-[E]-(o)$_t$ being derived from an amino alcohol, o being an ester function and Hy being derived from a fatty alcohol, in particular the radical -k-[E]-(o)$_t$ being derived from 2-(2-aminoethoxy)ethanol and Hy being derived from dodecanol.

The invention also relates to a hydrophobized anionic polymer of formula II-XII:

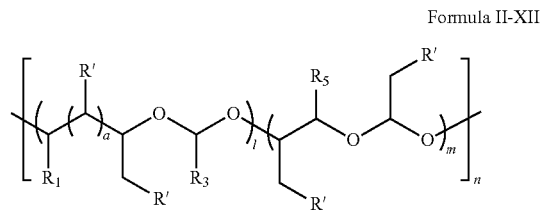

Formula II-XII in which,
l=0 or 1,
m=0, 1 or 2,
a=0 or 1,
n is the degree of polymerization, of between 3 and 1000, and
—R$_1$ is a hydrogen —H,
—R$_3$ is a radical —CH$_2$R',
—R$_5$ is either a —COOH group, or a radical —CH$_2$R', or a radical -k-[D],
in which:
-[D] is a radical -[Hy] or -[E]-(o-[Hy]) t;
-[E]- is an at least divalent radical comprising from 1 to 15 carbon atoms comprising at least one heteroatom chosen from O, N and S, optionally bearing carboxyl or amine functions and/or -k-[E]-(o)$_t$, comprising from 2 to 16 carbon atoms, is derived from an amino acid, from a dialcohol, from a diamine or from an amine alcohol;
-[Hy] is a C$_8$ to C$_{30}$ linear or cyclic alkyl group or a C$_8$ to C$_{30}$ alkylaryl or arylalkyl, optionally substituted with one or more C$_1$ to C$_3$ alkyl groups, which is derived from a hydrophobic compound;
k resulting from the reaction between a carboxyl, amine or alcohol function of the precursor of -k-[E]-(o)$_t$ and an alcohol, carboxyl or amine function of the polymer and is a function chosen from the group consisting of ester, amide, carbonate and carbamate functions;
o resulting from the reaction between a carboxyl, amine or alcohol function of the precursor of -k-[E]-(o)$_t$ and an alcohol or acid function of the precursor of -[Hy] is a function chosen from the group consisting of ester, amide, urea (carbamide), carbonate and carbamate functions;
t is a positive integer equal to 1 or 2;
or
—R$_1$ and —R$_3$ form a six-membered ring —R$_1$-R$_3$—=—CH(NHCOCH$_3$)—,
and
—R' is chosen from the group consisting of the radicals:
—OH
—O-Alk, Alk being a C$_1$ to C$_3$ alkyl chain,
-(f-[A]-COOH), in which:
-[A]- is an at least divalent radical comprising from 1 to 15 carbon atoms comprising at least one heteroatom chosen from O, N and S, optionally bearing carboxyl or amine functions and/or -f-[A]-COOH is derived from an amino acid, from a diacid or from an alcohol acid and is bonded to the backbone of the molecule via a function f;
f resulting from the reaction between a carboxyl or alcohol or amine function of the precursor of -f-[A]-COOH and a hydroxyl function of the backbone is chosen from the group consisting of ether, ester, carbamate or carbonate functions;

-g-[B]-(k-[D])$_p$, in which:
- -[B]- is an at least divalent radical comprising from 1 to 15 carbon atoms comprising at least one heteroatom chosen from O, N and S, optionally bearing carboxyl or amine functions and/or -g-[B]-(k-)$_p$ is derived from an amino acid, from a diacid, from a dialcohol, from an alcohol acid, from a diamine or from an amine alcohol and is bonded to the backbone of the molecule via a function g and is bonded to at least one radical -[D] via a function k,
- g resulting from the reaction between a carboxyl or alcohol or amine function of the precursor of -g-[B]-(k-)$_p$ and a function of the backbone is chosen from the group consisting of ether, amine, ester, carbamate or carbonate functions,
- k resulting from the reaction between a carboxyl or alcohol or amine function of the precursor of -g-[B]-(k-)$_p$ and an alcohol or acid function of the precursor of -[D] is chosen from the group consisting of ester, amide or carbamate functions;
- p is a positive integer equal to 1 or 2;

and -[A]-, -[B]- and -[E]- are identical or different, and k and o are identical or different;

and, if -[B]- is a trivalent radical, then -[D] is a radical -[Hy], and the degree of substitution with carboxylate charges is the average number of carboxylate charges per monomer divided by (l+m) and is greater than or equal to 0.4, and the degree of substitution with hydrophobic radicals is the average number of hydrophobic radicals per monomer divided by (l+m) and is less than or equal to 0.5, and, if the hydrophobized anionic polymer is a polysaccharide, then the identical or different glycosidic linkages may be of or type and/or of β type.

In one embodiment, the hydrophobized anionic polymer according to the invention is chosen from the hydrophobized anionic polymers of formula II-XII in which l=0 and m=1, in other words it is chosen from the hydrophobized anionic polymers of formula II-IV,

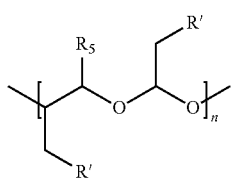

Formula II-IV in which —R$_5$ is either a —COOH group, or a radical —CH$_2$R', or a radical -k-[D], —R' and n being as defined above.

In one embodiment, the hydrophobized anionic polymer according to the invention is chosen from the hydrophobized anionic polymers of formula II-IV:

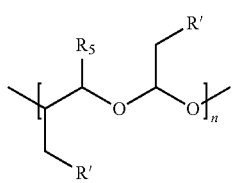

Formula II-IV in which —R$_5$ is either a —COOH group, or a radical -k-[D], —R' and n being as defined above.

In one embodiment, the hydrophobized anionic polymer according to the invention is chosen from the hydrophobized anionic polymers of formula II-IV:

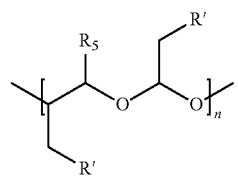

Formula II-IV in which —R$_5$ is a radical —CH$_2$R', —R' and n being as defined above.

In one embodiment, the hydrophobized anionic polymer according to the invention is chosen from the hydrophobized anionic polymers of formula II-XII in which m=0, l=1 and a=0, in other words it is chosen from the hydrophobized anionic polymers of formula II-V:

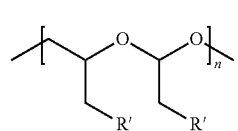

Formula II-V

—R' and n being as defined above.

In one embodiment, the hydrophobized anionic polymer according to the invention is chosen from the hydrophobized anionic polymers of formula II-XII in which l=1, m=2 and a=0, in other words it is chosen from the hydrophobized anionic polymers of formula II-VI:

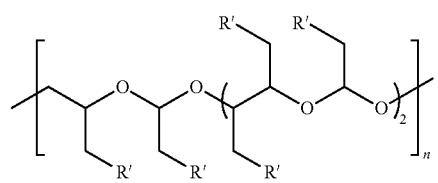

Formula II-VI

—R' and n being as defined above.

In one embodiment, the hydrophobized anionic polymer according to the invention is chosen from the hydrophobized anionic polymers of formula II-XII in which m=1, l=1, a=1, —R$_1$-R$_3$——CH(NHCOCH$_3$)—, —R$_2$=—CH$_2$R', —R$_4$=—CH$_2$R', —R$_5$ is either a —COOH group, or a radical -k-[D], —R$_6$=—CH$_2$R', in other words it is chosen from the hydrophobized anionic polymers of formula II-VII:

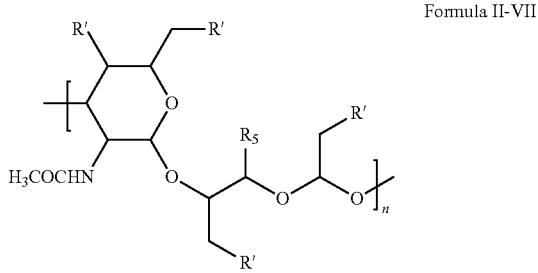

Formula II-VII

R' and n being as defined above.

In one embodiment, the hydrophobized anionic polymer according to the invention is chosen from the hydrophobized anionic polymers of formulae II-IV to II-VII and II-XII, in which the radical -f-[A]-COOH is chosen from the radicals of formula II-II below:

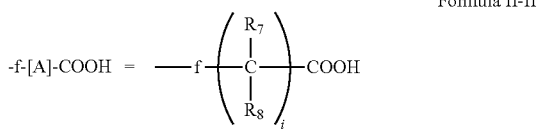

Formula II-II in which:
- i is greater than or equal to 1 and less than or equal to 12, and
- —$R_7$ and —$R_8$, which may be identical or different, are chosen from the group consisting of a hydrogen atom, a saturated or unsaturated, linear, branched or cyclic $C_1$ to $C_6$ alkyl, a benzyl, an alkylaryl, optionally comprising heteroatoms chosen from the group consisting of O, N and/or S, or functions chosen from the group consisting of carboxylic acid, amine, alcohol and thiol functions.

In one embodiment, the hydrophobized anionic polymer according to the invention is chosen from the compounds of formula II-I in which the radical -f-[A]—COOH, comprising from 2 to 8 carbon atoms, is derived from an amino acid, from a dialcohol, from a diamine, from a diacid or from an amine alcohol.

In one embodiment, the hydrophobized anionic polymer according to the invention is chosen from the compounds of formula II-I in which the radical -f-[A]-COOH, comprising from 2 to 6 carbon atoms, is derived from an amino acid, from a dialcohol, from a diamine, from a diacid or from an amine alcohol.

In one particular embodiment, the hydrophobized anionic polymer according to the invention is chosen from the hydrophobized anionic polymers of formulae II-IV to II-VII and II-XII corresponding to the following conditions:
- when -g-[B]-(k-[D])$_p$ comprises one Hy chain and Hy is a $C_8$ to $C_{15}$ alkyl, then the product of the degree of substitution with hydrophobic radicals and the average degree of polymerization (n) is greater than or equal to 2,
- when -g-[B]-(k-[D])$_p$ comprises one Hy chain and Hy is a $C_{16}$ to $C_{20}$ alkyl, then the product of the degree of substitution with hydrophobic radicals and the average degree of polymerization (n) is greater than or equal to 1,
- when -g-[B]-(k-[D])$_p$ comprises two Hy chains and Hy is a $C_8$ to $C_9$ alkyl, then the product of the degree of substitution with hydrophobic radicals and the average degree of polymerization (n) is greater than or equal to 2,
- when -g-[B]-(k-[D])$_p$ comprises two Hy chains and Hy is a $C_{10}$ to $C_{16}$ alkyl, then the product of the degree of substitution with hydrophobic radicals and the average degree of polymerization (n) is greater than or equal to 0.2.

In one embodiment, the hydrophobized anionic polymer according to the invention is chosen from the hydrophobized anionic polymers of formulae II-IV to II-VII and II-XII, in which the radical -f-[A]-COOH is chosen from the group consisting of the following radicals, f having the meaning given above:

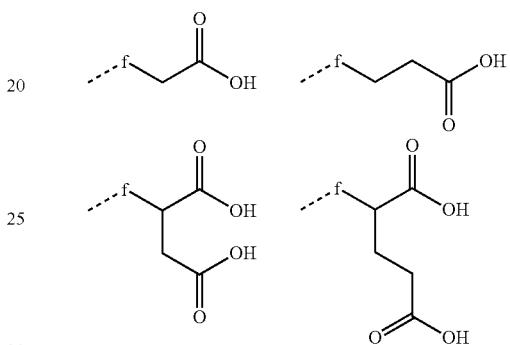

or the salts thereof with alkali metal cations chosen from the group consisting of $Na^+$ and $K^+$.

In one embodiment, the hydrophobized anionic polymer according to the invention is chosen from the hydrophobized anionic polymers of formulae II-IV to II-VII and II-XII, in which the radical -[A]- is a radical —$CH_2$—.

In one embodiment, the hydrophobized anionic polymer according to the invention is chosen from the hydrophobized anionic polymers of formulae II-IV to II-VII and II-XII, in which the radical -f-[A]-COOH is derived from an amino acid.

In one embodiment, the hydrophobized anionic polymer according to the invention is chosen from the hydrophobized anionic polymers of formulae II-IV to II-VII and II-XII, in which the radical -f-[A]-COOH is derived from glycine.

In one embodiment, the hydrophobized anionic polymer according to the invention is chosen from the hydrophobized anionic polymers of formulae II-IV to II-VII and II-XII, in which the radical -f-[A]-COOH is derived from aspartic acid.

In one embodiment, the hydrophobized anionic polymer according to the invention is chosen from the hydrophobized anionic polymers of formulae II-IV to II-VII and II-XII, in which the radical -f-[A]-COOH is derived from glutamic acid.

In one embodiment, the hydrophobized anionic polymer according to the invention is chosen from the hydrophobized anionic polymers of formulae II-IV to II-VII and II-XII, in which the radical -f-[A]-COOH is derived from succinic acid.

In one embodiment, the hydrophobized anionic polymer according to the invention is chosen from the hydrophobized anionic polymers of formulae II-IV to II-VII and II-XII, in which the function f is an ether function.

In one embodiment, the hydrophobized anionic polymer according to the invention is chosen from the hydrophobized anionic polymers of formulae II-IV to II-VII and II-XII, in which the function f is a carbamate function.

In one embodiment, the hydrophobized anionic polymer according to the invention is chosen from the hydrophobized anionic polymers of formulae II-IV to II-VII and II-XII, in which the function f is an ester function.

In one embodiment, the hydrophobized anionic polymer according to the invention is chosen from the hydrophobized anionic polymers of formulae II-IV to II-VII and II-XII, in which the function f is a carbonate function.

In one embodiment, the hydrophobized anionic polymer according to the invention is chosen from the hydrophobized anionic polymers of formulae II-IV to II-VII and II-XII, in which the function f is an amide function.

In one embodiment, the hydrophobized anionic polymer according to the invention is chosen from the hydrophobized anionic polymers of formulae II-IV to II-VII and II-XII, in which the radical -g-[B]- is chosen from the radicals of formula II-III below:

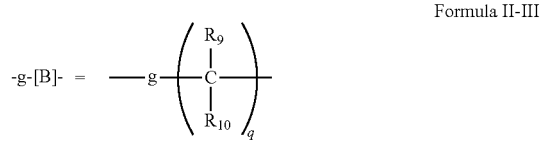

Formula II-III in which:
q is greater than or equal to 1 and less than or equal to 12, and
—$R_9$ and —$R_{10}$, which may be identical or different, are chosen from the group consisting of a hydrogen atom, a saturated or unsaturated, linear, branched or cyclic $C_1$ to $C_6$ alkyl, a benzyl, an alkylaryl, optionally comprising heteroatoms chosen from the group consisting of O, N and/or S, or functions chosen from the group consisting of carboxylic acid, amine, alcohol and thiol functions.

In one embodiment, the hydrophobized anionic polymer according to the invention is chosen from the hydrophobized anionic polymers of formulae II-IV to II-VII, in which the radical -g-[B]-k-[D] is chosen from the group consisting of the following radicals; g, k and -[D] having the meanings given above:

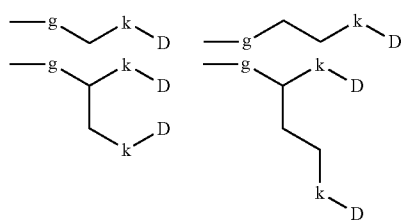

In one embodiment, the hydrophobized anionic polymer according to the invention is chosen from the hydrophobized anionic polymers of formulae II-IV to II-VII and II-XII, in which the radical -[B]- is a radical —$CH_2$—.

In one embodiment, the hydrophobized anionic polymer according to the invention is chosen from the hydrophobized anionic polymers of formulae II-IV to II-VII and II-XII, in which the radical -g-[B]-(k-[D])p is such that -g-[B]-k- is derived from an amino acid.

In one embodiment, the hydrophobized anionic polymer according to the invention is chosen from the hydrophobized anionic polymers of formulae II-IV to II-VII and II-XII, in which the radical -g-[B]-(k-[D])p is such that -g-[B]-k- is derived from glycine.

In one embodiment, the hydrophobized anionic polymer according to the invention is chosen from the hydrophobized anionic polymers of formulae II-IV to II-VII and II-XII, in which the radical -g-[B]-(k-[D])p is such that -g-[B]-k- is derived from aspartic acid.

In one embodiment, the hydrophobized anionic polymer according to the invention is chosen from the hydrophobized anionic polymers of formulae II-IV to II-VII and II-XII, in which the radical -g-[B]-(k-[D])p is such that -g-[B]-k- is derived from glutamic acid.

In one embodiment, the hydrophobized anionic polymer according to the invention is chosen from the hydrophobized anionic polymers of formulae II-IV to II-VII and II-XII, in which the radical -g-[B]-(k-[D])p is such that -g-[B]-k- is derived from succinic acid.

In one embodiment, the hydrophobized anionic polymer according to the invention is chosen from the hydrophobized anionic polymers of formulae II-IV to II-VII and II-XII, in which the function g is an ether function.

In one embodiment, the hydrophobized anionic polymer according to the invention is chosen from the hydrophobized anionic polymers of formulae II-IV to II-VII and II-XII, in which the function g is a carbamate function.

In one embodiment, the hydrophobized anionic polymer according to the invention is chosen from the hydrophobized anionic polymers of formulae II-IV to II-VII and II-XII, in which the function g is an ester function.

In one embodiment, the hydrophobized anionic polymer according to the invention is chosen from the hydrophobized anionic polymers of formulae II-IV to II-VII and II-XII, in which the function g is an amine function.

In one embodiment, the hydrophobized anionic polymer according to the invention is chosen from the hydrophobized anionic polymers of formulae II-IV to II-VII and II-XII, in which the function g is a carbonate function.

In one embodiment, the hydrophobized anionic polymer according to the invention is chosen from the hydrophobized anionic polymers of formulae II-IV to II-VII and II-XII, in which the function k is an amide function.

In one embodiment, the hydrophobized anionic polymer according to the invention is chosen from the hydrophobized anionic polymers of formulae II-IV to II-VII and II-XII, in which the function k is a carbamate function.

In one embodiment, the hydrophobized anionic polymer according to the invention is chosen from the hydrophobized anionic polymers of formulae II-IV to II-VII and II-XII, in which the function k is an ester function.

In one embodiment, the hydrophobized anionic polymer according to the invention is chosen from the hydrophobized anionic polymers of formulae II-IV to II-VII and II-XII, in which the radical -k-[E]-(o)t is an at least divalent radical derived from an amino acid.

In one embodiment, the hydrophobized anionic polymer according to the invention is chosen from the hydrophobized anionic polymers of formulae II-IV to II-VII and II-XII, in which the radical -k-[E]-(o)t is an at least divalent radical derived from an alpha amino acid.

In one embodiment, the hydrophobized anionic polymer according to the invention is chosen from the hydrophobized anionic polymers of formulae II-IV to II-VII and II-XII, in which the radical -k-[E]-(o)t is an at least divalent radical derived from a natural alpha amino acid chosen from the group consisting of glycine, leucine, phenylalanine, lysine, isoleucine, alanine, valine, aspartic acid and glutamic acid, in their L, D or racemic forms.

In one embodiment, the hydrophobized anionic polymer according to the invention is chosen from the hydrophobized anionic polymers of formulae II-IV to II-VII and II-XII, in which the radical -k-[E]-(o)t is an at least divalent radical derived from a mono- or polyethylene glycol.

In one embodiment, the hydrophobized anionic polymer according to the invention is chosen from the hydrophobized anionic polymers of formulae II-IV to II-VII and II-XII, in which the radical -k-[E]-(o)t is an at least divalent radical derived from ethylene glycol.

In one embodiment, the hydrophobized anionic polymer according to the invention is chosen from the hydrophobized anionic polymers of formulae II-IV to II-VII and II-XII, in which the radical -k-[E]-(o)t is an at least divalent radical derived from a polyethylene glycol chosen from the group consisting of diethylene glycol, triethylene glycol and tetraethylene glycol.

In one embodiment, the hydrophobized anionic polymer according to the invention is chosen from the hydrophobized anionic polymers of formulae II-IV to II-VII and II-XII, in which the radical -k-[E]-(o)t is an at least divalent radical derived from a mono- or polyethylene glycol amine.

In one embodiment, the hydrophobized anionic polymer according to the invention is chosen from the hydrophobized anionic polymers of formulae II-IV to II-VII and II-XII, in which the radical -k-[E]-(o)t is an at least divalent radical derived from a mono- or polyethylene glycol amine chosen from the group consisting of ethanolamine, diethylene glycol amine and triethylene glycol amine.

In one embodiment, the hydrophobized anionic polymer according to the invention is chosen from the hydrophobized anionic polymers of formulae II-IV to II-VII and II-XII, in which the radical -k-[E]-(o)t is an at least divalent radical derived from a mono- or polyethylene glycol diamine.

In one embodiment, the hydrophobized anionic polymer according to the invention is chosen from the hydrophobized anionic polymers of formulae II-IV to II-VII and II-XII, in which the radical -k-[E]-(o)t is an at least divalent radical derived from a mono- or polyethylene glycol diamine chosen from the group consisting of diethylene glycol diamine and triethylene glycol diamine.

In one embodiment, the hydrophobized anionic polymer according to the invention is chosen from the hydrophobized anionic polymers of formulae II-IV to II-VII and II-XII, in which the radical -k-[E]-(o)t is an at least divalent radical derived from ethylenediamine.

In one embodiment, the hydrophobized anionic polymer according to the invention is chosen from the hydrophobized anionic polymers of formulae II-IV to II-VII and II-XII, in which the function o is an ester function.

In one embodiment, the hydrophobized anionic polymer according to the invention is chosen from the hydrophobized anionic polymers of formulae II-IV to II-VII and II-XII, in which the function o is an amide function.

In one embodiment, the hydrophobized anionic polymer according to the invention is chosen from the hydrophobized anionic polymers of formulae II-IV to II-VII and II-XII, in which the function o is a carbamate function.

In one embodiment, the hydrophobized anionic polymer according to the invention is chosen from the hydrophobized anionic polymers of formulae II-IV to II-VII and II-XII, in which the function o is a carbonate function.

In one embodiment, the hydrophobized anionic polymer according to the invention is chosen from the hydrophobized anionic polymers of formulae II-IV to II-VII and II-XII, in which the -[Hy] group is an alkyl group derived from a hydrophobic alcohol having a Log P greater than or equal to 2.

In one embodiment, the hydrophobized anionic polymer according to the invention is chosen from the hydrophobized anionic polymers of formulae II-IV to II-VII and II-XII, in which the -[Hy] group is an alkyl group derived from a branched or unbranched, unsaturated and/or saturated, hydrophobic alcohol comprising from 8 to 30 carbons.

In one embodiment, the hydrophobized anionic polymer according to the invention is chosen from the hydrophobized anionic polymers of formulae II-IV to II-VII and II-XII, in which the -[Hy] group is an alkyl group derived from a hydrophobic alcohol chosen from the group consisting of octanol, decanol, dodecanol (lauryl alcohol), tetradecanol (myristyl alcohol), hexadecanol (cetyl alcohol), stearyl alcohol, cetearyl alcohol and oleyl alcohol.

In one embodiment, the hydrophobized anionic polymer according to the invention is chosen from the hydrophobized anionic polymers of formulae II-IV to II-VII and II-XII, in which the -[Hy] group is a group derived from a sterol.

In one embodiment, the hydrophobized anionic polymer according to the invention is chosen from the hydrophobized anionic polymers of formulae II-IV to II-VII and II-XII, in which the -[Hy] group is a group derived from a sterol, chosen from the group consisting of cholesterol and derivatives thereof.

In one embodiment, the hydrophobized anionic polymer according to the invention is chosen from the hydrophobized anionic polymers of formulae II-IV to II-VII and II-XII, in which the -[Hy] group is a group derived from cholesterol.

In one embodiment, the hydrophobized anionic polymer according to the invention is chosen from the hydrophobized anionic polymers of formulae II-IV to II-VII and II-XII, in which the -[Hy] group is a group derived from a tocopherol.

In one embodiment, the hydrophobized anionic polymer according to the invention is chosen from the hydrophobized anionic polymers of formulae II-IV to II-VII and II-XII, in which the -[Hy] group is a group derived from a tocopherol derivative, chosen from the racemate, the L isomer or the D isomer of α-tocopherol.

In one embodiment, the hydrophobized anionic polymer according to the invention is chosen from the hydrophobized anionic polymers of formulae II-IV to II-VII and II-XII, in which the -[Hy] group is a group derived from DL-α-tocopherol.

In one embodiment, the hydrophobized anionic polymer according to the invention is chosen from the hydrophobized anionic polymers of formulae II-IV to II-VII and II-XII, in which the -[Hy] group is a group derived from menthol.

In one embodiment, the hydrophobized anionic polymer according to the invention is chosen from the hydrophobized anionic polymers of formulae II-IV to II-VII and II-XII, in which the -[Hy] group is a group derived from menthol or derivatives thereof, chosen from the racemate, the L isomer or the D isomer of menthol.

In one embodiment, the hydrophobized anionic polymer according to the invention is chosen from the hydrophobized anionic polymers of formulae II-IV to II-VII and II-XII, in which the -[Hy] group is an alkyl group derived from a hydrophobic acid.

In one embodiment, the hydrophobized anionic polymer according to the invention is chosen from the hydrophobized anionic polymers of formulae II-IV to II-VII and II-XII, in which the -[Hy] group is an alkyl group derived from a hydrophobic acid having a Log P greater than or equal to 2.

In one embodiment, the hydrophobized anionic polymer according to the invention is chosen from the hydrophobized anionic polymers of formulae II-IV to II-VII and II-XII, in which the -[Hy] group is an alkyl group derived from a linear hydrophobic acid, chosen from the group consisting of dodecanoic acid, tetradecanoic acid and hexadecanoic acid.

In one embodiment, the hydrophobized anionic polymer according to the invention is chosen from the hydrophobized anionic polymers of formulae II-IV to II-VII and II-XII, in which the -[Hy] group is an alkyl group derived from a fatty acid.

In one embodiment, the hydrophobized anionic polymer according to the invention is chosen from the hydrophobized anionic polymers of formulae II-IV to II-VII and II-XII, in which the -[Hy] group is an alkyl group derived from a fatty acid chosen from the group consisting of the acids consisting of a branched or unbranched, unsaturated or saturated, alkyl chain comprising from 8 to 30 carbons.

In one embodiment, the hydrophobized anionic polymer according to the invention is chosen from the hydrophobized anionic polymers of formulae II-IV to II-VII and II-XII, in which the -[Hy] group is an alkyl group derived from a fatty acid chosen from the group consisting of linear fatty adds.

In one embodiment, the hydrophobized anionic polymer according to the invention is chosen from the hydrophobized anionic polymers of formulae II-IV to II-VII and II-XII, in which the -[Hy] group is an alkyl group derived from a saturated linear fatty acid chosen from the group consisting of caprylic acid (octanoic add), nonanoic acid, capric acid (decanoic acid), undecanoic acid, lauric acid (dodecanoic acid), myristic (tetradecanoic) acid, palmitic (hexadecanoic) acid, stearic (octadecanoic) acid, arachidic (eicosanoic) acid, behenic (docosanoic) acid, tricosanoic acid, lignoceric (tetracosanoic) acid, heptacosanoic acid, octacosanoic acid and melissic (tricontanoic) add.

In one embodiment, the hydrophobized anionic polymer according to the invention is chosen from the hydrophobized anionic polymers of formulae II-IV to II-VII and II-XII, in which the -[Hy] group is an alkyl group derived from an unsaturated fatty acid.

In one embodiment, the hydrophobized anionic polymer according to the invention is chosen from the hydrophobized anionic polymers of formulae II-IV to II-VII and II-XII, in which the -[Hy] group is an alkyl group derived from an unsaturated fatty add chosen from the group consisting of myristoleic ((Z)-tetradec-9-enoic) acid, palmitoleic ((Z)-hexadec-9-enoic) acid, oleic ((Z)-octadec-9-enoic) acid, elaidic ((E)-octadec-9-enoic) acid, linoleic ((9Z,12Z)-octadeca-9,12-dienoic) add, alpha-linoleic ((9Z,12Z,15Z)-octadeca-9,12,15-trienoic) acid, arachidonic ((5Z,8Z,11Z,14Z)-octadeca-5,8,11,14-tetraenoic) acid, eicosapentaenoic ((5Z,8Z,11Z,14Z,17Z)-eicosa-5,8,11,14,17-pentaenoic) acid, erucic (13-docoenoic) acid and docosahexaenoic ((4Z,7Z,10Z,13Z,16Z,19Z)-docosa-4,7,10,13,16,19-hexaenoic) add.

In one embodiment, the hydrophobized anionic polymer according to the invention is chosen from the hydrophobized anionic polymers of formulae II-IV to II-VII and II-XII, in which the -[Hy] group is an alkyl group derived from a bile acid and derivatives thereof.

In one embodiment, the hydrophobized anionic polymer according to the invention is chosen from the hydrophobized anionic polymers of formulae II-IV to II-VII and II-XII, in which the -[Hy] group is an alkyl group derived from a bile acid and derivatives thereof, chosen from the group consisting of cholic acid, dehydrocholic add, deoxycholic acid and chenodeoxycholic acid.

In one embodiment, the hydrophobized anionic polymer according to the invention is chosen from the hydrophobized anionic polymers of formula II-V in which —R' is either an —OH group, or a radical -f-[A]-COOH, or a radical -g-[B]-k-[D], f being an ether function, the radical -[A]- being a radical —$CH_2$—, g being an ether function, the radical -[B]- being a radical —$CH_2$—, k being an amide function, -[D] being a radical -[E]-o-Hy, p and t=1, the radical -[E]- being derived from leucine, o being an ester function and Hy being derived from cholesterol.

The precursors of the hydrophobized anionic polymers of formula II-I, in which —$R_2$, —$R_4$ and —$R_6$ are radicals —$CH_2R'$, or of formulae II-IV to II-VII and II-XII can be obtained by means of a process such as that described in Biomacromolecules, 2005, 6, 2659-2670. This process can result in polymers comprising units other than that which is repeated in formula II-I, in which —$R_2$, —$R_4$ and —$R_6$ are radicals —$CH_2R'$, in particular hemiacetal rings, for example as described in the publication Carbohydrate Research 1978, 64, 189-197.

Thus, according to one embodiment, the hydrophobized anionic polymers according to the invention comprise at least 75% of their repeat units in the form of that defined in formula II-I, in which —$R_2$, —$R_4$ and —$R_6$ are radicals —$CH_2R'$, or in formulae II-IV to II-VII and II-XII.

According to one embodiment, the hydrophobized anionic polymers according to the invention comprise at least 85% of their repeat units in the form of that defined in formula II-I, in which —$R_2$, —$R_4$ and —$R_6$ are radicals —$CH_2R'$, or in formulae II-IV to II-VII and II-XII.

According to one embodiment, the hydrophobized anionic polymers according to the invention comprise at least 95% of their repeat units in the form of that defined in formula II-I, in which —$R_2$, —$R_4$ and —$R_6$ are radicals —$CH_2R'$, or in formulae II-IV to II-VII and II-XII.

According to one embodiment, the hydrophobized anionic polymers according to the invention comprise at least 98% of their repeat units in the form of that defined in formula II-I, in which —$R_2$, —$R_4$ and —$R_6$ are radicals —$CH_2R'$, or in formulae II-IV to II-VII and II-XII.

According to one embodiment, the hydrophobized anionic polymers according to the invention comprise 100% of their repeat units in the form of that defined in formula II-I, in which —$R_2$, —$R_4$ and —$R_6$ are radicals —$CH_2R'$, or in formulae II-IV to II-VII and II-XII.

According to one embodiment, the hydrophobized anionic polymer according to the invention is chosen from the hydrophobized anionic polymers of formula II-V having a weight-average molar mass ranging from 2 to 40 kg/mol.

According to one embodiment, the hydrophobized anionic polymer according to the invention is chosen from the hydrophobized anionic polymers of formula II-V having a weight-average molar mass ranging from 2 to 20 kg/mol.

According to one embodiment, the hydrophobized anionic polymer according to the invention is chosen from the hydrophobized anionic polymers of formula II-V having a weight-average molar mass ranging from 2 to 12 kg/mol.

In one particular embodiment, the hydrophobized anionic polymer according to the invention is chosen from the hydrophobized anionic polymers of formula II-V corresponding to the following conditions:
when -g-[B]-(k-[D])$_p$ comprises one Hy chain and Hy is a $C_8$ to $C_{15}$ alkyl, then the product of the degree of substitution with hydrophobic radicals and the average degree of polymerization (n) is greater than or equal to 2, when -g-[B]-(k-[D])$_p$ comprises one Hy chain and Hy is a $C_{16}$ to $C_{20}$ alkyl, then the product of the degree of substitution with hydrophobic radicals and the average degree of polymerization (n) is greater than or equal to 1, when -g-[B]-(k-[D])$_p$ comprises two Hy chains and Hy is a $C_8$ to $C_9$ alkyl, then the product of the degree of substitution with hydrophobic radicals and the average degree of polymerization (n) is greater than or equal to 2, when -g-[B]-(k-[D])$_p$ comprises two Hy chains and Hy is a $C_{10}$ to $C_{16}$ alkyl, then the product of the degree of substitution with hydrophobic radicals and the average degree of polymerization (n) is greater than or equal to 0.2.

According to one embodiment, the hydrophobized anionic polymer according to the invention is chosen from the hydrophobized anionic polymers of formula II-V in which the radical -f-[A]-COOH is chosen from the group consisting of the following radicals, f having the meaning given above:

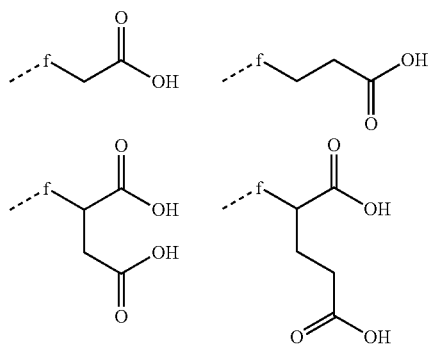

or the salts thereof with alkali metal cations chosen from the group consisting of Na$^+$ and K$^+$.

In one embodiment, the hydrophobized anionic polymer according to the invention is chosen from the hydrophobized anionic polymers of formula II-V in which the radical -[A]- is a radical —CH$_2$—.

In one embodiment, the hydrophobized anionic polymer according to the invention is chosen from the hydrophobized anionic polymers of formula II-V in which the function f is an ether function.

In one embodiment, the hydrophobized anionic polymer according to the invention is chosen from the hydrophobized anionic polymers of formula II-V in which the radical -g-[B]-k-[D] is chosen from the group consisting of the following radicals; g, k and -[D] having the meanings given above:

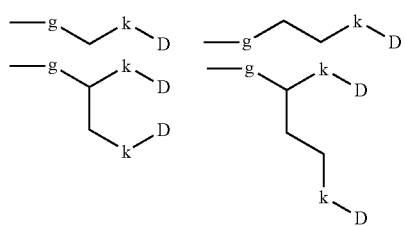

In one embodiment, the hydrophobized anionic polymer according to the invention is chosen from the hydrophobized anionic polymers of formula II-V in which the radical -[B]- is a radical —CH$_2$—.

In one embodiment, the hydrophobized anionic polymer according to the invention is chosen from the hydrophobized anionic polymers of formula II-V in which the function g is an ether function.

In one embodiment, the hydrophobized anionic polymer according to the invention is chosen from the hydrophobized anionic polymers of formula II-V in which the function k is an amide function.

In one embodiment, the hydrophobized anionic polymer according to the invention is chosen from the hydrophobized anionic polymers of formula II-V in which the radical -k-[E]-(o)t is an at least divalent radical derived from an amino acid.

In one embodiment, the hydrophobized anionic polymer according to the invention is chosen from the hydrophobized anionic polymers of formula II-V in which the radical -k-[E]-(o)t is an at least divalent radical derived from an alpha amino acid.

In one embodiment, the hydrophobized anionic polymer according to the invention is chosen from the hydrophobized anionic polymers of formula II-V in which the radical -[E]- is an at least divalent radical derived from a natural alpha amino acid chosen from the group consisting of glycine, leucine, phenylalanine, lysine, isoleucine, alanine, valine, aspartic acid and glutamic acid, in their L, D or racemic forms.

In one embodiment, the hydrophobized anionic polymer according to the invention is chosen from the hydrophobized anionic polymers of formula II-V in which the radical -k-[E]-(o)t is an at least divalent radical derived from a mono- or polyethylene glycol amine chosen from the group consisting of ethanolamine, diethylene glycol amine and triethylene glycol amine.

In one embodiment, the hydrophobized anionic polymer according to the invention is chosen from the hydrophobized anionic polymers of formula II-V in which the radical -k-[E]-(o)t is an at least divalent radical derived from ethylenediamine.

In one embodiment, the hydrophobized anionic polymer according to the invention is chosen from the hydrophobized anionic polymers of formula II-V in which the function o is an ester function.

In one embodiment, the hydrophobized anionic polymer according to the invention is chosen from the hydrophobized anionic polymers of formula II-V in which the function o is an amide function.

In one embodiment, the hydrophobized anionic polymer according to the invention is chosen from the hydrophobized anionic polymers of formula II-V in which the function o is a carbamate function.

In one embodiment, the hydrophobized anionic polymer according to the invention is chosen from the hydrophobized anionic polymers of formula II-V in which the -[Hy] group is an alkyl group derived from a hydrophobic alcohol having a Log P greater than or equal to 2.

In one embodiment, the hydrophobized anionic polymer according to the invention is chosen from the hydrophobized anionic polymers of formula II-V in which the -[Hy] group is an alkyl group derived from a branched or unbranched, unsaturated and/or saturated, hydrophobic alcohol comprising from 8 to 30 carbons.

In one embodiment, the hydrophobized anionic polymer according to the invention is chosen from the hydrophobized anionic polymers of formula II-V in which the -[Hy] group is an alkyl group derived from a hydrophobic alcohol chosen from the group consisting of octanol, decanol, dodecanol (lauryl alcohol), tetradecanol (myristyl alcohol), hexadecanol (cetyl alcohol), stearyl alcohol, cetearyl alcohol and oleyl alcohol.

In one embodiment, the hydrophobized anionic polymer according to the invention is chosen from the hydrophobized anionic polymers of formula II-V in which the -[Hy] group is a group derived from a sterol.

In one embodiment, the hydrophobized anionic polymer according to the invention is chosen from the hydrophobized anionic polymers of formula II-V in which the -[Hy] group is a group derived from a sterol, chosen from the group consisting of cholesterol and derivatives thereof.

In one embodiment, the hydrophobized anionic polymer according to the invention is chosen from the hydrophobized anionic polymers of formula II-V in which the -[Hy] group is a group derived from cholesterol.

In one embodiment, the hydrophobized anionic polymer according to the invention is chosen from the hydrophobized anionic polymers of formula II-V in which the -[Hy] group is a group derived from a tocopherol.

In one embodiment, the hydrophobized anionic polymer according to the invention is chosen from the hydrophobized anionic polymers of formula II-V in which the -[Hy] group is a group derived from a tocopherol derivative, chosen from the racemate, the L isomer or the D isomer of α-tocopherol.

In one embodiment, the hydrophobized anionic polymer according to the invention is chosen from the hydrophobized anionic polymers of formula II-V in which the -[Hy] group is a group derived from DL-α-tocopherol.

In one embodiment, the hydrophobized anionic polymer according to the invention is chosen from the hydrophobized anionic polymers of formula II-V in which the -[Hy] group is a group derived from menthol.

In one embodiment, the hydrophobized anionic polymer according to the invention is chosen from the hydrophobized anionic polymers of formula II-V in which the -[Hy] group is a group derived from menthol or derivatives thereof, chosen from the racemate, the L isomer or the D isomer of menthol.

In one embodiment, the hydrophobized anionic polymer according to the invention is chosen from the hydrophobized anionic polymers of formula II-V in which the -[Hy] group is an alkyl group derived from a hydrophobic add.

In one embodiment, the hydrophobized anionic polymer according to the invention is chosen from the hydrophobized anionic polymers of formula II-V in which the -[Hy] group is an alkyl group derived from a hydrophobic acid having a Log P greater than or equal to 2.

In one embodiment, the hydrophobized anionic polymer according to the invention is chosen from the hydrophobized anionic polymers of formula II-V in which the -[Hy] group is an alkyl group derived from a linear hydrophobic acid, chosen from the group consisting of dodecanoic add, tetradecanoic acid and hexadecanoic acid.

In one embodiment, the hydrophobized anionic polymer according to the invention is chosen from the hydrophobized anionic polymers of formula II-V in which the -[Hy] group is an alkyl group derived from a fatty acid.

In one embodiment, the hydrophobized anionic polymer according to the invention is chosen from the hydrophobized anionic polymers of formula II-V in which the -[Hy] group is an alkyl group derived from a fatty acid chosen from the group consisting of the acids consisting of a branched or unbranched, unsaturated or saturated, alkyl chain comprising from 8 to 30 carbons.

In one embodiment, the hydrophobized anionic polymer according to the invention is chosen from the hydrophobized anionic polymers of formula II-V in which the -[Hy] group is an alkyl group derived from a fatty acid chosen from the group consisting of linear fatty acids.

In one embodiment, the hydrophobized anionic polymer according to the invention is chosen from the hydrophobized anionic polymers of formula II-V in which the -[Hy] group is an alkyl group derived from a saturated linear fatty acid chosen from the group consisting of caprylic add (octanoic add), nonanoic acid, capric acid (decanoic acid), undecanoic add, lauric add (dodecanoic acid), myristic (tetradecanoic) acid, palmitic (hexadecanoic) add, stearic (octadecanoic) acid, arachidic (eicosanoic) acid, behenic (docosanoic) acid, tricosanoic acid, lignoceric (tetracosanoic) acid, heptacosanoic acid, octacosanoic acid and melissic (tricontanoic) acid.

In one embodiment, the hydrophobized anionic polymer according to the invention is chosen from the hydrophobized anionic polymers of formula II-V in which the -[Hy] group is an alkyl group derived from an unsaturated fatty acid.

In one embodiment, the hydrophobized anionic polymer according to the invention is chosen from the hydrophobized anionic polymers of formula II-V in which the -[Hy] group is an alkyl group derived from an unsaturated fatty acid chosen from the group consisting of myristoleic ((Z)-tetradec-9-enoic) acid, palmitoleic ((Z)-hexadec-9-enoic) acid, oleic ((Z)-octadec-9-enoic) add, elaidic ((E)-octadec-9-enoic) acid, linoleic ((9Z,12Z)-octadeca-9,12-dienoic) acid, alpha-linoleic ((9Z,12Z,15Z)-octadeca-9,12,15-trienoic) acid, arachidonic ((5Z,8Z,11Z,14Z)-octadeca-5,8,11,14-tetraenoic) acid, eicosapentaenoic ((5Z,8Z,11Z,14Z,17Z)-eicosa-5,8,11,14,17-pentaenoic) add, erucic (13-docoenoic) acid and docosahexaenoic ((4Z,7Z,10Z,13Z,16Z,19Z)-docosa-4,7,10,13,16,19-hexaenoic) add.

In one embodiment, the hydrophobized anionic polymer according to the invention is chosen from the hydrophobized anionic polymers of formula II-V in which the -[Hy] group is an alkyl group derived from a bile acid and derivatives thereof.

In one embodiment, the hydrophobized anionic polymer according to the invention is chosen from the hydrophobized anionic polymers of formula II-V in which the -[Hy] group is an alkyl group derived from a bile acid and derivatives thereof, chosen from the group consisting of cholic acid, dehydrocholic acid, deoxycholic acid and chenodeoxycholic add.

In one embodiment, the hydrophobized anionic polymer according to the invention is chosen from the hydrophobized anionic polymers of formula II-V in which —R' is either an —OH group, or a radical -f-[A]-COOH, or a radical -g-[B]-k-[D], f being an ether function, the radical -[A]- being a radical —CH$_2$—, g being an ether function, the radical -[B]- being a radical —CH$_2$—, k being an amide function, -[D] being a radical -[E]-o-Hy, p and t=1, the radical -k-[E]-(o)$_t$ being derived from an amino acid, o being an ester function and Hy being derived from a sterol or from a fatty alcohol, in particular:

the radical -k-[E]-(o)$_t$ being derived from leucine and Hy being derived from cholesterol, the radical -k-[E]-(o)$_t$ being derived from glycine and Hy being derived from dodecanol, the radical -k-[E]-(o)$_t$ being derived from leucine and Hy being derived from tocopherol, and the radical -k-[E]-(o)$_t$ being derived from phenylalanine and Hy being derived from octanol, and the radical -k-[E]-(o)$_t$ being derived from phenylalanine and Hy being derived from 3,7-dimethyloctan-1-ol.

In one embodiment, the hydrophobized anionic polymer according to the invention is chosen from the hydrophobized anionic polymers of formula II-V in which —R' is either an —OH group, or a radical -f-[A]-COOH, or a radical -g-[B]-k-[D], f being an ether function, the radical -[A]- being a radical —CH$_2$—, g being an ether function, the radical -[B]- being a radical —CH$_2$—, k being an amide function, -[D] being a radical -[E]-(o-Hy)$_2$, p=1 and t=2, the radical -k-[E]-(o)$_t$ being derived from an amino acid, o being an ester function and Hy being derived from a fatty alcohol, in particular the radical -k-[E]-(o)$_t$ being derived from aspartic acid and Hy being derived from dodecanol or decanol.

In one embodiment, the hydrophobized anionic polymer according to the invention is chosen from the hydrophobized anionic polymers of formula II-V in which —R' is either an —OH group, or a radical -f-[A]-COOH, or a radical -g-[B]-k-[D], f being an ether function, the radical -[A]- being a radical —CH$_2$—, g being an ether function, the radical -[B]- being a radical —CH$_2$—, k being an amide function, -[D] being a radical -[E]-o-Hy, p and t=1, the radical -k-[E]-(o)t being derived from a diamine, o being an amide function and Hy being derived from a fatty acid, in particular the radical -k-[E]-(o)t being derived from ethylenediamine and Hy being derived from dodecanoic acid.

In one embodiment, the hydrophobized anionic polymer according to the invention is chosen from the hydrophobized anionic polymers of formula II-V in which —R' is either an —OH group, or a radical -f-[A]-COOH, or a radical -g-[B]-k-[D], f being an ether function, the radical -[A]- being a radical —CH$_2$—, g being an ether function, the radical -[B]- being a radical —CH$_2$—, k being an amide function, -[D] being a radical -[E]-o-Hy, p and t=1, the radical -k-[E]-(o)t being derived from a diamine, o being a carbamate function and Hy being derived from a sterol, in particular the radical -k-[E]-(o)t being derived from ethylenediamine and Hy being derived from cholesterol.

In one embodiment, the hydrophobized anionic polymer according to the invention is chosen from the hydrophobized anionic polymers of formula II-V in which —R' is either an —OH group, or a radical -f-[A]-COOH, or a radical -g-[B]-k-[D], f being an ether function, the radical -[A]- being a radical —CH$_2$—, g being an ether function, the radical -[B]- being a radical —CH$_2$—, k being an amide function, -[D] being a radical -[E]-o-Hy, p and t=1, the radical -k-[E]-(o)t being derived from an amino alcohol, o being an ester function and Hy being derived from a fatty alcohol, in particular the radical -k-[E]-(o)t being derived from 2-(2-aminoethoxy)ethanol and Hy being derived from dodecanol.

In one embodiment, the composition according to the invention is characterized in that the hydrophobized anionic polymer is chosen from the hydrophobized anionic polymers of formula II-I in which —R$_4$ and —R$_6$ form a six-membered ring and —R$_4$-R$_6$═══(CH(R'))$_2$—.

In one embodiment, the composition according to the invention is characterized in that the hydrophobized anionic polymer of formula II-I, in which —R$_4$ and —R$_6$ form a six-membered ring and —R$_4$-R$_6$═══(CH(R'))$_2$—, is chosen from the hydrophobized anionic polysaccharides of formula II-XI:

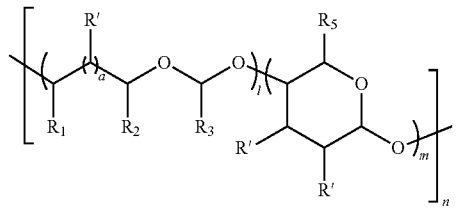

Formula II-XI in which,
l=0 or 1,
m=0, 1 or 2,
a=0 or 1,
n being the degree of polymerization, of between 3 and 1000,
and
—R$_1$ is a hydrogen,
—R$_2$ is a radical —CH$_2$R',
—R$_5$ is either a —COOH group, or a radical —CH$_2$R', or a radical -k-[D],
or
—R$_2$ and —R$_3$ form a six-membered ring and —R$_2$-R$_3$—═══(CH(R'))$_3$— and —R$_1$ is a hydrogen,
and
—R', n and -k-[D] being as defined above,
and the degree of substitution with carboxylate charges is the average number of carboxylate charges per monomer divided by (l+m) and is greater than or equal to 0.4,
and the degree of substitution with hydrophobic radicals is the average number of hydrophobic radicals per monomer divided by (l+m) and is less than or equal to 0.5.

In one embodiment, the composition according to the invention is characterized in that the hydrophobized anionic polymer is a polysaccharide of formula II-XI in which the identical or different six-membered ring(s) is (are) saccharide units chosen from the group consisting of hexoses, uronic acids and N-acetylhexosamines.

In one embodiment, the composition according to the invention is characterized in that the saccharide units are chosen from the group consisting of hexoses in cyclic form.

In one embodiment, the composition according to the invention is characterized in that the saccharide units are chosen from the group consisting of fructose, sorbose, tagatose, psicose, glucose, mannose, galactose, allose, altrose, talose, idose, gulose, fucose, fuculose and rhamnose.

In one embodiment, the composition according to the invention is characterized in that the saccharide units are chosen from the group consisting of uronic acids.

In one embodiment, the composition according to the invention is characterized in that the saccharide units are chosen from the group consisting of glucuronic acid, iduronic acid and galacturonic acid.

In one embodiment, the composition according to the invention is characterized in that the saccharide units are chosen from the group consisting of N-acetyl hexosamines.

In one embodiment, the composition according to the invention is characterized in that the saccharide units are chosen from the group consisting of N-acetylglucosamine, N-acetylgalactosamine and N-acetylmannosamine.

In one embodiment, the composition according to the invention is characterized in that the polysaccharides of formula II-XI are linked via glycosidic linkages of a and/or β type, which may be identical or different.

In one embodiment, the composition according to the invention is characterized in that the hydrophobized anionic polysaccharide of formula II-XI, in which l=0, m=1, and —$R_5$ is a radical —$CH_2R'$, in other words it is chosen from celluloses and water-soluble celluloses of formula II-VIII:

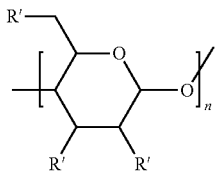

Formula II-VIII

—R' being as defined above.

In one embodiment, the composition according to the invention is characterized in that the hydrophobized anionic polysaccharide of formula II-XI, in which l=0, m=2, and —$R_5$ is either a —COOH group, or a radical -k-[D], in other words it is chosen from the alginates of formula I-IX:

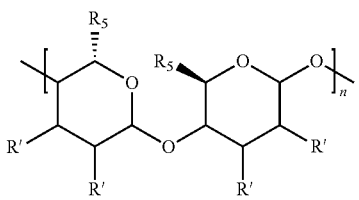

Formula II-IX

—R', n and -k-[D] being as defined above.

In one embodiment, the composition according to the invention is characterized in that the hydrophobized anionic polysaccharide of formula III-XI, in which l=1, m=2, a=0, —$R_1$ is an —H, —$R_2$ and —$R_3$ form a six-membered ring and —$R_2$-$R_3$—=—$(CH(R')_3)$—, and —$R_5$ is a radical —$CH_2R'$, in other words it is chosen from the pullulans of formula II-X:

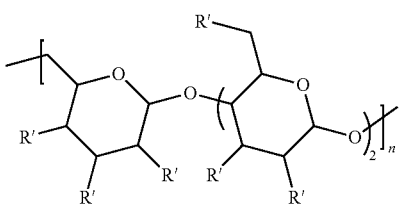

Formula II-X

—R' being as defined above.

In one embodiment, the composition according to the invention is characterized in that the hydrophobized anionic polymer is chosen from the hydrophobized anionic polymers of formulae II-VIII to II-XI, in which the radical -f-[A]-COOH is chosen from the radicals of formula II-II below:

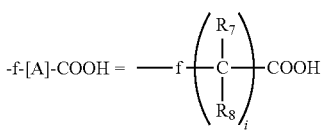

Formula II-II in which:
i is greater than or equal to 1 and less than or equal to 12, and
—$R_7$ and —$R_8$, which may be identical or different, are chosen from the group consisting of a hydrogen atom, a saturated or unsaturated, linear, branched or cyclic $C_1$ to $C_6$ alkyl, a benzyl, an alkylaryl, optionally comprising heteroatoms chosen from the group consisting of O, N and/or S, or functions chosen from the group consisting of carboxylic acid, amine, alcohol and thiol functions.

In one embodiment, the composition according to the invention is characterized in that the hydrophobized anionic polymer is chosen from the hydrophobized anionic polymers of formulae II-VII to II-XI, in which the radical -f-[A]-COOH is chosen from the group consisting of the following radicals, f having the meaning given above:

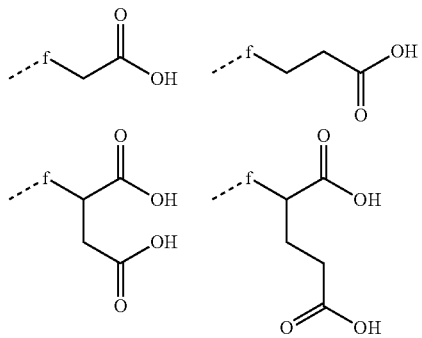

or the salts thereof with alkali metal cations chosen from the group consisting of $Na^+$ and $K^+$.

In one embodiment, the composition according to the invention is characterized in that the hydrophobized anionic polymer is chosen from the hydrophobized anionic polymers of formulae II-VIII to II-XI, in which the radical -[A]- is a radical —$CH_2$—.

In one embodiment, the composition according to the invention is characterized in that the hydrophobized anionic polymer is chosen from the hydrophobized anionic polymers of formulae II-VIII to II-XI, in which the radical -f-[A]-COOH is derived from an amino acid.

In one embodiment, the composition according to the invention is characterized in that the hydrophobized anionic polymer is chosen from the hydrophobized anionic polymers of formulae II-VIII to II-XI, in which the radical -f-[A]-COOH is derived from glycine.

In one embodiment, the composition according to the invention is characterized in that the hydrophobized anionic polymer is chosen from the hydrophobized anionic polymers of formulae II-VIII to II-XI, in which the radical -f-[A]-COOH is derived from aspartic acid.

In one embodiment, the composition according to the invention is characterized in that the hydrophobized anionic polymer is chosen from the hydrophobized anionic polymers of formulae II-VIII to II-XI, in which the radical -f-[A]-COOH is derived from glutamic acid.

In one embodiment, the composition according to the invention is characterized in that the hydrophobized anionic polymer is chosen from the hydrophobized anionic polymers of formulae II-VIII to II-XI, in which the radical -f-[A]-COOH is derived from succinic acid.

In one embodiment, the composition according to the invention is characterized in that the hydrophobized anionic polymer is chosen from the hydrophobized anionic polymers of formulae II-VIII to II-XI, in which the function f is an ether function.

In one embodiment, the composition according to the invention is characterized in that the hydrophobized anionic polymer is chosen from the hydrophobized anionic polymers of formulae II-VIII to II-XI, in which the function f is a carbamate function.

In one embodiment, the composition according to the invention is characterized in that the hydrophobized anionic polymer is chosen from the hydrophobized anionic polymers of formulae II-VIII to II-XI, in which the function f is an ester function.

In one embodiment, the composition according to the invention is characterized in that the hydrophobized anionic polymer is chosen from the hydrophobized anionic polymers of formulae II-VIII to II-XI, in which the function f is a carbonate function.

In one embodiment, the composition according to the invention is characterized in that the hydrophobized anionic polymer is chosen from the hydrophobized anionic polymers of formulae II-VIII to II-XI, in which the function f is an amide function.

In one embodiment, the composition according to the invention is characterized in that the hydrophobized anionic polymer is chosen from the hydrophobized anionic polymers of formulae II-VIII to II-XI, in which the radical -g-[B]- is chosen from the radicals of formula II-III below:

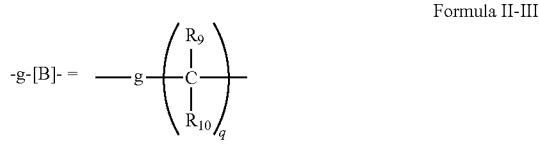

Formula II-III in which:
  q is greater than or equal to 1 and less than or equal to 12, and
  —$R_9$ and —$R_{10}$, which may be identical or different, are chosen from the group consisting of a hydrogen atom, a saturated or unsaturated, linear, branched or cyclic $C_1$ to $C_6$ alkyl, a benzyl, an alkylaryl, optionally comprising heteroatoms chosen from the group consisting of O, N and/or S, or functions chosen from the group consisting of carboxylic acid, amine, alcohol and thiol functions.

In one embodiment, the composition according to the invention is characterized in that the hydrophobized anionic polymer is chosen from the hydrophobized anionic polymers of formulae II-VIII to II-XI, in which the radical -g-[B]-k-[D] is chosen from the group consisting of the following radicals; g, k and -[D] having the meanings given above:

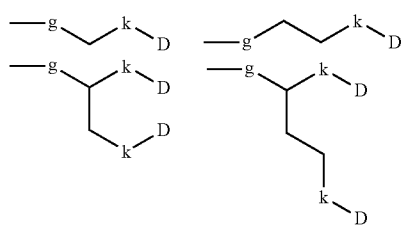

In one embodiment, the composition according to the invention is characterized in that the hydrophobized anionic polymer is chosen from the hydrophobized anionic polymers of formulae II-VIII to II-XI, in which the radical -[B]- is a radical —$CH_2$—.

In one embodiment, the composition according to the invention is characterized in that the hydrophobized anionic polymer is chosen from the hydrophobized anionic polymers of formulae II-VIII to II-XI, in which the radical -g-[B]-(k-[D])p is such that -g-[B]-k- Is derived from an amino acid.

In one embodiment, the composition according to the invention is characterized in that the hydrophobized anionic polymer is chosen from the hydrophobized anionic polymers of formulae II-VIII to II-XI, in which the radical -g-[B]-(k-[D])p is such that -g-[B]-k- is derived from glycine.

In one embodiment, the composition according to the invention is characterized in that the hydrophobized anionic polymer is chosen from the hydrophobized anionic polymers of formulae II-VIII to II-XI, in which the radical -g-[B]-(k-[D])p is such that -g-[B]-k- is derived from aspartic acid.

In one embodiment, the composition according to the invention is characterized in that the hydrophobized anionic polymer is chosen from the hydrophobized anionic polymers of formulae II-VIII to II-XI, in which the radical -g-[B]-(k-[D])p is such that -g-[B]-k- is derived from glutamic acid.

In one embodiment, the composition according to the invention is characterized in that the hydrophobized anionic polymer is chosen from the hydrophobized anionic polymers of formulae II-VIII to II-XI, in which the radical -g-[B]-(k-[D])p is such that -g-[B]-k- is derived from succinic acid.

In one embodiment, the composition according to the invention is characterized in that the hydrophobized anionic polymer is chosen from the hydrophobized anionic polymers of formulae II-VIII to II-XI, in which the function g is an ether function.

In one embodiment, the composition according to the invention is characterized in that the hydrophobized anionic polymer is chosen from the hydrophobized anionic polymers of formulae II-VIII to II-XI, in which the function g is a carbamate function.

In one embodiment, the composition according to the invention is characterized in that the hydrophobized anionic polymer is chosen from the hydrophobized anionic polymers of formulae II-VIII to II-XI, in which the function g is an ester function.

In one embodiment, the composition according to the invention is characterized in that the hydrophobized anionic polymer is chosen from the hydrophobized anionic polymers of formulae II-VIII to II-XI, in which the function g is an amine function.

In one embodiment, the composition according to the invention is characterized in that the hydrophobized anionic polymer is chosen from the hydrophobized anionic polymers of formulae II-VIII to II-XI, in which the function g is a carbonate function.

In one embodiment, the composition according to the invention is characterized in that the hydrophobized anionic polymer is chosen from the hydrophobized anionic polymers of formulae II-VIII to II-XI, in which the function k is an amide function.

In one embodiment, the composition according to the invention is characterized in that the hydrophobized anionic polymer is chosen from the hydrophobized anionic polymers of formulae II-VIII to II-XI, in which the function k is a carbamate function.

In one embodiment, the composition according to the invention is characterized in that the hydrophobized anionic polymer is chosen from the hydrophobized anionic polymers of formulae II-VIII to II-XI, in which the function k is an ester function.

In one embodiment, the composition according to the invention is characterized in that the hydrophobized anionic polymer is chosen from the hydrophobized anionic polymers of formulae II-VIII to II-XI, in which the radical -k-[E]-(o)t is an at least divalent radical derived from an amino acid.

In one embodiment, the composition according to the invention is characterized in that the hydrophobized anionic polymer is chosen from the hydrophobized anionic polymers of formulae II-VIII to II-XI, in which the radical -k-[E]-(o)t is an at least divalent radical derived from an alpha amino acid.

In one embodiment, the composition according to the invention is characterized in that the hydrophobized anionic polymer is chosen from the hydrophobized anionic polymers of formulae II-VIII to II-XI, in which the radical -k-[E]-(o)t is an at least divalent radical derived from a natural alpha amino acid chosen from the group consisting of glycine, leucine, phenylalanine, lysine, isoleucine, alanine, valine, aspartic acid and glutamic acid, in their L, D or racemic forms.

In one embodiment, the composition according to the invention is characterized in that the hydrophobized anionic polymer is chosen from the hydrophobized anionic polymers of formulae II-VIII to II-XI, in which the radical -k-[E]-(o)t is an at least divalent radical derived from a mono- or polyethylene glycol.

In one embodiment, the composition according to the invention is characterized in that the hydrophobized anionic polymer is chosen from the hydrophobized anionic polymers of formulae II-VIII to II-XI, in which the radical -k-[E]-(o)t is an at least divalent radical derived from ethylene glycol.

In one embodiment, the composition according to the invention is characterized in that the hydrophobized anionic polymer is chosen from the hydrophobized anionic polymers of formulae II-VIII to II-XI, in which the radical -k-[E]-(o)t is an at least divalent radical derived from a polyethylene glycol chosen from the group consisting of diethylene glycol, triethylene glycol and tetraethylene glycol.

In one embodiment, the composition according to the invention is characterized in that the hydrophobized anionic polymer is chosen from the hydrophobized anionic polymers of formulae II-VIII to II-XI, in which the radical -k-[E]-(o)t is an at least divalent radical derived from a mono- or polyethylene glycol amine.

In one embodiment, the composition according to the invention is characterized in that the hydrophobized anionic polymer is chosen from the hydrophobized anionic polymers of formulae II-VIII to II-XI, in which the radical -k-[E]-(o)t is an at least divalent radical derived from a mono- or polyethylene glycol amine chosen from the group consisting of ethanolamine, diethylene glycol amine and triethylene glycol amine.

In one embodiment, the composition according to the invention is characterized in that the hydrophobized anionic polymer is chosen from the hydrophobized anionic polymers of formulae II-VIII to II-XI, in which the radical -k-[E]-(o)t is an at least divalent radical derived from a mono- or polyethylene glycol diamine.

In one embodiment, the composition according to the invention is characterized in that the hydrophobized anionic polymer is chosen from the hydrophobized anionic polymers of formulae II-VIII to II-XI, in which the radical -k-[E]-(o)t is an at least divalent radical derived from a mono- or polyethylene glycol diamine chosen from the group consisting of diethylene glycol diamine and triethylene glycol diamine.

In one embodiment, the composition according to the invention is characterized in that the hydrophobized anionic polymer is chosen from the hydrophobized anionic polymers of formulae II-VIII to II-XI, in which the radical -k-[E]-(o)t is an at least divalent radical derived from ethylenediamine.

In one embodiment, the composition according to the invention is characterized in that the hydrophobized anionic polymer is chosen from the hydrophobized anionic polymers of formulae II-VIII to II-XI, in which the function o is an ester function.

In one embodiment, the composition according to the invention is characterized in that the hydrophobized anionic polymer is chosen from the hydrophobized anionic polymers of formulae II-VIII to II-XI, in which the function o is an amide function.

In one embodiment, the composition according to the invention is characterized in that the hydrophobized anionic polymer is chosen from the hydrophobized anionic polymers of formulae II-VIII to II-XI, in which the function o is a carbamate function.

In one embodiment, the composition according to the invention is characterized in that the hydrophobized anionic polymer is chosen from the hydrophobized anionic polymers of formulae II-VIII to II-XI, in which the function o is a urea (carbamide) function.

In one embodiment, the composition according to the invention is characterized in that the hydrophobized anionic polymer is chosen from the hydrophobized anionic polymers of formulae II-VIII to II-XI, in which the -[Hy] group is an alkyl group derived from a branched or unbranched, unsaturated and/or saturated, hydrophobic alcohol comprising from 8 to 30 carbons.

In one embodiment, the composition according to the invention is characterized in that the hydrophobized anionic polymer is chosen from the hydrophobized anionic polymers of formulae II-VIII to II-XI, in which the -[Hy] group is an alkyl group derived from a hydrophobic alcohol chosen from the group consisting of octanol, decanol, dodecanol (lauryl alcohol), tetradecanol (myristyl alcohol), hexadecanol (cetyl alcohol), stearyl alcohol, cetearyl alcohol and oleyl alcohol.

In one embodiment, the composition according to the invention is characterized in that the hydrophobized anionic polymer is chosen from the hydrophobized anionic polymers of formulae II-VIII to II-XI, in which the -[Hy] group is a group derived from a sterol.

In one embodiment, the composition according to the invention is characterized in that the hydrophobized anionic polymer is chosen from the hydrophobized anionic polymers of formulae II-VIII to II-XI, in which the -[Hy] group is a group derived from a sterol, chosen from the group consisting of cholesterol and derivatives thereof.

In one embodiment, the composition according to the invention is characterized in that the hydrophobized anionic polymer is chosen from the hydrophobized anionic polymers of formulae II-VIII to II-XI, in which the -[Hy] group is a group derived from cholesterol.

In one embodiment, the composition according to the invention is characterized in that the hydrophobized anionic polymer is chosen from the hydrophobized anionic polymers of formulae II-VIII to II-XI, in which the -[Hy] group is a group derived from a tocopherol.

In one embodiment, the composition according to the invention is characterized in that the hydrophobized anionic polymer is chosen from the hydrophobized anionic polymers of formulae II-VIII to II-XI, in which the -[Hy] group is a group derived from a tocopherol derivative, chosen from the racemate, the L isomer or the D isomer of α-tocopherol.

In one embodiment, the composition according to the invention is characterized in that the hydrophobized anionic polymer is chosen from the hydrophobized anionic polymers of formulae II-VIII to II-XI, in which the -[Hy] group is a group derived from DL-α-tocopherol.

In one embodiment, the composition according to the invention is characterized in that the hydrophobized anionic polymer is chosen from the hydrophobized anionic polymers of formulae II-VIII to II-XI, in which the -[Hy] group is a group derived from menthol.

In one embodiment, the composition according to the invention is characterized in that the hydrophobized anionic polymer is chosen from the hydrophobized anionic polymers of formulae II-VIII to II-XI, in which the -[Hy] group is a group derived from menthol or derivatives thereof, chosen from the racemate, the L isomer or the D isomer of menthol.

In one embodiment, the composition according to the invention is characterized in that the hydrophobized anionic polymer is chosen from the hydrophobized anionic polymers of formulae II-VIII to II-XI, in which the -[Hy] group is an alkyl group derived from a hydrophobic acid.

In one embodiment, the composition according to the invention is characterized in that the hydrophobized anionic polymer is chosen from the hydrophobized anionic polymers of formulae II-VIII to II-XI, in which the -[Hy] group is an alkyl group derived from a linear hydrophobic acid, chosen from the group consisting of dodecanoic acid, tetradecanoic acid and hexadecanoic acid.

In one embodiment, the composition according to the invention is characterized in that the hydrophobized anionic polymer is chosen from the hydrophobized anionic polymers of formulae II-VIII to II-XI, in which the -[Hy] group is an alkyl group derived from a fatty acid.

In one embodiment, the composition according to the invention is characterized in that the hydrophobized anionic polymer is chosen from the hydrophobized anionic polymers of formulae II-VIII to II-XI, in which the -[Hy] group is an alkyl group derived from a fatty acid chosen from the group consisting of the acids consisting of a branched or unbranched, unsaturated or saturated, alkyl chain comprising from 8 to 30 carbons.

In one embodiment, the composition according to the invention is characterized in that the hydrophobized anionic polymer is chosen from the hydrophobized anionic polymers of formulae II-VIII to II-XI, in which the -[Hy] group is an alkyl group derived from a fatty acid chosen from the group consisting of linear fatty acids.

In one embodiment, the composition according to the invention is characterized in that the hydrophobized anionic polymer is chosen from the hydrophobized anionic polymers of formulae II-VIII to II-XI, in which the -[Hy] group is an alkyl group derived from a saturated linear fatty acid chosen from the group consisting of caprylic acid (octanoic acid), nonanoic acid, capric acid (decanoic acid), undecanoic acid, lauric acid (dodecanoic acid), myristic (tetradecanoic) acid, palmitic (hexadecanoic) acid, stearic (octadecanoic) acid, arachidic (eicosanoic) acid, behenic (docosanoic) acid, tricosanoic acid, lignoceric (tetracosanoic) acid, heptacosanoic add, octacosanoic acid and melissic (tricontanoic) acid.

In one embodiment, the composition according to the invention is characterized in that the hydrophobized anionic polymer is chosen from the hydrophobized anionic polymers of formulae II-VIII to II-XI, in which the -[Hy] group is an alkyl group derived from an unsaturated fatty acid.

In one embodiment, the composition according to the invention is characterized in that the hydrophobized anionic polymer is chosen from the hydrophobized anionic polymers of formulae II-VIII to II-XI, in which the -[Hy] group is an alkyl group derived from an unsaturated fatty add chosen from the group consisting of myristoleic ((Z)-tetradec-9-enoic) acid, palmitoleic ((Z)-hexadec-9-enoic) acid, oleic ((Z)-octadec-9-enoic) add, elaidic ((E)-octadec-9-enoic) acid, linoleic ((9Z,12Z)-octadeca-9,12-dienoic) acid, alpha-linoleic ((9Z,12Z,15Z)-octadeca-9,12,15-trienoic) acid, arachidonic ((5Z,8Z,11Z,14Z)-octadeca-5,8,11,14-tetraenoic) acid, eicosapentaenoic ((5Z,8Z,11Z,14Z,17Z)-eicosa-5,8,11,14,17-pentaenoic) acid, erucic (13-docoenoic) acid and docosahexaenoic ((4Z,7Z,10Z,13Z,16Z,19Z)-docosa-4,7,10,13,16,19-hexaenoic) acid.

In one embodiment, the composition according to the invention is characterized in that the hydrophobized anionic polymer is chosen from the hydrophobized anionic polymers of formulae II-VIII to II-XI, in which the -[Hy] group is an alkyl group derived from a bile acid and derivatives thereof.

In one embodiment, the composition according to the invention is characterized in that the hydrophobized anionic polymer is chosen from the hydrophobized anionic polymers of formulae II-VIII to II-XI, in which the -[Hy] group is an alkyl group derived from a bile acid and derivatives thereof, chosen from the group consisting of cholic acid, dehydrocholic acid, deoxycholic acid and chenodeoxycholic acid.

In one embodiment, the composition according to the invention is characterized in that the hydrophobized anionic polymer is chosen from the hydrophobized anionic polymers of formula II-XI in which —$R_5$ is either a —COOH group, or a radical -k-[D], in which -[D] is a radical -[E]-o-[Hy], k being an amide function, the radical -[E]- being derivas clameded from leucine, o being an ester function and -[Hy] being derived from cholesterol.

In one embodiment, the composition according to the invention is characterized in that the hydrophobized anionic polymer is chosen from the hydrophobized anionic polymers of formula II-X in which —R' is either an —OH group, or a radical -f-[A]-COOH, or a radical -g-[B]-k-[D], f being an ether function, the radical -[A]- being a radical —$CH_2$—, g being an ether function, the radical -[B]- being a radical —$CH_2$—, k being an amide function, -[D] being a radical -[E]-o-Hy, the radical -[E]-being derived from ethylenediamine, o being an amide function, p and t=1 and -[Hy] being derived from lauric acid.

The expression "basal insulin, the isoelectric point of which is between 5.8 and 8.5" is intended to mean an insulin which is insoluble at pH 7 and the duration of action of which is between 8 and 24 hours or more in the standard diabetes models.

These basal insulins, the isoelectric point of which is between 5.8 and 8.5, are recombinant insulins of which the primary structure has been modified mainly by introducing basic amino adds such as arginine or lysine. They are described, for example, in the following patents, patent applications or publications WO 2003/053339, WO 2004/096854, U.S. Pat. Nos. 5,656,722 and 6,100,376, the content of which is incorporated by way of reference.

In one embodiment, the basal insulin, the isoelectric point of which is between 5.8 and 8.5, is insulin glargine.

In one embodiment, the compositions according to the invention comprise between 40 and 500 IU/ml of basal insulin, the isoelectric point of which is between 5.8 and 8.5.

In one embodiment, the compositions according to the invention comprise between 100 and 350 IU/ml of basal insulin, the isoelectric point of which is between 5.8 and 8.5.

In one embodiment, the compositions according to the invention comprise 40 IU/ml of basal insulin, the isoelectric point of which is between 5.8 and 8.5.

In one embodiment, the compositions according to the invention comprise 100 IU/ml (i.e. approximately 3.6 mg/ml) of basal insulin, the isoelectric point of which is between 5.8 and 8.5.

In one embodiment, the compositions according to the invention comprise 200 IU/ml of basal insulin, the isoelectric point of which is between 5.8 and 8.5.

In one embodiment, the compositions according to the invention comprise 300 IU/ml of basal insulin, the isoelectric point of which is between 5.8 and 8.5.

In one embodiment, the compositions according to the invention comprise 400 IU/ml of basal insulin, the isoelectric point of which is between 5.8 and 8.5.

In one embodiment, the compositions according to the invention comprise 500 IU/ml of basal insulin, the isoelectric point of which is between 5.8 and 8.5.

In one embodiment, the weight ratio between the basal insulin, the isoelectric point of which is between 5.8 and 8.5, and the hydrophobized anionic polymer, that is to say the hydrophobized anionic polymer/basal insulin weight ratio, is between 0.2 and 30.

In one embodiment, the weight ratio is between 0.2 and 15.

In one embodiment, the weight ratio is between 0.2 and 10.

In one embodiment, the weight ratio is between 0.2 and 4.
In one embodiment, the weight ratio is between 0.2 and 3.
In one embodiment, the weight ratio is between 0.2 and 2.
In one embodiment, the weight ratio is between 0.2 and 1.
In one embodiment, the weight ratio is equal to 1.
In one embodiment, the weight ratio is between 0.5 and 3.
In one embodiment, the weight ratio is between 1 and 3.

In one embodiment, the weight ratio between the basal insulin, the isoelectric point of which is between 5.8 and 8.5, and the substituted dextran, i.e. the substituted dextran/basal insulin weight ratio, is between 0.2 and 5.

In one embodiment, the weight ratio between the basal insulin, the isoelectric point of which is between 5.8 and 8.5, and the substituted dextran, i.e. the substituted dextran/basal insulin weight ratio, is between 0.2 and 4.

In one embodiment, the weight ratio between the basal insulin, the isoelectric point of which is between 5.8 and 8.5, and the substituted dextran, i.e. the substituted dextran/basal insulin weight ratio, is between 0.2 and 3.

In one embodiment, the weight ratio between the basal insulin, the isoelectric point of which is between 5.8 and 8.5, and the substituted dextran, i.e. the substituted dextran/basal insulin weight ratio, is between 0.5 and 3.

In one embodiment, the weight ratio between the basal insulin, the isoelectric point of which is between 5.8 and 8.5, and the substituted dextran, i.e. the substituted dextran/basal insulin weight ratio, is between 0.8 and 3.

In one embodiment, the weight ratio between the basal insulin, the isoelectric point of which is between 5.8 and 8.5, and the substituted dextran, i.e. the substituted dextran/basal insulin weight ratio, is between 1 and 3.

In one embodiment, the concentration of hydrophobized anionic polymer is at most 100 mg/ml.

In one embodiment, the concentration of hydrophobized anionic polymer is at most 80 mg/ml.

In one embodiment, the concentration of hydrophobized anionic polymer is at most 60 mg/ml.

In one embodiment, the concentration of hydrophobized anionic polymer is at most 40 mg/ml.

In one embodiment, the concentration of hydrophobized anionic polymer is at most 20 mg/ml.

In one embodiment, the concentration of hydrophobized anionic polymer is at most 10 mg/ml.

In one embodiment, the concentration of hydrophobized anionic polymer is at most 5 mg/ml.

In one embodiment, the compositions according to the invention also comprise a prandial insulin. The prandial insulins are soluble at pH 7.

In one embodiment, the concentration of substituted dextran is between 1 and 100 mg/ml.

In one embodiment, the concentration of substituted dextran is between 1 and 80 mg/ml.

In one embodiment, the concentration of substituted dextran is between 1 and 60 mg/ml.

In one embodiment, the concentration of substituted dextran is between 1 and 50 mg/ml.

In one embodiment, the concentration of substituted dextran is between 1 and 30 mg/ml.

In one embodiment, the concentration of substituted dextran is between 1 and 20 mg/ml.

In one embodiment, the concentration of substituted dextran is between 1 and 10 mg/ml.

In one embodiment, the concentration of polysaccharide is between 5 and 20 mg/ml.

In one embodiment, the concentration of polysaccharide is between 5 and 10 mg/ml.

In one embodiment, the compositions according to the invention also comprise a prandial insulin. The prandial insulins are soluble at pH 7.

The term "prandial insulin" is intended to mean an insulin termed fast-acting or "regular".

The prandial insulins termed fast-acting insulins are insulins which must respond to the needs caused by the ingestion of proteins and carbohydrates during a meal; they must act in less than 30 minutes.

In one embodiment, the prandial insulin termed "regular" is human insulin.

In one embodiment, the insulin is a recombinant human insulin as described in the European Pharmacopeia and the US Pharmacopeia.

In one embodiment, the prandial insulins termed "regular" are chosen from the group comprising Humulin® (human insulin) and Novolin® (human insulin).

Human insulin is, for example, sold under the brand names Humulin® (Eli Lilly) and Novolin® (Novo Nordisk).

The prandial insulins termed fast-acting are insulins which are obtained by recombination and the primary structure of which has been modified so as to reduce their action time.

In one embodiment, the prandial insulins termed fast-acting are chosen from the group comprising insulin lispro (Humalog®), insulin glulisine (Apidra®) and insulin aspart (NovoLog®).

In one embodiment, the prandial insulin is insulin lispro.
In one embodiment, the prandial insulin is insulin glulisine.
In one embodiment, the prandial insulin is insulin aspart.

In one embodiment, the compositions according to the invention comprise in total between 40 and 800 IU/ml of insulin with a combination of prandial insulin and basal insulin, the isoelectric point of which is between 5.8 and 8.5.

In one embodiment, the compositions according to the invention comprise in total between 40 and 500 IU/ml of insulin with a combination of prandial insulin and basal insulin, the isoelectric point of which is between 5.8 and 8.5.

In one embodiment, the compositions according to the invention comprise in total 800 IU/ml of insulin with a combination of prandial insulin and basal insulin, the isoelectric point of which is between 5.8 and 8.5.

In one embodiment, the compositions according to the invention comprise in total 700 IU/ml of insulin with a combination of prandial insulin and basal insulin, the isoelectric point of which is between 5.8 and 8.5.

In one embodiment, the compositions according to the invention comprise in total 600 IU/ml of insulin with a combination of prandial insulin and basal insulin, the isoelectric point of which is between 5.8 and 8.5.

In one embodiment, the compositions according to the invention comprise in total 500 IU/ml of insulin with a combination of prandial insulin and basal insulin, the isoelectric point of which is between 5.8 and 8.5.

In one embodiment, the compositions according to the invention comprise in total 400 IU/ml of insulin with a combination of prandial insulin and basal insulin, the isoelectric point of which is between 5.8 and 8.5.

In one embodiment, the compositions according to the invention comprise in total 300 IU/ml of insulin with a combination of prandial insulin and basal insulin, the isoelectric point of which is between 5.8 and 8.5.

In one embodiment, the compositions according to the invention comprise in total 200 IU/ml of insulin with a combination of prandial insulin and basal insulin, the isoelectric point of which is between 5.8 and 8.5.

In one embodiment, the compositions according to the invention comprise in total 100 IU/ml of insulin with a combination of prandial insulin and basal insulin, the isoelectric point of which is between 5.8 and 8.5.

In one embodiment, the compositions according to the invention comprise in total 40 IU/ml of insulin with a combination of prandial insulin and basal insulin, the isoelectric point of which is between 5.8 and 8.5.

The proportions between the basal insulin, the isoelectric point of which is between 5.8 and 8.5, and the prandial insulin are, for example, as a percentage, 25/75, 30/70, 40/60, 50/50, 60/40, 70/30, 75/25, 80/20, 90/10 for formulations as described above comprising from 40 to 800 IU/ml. However, any other proportion can be used.

For a formulation at 100 IU/ml of total insulin, the proportions between the basal insulin, the isoelectric point of which is between 5.8 and 8.5, and the prandial insulin are, for example, in IU/ml, 25/75, 30/70, 40/60, 50/50, 60/40, 70/30, 80/20 or 90/10. However, any other proportion can be used.

In one embodiment, the compositions according to the invention also comprise a gut hormone.

The term "gut hormones" is intended to mean the hormones chosen from the group consisting of GLP-1 (Glucagon like peptide-1) and GIP (Glucose-dependent insulinotropic peptide), oxyntomodulin (a proglucagon derivative), peptide YY, amylin, cholecystokinin, pancreatic polypeptide (PP), ghrelin and enterostatin, analogs or derivatives thereof and/or pharmaceutically acceptable salts thereof.

In one embodiment, the gut hormones are GLP-1 analogs or derivatives chosen from the group consisting of exenatide or Byetta®, developed by ELI LILLY & CO and AMYLIN PHARMACEUTICALS, liraglutide or Victoza® developed by NOVO NORDISK, or lixisenatide or Lyxumia® developed by SANOFI-AVENTIS, analogs or derivatives thereof and pharmaceutically acceptable salts thereof.

In one embodiment, the gut hormone is exenatide or Byetta®, analogs or derivatives thereof and pharmaceutically acceptable salts thereof.

In one embodiment, the gut hormone is liraglutide or Victoza®, analogs or derivatives thereof and pharmaceutically acceptable salts thereof.

In one embodiment, the gut hormone is lixisenatide or Lyxumia®, analogs or derivatives thereof and pharmaceutically acceptable salts thereof.

The term "analog", when it is used with reference to a peptide or a protein, is intended to mean a peptide or protein in which one or more constituent amino add residues have been substituted with other amino acid residues and/or in which one or more constituent amino acid residues have been deleted and/or in which one or more constituent amino acid residues have been added. The percentage homology accepted for the present definition of an analog is 50%.

The term "derivative", when it is used with reference to a peptide or a protein, is intended to mean a peptide or a protein or an analog chemically modified with a substituent which is not present in the reference peptide, protein or analog, i.e. a peptide or a protein which has been modified by creating covalent bonds, so as to introduce substituents.

In one embodiment, the substituent is chosen from the group consisting of fatty chains.

In one embodiment, the concentration of GLP-1 or of GLP-1 analog or derivative is included in a range of from 0.01 to 10 mg/ml.

In one embodiment, the concentration of exenatide, analogs or derivatives thereof and pharmaceutically acceptable salts thereof is included in a range of from 0.05 to 0.5 mg/ml.

In one embodiment, the concentration of liraglutide, analogs or derivatives thereof and pharmaceutically acceptable salts thereof is included in a range of from 1 to 10 mg/ml.

In one embodiment, the concentration of lixisenatide, analogs or derivatives thereof and pharmaceutically acceptable salts thereof is included in a range of from 0.01 to 1 mg/ml.

In one embodiment, the compositions according to the invention are prepared by mixing commercial solutions of basal insulin, the isoelectric point of which is between 5.8 and 8.5, and commercial solutions of GLP-1 or of GLP-1 analog or derivative in volume ratios included in a range of from 10/90 to 90/10.

In one embodiment, the composition according to the invention comprises a daily dose of basal insulin and a daily dose of GLP-1 or of GLP-1 analog or derivative.

In one embodiment, the compositions according to the invention comprise 500 IU/ml of basal insulin, the isoelectric point of which is between 5.8 and 8.5, and from 0.05 to 0.5 mg/ml of exenatide.

In one embodiment, the compositions according to the invention comprise 500 IU/ml of basal insulin, the isoelectric point of which is between 5.8 and 8.5, and from 1 to 10 mg/ml of liraglutide.

In one embodiment, the compositions according to the invention comprise 500 IU/ml of basal insulin, the isoelectric point of which is between 5.8 and 8.5, and from 0.05 to 0.5 mg/ml of lixisenatide.

In one embodiment, the compositions according to the invention comprise 100 IU/ml of basal insulin, the isoelectric point of which is between 5.8 and 8.5, and from 0.05 to 0.5 mg/ml of exenatide.

In one embodiment, the compositions according to the invention comprise 100 IU/ml of basal insulin, the isoelectric point of which is between 5.8 and 8.5, and from 1 to 10 mg/ml of liraglutide.

In one embodiment, the compositions according to the invention comprise 100 IU/ml of basal insulin, the isoelectric point of which is between 5.8 and 8.5, and from 0.05 to 0.5 mg/ml of lixisenatide.

In one embodiment, the compositions according to the invention comprise 40 IU/ml of basal insulin, the isoelectric point of which is between 5.8 and 8.5, and from 0.05 to 0.5 mg/ml of exenatide.

In one embodiment, the compositions according to the invention comprise 40 IU/ml of basal insulin, the isoelectric point of which is between 5.8 and 8.5, and from 1 to 10 mg/ml of liraglutide.

In one embodiment, the compositions according to the invention comprise 40 IU/ml of basal insulin, the isoelectric point of which is between 5.8 and 8.5, and from 0.05 to 0.5 mg/ml of lixisenatide.

In one embodiment, the compositions according to the invention comprise 200 IU/ml of basal insulin, the isoelectric point of which is between 5.8 and 8.5, and from 0.05 to 0.5 mg/ml of exenatide.

In one embodiment, the compositions according to the invention comprise 200 IU/ml of basal insulin, the isoelectric point of which is between 5.8 and 8.5, and from 1 to 10 mg/ml of liraglutide.

In one embodiment, the compositions according to the invention comprise 200 IU/ml of basal insulin, the isoelectric point of which is between 5.8 and 8.5, and from 0.05 to 0.5 mg/ml of lixisenatide.

In one embodiment, the compositions according to the invention also comprise zinc salts at a concentration of between 0 and 5000 µM.

In one embodiment, the compositions according to the invention also comprise zinc salts at a concentration of between 50 and 4000 µM.

In one embodiment, the compositions according to the invention also comprise zinc salts at a concentration of between 0 and 4000 µM.

In one embodiment, the compositions according to the invention also comprise zinc salts at a concentration of between 0 and 3000 µM.

In one embodiment, the compositions according to the invention also comprise zinc salts at a concentration of between 200 and 3000 µM.

In one embodiment, the compositions according to the invention also comprise zinc salts at a concentration of between 0 and 2000 µM.

In one embodiment, the compositions according to the invention also comprise zinc salts at a concentration of between 0 and 1000 µM.

In one embodiment, the compositions according to the invention also comprise zinc salts at a concentration of between 50 and 600 µM.

In one embodiment, the compositions according to the invention also comprise zinc salts at a concentration of between 20 and 600 µM.

In one embodiment, the compositions according to the invention also comprise zinc salts at a concentration of between 50 and 500 µM.

In one embodiment, the compositions according to the invention also comprise zinc salts at a concentration of between 100 and 500 µM.

In one embodiment, the compositions according to the invention also comprise zinc salts at a concentration of between 200 and 500 µM.

In one embodiment, the compositions according to the invention also comprise buffers.

In one embodiment, the compositions according to the invention comprise buffers at concentrations of between 0 and 100 mM.

In one embodiment, the compositions according to the invention comprise buffers at concentrations of between 15 and 50 mM.

In one embodiment, the compositions according to the invention comprise buffers chosen from the group comprising Tris, citrates and phosphates, at concentrations of between 0 and 100 mM, preferably between 0 and 50 mM or between 15 and 50 mM.

In one embodiment, the compositions according to the invention comprise a buffer chosen from the group consisting of a phosphate buffer, Tris (trishydroxymethylaminomethane) or sodium citrate.

In one embodiment, the buffer is sodium phosphate.

In one embodiment, the buffer is Tris (trishydroxymethylaminomethane).

In one embodiment, the buffer is sodium citrate.

In one embodiment, the compositions according to the invention also comprise preserving agents.

In one embodiment, the preserving agents are chosen from the group consisting of m-cresol and phenol, alone or as a mixture.

In one embodiment, the concentration of preserving agents is between 10 and 50 mM.

In one embodiment, the concentration of preserving agents is between 10 and 40 mM.

In one embodiment, the compositions according to the invention also comprise a surfactant.

In one embodiment, the surfactant is chosen from the group consisting of propylene glycol and polysorbate.

The compositions according to the invention may also comprise additives, such as tonicity agents.

In one embodiment, the tonicity agents are chosen from the group consisting of glycerol, sodium chloride, mannitol and glycine.

The compositions according to the invention may also comprise any excipients in accordance with the Pharmacopeias and which are compatible with the insulins used at the working concentrations.

The invention also relates to a pharmaceutical formulation according to the invention, which is obtained by drying and/or lyophilization.

In the case of local and systemic release, the envisioned modes of administration are intravenous, subcutaneous, intradermal or intramuscular.

Transdermal, oral, nasal, vaginal, ocular, buccal and pulmonary administration routes are also envisioned.

The invention also relates to single-dose formulations at a pH of between 6.6 and 7.8 comprising a basal insulin, the isoelectric point of which is between 5.8 and 8.5.

The invention also relates to single-dose formulations at a pH of between 6.6 and 7.8 comprising a basal insulin, the isoelectric point of which is between 5.8 and 8.5, and a prandial insulin.

The invention also relates to single-dose formulations at a pH of between 6.6 and 7.8 comprising a basal insulin, the isoelectric point of which is between 5.8 and 8.5, and a gut hormone, as previously defined.

The invention also relates to single-dose formulations at a pH of between 6.6 and 7.8 comprising a basal insulin, the isoelectric point of which is between 5.8 and 8.5, a prandial insulin and a gut hormone, as previously defined.

The invention also relates to single-dose formulations at a pH of between 7 and 7.8 comprising a basal insulin, the isoelectric point of which is between 5.8 and 8.5.

The invention also relates to single-dose formulations at a pH of between 7 and 7.8 comprising a basal insulin, the isoelectric point of which is between 5.8 and 8.5, and a prandial insulin.

The invention also relates to single-dose formulations at a pH of between 7 and 7.8 comprising a basal insulin, the isoelectric point of which is between 5.8 and 8.5, and a gut hormone, as previously defined.

The invention also relates to single-dose formulations at a pH of between 7 and 7.8 comprising a basal insulin, the isoelectric point of which is between 5.8 and 8.5, a prandial insulin and a gut hormone, as previously defined.

In one embodiment, the single-dose formulations also comprise a hydrophobized anionic polymer, as previously defined.

In one embodiment, the formulations are in the form of an injectable solution.

In one embodiment, the basal insulin, the isoelectric point of which is between 5.8 and 8.5, is insulin glargine.

In one embodiment, the prandial insulin is human insulin.

In one embodiment, the prandial insulin is chosen from the group comprising Humulin® (human insulin) and Novolin® (human insulin).

In one embodiment, the insulin is a recombinant human insulin as described in the European Pharmacopeia and the US Pharmacopeia.

In one embodiment, the prandial insulin is chosen from the group comprising insulin lispro (Humalog®), insulin glulisine (Apidra®) and insulin aspart (NovoLog®).

In one embodiment, the prandial insulin is insulin lispro.

In one embodiment, the prandial insulin is insulin glulisine.

In one embodiment, the prandial insulin is insulin aspart.

In one embodiment, the GLP-1 or GLP-1 analog or derivative is chosen from the group comprising exenatide (Byetta®), liraglutide (Victoza®) and lixisenatide (Lyxumia®), or a derivative thereof.

In one embodiment, the gut hormone is exenatide.

In one embodiment, the gut hormone is liraglutide.

In one embodiment, the gut hormone is lixisenatide.

The solubilization, at a pH of between 6.6 and 7.8, of the basal insulins, the isoelectric point of which is between 5.8 and 8.5, by the polysaccharides of formula I, II, III or IV, can be simply observed and controlled, with the naked eye, through a change in appearance of the solution.

The solubilization, at a pH of between 7 and 7.8, of the basal insulins, the isoelectric point of which is between 5.8 and 8.5, by the polysaccharides of formula I, II, III or IV, can be simply observed and controlled, with the naked eye, through a change in appearance of the solution.

Moreover and just as importantly, the applicant has been able to verify that a basal insulin, the isoelectric point of which is between 5.8 and 8.5, solubilized in the presence of a polysaccharide of formula I, II, III or IV, has lost nothing of its slow insulin action.

The preparation of a composition according to the invention has the advantage of being able to be carried out by simply mixing an aqueous solution of basal insulin, the isoelectric point of which is between 5.8 and 8.5, a solution of prandial insulin, and a polysaccharide of formula I, II, III or IV, in aqueous solution or in lyophilized form. If necessary, the pH of the preparation is adjusted to pH 7.

The preparation of a composition according to the invention has the advantage of being able to be carried out by simply mixing an aqueous solution of basal insulin, the isoelectric point of which is between 5.8 and 8.5, a polysaccharide of formula I, II, III or IV in aqueous solution or in lyophilized form, and a prandial insulin in aqueous solution or in lyophilized form.

The solubilization, at a pH of between 6.6 and 7.8, of the basal insulins, the isoelectric point of which is between 5.8 and 8.5, by the hydrophobized anionic polymers of formulae II-I and II-IV to II-XII, can be simply observed and controlled, with the naked eye, through a change in appearance of the solution.

The solubilization, at a pH of between 7 and 7.8, of the basal insulins, the isoelectric point of which is between 5.8 and 8.5, by the hydrophobized anionic polymers of formulae II-I and II-IV to II-XII, can be simply observed and controlled, with the naked eye, through a change in appearance of the solution.

Moreover and just as importantly, the applicant has been able to verify that a basal insulin, the isoelectric point of which is between 5.8 and 8.5, solubilized at a pH of between 6.6 and 7.8, in the presence of a hydrophobized anionic polymer of formulae II-I and II-IV to II-XII, retains a slow insulin action, whether alone or in combination with a prandial insulin or a gut hormone.

The applicant has also been able to verify that a prandial insulin mixed at a pH of between 6.6 and 7.8 in the presence of a hydrophobized anionic polymer of formulae II-I and II-IV to II-XII, and of a basal insulin, the isoelectric point of which is between 5.8 and 8.5, retains a fast insulin action.

The preparation of a composition according to the invention has the advantage of being able to be carried out by simply mixing an aqueous solution of basal insulin, the isoelectric point of which is between 5.8 and 8.5, and a hydrophobized anionic polymer of formulae II-I and II-IV to II-XII, in aqueous solution or in lyophilized form. If necessary, the pH of the preparation is adjusted to pH 7.

The preparation of a composition according to the invention has the advantage of being able to be carried out by simply mixing an aqueous solution of basal insulin, the isoelectric point of which is between 5.8 and 8.5, a solution of prandial insulin, and a hydrophobized anionic polymer of formulae II-I and II-IV to II-XII, in aqueous solution or in lyophilized form. If necessary, the pH of the preparation is adjusted to pH 7.

The preparation of a composition according to the invention has the advantage of being able to be carried out by simply mixing an aqueous solution of basal insulin, the isoelectric point of which is between 5.8 and 8.5, a solution of GLP-1 or a GLP-1 analog or derivative, and a hydrophobized anionic polymer of formulae II-I and II-IV to II-XII, in aqueous solution or in lyophilized form. If necessary, the pH of the preparation is adjusted to pH 7.

The preparation of a composition according to the invention has the advantage of being able to be carried out by simply mixing an aqueous solution of basal insulin, the isoelectric point of which is between 5.8 and 8.5, a solution of prandial insulin, a solution of GLP-1 or a GLP-1 analog or derivative, and a hydrophobized anionic polymer of formulae II-I and II-IV to II-XII, in aqueous solution or in lyophilized form. If necessary, the pH of the preparation is adjusted to pH 7.

In one embodiment, the mixture of basal insulin and hydrophobized anionic polymer is in aqueous or in lyophilized form.

In one embodiment, the mixture of basal insulin and polysaccharide is concentrated by ultrafiltration before mixing with the prandial insulin in aqueous solution or in lyophilized form.

If necessary, the composition of the mixture is adjusted in terms of excipients such as glycerol, m-cresol, zinc chloride and tween by addition of concentrated solutions of these excipients to the mixture. If necessary, the pH of the preparation is adjusted to 7.

DESCRIPTION OF THE FIGURES

FIG. 1: Curves of mean+standard deviation of the mean for the sequential administrations of Apidra® and Lantus® (□) in comparison with a Polysaccharide 4/Lantus®/Apidra® (75/25) composition according to the invention (●).

FIG. 2: Individual Apidra® Lantus® curves (tested on 6 pigs).

FIG. 3: Individual Polysaccharide 4/Apidra®/Lantus® curves (tested on 6 pigs).

FIG. 4: Curves of mean+standard deviation of the mean for the sequential administrations of Humalog® and Lantus® (□) in comparison with the administration of a Polysaccharide 4/Humalog®/Lantus® composition according to the invention (●).

FIG. 5: Individual Humalog® Lantus® curves (tested on 6 pigs).

FIG. 6: Individual Polysaccharide 4/Humalog®/Lantus® curves (tested on 5 pigs).

FIG. 7: Curves of mean+standard deviation of the mean for the sequential administrations of Humalog® (100 IU/ml, 0.13 IU/kg) and Lantus® (100 IU/ml, 0.4 IU/kg) (···✱···) in comparison with a composition according to the invention described in example B28 (0.53 IU/kg) (—✱—).

FIG. 8: Curves of mean+standard deviation of the mean for the sequential administrations of Humalog® (100 IU/ml, 0.13 IU/kg) and Lantus® (100 IU/ml, 0.4 IU/kg) (···✱···) in comparison with a composition according to the invention described in example B27 (0.47 IU/kg) (—✱—).

FIG. 9: Curves of mean+standard deviation of the mean for the sequential administrations of Humalog® (100 IU/ml, 0.13 IU/kg) and Lantus® (100 IU/ml, 0.4 IU/kg) (···✱···) in comparison with a composition according to the invention described in example B29 (0.53 IU/kg) (—✱—).

FIG. 10: Curves of mean+standard deviation of the mean for the sequential administrations of Humalog® (100 IU/ml, 0.13 IU/kg) and Lantus® (100 IU/ml, 0.4 IU/kg) (···✱···) in comparison with a composition according to the invention described in example B31 (0.48 IU/kg) (—✱—).

FIG. 11: Curves of mean+standard deviation of the mean for the sequential administrations of Humalog® (100 IU/ml, 0.24 IU/kg) and Lantus® (100 IU/ml, 0.4 IU/kg) (···✱···) in comparison with a composition according to the invention described in example B30 (0.64 IU/kg) (—✱—).

FIG. 12: Curves of mean+standard deviation of the mean for the sequential administrations of Humalog® (100 IU/ml, 0.13 IU/kg) and Lantus® (100 IU/ml, 0.4 IU/kg (···✱···) in comparison with a composition according to the invention described in example B32 (0.53 IU/kg) (—✱—).

EXAMPLES

Figure 1:
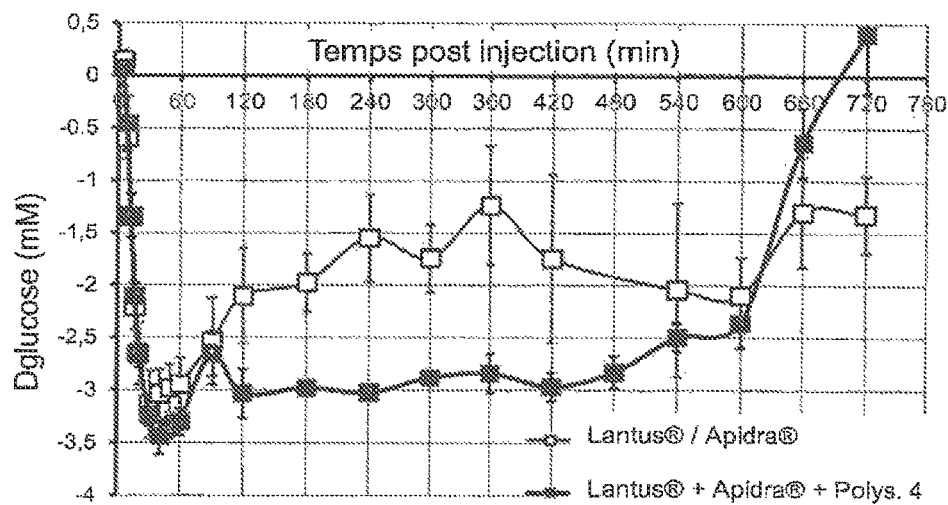
FIGS. 1 to 6 show the results obtained in the form of glucose pharmacodynamics curves. The γ-axis represents the D-glucose (expressed in mM) as a function of the time post-injection (expressed in minutes).

I. Dextrans Substituted with Radicals Bearing Carboxylate Charges and Hydrophobic Radicals, and Corresponding Formulations Part A Polysaccharides Table 1 below presents, without implied limitation, examples of polysaccharides that can be used in the compositions according to the invention.

TABLE 1

| POLYSACCHARIDES | SUBSTITUENTS -f-A-COONa -g-B-k-D | USUAL NAME |
|---|---|---|
| Polysaccharide 1 q: 38 n: 0.9 m: 0.2 | 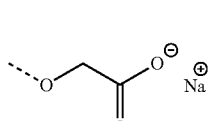 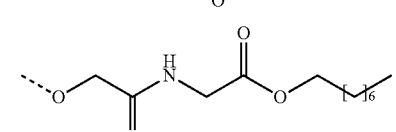 | Sodium dextranmethyl-carboxylate modified with octyl glycinate |

TABLE 1-continued

| | | |
|---|---|---|
| Polysaccharide 2<br>q: 19<br>n: 1.0<br>m: 0.1<br>Polysaccharide 16<br>q: 19<br>n: 1.05<br>m: 0.05<br>Polysaccharide 17<br>q: 38<br>n: 0.37<br>m: 0.05 | 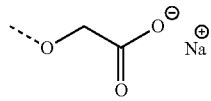<br>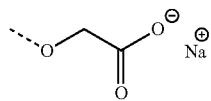 | Sodium dextranmethyl-carboxylate modified with cetyl glycinate |
| Polysaccharide 3<br>q: 38<br>n: 1.0<br>m: 0.1<br>Polysaccharide 4<br>q: 19<br>n: 1.0<br>m: 0.2 | 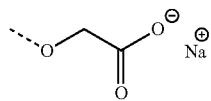<br>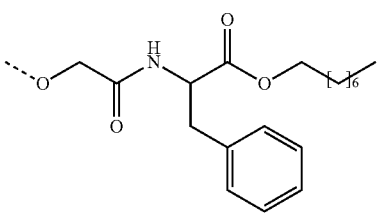 | Sodium dextranmethyl-carboxylate modified with octyl phenylalaninate |
| Polysaccharide 5<br>q: 38<br>n: 1.0<br>m: 0.1 | 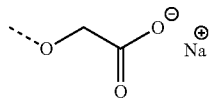<br>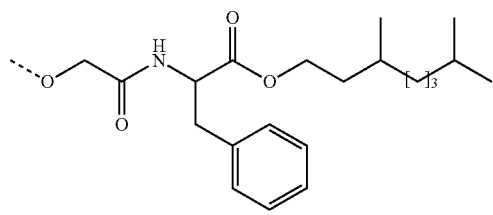 | Sodium dextranmethyl-carboxylate modified with 3,7-dimethyl-1-octyl phenylalaninate |
| Polysaccharide 6<br>q: 38<br>n: 1.05<br>m: 0.05 | 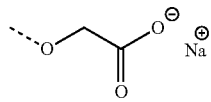<br>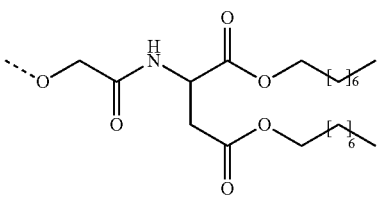 | Sodium dextranmethyl-carboxylate modified with dioctyl aspartate |
| Polysaccharide 7<br>q: 38<br>n: 1.05<br>m: 0.05<br>Polysaccharide 29<br>q: 4<br>n: 1.05<br>m: 0.05 | 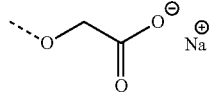<br>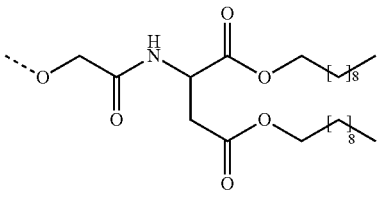 | Sodium dextranmethyl-carboxylate modified with didecyl aspartate |

TABLE 1-continued

| | | |
|---|---|---|
| Polysaccharide 8<br>q: 19<br>n: 1.05<br>m: 0.05 | 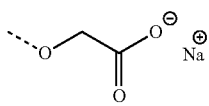 | Sodium dextranmethyl-carboxylate modified with dilauryl aspartate |
| Polysaccharide 27<br>q: 4<br>n: 1.41<br>m: 0.16 | | |
| Polysaccharide 28<br>q: 4<br>n: 1.50<br>m: 0.07 | 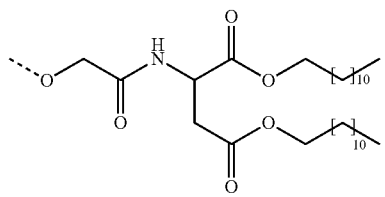 | |
| Polysaccharide 9<br>q: 38<br>n: 1.0<br>m: 0.1 | 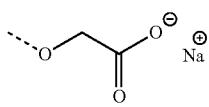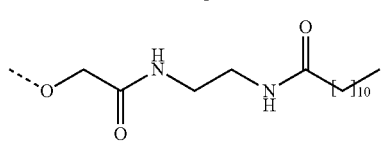 | Sodium dextranmethyl-carboxylate modified with N-(2-aminoethyl)-dodecanamide |
| Polysaccharide 10<br>q: 38<br>n: 1.3<br>m: 0.1 | 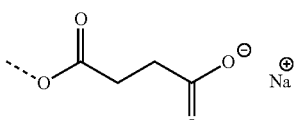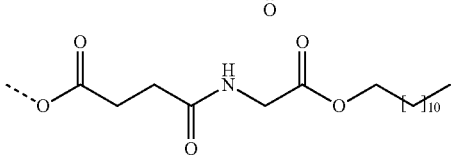 | Sodium dextransuccinate modified with lauryl glycinate |
| Polysaccharide 11<br>q: 38<br>n: 1.3<br>m: 0.1 | 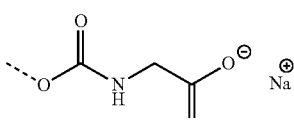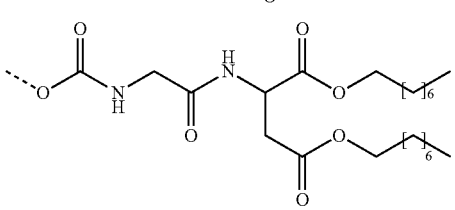 | N-(sodium methyl-carboxylate) dextran carbamate modified with dioctyl aspartate |
| Polysaccharide 12<br>q: 4<br>n: 0.96<br>m: 0.07 | 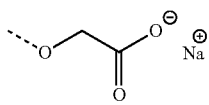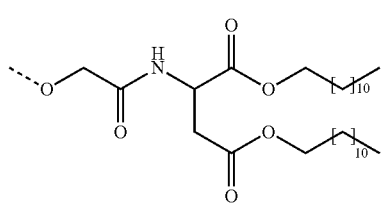 | Sodium dextranmethyl-carboxylate modified with dilauryl aspartate |

TABLE 1-continued

| | | |
|---|---|---|
| Polysaccharide 13<br>q: 38<br>n: 1.0<br>m: 0.1 | 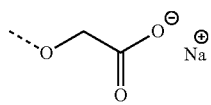 | Sodium dextranmethyl-carboxylate modified with 2-(2-amino-ethoxy)ethyl dodecanoate |
| Polysaccharide 14<br>q: 38<br>n: 1.0<br>m: 0.1 | 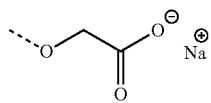 | Sodium dextranmethyl-carboxylate modified with 2-(2-{2-[dodecanoyl-amino]ethoxy}-ethoxy)ethylamine |
| Polysaccharide 15<br>q: 38<br>n: 1.05<br>m: 0.05 | 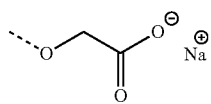 | Sodium dextranmethyl-carboxylate modified with 2-(2-{2-[hexadecanoyl-amino]ethoxy}-ethoxy)ethylamine |
| Polysaccharide 18<br>q: 19<br>n: 1.61<br>m: 0.04<br>Polysaccharide 19<br>q: 19<br>n: 1.06<br>m: 0.04<br>Polysaccharide 20<br>q: 19<br>n: 0.66<br>m: 0.04<br>Polysaccharide 21<br>q: 19<br>n: 0.46<br>m: 0.04<br>Polysaccharide 22<br>q: 4<br>n: 1.61<br>m: 0.04<br>Polysaccharide 26<br>q: 38<br>n: 0.99<br>m: 0.05 | 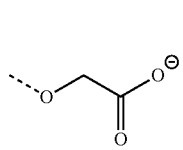 | Sodium dextranmethyl-carboxylate modified with cholesteryl leucinate |
| Polysaccharide 23<br>q: 19<br>n: 1.61<br>m: 0.04 | 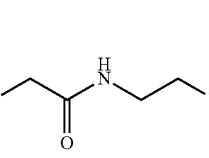 | Sodium dextranmethyl-carboxylate modified with cholesteryl 1-ethylenediamine-carboxylate |

| POLYSACCHARIDES | SUBSTITUENTS -f-A-COONa -[E]-o-[F] | USUAL NAME |
|---|---|---|
| Polysaccharide 24<br>q: 19<br>n: 1.96<br>m: 0.04 | 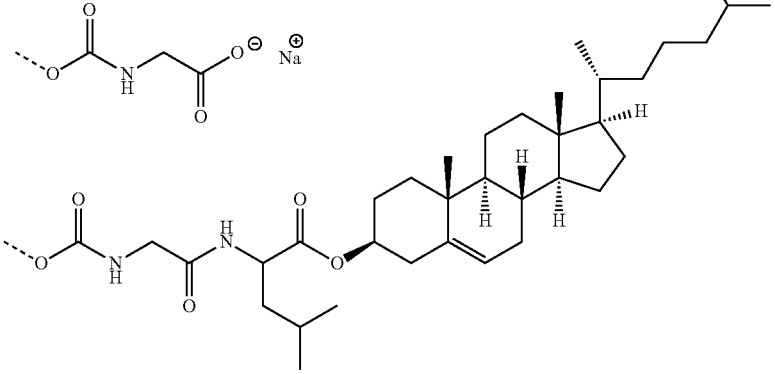 | N-(sodium methyl-carboxylate) dextran carbamate modified with cholesteryl leucinate |
| Polysaccharide 25<br>q: 19<br>n: 1.65 | 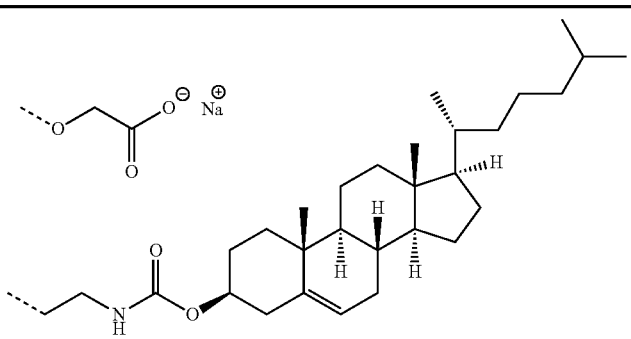 | Sodium dextranmethyl-carboxylate modified with cholesteryl 1-ethylenediamine-carboxylate grafted by reductive amination onto the reducing chain end |

Example A1: Preparation of Polysaccharide 1

16 g (i.e. 296 mmol of hydroxyls) of dextran having a weight-average molar mass of approximately 10 kg/mol (q=38, Pharmacosmos) are dissolved in water at 420 g/l. 30 ml of 10 N NaOH (296 mmol) are added to this solution. The mixture is brought to 35° C., then 46 g (396 mmol) of sodium chloroacetate are added. The temperature of the reaction medium is brought to 60° C. at 0.5° C./min and then maintained at 60° C. for 100 minutes. The reaction medium is diluted with 200 ml of water, neutralized with acetic acid and purified by ultrafiltration on a 5 kDa PES membrane against 6 volumes of water. The final solution is assayed by dry extract to determine the polysaccharide concentration, and then assayed by acid/base titration in 50/50 (V/V) water/acetone to determine the average number of methyl-carboxylate units per glucoside unit.

According to the dry extract: [polysaccharide]=31.5 mg/g

According to the acid/base titration: the average number of methylcarboxylate units per glucoside unit is 1.1.

The sodium dextranmethylcarboxylate solution is passed over a Purolite resin (anionic) to obtain dextranmethylcar-boxylic acid, which is then lyophilized for 18 hours.

Octyl glycinate, para-toluenesulfonic acid salt, is obtained according to the process described in U.S. Pat. No. 4,826, 818.

10 g of dextranmethylcarboxylic add (44.86 mmol methylcarboxylic acid) are dissolved in DMF at 60 g/l and then cooled to 0° C. 3.23 g of octyl glycinate, para-toluenesulfonic acid salt (8.97 mmol), are suspended in DMF at 100 g/l. 0.91 g (8.97 mmol) of triethylamine is then added to this suspension. Once the polysaccharide solution is at 0° C., a solution of NMM (5.24 g, 51.8 mmol) in DMF (530 g/l) and 5.62 g (51.8 mmol) of EtOCOCl are then added. After reaction for 10 min, the octyl glycinate suspension is added. The medium is then maintained at 10° C. for 45 minutes. The medium is then heated to 30° C. A solution of imidazole (10.38 g in 17 ml of water) and 52 ml of water are added to the reaction medium. The polysaccharide solution is ultra-filtered on a 10 kDa PES membrane against 15 volumes of 0.9% NaCl solution and 5 volumes of water. The concentration of the polysaccharide solution is determined by dry extract. A fraction of solution is lyophilized and analyzed by 1H NMR in D2O to determine the degree of substitution of the methylcarboxylates with octyl glycinate per glucoside unit.

According to the dry extract: [Polysaccharide 1]=36.4 mg/g

According to the acid/base titration: n=0.9

According to the $^1$H NMR: m=0.2.

Example A2: Preparation of Polysaccharide 2

Cetyl glycinate, para-toluenesulfonic acid salt, is obtained according to the process described in U.S. Pat. No. 4,826, 818.

Via a process similar to that described in example A1, a sodium dextranmethylcarboxylate, synthesized according to the process described in example A1 using a dextran with a weight-average molecular weight of approximately 5 kg/mol (q=19, Pharmacosmos), modified with cetyl glycinate, is obtained.

According to the dry extract: [Polysaccharide 2]=15.1 mg/g
According to the acid/base titration: n=1.05
According to the $^1$H NMR: m=0.05.

Example A3: Preparation of Polysaccharide 3

Octyl phenylalaninate, para-toluenesulfonic acid salt, is obtained according to the process described in U.S. Pat. No. 4,826,818.

Via a process similar to that described in example A1, a sodium dextranmethylcarboxylate, synthesized according to the process described in example A1 using a dextran with a weight-average molecular weight of approximately 10 kg/mol (q=38, Pharmacosmos), modified with octyl phenylalaninate, is obtained.

According to the dry extract: [Polysaccharide 3]=27.4 mg/g
According to the acid/base titration: n=1.0
According to the $^1$H NMR: m=0.1.

Example A4: Preparation of Polysaccharide 4

Via a process similar to that described in example A3, a sodium dextranmethylcarboxylate, synthesized according to the process described in example A1 using a dextran with a weight-average molecular weight of approximately 5 kg/mol (q=19, Pharmacosmos), modified with octyl phenylalaninate, is obtained.

According to the dry extract: [Polysaccharide 4]=21.8 mg/g
According to the acid/base titration: n=1.0
According to the $^1$H NMR: m=0.2.

Example A5: Preparation of Polysaccharide 5

3,7-Dimethyl-1-octyl phenylalaninate, para-toluenesulfonic acid salt, is obtained according to the process described in U.S. Pat. No. 4,826,818.

Via a process similar to that described in example A1, a sodium dextranmethylcarboxylate, synthesized according to the process described in example A1 using a dextran with a weight-average molecular weight of approximately 10 kg/mol (q=38, Pharmacosmos), modified with 3,7-dimethyl-1-octyl phenylalaninate, is obtained.

According to the dry extract: [Polysaccharide 5]=24.3 mg/g
According to the acid/base titration: n=1.0
According to the $^1$H NMR: m=0.1.

Example A6: Preparation of Polysaccharide 6

Dioctyl aspartate, para-toluenesulfonic acid salt, is obtained according to the process described in U.S. Pat. No. 4,826,818.

Via a process similar to that described in example A1, a sodium dextranmethylcarboxylate, synthesized according to the process described in example A1 using a dextran with a weight-average molecular weight of approximately 10 kg/mol (q=38, Pharmacosmos), modified with dioctyl aspartate, is obtained.

According to the dry extract: [Polysaccharide 6]=22.2 mg/g
According to the acid/base titration: n=1.05
According to the $^1$H NMR: m=0.05.

Example A7: Preparation of Polysaccharide 7

Didecyl aspartate, para-toluenesulfonic acid salt, is obtained according to the process described in U.S. Pat. No. 4,826,818.

Via a process similar to that described in example A1, a sodium dextranmethylcarboxylate, synthesized according to the process described in example A1 using a dextran with a weight-average molecular weight of approximately 10 kg/mol (q=38, Pharmacosmos), modified with didecyl aspartate, is obtained.

According to the dry extract: [Polysaccharide 7]=19.8 mg/g
According to the acid/base titration: n=1.05
According to the $^1$H NMR: m=0.05.

Example A8: Preparation of Polysaccharide 8

Dilauryl aspartate, para-toluenesulfonic acid salt, is obtained according to the process described in U.S. Pat. No. 4,826,818.

Via a process similar to that described in example A1, a sodium dextranmethylcarboxylate, synthesized according to the process described in example A1 using a dextran with a weight-average molecular weight of approximately 5 kg/mol (q=19, Pharmacosmos), modified with dilauryl aspartate, is obtained.

According to the dry extract: [Polysaccharide 8]=22.8 mg/g
According to the acid/base titration: n=1.05
According to the $^1$H NMR: m=0.05.

Example A9: Preparation of Polysaccharide 9

N-(2-Aminoethyl)dodecanamide is obtained according to the process described in U.S. Pat. No. 2,387,201 from the methyl ester of dodecanoic add (Sigma) and ethylenediamine (Roth).

Via a process similar to that described in example A1, a sodium dextranmethylcarboxylate, synthesized according to the process described in example A1 using a dextran with a weight-average molecular weight of approximately 10 kg/mol (q=38, Pharmacosmos), modified with N-(2-aminoethyl)dodecanamide, is obtained.

According to the dry extract: [Polysaccharide 9]=23.8 mg/g
According to the acid/base titration: n=1.0
According to the $^1$H NMR: m=0.1.

Example A10: Preparation of Polysaccharide 10

Sodium dextransuccinate is obtained from a dextran having a weight-average molar mass of approximately 10 kg/mol (q=38, Pharmacosmos) according to the method described in the article by Sanchez-Chaves et al., 1998 (Manuel et al., Polymer 1998, 39 (13), 2751-2757). According to the 1H NMR in D2O/NaOD, the average number of succinate groups per glucoside unit is 1.4.

Lauryl glycinate, para-toluenesulfonic acid salt, is obtained according to the process described in U.S. Pat. No. 4,826,818.

Via a process similar to that described in example A1, a sodium dextransuccinate modified with lauryl glycinate is obtained.

According to the dry extract: [Polysaccharide 10]=16.1 mg/g

According to the acid/base titration: n=1.3

According to the $^1$H NMR: m=0.1.

Example A11: Preparation of Polysaccharide 11

Dioctyl aspartate, para-toluenesulfonic add salt, is obtained according to the process described in U.S. Pat. No. 4,826,818.

12 g (i.e. 0.22 mol of hydroxyls) of dextran having a weight-average molar mass of approximately 10 kg/mol (q=38, Pharmacosmos) are dissolved in a DMF/DMSO mixture. The mixture is brought to 80° C. with stirring. 3.32 g (0.03 mol) of 1,4-diazabicyclo[2.2.2]octane and then 14.35 g (0.11 mol) of ethyl isocyanatoacetate are gradually introduced. After reaction for 5 h, the medium is diluted with water and purified by diafiltration on a 5 kD PES membrane against 0.1 N NaOH, 0.9% NaCl and water. The final solution is assayed by dry extract to determine the polysaccharide concentration, and then assayed by acid/base titration in 50/50 (V/V) water/acetone to determine the average number of N-methylcarboxylate carbamate units per glucoside unit.

According to the dry extract: [polysaccharide]=30.5 mg/g

According to the acid/base titration: the average number of N-methylcarboxylate carbamate units per glucoside unit is 1.4.

Via a process similar to that described in example A1, an N-(sodium methylcarboxylate) dextran carbamate modified with dioctyl aspartate is obtained.

According to the dry extract: [Polysaccharide 11]=17.8 mg/g

According to the acid/base titration: n=1.3

According to the $^1$H NMR: m=0.1.

Example A12: Preparation of Polysaccharide 12

Dilauryl aspartate, para-toluenesulfonic acid salt, is obtained according to the process described in U.S. Pat. No. 4,826,818.

Via a process similar to that described in example A1, a sodium dextranmethylcarboxylate, synthesized according to the process described in example A1 using a dextran with a weight-average molecular weight of approximately 1 kg/mol (q=4, Pharmacosmos), modified with dilauryl aspartate, is obtained.

According to the dry extract: [Polysaccharide 12]=12.3 mg/g

According to the acid/base titration: n=0.96

According to the $^1$H NMR: m=0.07.

Example A13: Preparation of Polysaccharide 13

2-(2-Aminoethoxy)ethyl dodecanoate, para-toluenesulfonic add salt, is obtained according to the process described in U.S. Pat. No. 4,826,818.

Via a process similar to that described in example A1, a sodium dextranmethylcarboxylate, synthesized according to the process described in example A1 using a dextran with a weight-average molecular weight of approximately 10 kg/mol (q=38, Pharmacosmos), modified with 2-(2-aminoethoxy)ethyl dodecanoate, is obtained.

According to the dry extract: [Polysaccharide 13]=25.6 mg/g

According to the acid/base titration: n=1.0

According to the 1H NMR: m=0.1.

Example A14: Preparation of Polysaccharide 14

2-(2-{2-[Dodecanoylamino]ethoxy}ethoxy)ethylamine is obtained according to the process described in U.S. Pat. No. 2,387,201 from the methyl ester of dodecanoic acid (Sigma) and triethylene glycol diamine (Huntsman).

Via a process similar to that described in example A1, a sodium dextranmethylcarboxylate, synthesized according to the process described in example A1 using a dextran with a weight-average molecular weight of approximately 10 kg/mol (q=38, Pharmacosmos), modified with 2-(2-{2-[dodecanoylamino]ethoxy}ethoxy)ethylamine, is obtained.

According to the dry extract: [Polysaccharide 14]=24.9 mg/g

According to the acid/base titration: n=1.0

According to the $^1$H NMR: m=0.1.

Example A15: Preparation of Polysaccharide 15

2-(2-{2-[Hexadecanoylamino]ethoxy}ethoxy)ethylamine is obtained according to the process described in U.S. Pat. No. 2,387,201 from the methyl ester of palmitic acid (Sigma) and triethylene glycol diamine (Huntsman).

Via a process similar to that described in example A1, a sodium dextranmethylcarboxylate, synthesized according to the process described in example A1 using a dextran with a weight-average molecular weight of approximately 10 kg/mol (q=38, Pharmacosmos), modified with 2-(2-{2-[hexadecanoylamino]ethoxy}ethoxy)ethylamine, is obtained.

According to the dry extract: [Polysaccharide 15]=22.2 mg/g

According to the acid/base titration: n=1.05

According to the $^1$H NMR: m=0.05.

Example A16: Preparation of Polysaccharide 16

Cetyl glycinate, para-toluenesulfonic acid salt, is obtained according to the process described in U.S. Pat. No. 4,826,818.

Via a process similar to that described in example A1, a sodium dextranmethylcarboxylate, synthesized according to the process described in example A1 using a dextran with a weight-average molecular weight of approximately 5 kg/mol (q=19, Pharmacosmos), modified with cetyl glycinate, is obtained.

According to the dry extract: [Polysaccharide 16]=23 mg/g

According to the acid/base titration: n=1.05

According to the $^1$H NMR: m=0.05.

Example A17: Preparation of Polysaccharide 17

10 g (i.e. 185 mmol of hydroxyls) of dextran having a weight-average molar mass of approximately 10 kg/mol (q=38, Pharmacosmos) are dissolved in water at 420 g/l. 19 ml of 10 N NaOH (185 mmol) are added to this solution. The mixture is brought to 35° C., then 8.6 g (74 mmol) of sodium chloroacetate are added. The temperature of the reaction medium is brought to 60° C. at 0.5° C./min and then maintained at 60° C. for 100 minutes. The reaction medium is diluted with 200 ml of water, neutralized with acetic acid and purified by ultrafiltration on a 5 kDa PES membrane against 6 volumes of water. The final solution is assayed by dry extract to determine the polysaccharide concentration, and then assayed by acid/base titration in 50/50 (V/V) water/acetone to determine the average number of methylcarboxylate units per glucoside unit.

According to the dry extract: [polysaccharide]=35.1 mg/g
According to the acid/base titration: the average number of methylcarboxylate units per glucoside unit is 0.42.

The sodium dextranmethylcarboxylate solution is passed over a Purolite resin (anionic) to obtain dextranmethylcarboxylic acid, which is then lyophilized for 18 hours.

Cetyl glycinate, para-toluenesulfonic acid salt, is obtained according to the process described in U.S. Pat. No. 4,826,818.

Via a process similar to that described in example A1, a sodium dextranmethylcarboxylate modified with cetyl glycinate is obtained.

According to the dry extract: [Polysaccharide 17]=18 mg/g
According to the acid/base titration: n=0.37
According to the $^1$H NMR: m=0.05.

Example A18: Preparation of Polysaccharide 18

10 g of sodium dextranmethylcarboxylate characterized by a degree of substitution with methylcarboxylate of 1.10 per glucoside unit are synthesized from a dextran having a weight-average molar mass of 5 kg/mol (q=19, Pharmacosmos), according to a process similar to that described for Polysaccharide 1, and then lyophilized.

8 g (i.e. 64 mmol of hydroxyls) of sodium dextranmethylcarboxylate characterized by a degree of substitution with methylcarboxylate of 1.05 per glucoside unit are dissolved in water at 1000 g/l. 6 ml of 10 N NaOH (64 mmol) are added. The mixture is heated to 35° C. and 7.6 g (65 mmol) of sodium chloroacetate are added. The mixture is gradually brought to a temperature of 60° C., and maintained at this temperature for a further 100 minutes. The mixture is diluted with water, neutralized with acetic acid and then purified by ultrafiltration on a 5 kDa PES membrane against water. The final solution is assayed by dry extract to determine the polysaccharide concentration, and then assayed by acid/base titration in 50/50 (V/V) water/acetone to determine the average number of methylcarboxylate units per glucoside unit.

According to the dry extract: [polysaccharide]=45.8 mg/g
According to the acid/base titration: the average number of methylcarboxylate units per glucoside unit is 1.65.

The sodium dextranmethylcarboxylate solution is passed over a Purolite resin (anionic) to obtain dextranmethylcarboxylic acid, which is then lyophilized for 18 hours.

Cholesteryl leucinate, para-toluenesulfonic acid salt, is obtained according to the process described in U.S. Pat. No. 4,826,818.

Via a process similar to that described in example A1, a sodium dextranmethylcarboxylate modified with cholesteryl leucinate is obtained.

According to the dry extract: [Polysaccharide 18]=21 mg/g
According to the acid/base titration: n=1.61
According to the 1H NMR: m=0.04.

Example A19: Preparation of Polysaccharide 19

Via a process similar to that described in example A1, a sodium dextranmethylcarboxylate, synthesized according to the process described in example A1 using a dextran with a weight-average molecular weight of approximately 5 kg/mol (q=19, Pharmacosmos), modified with cholesteryl leucinate, is obtained.

According to the dry extract: [Polysaccharide 19]=19.4 mg/g
According to the acid/base titration: n=1.06
According to the $^1$H NMR: m=0.04.

Example A20: Preparation of Polysaccharide 20

16 g (i.e. 296 mmol of hydroxyls) of dextran having a weight-average molar mass of approximately 5 kg/mol (q=19, Pharmacosmos) are dissolved in water at 420 g/l. 30 ml of 10 N NaOH (296 mmol) are added to this solution. The mixture is brought to 35° C., then 26 g (222 mmol) of sodium chloroacetate are added. The temperature of the reaction medium is gradually brought to 60° C. and then maintained at 60° C. for 100 minutes. The reaction medium is diluted with water, neutralized with acetic acid and purified by ultrafiltration on a 5 kDa PES membrane against water. The final solution is assayed by dry extract to determine the polysaccharide concentration, and then assayed by acid/base titration in 50/50 (V/V) water/acetone to determine the average number of methylcarboxylate units per glucoside unit.

According to the dry extract: [polysaccharide]=33.1 mg/g
According to the acid/base titration: the average number of methylcarboxylate units per glucoside unit is 0.70.

The sodium dextranmethylcarboxylate solution is passed over a Purolite resin (anionic) to obtain dextranmethylcarboxylic acid, which is then lyophilized for 18 hours.

Via a process similar to that described in example A1, a sodium dextranmethylcarboxylate modified with cholesteryl leucinate is obtained.

According to the dry extract: [Polysaccharide 20]=18.9 mg/g
According to the acid/base titration: n=0.66
According to the $^1$H NMR: m=0.04.

Example A21: Preparation of Polysaccharide 21

16 g (i.e. 296 mmol of hydroxyls) of dextran having a weight-average molar mass of approximately 5 kg/mol (q=19, Pharmacosmos) are dissolved in water at 420 g/l. 30 ml of 10 N NaOH (296 mmol) are added to this solution. The mixture is brought to 35° C., then 18 g (158 mmol) of sodium chloroacetate are added. The temperature of the reaction medium is gradually brought to 60° C. and then maintained at 60° C. for 100 minutes. The reaction medium is diluted with water, neutralized with acetic acid and purified by ultrafiltration on a 1 kDa PES membrane against water. The final solution is assayed by dry extract to determine the polysaccharide concentration, and then assayed by acid/base titration in 50/50 (V/V) water/acetone to determine the average number of methylcarboxylate units per glucoside unit.

According to the dry extract: [polysaccharide]=52.6 mg/g
According to the acid/base titration: the average number of methylcarboxylate units per glucoside unit is 0.50.

The sodium dextranmethylcarboxylate solution is passed over a Purolite resin (anionic) to obtain dextranmethylcarboxylic acid, which is then lyophilized for 18 hours.

Via a process similar to that described in example A1, a sodium dextranmethylcarboxylate modified with cholesteryl leucinate is obtained.

According to the dry extract: [Polysaccharide 21]=18.9 mg/g
According to the acid/base titration: n=0.46
According to the $^1$H NMR: m=0.04.

Example A22: Preparation of Polysaccharide 22

Via a process similar to that described in example A18, a sodium dextranmethylcarboxylate, synthesized according to the process described in example A18 using a dextran with a weight-average molecular weight of approximately 1 kg/mol (q=4, Pharmacosmos), modified with cholesteryl leucinate, is obtained.

According to the dry extract: [Polysaccharide 22]=20.2 mg/g
According to the acid/base titration: n=1.61
According to the $^1$H NMR: m=0.04.

Example A23: Preparation of Polysaccharide 23

Cholesteryl 1-ethylenediaminecarboxylate hydrochloride is obtained according to the process described in patent (Akiyoshi, K et al. WO 2010/053140).

Via a process similar to that described in example A18, a sodium dextranmethylcarboxylate, synthesized according to the process described in example A18 using a dextran with a weight-average molecular weight of approximately 5 kg/mol (q=19, Pharmacosmos), modified with cholesteryl 1-ethylenediaminecarboxylate, is obtained.

According to the dry extract: [Polysaccharide 23]=20.1 mg/g
According to the add/base titration: n=1.61
According to the $^1$H NMR: m=0.04.

Example A24: Preparation of Polysaccharide 24

12 g (i.e. 0.22 mol of hydroxyls) of dextran having a weight-average molar mass of approximately 5 kg/mol (q=19, Pharmacosmos) are dissolved in a DMF/DMSO mixture. The mixture is brought to 80° C. with stirring. 3.32 g (0.03 mol) of 1,4-diazabicyclo[2.2.2]octane and then 26.8 g (0.21 mol) of ethyl isocyanatoacetate are gradually introduced. After reaction for 5 h, the medium is diluted with water and purified by diafiltration on a 5 kD PES membrane against 0.1 N NaOH, 0.9% NaCl and water. The final solution is assayed by dry extract to determine the polysaccharide concentration, and then assayed by acid/base titration in 50/50 (V/V) water/acetone to determine the average number of N-methylcarboxylate carbamate units per glucoside unit.

According to the dry extract: [polysaccharide]=30.1 mg/g
According to the add/base titration: the average number of N-methylcarboxylate carbamate units per glucoside unit is 2.0.

Via a process similar to that described in example A1, an N-(sodium methylcarboxylate) dextran carbamate modified with cholesteryl leucinate is obtained.

According to the dry extract: [Polysaccharide 24]=17.9 mg/g
According to the acid/base titration: n=1.96
According to the $^1$H NMR: m=0.04.

Example A25: Preparation of Polysaccharide 25

Cholesteryl 1-ethylenediaminecarboxylate hydrochloride is obtained according to the process described in patent (Aklyoshi, K et al. WO 2010/053140).

10 g of dextran having a weight-average molar mass of approximately 5 kg/mol (q=19, Pharmacosmos, 3.2 mmol of chain ends) are dissolved in DMSO at 80° C. 4.8 g of cholesteryl 1-ethylenediaminecarboxylate hydrochloride (9.5 mmol), 0.96 g of triethylamine (9.5 mmol) and 2.0 g of sodium cyanoborohydride (32 mmol) are added to the reaction medium which is stirred at 80° C. for 24 hours. After cooling, the mixture is precipitated from dichloromethane and then from acetone, and dried under vacuum. According to the $^1$H NMR, a dextran modified at the chain end with cholesteryl 1-ethylenediaminecarboxylate is obtained. A sodium dextranmethylcarboxylate characterized by a degree of substitution with methylcarboxylate of 1.65 per glucoside unit and modified at the chain end with cholesteryl 1-ethylenediaminecarboxylate was synthesized via a process similar to that described in example A18 using the dextran modified at the chain end with cholesteryl 1-ethylenediaminecarboxylate.

According to the dry extract: [Polysaccharide 25]=13.7 mg/g
According to the acid/base titration: n=1.65
According to the $^1$H NMR: each polymer chain bears a cholesteryl 1-ethylenediaminecarboxylate group grafted onto the reducing chain end.

Example A26: Preparation of Polysaccharide 26

Cholesteryl leucinate, para-toluenesulfonic acid salt, is obtained according to the process described in U.S. Pat. No. 4,826,818.

Via a process similar to that described in example A1, a sodium dextranmethylcarboxylate, synthesized according to the process described in example A1 using a dextran with a weight-average molecular weight of approximately 10 kg/mol (q=38, Pharmacosmos), modified with cholesteryl leucinate, is obtained.

According to the dry extract: [Polysaccharide 26]=26.6 mg/g
According to the acid/base titration: n=0.99
According to the $^1$H NMR: m=0.05.

Example A27: Preparation of Polysaccharide 27

Dilauryl aspartate, para-toluenesulfonic acid salt, is obtained according to the process described in U.S. Pat. No. 4,826,818.

Via a process similar to that described in example A1, a sodium dextranmethylcarboxylate, synthesized according to the process described in example A18 using a dextran with a weight-average molecular weight of approximately 1 kg/mol (q=4, Pharmacosmos), modified with dilauryl aspartate, is obtained.

According to the dry extract: [Polysaccharide 27]=16.7 mg/g
According to the acid/base titration: n=1.41
According to the $^1$H NMR: m=0.16.

Example A28: Preparation of Polysaccharide 28

Dilauryl aspartate, para-toluenesulfonic acid salt, is obtained according to the process described in U.S. Pat. No. 4,826,818.

Via a process similar to that described in example A1, a sodium dextranmethylcarboxylate, synthesized according to the process described in example A18 using a dextran with a weight-average molecular weight of approximately 1 kg/mol (q=4, Pharmacosmos), modified with dilauryl aspartate, is obtained.

According to the dry extract: [Polysaccharide 28]=25 mg/g
According to the acid/base titration: n=1.50
According to the $^1$H NMR: m=0.07.

Example A29: Preparation of Polysaccharide 29

Didecyl aspartate, para-toluenesulfonic acid salt, is obtained according to the process described in U.S. Pat. No. 4,826,818.

Via a process similar to that described in example A1, a sodium dextranmethylcarboxylate, synthesized according to the process described in example A1 using a dextran with a weight-average molecular weight of approximately 1 kg/mol (q=4, Pharmacosmos), modified with didecyl aspartate, is obtained.

According to the dry extract: [Polysaccharide 29]=15 mg/g
According to the acid/base titration: n=1.05
According to the $^1$H NMR: m=0.05.

Examples

Part B Demonstration of the Properties of the Compositions According to the Invention Example B1: 100 IU/ml Solution of Fast-Acting Insulin Analog (Novolog®)

This solution is a commercial solution of insulin aspart sold by the company Novo Nordisk under the name Novolog® in the USA and Novorapid® in Europe. This product is a fast-acting insulin analog.

Example B2: 100 IU/ml Solution of Fast-Acting Insulin Analog (Humalog®)

This solution is a commercial solution of insulin lispro sold by the company Eli Lilly under the name Humalog®. This product is a fast-acting insulin analog.

Example B3: 100 IU/ml Solution of Fast-Acting Insulin Analog (Apidra®)

This solution is a commercial solution of insulin glulisine sold by the company Sanofi-Aventis under the name Apidra®. This product is a fast-acting insulin analog.

Example B4: 100 IU/ml Solution of Slow-Acting Insulin Analog (Lantus®)

This solution is a commercial solution of insulin glargine sold by the company Sanofi-Aventis under the name Lantus®. This product is a slow-acting insulin analog.

Example B5: 100 IU/ml Solution of Human Insulin (ActRapid®)

This solution is a commercial solution from Novo Nordisk sold under the name ActRapid®. This product is a human insulin.

Example B6: Solubilization of Lantus® at 100 IU/ml and at pH 7 Using a Substituted Dextran 20 mg of Polysaccharide 4 described in example A4 are accurately weighed out. This lyophilizate is taken up with 2 ml of Lantus® in its commercial formulation. A temporary precipitate appears, but the solution becomes clear after approximately 30 minutes. The pH of this solution is 6.3. The pH is adjusted to 7 with a 0.1 N sodium hydroxide solution. This clear solution is filtered through a 0.22 μm filter and is then placed at +4° C.

Example B7: Preparation of a Substituted Dextran/Lantus®/Apidra® 75/25 Composition at pH 7

0.25 ml of Apidra® (in its commercial formulation) is added to 0.75 ml of the Polysaccharide 4/Lantus® solution prepared in example B6, so as to form 1 ml of a composition at pH 7. The composition is clear, attesting to the good solubility of Lantus® and of Apidra® under these formulation conditions. This clear solution is filtered through a 0.22 μm filter and then placed at +4° C.

Example B8: Preparation of a Substituted Dextran/Lantus®/Humalog® 75/25 Composition at pH 7

0.25 ml of Humalog® (in its commercial formulation) is added to 0.75 ml of the Polysaccharide 4/Lantus® solution prepared in example B6, so as to form 1 ml of a composition at pH 7. The composition is clear, attesting to the good solubility of Lantus® and of Humalog® under these formulation conditions. This clear solution is filtered through a 0.22 μm filter and then placed at +4° C.

Example B9: Preparation of a Substituted Dextran/Lantus®/Novolog® 75/25 Composition at pH 7

0.25 ml of Novolog® (in its commercial formulation) is added to 0.75 ml of the Polysaccharide 4/Lantus® solution prepared in example B6, so as to form 1 ml of a composition at pH 7. The composition is clear, attesting to the good solubility of Lantus® and of Novolog® under these formulation conditions. This clear solution is filtered through a 0.22 μm filter and then placed at +4° C.

Example B10: Preparation of a Substituted Dextran/Lantus®/ActRapid® 75/25 Composition at pH 7

0.25 ml of ActRapid® (in its commercial formulation) is added to 0.75 ml of the Polysaccharide 4/Lantus® solution prepared in example B6, so as to form 1 ml of a composition at pH 7. The composition is clear, attesting to the good solubility of Lantus® and of ActRapid® under these formulation conditions. This clear solution is filtered through a 0.22 μm filter and then placed at +4° C.

Example 811: Preparation of a Substituted Dextran/Lantus®/Apidra® 60/40 Composition at pH 7

0.4 ml of Apidra® (in its commercial formulation) is added to 0.6 ml of the Polysaccharide 4/Lantus® solution prepared in example B6, so as to form 1 ml of a composition at pH 7. The composition is clear, attesting to the good solubility of Lantus® and of Apidra® under these formulation conditions. This clear solution is filtered through a 0.22 μm filter and then placed at +4° C.

Example B12: Preparation of a Substituted Dextran/Lantus®/Apidra® 40/60 Composition at pH 7

0.6 ml of Apidra® (in its commercial formulation) is added to 0.4 ml of the Polysaccharide 4/Lantus® solution prepared in example B6, so as to form 1 ml of a composition at pH 7. The composition is clear, attesting to the good solubility of Lantus® and of Apidra® under these formulation conditions. This clear solution is filtered through a 0.22 µm filter and then placed at +4° C.

Example B13: Precipitation of Lantus®

1 ml of Lantus® is added to 2 ml of a solution of PBS containing 20 mg/ml of BSA (bovine serum albumin). The PBS/BSA mixture simulates the composition of the subcutaneous medium. A precipitate appears, which is in good agreement with the mechanism via which Lantus® functions (precipitation upon injection due to the increase in pH).

Centrifugation at 4000 rpm is carried out in order to separate the precipitate from the supernatant. Lantus® is then assayed in the supernatant. It results from this that 86% of Lantus® is found in a precipitated form.

Example B14: Precipitation of a Substituted Dextran/Lantus® Composition 1 ml of Polysaccharide 4/Lantus® solution prepared in example B6 is added to 2 ml of a solution of PBS containing 20 mg/ml of BSA (bovine serum albumin). The PBS/BSA mixture simulates the composition of the subcutaneous medium. A precipitate appears.

Centrifugation at 4000 rpm is carried out in order to separate the precipitate from the supernatant. Lantus® is then assayed in the supernatant. It results from this that 85% of Lantus® is found in a precipitated form. This percentage precipitation of Lantus® is identical to that obtained for the control described in example B13.

Solubilization and precipitation tests identical to those described in examples B6 and B14 were carried out with other substituted dextrans at the same concentration of 10 mg/ml of polysaccharde for 100 IU/ml of Lantus®. 20 mg of polysaccharide in lyophilizate form are accurately weighed out. This lyophilizate is taken up with 2 ml of Lantus® in its commercial formulation. A temporary precipitate appears, but the solution becomes clear after approximately 30 minutes to a few hours (depending on the nature of the polysaccharide). The pH of this solution is 6.3. The pH is adjusted to 7 with a 0.1 N sodium hydroxide solution. This clear solution is filtered through a 0.22 µm filter and is then placed at +4° C. The results are summarized in table 2.

TABLE 2

| Polysaccharide No. | Solubilization of Lantus ® | Precipitation of Lantus ® | % precipitation |
|---|---|---|---|
| 2 | Yes | Yes | 85 |
| 1 | Yes | Yes | Not measured |
| 4 | Yes | Yes | 87 |
| 3 | Yes | Yes | Not measured |
| 5 | Yes | Yes | 94 |
| 6 | Yes | Yes | Not measured |
| 7 | Yes | Yes | Not measured |
| 8 | Yes | Yes | Not measured |
| 9 | Yes | Yes | 94 |
| 10 | Yes | Yes | Not measured |
| 15 | Yes | Yes | Not measured |
| 14 | Yes | Yes | Not measured |
| 13 | Yes | Yes | Not measured |
| 12 | Yes | Yes | Not measured |
| 11 | Yes | Yes | Not measured |
| 16 | Yes | Yes | Not measured |
| 17 | Yes | Yes | Not measured |
| 18 | Yes | Yes | Not measured |
| 19 | Yes | Yes | Not measured |
| 20 | Yes | Yes | Not measured |
| 21 | Yes | Yes | Not measured |
| 22 | Yes | Yes | Not measured |
| 23 | Yes | Yes | Not measured |
| 24 | Yes | Yes | Not measured |
| 25 | Yes | Yes | Not measured |
| 26 | Yes | Yes | Not measured |

Example B15: Preparation of a Substituted Dextran/Lantus®/Apidra® 75/25 Composition at pH 7

1 ml of the substituted dextran/Lantus®/Apidra® 75/25 composition (containing 7.5 mg/ml of polysaccharide, 75 IU/ml of Lantus® and 25 IU/ml of Apidra®) prepared in example B7 is added to 2 ml of a solution of PBS containing 20 mg/ml of BSA (bovine serum albumin). The PBS/BSA mixture simulates the composition of the subcutaneous medium. A precipitate appears.

Centrifugation at 4000 rpm is carried out in order to separate the precipitate from the supernatant. Lantus® is then assayed in the supernatant. The Lantus® precipitation percentages are similar to the control described in example B13.

Example B16: Precipitation of Various Compositions while Varying the Nature of the Substituted Dextran Other tests under the same conditions as those of example B15 were carried out in the presence of other substituted dextrans.

The results are grouped together in table 3 below and it is observed that the solubilization and the precipitation of Lantus® are preserved.

TABLE 3

| Polysaccharide No. | Solubilization Lantus ®/Apidra ® 75/25 | Percentage precipitation of Lantus ® |
|---|---|---|
| 2 | Yes | 85 |
| 1 | Yes | Not measured |
| 4 | Yes | 87 |
| 3 | Yes | Not measured |
| 5 | Yes | 86 |
| 6 | Yes | Not measured |
| 7 | Yes | Not measured |
| 8 | Yes | Not measured |
| 9 | Yes | 86 |
| 10 | Yes | 85 |
| 15 | Yes | 87 |
| 14 | Yes | 86 |
| 13 | Yes | 88 |
| 12 | Yes | 91 |
| 18 | Yes | Not measured |
| 19 | Yes | Not measured |

TABLE 3-continued

| Polysaccharide No. | Solubilization Lantus®/Apidra® 75/25 | Percentage precipitation of Lantus® |
|---|---|---|
| 20 | Yes | Not measured |
| 21 | Yes | Not measured |
| 22 | Yes | Not measured |
| 23 | Yes | Not measured |
| 24 | Yes | Not measured |
| 25 | Yes | Not measured |
| 26 | Yes | Not measured |

Example B17: Precipitation of Various Compositions while Varying the Nature of the Prandial Insulin Compositions are prepared by mixing 0.75 ml of the solution of Polysaccharide 4/Lantus® prepared in example B6 with 0.25 ml of a prandial insulin so as to form 1 ml of substituted dextran/Lantus®/prandial insulin composition (containing 7.5 mg/ml of polysaccharide, 75 IU/ml of Lantus® and 25 IU/ml of prandial insulin).

This composition is added to 2 ml of PBS containing 20 mg/ml of BSA (bovine serum albumin). The PBS/BSA mixture simulates the composition of the subcutaneous medium. A precipitate appears.

Centrifugation at 4000 rpm is carried out in order to separate the precipitate from the supernatant. Lantus® is then assayed in the supernatant. In the presence of the 4 prandial insulins tested, Lantus® is at least 90% precipitated. This percentage precipitation of Lantus® is similar to the control described in example B13; the results are grouped together in table 4.

TABLE 4

| Nature of the prandial insulin | Solubilization of Lantus®/prandial insulin 75/25 | Percentage precipitation of Lantus® |
|---|---|---|
| Apidra® | Yes | 88 |
| Novolog® | Yes | 92 |
| Humalog® | Yes | 89 |
| ActRapid® | Yes | 90 |

Example B18: Preparation of a Concentrated Solution of Slow-Acting Insulin Analog (Glargine)

A commercial solution of insulin glargine sold by the company Sanofi-Aventis under the name Lantus® is concentrated by ultrafiltration on a 3 kDa regenerated cellulose membrane (Amicon® Ultra-15 sold by the company Millipore). At the end of this ultrafiltration step, the insulin glargine concentration is assayed in the retentate by reverse-phase liquid chromatography (RP-HPLC). The final concentration of insulin glargine is then adjusted by adding a commercial solution of glargine at 100 IU/ml, so as to obtain the desired final concentration. This process makes it possible to obtain concentrated solutions of glargine denoted $C_{glargine}$ at various concentrations greater than 100 IU/ml, such that $C_{glargine}$=200, 250, 300 and 333 IU/ml. The concentrated solutions are filtered through a 0.22 µm filter and then stored at +4° C.

Example B19: Dialysis of a Commercial Solution of Fast-Acting Insulin Analog (Lispro)

A commercial solution of insulin lispro sold by the company Eli Lilly under the name Humalog® is dialyzed by ultrafiltration on a 3 kDa regenerated cellulose membrane (Amicon® Ultra-15 sold by the company Millipore). The dialysis is carried out in a 1 mM phosphate buffer at pH 7. At the end of this dialysis step, the concentration $C_{Humalog\ dialyzed}$ of lispro in the retentate is determined by reverse-phase liquid chromatography (RP-HPLC). The dialyzed solution is stored in a freezer at −80° C.

Example B20: Lyophilization of a Solution of Fast-Acting Insulin Analog (Lispro) in its Commercial Form A volume $V_{Humalog}$ of a solution of fast-acting insulin lispro at a concentration of 100 IU/ml in its commercial form is placed in a Lyogard® tray sterilized beforehand in an autoclave. The Lyogard® tray is placed in a freezer at −80° C. for approximately 1 h before undergoing lyophilization overnight at a temperature of 20° C. and a pressure of 0.31 mbar.

The resulting sterile lyophilizate is stored at ambient temperature.

Example B21: Lyophilization of a Commercial Solution of Fast-Acting Insulin Analog (Lispro) which has been Dialyzed A volume $V_{Humalog\ dialyzed}$ of a solution of fast-acting insulin lispro obtained according to example B19 at a concentration of $C_{Humalog\ dialyzed}$ is placed in a Lyogard® tray sterilized beforehand in an autoclave. The Lyogard® tray is placed in a freezer at −80° C. for approximately 1 h before undergoing lyophilization overnight at a temperature of 20° C. and a pressure of 0.31 mbar.

The resulting sterile lyophilizate is stored at ambient temperature.

Example B22: Preparation of a Substituted Dextran/Glargine Composition at pH 7 Using a Substituted Dextran, According to a Process Using Glargine in Liquid Form (in Solution) and a Polysaccharide in Solid Form (Lyophilized)

A weight $w_{polys.}$ of Polysaccharide 18 is accurately weighed out. This lyophilizate is taken up with a volume $V_{glargine}$ of a concentrated solution of glargine prepared according to example B18 so as to obtain a composition having a polysaccharide concentration $C_{polys.}$ (mg/ml)=$w_{polys.}/V_{glargine}$ and a glargine concentration $C_{glargine}$ (IU/ml). The solution is opalescent. The pH of this solution is approximately 6.3. The pH is adjusted to 7 by adding concentrated NaOH and then the solution is placed statically in an incubator at 37° C. for approximately 1 hour. A volume $V_{polys./glargine}$ of this visually clear solution is placed at +4° C.

Example B23: Preparation of a Substituted Dextran/Glargine Composition at pH 7 Using a Substituted Dextran, According to a Process Using Glargine in Liquid Form (in Solution) and a Polysaccharide in Liquid Form (in Solution)

Concentrated solutions of m-cresol, glycerol and Tween 20 are added to a stock solution of Polysaccharide 20 at pH 7 having a concentration $C_{polys.\ stock}$, so as to obtain a solution of polysaccharide of concentration $C_{polys.\ stock/excipients}$ (mg/ml) in the presence of these excipients at contents equivalent to those described in the commercial solution Lantus® in a 10 ml bottle.

In a sterile pot, a volume $V_{Lantus}$ of a commercial solution of slow-acting insulin glargine sold under the name Lantus® at a concentration of 100 IU/ml is added to a volume $V_{polys.\ stock/excipients}$ of a solution of polysaccharide at the concentration $C_{polys.\ stock/excipients}$ (mg/ml). A cloudiness appears. The pH is adjusted to pH 7 by adding 1 M NaOH and the solution is placed statically in an incubator at 37° C. for approximately 1 hour. This visually clear solution is placed at +4° C.

Example B24: Preparation of a Concentrated Polysaccharide/Glargine Composition at pH=7 Using a Substituted Dextran, According to a Process for Concentrating a Dilute Composition A dilute Polysaccharide 20/glargine composition at pH 7 described in example B23 is concentrated by ultrafiltration on a 3 kDa regenerated cellulose membrane (Amicon® Ultra-15 sold by the company Millipore). At the end of this ultrafiltration step, the retentate is clear and the concentration of insulin glargine in the composition is assayed by reverse-phase chromatography (RP-HPLC). If necessary, the insulin glargine concentration in the composition is then adjusted to the desired value by dilution in a solution of excipients m-cresol/glycerol/Tween 20 having, for each entity, a concentration equivalent to that described in the commercial solution Lantus® (in a 10 ml bottle). This solution at pH 7, which is visually clear, and which has a glargine concentration $C_{glargine}$ (IU/ml) and a polysaccharide concentration $C_{polys.}$ (mg/ml), is placed at +4° C.

Example B25: Preparation of a Substituted Dextran/Glargine/Lispro Composition at pH 7, from a Fast-Acting Insulin Lispro in its Commercial Form A volume $V_{glargine}$ of solution of polysaccharide/glargine pH 7 having a glargine concentration $C_{glargine}$ (IU/ml) and a Polysaccharide 18 concentration $C_{polys.}$ (mg/ml) prepared according to example B22 is added to a lyophilizate of insulin lispro obtained by lyophilization of a volume $V_{lispro}$, the preparation of which is described in example B19, such that the ratio $V_{poolysach./glargine}/V_{lispro}=100/C_{lispro}$ where $C_{lispro}$ is the concentration of lispro (IU/ml) targeted in the composition The solution is clear. The zinc content of the formulation is adjusted to the desired concentration $C_{zinc}$ (μM) by adding a concentrated solution of zinc chloride. The final pH is adjusted to 7 by adding concentrated NaOH or HCl.

The formulation is clear, attesting to the good solubility of glargine and lispro under these formulation conditions. This solution is filtered through a 0.22 μm filter and placed at +4° C.

Example B26: Preparation of a Substituted Dextran/Glargine/Lispro Composition at pH 7, from a Fast-Acting Insulin Lispro Obtained by Dialysis of a Commercial Solution A volume $V_{polysach./glargine}$ of solution of polysaccharide/glargine pH 7 having a glargine concentration $C_{glargine}$ (IU/ml) and a Polysaccharide 20 concentration $C_{polys.}$ (mg/ml) prepared according to example B24 is added to a lyophilizate of insulin lispro obtained by lyophilization of a volume $V_{Humalog\ dialyzed}$, the preparation of which is described in example B21, such that the ratio $V_{polysach./glargine}/V_{Humalog\ dialyzed}=C_{Humalog\ dialyzed}/C_{lispro}$ where $C_{Humalog\ dialyzed}$ is the concentration of lispro (IU/ml) obtained at the end of the dialysis of the commercial solution, which step is described in example B19, and $C_{lispro}$ is the concentration of lispro (IU/ml) targeted in the composition. The solution is clear. The zinc content of the formulation is adjusted to the desired concentration $C_{zinc}$ (μM) by adding a concentrated solution of zinc chloride. The final pH is adjusted to 7 by adding concentrated NaOH or HCl.

The formulation is clear, attesting to the good solubility of glargine and lispro under these formulation conditions. This solution is filtered through a 0.22 μm filter and placed at +4° C.

Example B27: Preparation of a Substituted Dextran/Glargine/Lispro Composition at pH 7 Having a Glargine Concentration of 200 IU/ml and a Lispro Concentration of 33 IU/ml (Proportion as Percentage of Insulin: Glargine/Lispro 85/15)

A concentrated solution of glargine at 200 IU/ml is prepared according to example B18. A Polysaccharide 18 (13 mg/ml)/glargine 300 IU/ml composition at pH 7 is prepared from Polysaccharide 18 and according to the method of preparation described in example B22. This Polysaccharide 18/glargine 200 IU/ml composition is added to a lyophilizate of insulin lispro obtained by lyophilization of the solution of fast-acting analog in its commercial form, according to the method of preparation described in example B25. The solution is clear. The zinc content of the formulation is adjusted to the concentration $C_{zinc}$ (μM)=750 μM by adding a concentrated solution of zinc chloride. The final pH is adjusted to 7 by adding concentrated NaOH or HCl.

This composition is described in table 5.

Example B28: Preparation of a Substituted Dextran/Glargine/Lispro Composition at pH 7 Having a Glargine Concentration of 200 IU/ml and a Lispro Concentration of 66 IU/ml (Proportion as Percentage of Insulin: Glargine/Lispro 75/25)

A concentrated solution of glargine at 200 IU/ml is prepared according to example B18. A Polysaccharide 18 (13 mg/ml)/glargine 300 IU/ml composition at pH 7 is prepared from Polysaccharide 18 and according to the method of preparation described in example B22. This Polysaccharide 18/glargine 200 IU/ml composition is added to a lyophilizate of insulin lispro obtained by lyophilization of the solution of fast-acting analog in its commercial form, according to the method of preparation described in example B25. The solution is clear. The zinc content of the formulation is adjusted to the concentration $C_{zinc}$ (μM)=1500 μM by adding a concentrated solution of zinc chloride. The final pH is adjusted to 7 by adding concentrated NaOH or HCl. The formulation is clear, attesting to the good solubility of glargine and lispro under these formulation conditions. This solution is filtered through a 0.22 μm filter and placed at +4° C.

This composition is described in table 5.

Example B29: Preparation of a Substituted Dextran/Glargine/Lispro Concentration at pH 7 Having a Glargine Concentration of 300 IU/ml and a Lispro Concentration of 100 IU/ml (Proportion as Percentage of Insulin: Glargine/Lispro 75/25)

A concentrated solution of glargine at 300 IU/ml is prepared according to example B18. A Polysaccharide 18 (23 mg/ml)/glargine 300 IU/ml composition at pH 7 is prepared from Polysaccharide 18 and according to the method of preparation described in example B22. This Polysaccharide 18/glargine 300 IU/ml composition is added to a lyophilizate of insulin lispro obtained by lyophilization of the solution of fast-acting analog in its commercial form, according to the method of preparation described in example B25. The solution is clear. The zinc content of the formulation is adjusted to the concentration $C_{zinc}$ (μM)=2000 μM by adding a concentrated solution of zinc chloride. The final pH is adjusted to 7 by adding concentrated NaOH or HCl.

The formulation is clear, attesting to the good solubility of glargine and lispro under these formulation conditions. This solution is filtered through a 0.22 μm filter and placed at +4° C.

This composition is described in table 5.

Example B30: Preparation of a Substituted Dextran/Glargine/Lispro Composition at pH 7 Having a Glargine Concentration of 250 IU/ml and a Lispro Concentration of 150 IU/ml (Proportion as Percentage of Insulin: Glargine/Lispro 63/37)

A concentrated solution of glargine at 300 IU/ml is prepared according to example B18. A Polysaccharide 18 (19 mg/ml)/glargine 300 IU/ml composition at pH 7 is prepared from Polysaccharide 18 and according to the method of preparation described in example B22. This Polysaccharide 18/glargine 250 IU/ml composition is added to a lyophilizate of insulin lispro obtained by lyophilization of the solution of fast-acting analog in its commercial form, according to the method of preparation described in example B25. The solution is clear. The zinc content of the formulation is adjusted to the concentration $C_{zinc}$ (μM)=1500 μM by adding a concentrated solution of zinc chloride. The final pH is adjusted to 7 by adding concentrated NaOH or HCl.

The formulation is clear, attesting to the good solubility of glargine and lispro under these formulation conditions. This solution is filtered through a 0.22 μm filter and placed at +4° C.

This composition is described in table 5.

Example B31: Preparation of a Substituted Dextran/Glargine/Lispro Composition at pH 7 Having a Glargine Concentration of 333 IU/ml and a Lispro Concentration of 67 IU/ml (Proportion as Percentage of Insulin: Glargine/Lispro 83/17)

A concentrated solution of glargine at 333 IU/ml is prepared according to example B18. A Polysaccharide 18 (20 mg/ml)/glargine 300 IU/ml composition at pH 7 is prepared from Polysaccharide 18 and according to the method of preparation described in example B22. This Polysaccharide 18/glargine 333 IU/ml composition is added to a lyophilizate of insulin lispro obtained by lyophilization of the solution of fast-acting analog in its commercial form, according to the method of preparation described in example B25. The solution is clear. The zinc content of the formulation is adjusted to the concentration $C_{zinc}$ (μM)=2000 μM by adding a concentrated solution of zinc chloride. The final pH is adjusted to 7 by adding concentrated NaOH or HCl.

The formulation is clear, attesting to the good solubility of glargine and lispro under these formulation conditions. This solution is filtered through a 0.22 μm filter and placed at +4° C.

This composition is described in table 5.

Example B32: Preparation of a Substituted Dextran/Glargine/Lispro Composition at pH 7 Having a Glargine Concentration of 300 IU/ml and a Lispro Concentration of 100 IU/ml (Proportion as Percentage of Insulin: Glargine/Lispro 75/25)

A concentrated solution of glargine at 300 IU/ml is prepared according to example B18. A Polysaccharide 19 (23 mg/ml)/glargine 300 IU/ml composition at pH 7 is prepared from Polysaccharide 19 and according to the method of preparation described in example B22. This Polysaccharide 19/glargine 300 IU/ml composition is added to a lyophilizate of insulin lispro obtained by lyophilization of the solution of fast-acting analog in its dialyzed form, according to the method of preparation described in example B26. The solution is clear. The zinc content of the formulation is adjusted to the concentration $C_{zinc}$ (μM)=3000 μM by adding a concentrated solution of zinc chloride. The final pH is adjusted to 7 by adding concentrated NaOH or HCl.

The formulation is clear, attesting to the good solubility of glargine and lispro under these formulation conditions. This solution is filtered through a 0.22 μm filter and placed at +4° C.

This composition is described in table 5.

Example B33: Preparation of a Substituted Dextran/Glargine/Lispro Composition at pH 7 Having a Glargine Concentration of 300 IU/ml and a Lispro Concentration of 100 IU/ml (Proportion as Percentage of Insulin: Glargine/Lispro 75/25)

A Polysaccharide 20 (23 mg/ml)/glargine 300 IU/ml composition at pH 7 is prepared from Polysaccharide 20 and according to the method of preparation described in example B23. This Polysaccharide 20/glargine 300 IU/ml composition is added to a lyophilizate of insulin lispro obtained by lyophilization of the solution of fast-acting analog derived from the dialysis of a commercial solution, according to the preparation method described in example B26. The solution is clear. The zinc content of the formulation is adjusted to the concentration $C_{zinc}$ (μM)=1500 μM by adding a concentrated solution of zinc chloride. The final pH is adjusted to 7 by adding concentrated NaOH or HCl.

The formulation is clear, attesting to the good solubility of glargine and lispro under these formulation conditions. This solution is filtered through a 0.22 μm filter and placed at +4° C.

This composition is described in table 5.

TABLE 5

Substituted dextran/glargine/lispro compositions at pH 7

| Example No. | Polysaccharide No. | $C_{polysach.}$ (mg/ml) | $C_{glargine}$ (IU/ml) | $C_{lispro}$ (IU/ml) | $C_{glargine}/C_{lispro}$ (%/%) | pH |
|---|---|---|---|---|---|---|
| B27 | 18 | 13 | 200 | 33 | 85/15 | 7 |
| B28 | 18 | 13 | 200 | 66 | 75/25 | 7 |

TABLE 5-continued

Substituted dextran/glargine/lispro compositions at pH 7

| Example No. | Polysaccharide No. | $C_{polysach.}$ (mg/ml) | $C_{glargine}$ (IU/ml) | $C_{lispro}$ (IU/ml) | $C_{glargine}/C_{lispro}$ (%/%) | pH |
|---|---|---|---|---|---|---|
| B29 | 18 | 23 | 300 | 100 | 75/25 | 7 |
| B30 | 18 | 19 | 250 | 150 | 63/37 | 7 |
| B31 | 18 | 20 | 333 | 67 | 83/17 | 7 |
| B32 | 19 | 23 | 300 | 100 | 75/25 | 7 |
| B33 | 20 | 23 | 300 | 100 | 75/25 | 7 |

Example B34: Precipitation of Various Substituted Dextran/Glargine/Lispro Compositions at pH 7 Having Various Concentrations of Insulins Glargine and Lispro and Various Relative Proportions of the 2 Insulins 1 ml of substituted dextran/Lantus®/Humalog® composition prepared in example B27 to B33 is added to 2 ml of a solution of PBS containing 20 mg/ml of BSA (bovine serum albumin). The PBS/BSA mixture simulates the composition of the subcutaneous medium. A precipitate appears.

Centrifugation at 4000 rpm is carried out in order to separate the precipitate from the supernatant. Lantus® is then assayed in the supernatant. The Lantus® precipitation percentages are similar to the control described in example B13. The results are summarized in table 6.

TABLE 6

| Example No. | Polysaccharide No. | $C_{polysach.}$ (mg/ml) | $C_{glargine}$ (IU/ml) | $C_{lispro}$ (IU/ml) | $C_{glargine}/C_{lispro}$ (%/%) | Solubilization of glargine and lispro at pH 7 | Glargine precipitation | % Precipitation |
|---|---|---|---|---|---|---|---|---|
| B27 | 18 | 13 | 200 | 33 | 85/15 | YES | YES | 96 |
| B28 | 18 | 13 | 200 | 66 | 75/25 | YES | YES | 86 |
| B29 | 18 | 23 | 300 | 100 | 75/25 | YES | YES | 91 |
| B30 | 18 | 19 | 250 | 150 | 63/37 | YES | YES | 90 |
| B31 | 18 | 20 | 333 | 67 | 83/17 | YES | YES | 93 |
| B32 | 19 | 23 | 300 | 100 | 75/25 | YES | YES | 98 |
| B33 | 20 | 23 | 300 | 100 | 75/25 | YES | YES | Not measured |

Example B35: Chemical Stability of the Compositions

The substituted dextran/Lantus®/prandial insulin compositions described in examples B7, B27, B28 and B29 and also the corresponding controls are placed at 30° C. for 4 weeks. Regulations require 95% of (non-degraded) native insulin after 4 weeks at 30° C.

After 4 weeks, the formulations studied meet the specifications defined by the regulations. The results are collated in table 7.

TABLE 7

| Compositions | Percentage of native glargine after 4 weeks at 30° C. | Percentage of native prandial insulin after 4 weeks at 30° C. |
|---|---|---|
| Lantus ® (commercial formulation) | 97 | na |
| Apidra ® (commercial formulation) | na | 95 |

TABLE 7-continued

| Compositions | Percentage of native glargine after 4 weeks at 30° C. | Percentage of native prandial insulin after 4 weeks at 30° C. |
|---|---|---|
| Humalog ® (commercial formulation) | na | 98 |
| B7 | 96 | 98 |
| B27 | 97 | 99 |
| B28 | 95 | 97 |
| B29 | 98 | 100 |

Whatever the formulation studied, a percentage of native insulin greater than 95% is thus obtained, which is in accordance with the regulatory requirements.

Example B36: Injectability of the Solutions

All the compositions prepared can be injected with the usual insulin injection systems. The solutions described in examples B7 to B12 and also the compositions described in examples B27 to B33 are injected without any difficulty, both with insulin syringes fitted with 31 gauge needles, and with insulin pens from Novo Nordisk sold under the name Novopen®, fitted with 31 gauge needles.

Example B37: Protocol for Measuring the Pharmacodynamics of the Insulin Solutions Preclinical Studies were Carried Out on Pigs with a View to Evaluating Two Compositions According to the Invention Lantus®/Apidra® (75/25), formulated with Polysaccharide 4 (6 mg/ml) described in example B7, and Lantus®/Humalog® (75/25), formulated with Polysaccharide 4 (6 mg/ml) described in example B8.

The hypoglycemic effects of these compositions were compared to injections carried out with simultaneous but separate injections of Lantus® (pH 4) and then of an Apidra® or Humalog® prandial insulin.

Six domestic pigs weighing approximately 50 kg, previously catheterized at the level of the jugular, are deprived of food for 2 to 3 hours before the beginning of the experiment. In the hour preceding the injection of insulin, three blood samples are taken in order to determine the basal level of glucose.

The injection of insulin at a dose of 0.4 IU/kg is carried out by subcutaneous injection in the neck, under the animal's ear, using the Novopen® insulin pen fitted with a 31 gauge needle.

Blood samples were then taken after 4, 8, 12, 16, 20, 30, 40, 50, 60, 90, 120, 240, 360, 480, 600, 660 and 720 minutes. After taking each sample, the catheter is rinsed with a dilute heparin solution.

A drop of blood is taken to determine the blood glucose level by means of a glucometer. The glucose pharmacodynamics curves are then plotted.

The results obtained are presented in the form of glucose pharmacodynamics curves represented in FIGS. 1 to 6.

Lantus®/Apidra® (75/25), formulated with Polysaccharide 4 (6 mg/ml).

Figure 2:
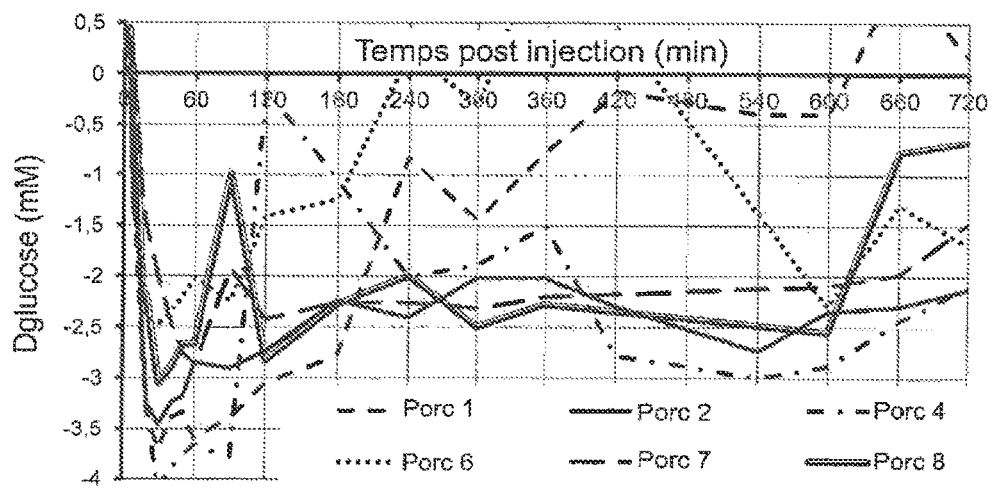
Figure 3:
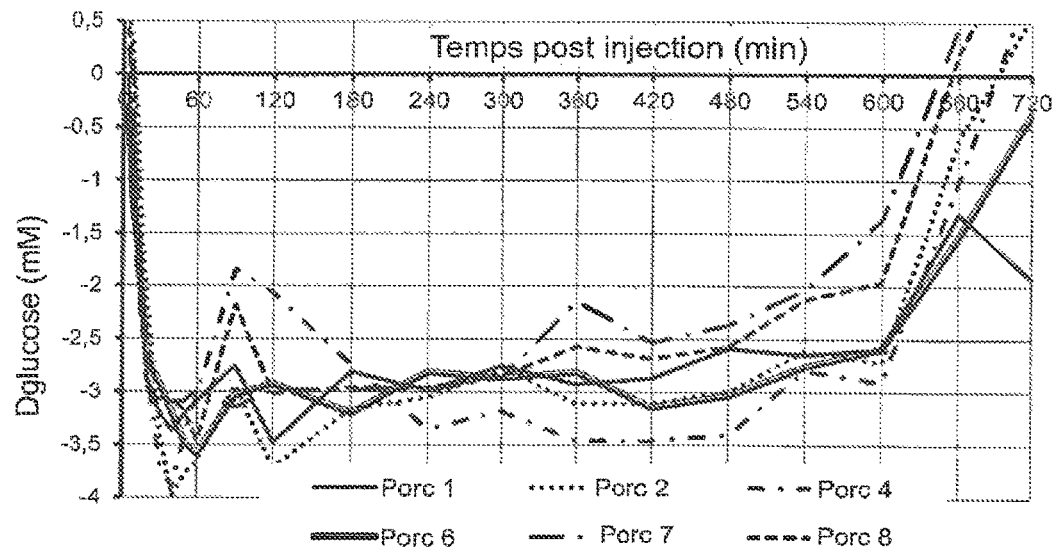

FIG. 1: Curves of mean+standard deviation of the mean for the sequential administrations of Apidra® and Lantus® in comparison with a Polysaccharide 4/Lantus®/Apidra® (75/25) composition according to the invention FIG. 2: Individual Apidra® Lantus® curves FIG. 3: Individual Polysaccharide 4/Apidra®/Lantus® curves FIG. 1 shows the curves of means of drop in blood glucose level and also the standard deviations of the mean for the pigs tested for each formulation. The drop in blood glucose level in the first 30 minutes is similar for the two formulations, indicating that the presence of a polysaccharide does not disrupt the fast-acting nature of Apidra®. On the other hand, between 90 min and 10 h (600 minutes), the sequential administration of Apidra® and Lantus® induces a heterogeneous glucose drop with a homogeneous plateau response in three pigs and a heterogeneous response in the other three pigs (FIG. 2). Conversely, the 6 pigs tested with the Polysaccharide 4/Apidra®/Lantus® formulation have a homogeneous response (FIG. 3). This is reflected by the analysis of the coefficients of variation (CV) between 60 min and 10 h which are on average 54% (between 21% and 113%) for the Apidra® Lantus® control and 12% (between 5% and 25%) for Polysaccharide 4/Apidra®/Lantus®.

Lantus®/Humalog® (75/25), formulated with Polysaccharide 4 (6 mg/ml).

Figure 4:
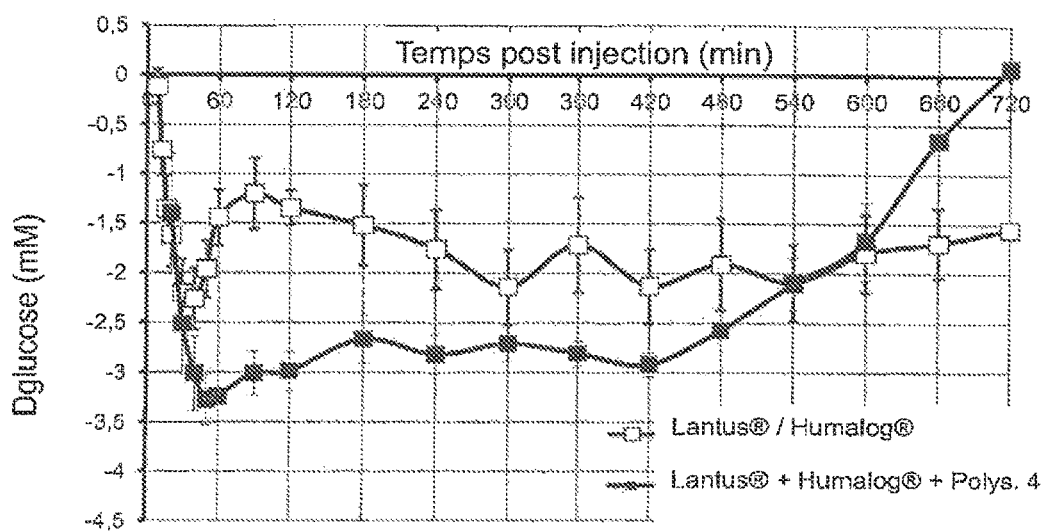
Figure 5:
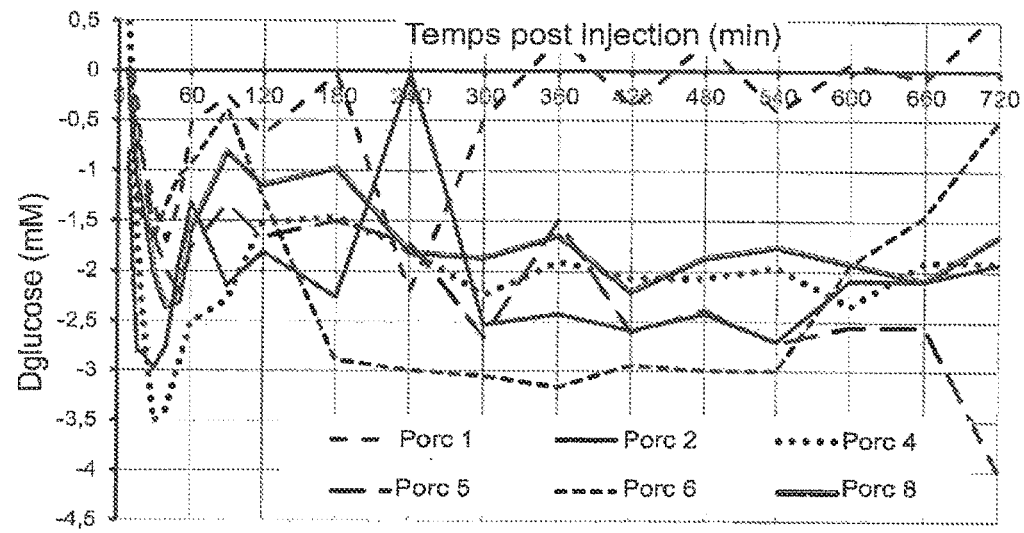
Figure 6:
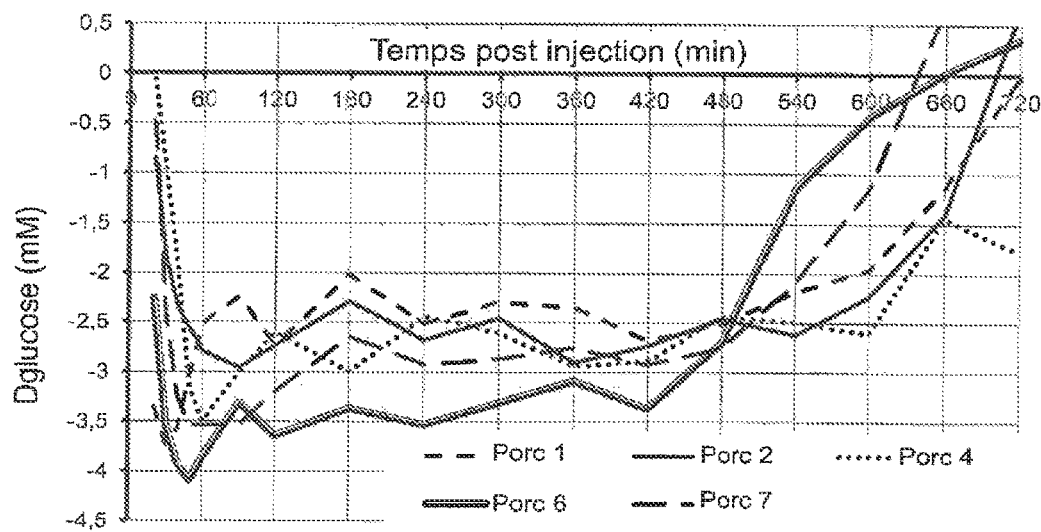

FIG. 4: Curves of mean+standard deviation of the mean for the sequential administrations of Humalog® and Lantus® in comparison with the administration of a Polysaccharide 4/Humalog®/Lantus® composition according to the invention FIG. 5: Individual Humalog® Lantus® curves FIG. 6: Individual Polysaccharide 4/Humalog®/Lantus® curves FIG. 4 shows the curves of means of drop in blood glucose level and also the standard deviations of the mean for the pigs tested for each formulation. The drop in blood glucose level in the first 30 minutes is similar for the two formulations, indicating that the presence of Polysaccharide 4 does not disrupt the fast-acting nature of Humalog®. On the other hand, between 60 min and 8 h (480 minutes), the sequential administration of Humalog® and Lantus® induces a heterogeneous glucose drop with a homogeneous plateau response in four pigs and a heterogeneous response in the other two pigs (FIG. 5). Conversely, the 5 pigs tested with the Polysaccharide 4/Humalog®/Lantus® formulation have a homogeneous response (FIG. 6). This is reflected by the analysis of the coefficients of variation (CV) on the data regarding drop in blood glucose level between 60 min and 8 h which are on average 54% (between 31% and 72%) for the Humalog® Lantus® control and 15% (between 6% and 28%) for Polysaccharide 4/Humalog®/Lantus®. The presence of Polysaccharide 4 therefore greatly reduces the variability of Lantus® on the drop in blood glucose level.

Example B38: Protocol for Measuring the Pharmacodynamics of the Insulin Solutions Preclinical Studies were Carried Out on Dogs with a View to Evaluating 6 Compositions According to the Invention The hypoglycemic effects of these compositions were compared to injections carried out with simultaneous but separate injections of Lantus® at 100 IU/ml (pH 4) and then of a Humalog® prandial insulin at 100 IU/ml.

10 domestic dogs (Beagles) weighing approximately 12 kg are deprived of food for 18 hours before the beginning of the experiment. In the hour preceding the injection of insulin, three blood samples are taken in order to determine the basal level of glucose.

The injection of insulin at a dose of 0.53 IU/kg (unless otherwise mentioned in the examples below) is carried out by subcutaneous injection in the animal's neck, using the Novopen® insulin pen fitted with a 31 G needle.

Blood samples were then taken after 10, 20, 30, 40, 50, 60, 90, 120, 180, 240, 300, 360, 420, 480, 540, 600, 660, 720, 780, 840, 900 and 960 minutes. The first samples are taken via a catheter (up to 180 min), and then directly from the jugular. After taking each sample, the catheter is rinsed with a dilute heparin solution.

A drop of blood is taken to determine the blood glucose level by means of a glucometer. The glucose pharmacodynamics curves are then plotted.

The results obtained are presented in the form of glucose pharmacodynamics curves represented in FIGS. 7 to 12. The Solution of Example B28.

Figure 7:
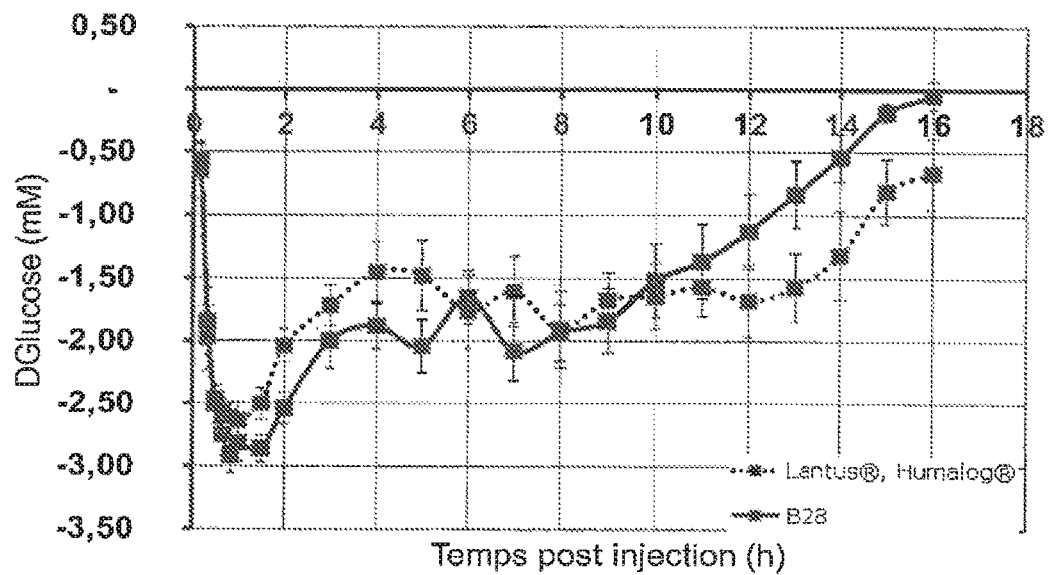
FIGS. 7 to 12 show the results obtained in the form of glucose pharmacodynamics curves. The y-axis represents the D-glucose (expressed in mM) as a function of the time post-injection (expressed in hours).

FIG. 7: Curves of mean+standard deviation of the mean for the sequential administrations of Humalog® (100 IU/ml, 0.13 IU/kg) and Lantus® (100 IU/ml, 0.4 IU/kg) in comparison with a composition according to the invention described in example B28 (0.53 IU/kg).

FIG. 7 shows the curves of means of drop in blood glucose level and also the standard deviations of the mean for the dogs tested for each formulation. The two curves are similar up to 12 hours with a rapid drop in blood glucose level indicating that the polysaccharide does not influence the rapid effect of Humalog®, a marked return between the peak due to Humalog® and the plateau due to glargine and then a glargine plateau up to 12 h indicating that the basal effect of glargine is indeed preserved.

The Solution of Example B27.

Figure 8:
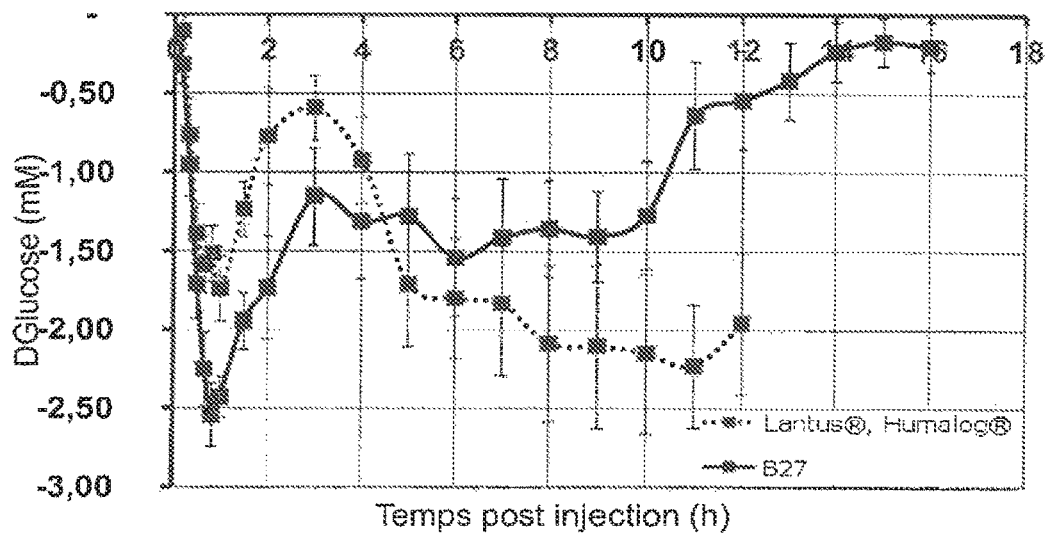

FIG. 8: Curves of mean+standard deviation of the mean for the sequential administrations of Humalog® (100 IU/ml, 0.13 IU/kg) and Lantus® (100 IU/ml, 0.4 IU/kg) in comparison with a composition according to the invention described in example B27 (0.47 IU/kg).

FIG. 8 shows the curves of means of drop in blood glucose level and also the standard deviations of the mean for the dogs tested for each formulation. In this comparison, the dose of basal insulin (Lantus®) is identical, whereas the dose of Humalog® is two times lower for the combination, compared with the control. The drop in glucose is greater in the case of formulation B27 compared with the control, even though this control contains twice as much Humalog®. On the other hand, the duration of the plateau is shorter in the case of the combination compared with the control. This indicates that, in this composition, part of the Lantus® is not precipitated upon injection and acts with Humalog®.

The Solution of Example B29.

Figure 9:
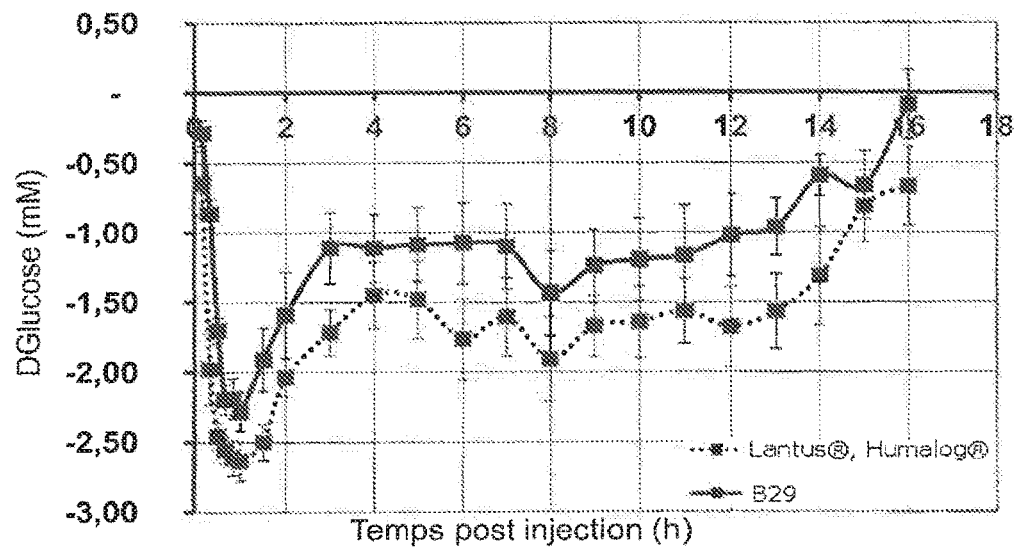

FIG. 9: Curves of mean+standard deviation of the mean for the sequential administrations of Humalog® (100 IU/ml, 0.13 IU/kg) and Lantus® (100 IU/ml, 0.4 IU/kg) in comparison with a composition according to the invention described in example B29 (0.53 IU/kg).

FIG. 9 shows the curves of means of drop in blood glucose level and also the standard deviations of the mean for the dogs tested for each formulation. The two curves are similar with a rapid drop in blood glucose level indicating that the polysaccharide does not influence the rapid effect of Humalog®, a marked return between the peak due to Humalog® and the plateau due to Lantus® and then a Lantus® plateau up to 13 h indicating that the basal effect of glargine is indeed preserved.

The Solution of Example B31.

Figure 10:
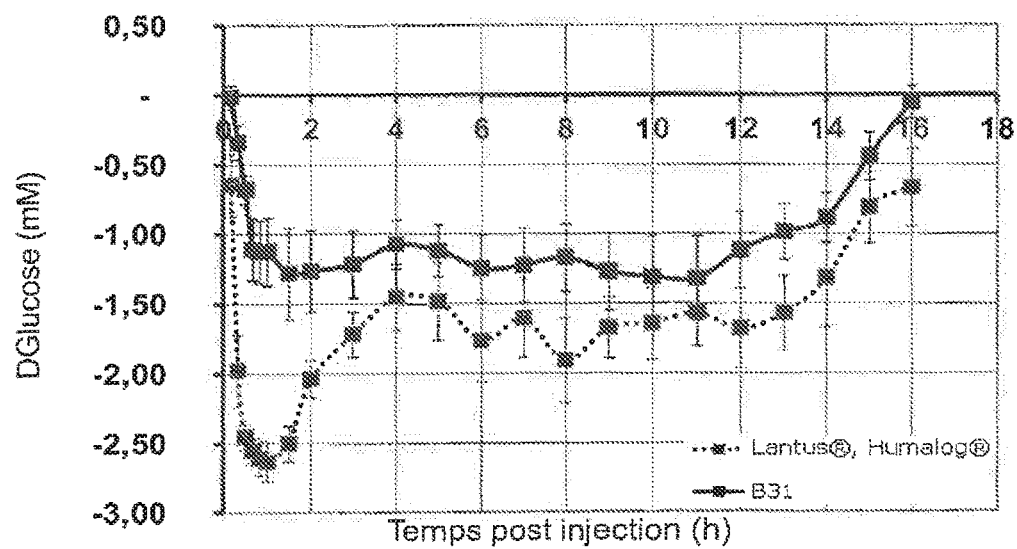

FIG. 10: Curves of mean+standard deviation of the mean for the sequential administrations of Humalog® (100 IU/ml, 0.13 IU/kg) and Lantus® (100 IU/ml, 0.4 IU/kg) in comparison with a composition according to the invention described in example B31 (0.48 IU/kg).

FIG. 10 shows the curves of means of drop in blood glucose level and also the standard deviations of the mean for the dogs tested for each formulation. In this comparison, the dose of basal insulin (Lantus®) is identical, whereas the dose of Humalog® is two times lower for the combination, compared with the control. The drop in glucose is greater in the case of the control compared with the combination corresponding to example B31. This response was expected given the two times lower concentration of Humalog® in the combination compared with the control. Moreover, the duration of the Lantus® plateau is identical in the case of the combination compared with the control. This indicates that, in this composition, and by comparison with the composition described in example B29 (FIG. 9), it is possible to modulate the amount of Humalog® in the combination without modifying the basal effect of Lantus®.

The Solution of Example B30.

Figure 11:
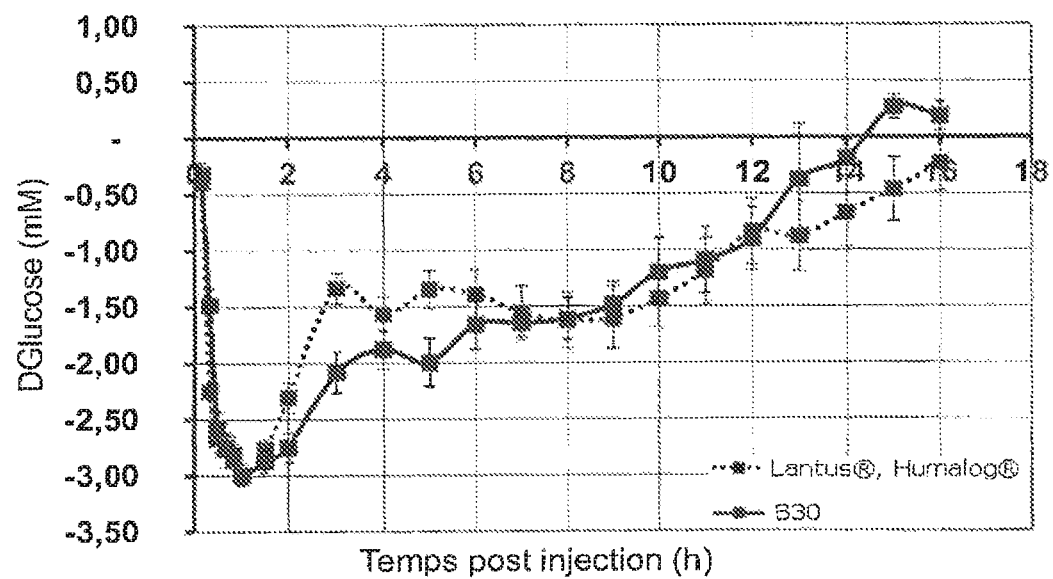

FIG. 11: Curves of mean+standard deviation of the mean for the sequential administrations of Humalog® (100 IU/ml, 0.24 IU/kg) and Lantus® (100 IU/ml, 0.4 IU/kg) in comparison with a composition according to the invention described in example B30 (0.64 IU/kg).

FIG. 11 shows the curves of means of drop in blood glucose level and also the standard deviations of the mean for the dogs tested for each formulation. The two curves are similar with a rapid drop in blood glucose level indicating that the polysaccharide does not influence the rapid effect of Humalog®, a marked return between the peak due to Humalog® and the plateau due to Lantus® and then a Lantus® plateau up to 10 h indicating that the basal effect of glargine is indeed preserved.

The Solution of Example B32.

Figure 12:
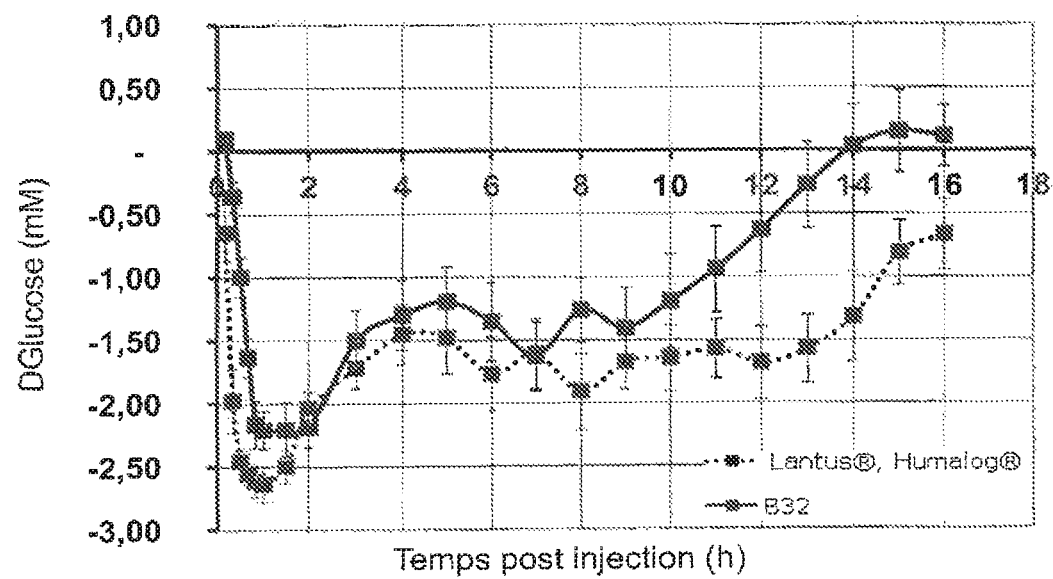

FIG. 12: Curves of mean+standard deviation of the mean for the sequential administrations of Humalog® (100 IU/ml, 0.13 IU/kg) and Lantus® (100 IU/ml, 0.4 IU/kg) in comparison with a composition according to the invention described in example B32 (0.53 IU/kg).

FIG. 12 shows the curves of means of drop in blood glucose level and also the standard deviations of the mean for the dogs tested for each formulation. The two curves are similar up to 10 hours with a rapid drop in blood glucose level indicating that the polysaccharide does not influence the rapid effect of Humalog®, a marked return between the peak due to Humalog® and the plateau due to Lantus® and then a glargine plateau indicating that the basal effect of glargine is preserved up to 10 h.

In conclusion, FIGS. 7 to 12 show that, by modulating the composition of the polysaccharide, the lispro and glargine concentrations, it is possible to obtain profiles identical to a double injection with different proportions of fast-acting insulin and of basal insulin. It is also possible to modulate the duration of the basal insulin without affecting the fast-acting insulin, or to modulate the amount of fast-acting insulin without affecting the effect of the basal insulin.

Examples

Part C: Demonstration of the Properties of the Compositions Comprising a GLP-1 Analog or Derivative According to the Invention Example C1: Solution of GLP-1 Analog Exenatide (Byetta®) at 0.25 mg/ml This solution is a solution of exenatide sold by the company Eli Lilly and Company under the name Byetta@.

Example C2: Solution of GLP-1 Derivative Liraglutide (Victoza®) at 6 mg/ml

This solution is a solution of liraglutide sold by the company Novo Nordisk under the name Victoza®.

Example C3: Solubilization of Lantus® at 100 IU/ml and at pH 7 Using a Substituted Dextran at the Concentration of 10 mg/ml 20 mg of a substituted dextran chosen from those described in table 1 are accurately weighed out. This lyophilizate is taken up with 2 ml of the insulin glargine solution of example B4 in order to obtain a solution of which the polysaccharide concentration is equal to 10 mg/ml. After mechanical stirring on rollers at ambient temperature, the solution becomes clear. The pH of this solution is 6.3. The pH is adjusted to 7 with a 0.1 N sodium hydroxide solution. This clear solution is filtered through a membrane (0.22 µm) and is then placed at +4° C.

Generalization: Clear solutions of Lantus® at 100 IU/ml and at pH 7 were also obtained with substituted dextran concentrations of 20 and 40 mg/ml according to the same protocol as that described in example C3. Thus, a weight of lyophilized polysaccharide among those described in table 1 is accurately weighed out. This lyophilizate is taken up with the insulin glargine solution of example B4 so as to obtain a solution of which the substituted dextran concentration is 20 or 40 mg/ml as described in table 8. After mechanical stirring on rollers at ambient temperature, the solution becomes clear. The pH of this solution is below 7. The pH is then adjusted to 7 with a 0.1 N sodium hydroxide solution. This clear final solution is filtered through a membrane (0.22 µm) and is then placed at +4° C.

TABLE 8

Preparation of a solution of Lantus ® at 100 IU/ml and at pH 7 using a substituted dextran at a concentration of 10, 20 or 40 mg/ml

| Final concentration of substituted dextran (mg/ml) | Weight of substituted dextran weighed out (mg) | Volume of the insulin glargine solution of example B4 added (ml) |
| --- | --- | --- |
| 10 | 20 | 2 |
| 20 | 40 | 2 |
| 40 | 80 | 2 |

Example C4: Preparation of a Lantus®/Byetta® 70/30 Composition at pH 7.5

0.09 ml of the solution of exenatide of example C1 is added to 0.21 ml of the solution of insulin glargine of example B4, so as to obtain 0.3 ml of a composition of which the pH is 4.5 on mixing. The composition containing 70 IU/ml of Lantus® and 0.075 mg/ml of Byetta® is clear, attesting to the good solubility of Lantus® and of Byetta® under these formulation conditions (pH 4.5). The pH is then adjusted to 7.5 with a 0.1 N sodium hydroxide solution. The composition then becomes cloudy, attesting to the poor solubility of the Lantus®/Byetta® composition at pH 7.5.

Lantus®/Byetta® 70/30 compositions were also prepared at pH 4.5-5.5-6.5-8.5 and 9.5 according to a protocol similar to that described in example C4. For each of these compositions, 0.09 ml of the solution of exenatide of example C1 is added to 0.21 ml of the solution of insulin glargine of example B4, so as to obtain 0.3 ml of a composition of which the pH is 4.5 on mixing. The composition is clear, attesting to the good solubility of Lantus® and of Byetta® under these formulation conditions (pH 4.5). The pH is adjusted to 5.5 or 6.5 or 8.5 or 9.5 with a 0.1 N sodium hydroxide solution. After adjustment of the pH, the composition at 5.5 is slightly cloudy, the compositions at 6.5-7.5 and 8.5 are very cloudy and the composition at pH 9.5 is clear. These compositions are placed at +4° C. for 48 h. After 48 h at +4° C., only the composition at pH 4.5 remains clear. The visual appearance after 48 h of the Lantus®/Byetta® 70/30 compositions at various pHs is summarized in table 9.

TABLE 9

Visual appearance after 48 h of the Lantus ®/
Byetta ® 70/30 compositions at various pHs
Lantus ®/Byetta ® 70/30 compositions at various pHs

| pH | Visual appearance at t = 48 h |
| --- | --- |
| 4.5 | Clear |
| 5.5 | Presence of a precipitate |
| 6.5 | Presence of a precipitate |
| 7.5 | Presence of a precipitate |
| 8.5 | Presence of a precipitate |
| 9.5 | Presence of a precipitate |

Example C5: Preparation of a Lantus®®/Victoza® 70/30 Composition at pH 7.5

0.09 ml of the solution of liraglutide of example C2 is added to 0.21 ml of the solution of insulin glargine of example B4, so as to obtain 0.3 ml of a composition of which the pH is 7 on mixing. The composition containing 70 IU/ml of glargine and 1.8 mg/ml of exenatide is cloudy, attesting to the poor solubility of the Lantus®/Victoza® composition under these formulation conditions. The pH is adjusted to 7.5 with a 0.1 N sodium hydroxide solution. After adjustment of the pH, the composition remains cloudy. This composition is placed at +4° C. for 48 h.

Lantus®/Victoza® 70/30 compositions were also prepared at pH 4.5-5.5-6.5-8.5 and 9.5 according to a protocol similar to that described in example C5. For each of these compositions, 0.09 ml of the solution of liraglutide of example C1 is added to 0.21 ml of the solution of insulin glargine of example B4, so as to obtain 0.3 ml of a composition of which the pH is 7. The composition is cloudy, attesting to the poor solubility of the Lantus®/Victoza® composition under these formulation conditions (pH 7). The pH is adjusted to 4.5 or 5.5 or 6.5 with a 0.1 N hydrochloric acid solution or to pH 9.5 with a 0.1 N sodium hydroxide solution. After adjustment of the pH, the compositions at pH 4.5-5.5 and 6.5 are cloudy, attesting to the poor solubility of the Lantus®/Victoza® composition under these formulation conditions. These compositions are placed at +4° C. for 48 h. After 48 h at 4° C., only the composition at pH 9.5 is clear. The visual appearance after 48 h of the Lantus®/Victoza® 70/30 compositions at various pHs is summarized in table 10.

TABLE 10

Visual appearance after 48 h of the Lantus ®/
Victoza ® 70/30 compositions at various pHs
Lantus ®/Victoza ® 70/30 compositions at various pHs

| pH | Visual appearance at t = 48 h |
| --- | --- |
| 4.5 | Presence of a precipitate |
| 5.5 | Presence of a precipitate |
| 6.5 | Presence of a precipitate |
| 7.5 | Presence of a precipitate |
| 8.5 | Presence of a precipitate |
| 9.5 | Clear |

Example C6: Preparation of a Substituted Dextran-Lantus®/Byetta® 70/30 Composition at pH 7

0.09 ml of the solution of exenatide of example C1 is added to 0.21 ml of the solution of substituted dextran/Lantus® prepared in example C3, so as to obtain 0.3 ml of a composition at pH 5.3. The pH is adjusted to 7 with a 0.1 N sodium hydroxide solution. The composition containing 7 mg/ml of polysaccharide, 70 IU/ml of Lantus® and 0.075 mg/ml of Byetta® is clear, attesting to the good solubility of Lantus® and of Byetta® in the presence of the substituted dextran at pH 7. This clear solution is placed at +4° C.

Generalization: Substituted dextran-Lantus®/Byetta® compositions at pH 7 were also prepared at $V_{Lantus}/V_{Byetta}$ volume ratios of 90/10, 50/50, 30/70 and 10/90 according to the same protocol as that described in example C6. Thus, one volume $V_{Byetta}$ of the solution of exenatide of example C1 is added to one volume $V_{Lantus}$ of the solution of substituted dextran/Lantus® prepared in example C3, so as to obtain a composition of which the pH is adjusted to 7 with a 0.1 N sodium hydroxide solution. The compositions obtained (see table 11) are clear, attesting to the good solubility of Lantus® and of Byetta® in the presence of a substituted dextran at pH 7. These clear solutions are placed at +4° C.

Example C7: Preparation of a Substituted Dextran-Lantus®/Byetta® 100/50 Composition at pH 7

0.150 ml of the solution of exenatide of example C1 are lyophilized, and then 0.3 ml of a solution of substituted dextran/Lantus® prepared in example C3 is added to the lyophilizate in order to obtain a composition of which the pH is adjusted to 7 with a 0.1 N sodium hydroxide solution. The composition containing 10 mg/ml of polysaccharide, 100 IU/ml of Lantus® and 0.125 mg/ml of Byetta® is clear, attesting to the good solubility of Lantus® and of Byetta® in the presence of the substituted dextran at pH 7. This clear solution is placed at +4° C.

TABLE 11

Final Lantus ®, substituted dextran and Byetta ® concentrations of the compositions obtained in examples C6 and C7

|  | Lantus ® | | [Polysaccharide No.] | Byetta ® |
|---|---|---|---|---|
|  | IU/ml | mg/ml | (mg/ml) | (mg/ml) |
| 100/50 | 100 | 3.5 | 10 | 0.125 |
| 90/10 | 90 | 3.15 | 9 | 0.025 |
| 70/30 | 70 | 2.45 | 7 | 0.075 |
| 50/50 | 50 | 1.75 | 5 | 0.125 |
| 30/70 | 30 | 1.05 | 3 | 0.175 |

Example C8: Preparation of a Substituted Dextran-Lantus®/Victoza® 70/30 Composition at pH 7

0.09 ml of the solution of liraglutide of example C2 is added to 0.21 ml of the solution of substituted dextran/Lantus® prepared in example C3, so as to obtain 0.3 ml of a composition at pH 7.6. The pH is adjusted to 7 with a 0.1 N hydrochloric acid solution. The composition containing 7 mg/ml of polysaccharide, 70 IU/ml of Lantus® and 1.8 mg/ml of Victoza® is clear, attesting to the good solubility of Lantus® and of Victoza® in the presence of the substituted dextran at pH 7. This clear solution is placed at +4° C.

Generalization: Substituted dextran-Lantus®/Victoza® compositions at pH 7 were also prepared at $V_{Lantus}/V_{Victoza}$ volume ratios of 90/10, 50/50, 30/70 and 90/10 according to the same protocol as that described in example C6. Thus, one volume $V_{Victoza}$ of the solution of liraglutide of example C2 is added to one volume $V_{Lantus}$ of the solution of substituted dextran/Lantus® prepared in example B3, so as to obtain a composition of which the pH is adjusted to 7 with a 0.1 N hydrochloric acid solution.

The compositions obtained (see table 12) are clear, attesting to the good solubility of Lantus® and of Victoza® in the presence of a substituted dextran at pH 7. These clear solutions are placed at +4° C.

Example C9: Preparation of a Substituted Dextran-Lantus®/Victoza® 100/50 Composition at pH 7

0.150 ml of the solution of liraglutide of example C2 are lyophilized, and then 0.3 ml of a solution of substituted dextran/Lantus® prepared in example C3 is added to the lyophilizate in order to obtain a composition of which the pH is adjusted to 7 with a 0.1 N sodium hydroxide solution. The composition containing 10 mg/ml of polysaccharide, 100 IU/ml of Lantus® and 3 mg/ml of Victoza® is clear, attesting to the good solubility of Lantus® and of Victoza® in the presence of the substituted dextran at pH 7. This clear solution is placed at +4° C.

TABLE 12

Final Lantus ®, substituted dextran and Victoza ® concentrations of the compositions obtained in examples C8 and C9

|  | Lantus ® | | [polysaccharide No.] | Victoza ® |
|---|---|---|---|---|
|  | IU/ml | mg/ml | (mg/ml) | (mg/ml) |
| 100/50 | 100 | 3.5 | 10 | 3 |
| 90/10 | 90 | 3.15 | 9 | 0.6 |
| 70/30 | 70 | 2.45 | 7 | 1.8 |
| 50/50 | 50 | 1.75 | 5 | 3 |
| 30/70 | 30 | 1.05 | 3 | 4.2 |

Example C10: Preparation of a Substituted Dextran-Lantus®/Apidra®/Byetta® 60/20/20 Composition at pH 7

20 mg of lyophilized Polysaccharide 4 described in example A3 are accurately weighed out. This lyophilizate is taken up with 2 ml of the solution of insulin glargine of example B4. After mechanical stirring on rollers at ambient temperature, the solution becomes clear. The pH of this solution is 6.3. The pH is adjusted to 7 with a 0.1 N sodium hydroxide solution. 0.2 ml of the solution of exenatide of example C1 and 0.2 ml of the solution of insulin glulisine of example B3 are added to 0.6 ml of the substituted dextran/Lantus® solution previously prepared so as to obtain 1 ml of a composition at pH 7. The composition containing 6 mg/ml of polysaccharide, 60 IU/ml of Lantus®, 20 IU/ml of Apidra® and 0.05 mg/ml of Byetta® is clear, attesting to the good solubility of Lantus®, of Apidra® and of Byetta® in the presence of the substituted dextran at pH 7. This clear solution is filtered through a (0.22 µm) membrane and then placed at +4° C.

Example C11: Precipitation of Lantus®

0.250 ml of Lantus® is added to 0.5 ml of a solution of PBS (Phosphate Buffered Saline) containing 20 mg/ml of BSA (Bovine Serum Albumin). The PBS/BSA mixture simulates the composition of the subcutaneous medium.

A precipitate appears, which is in good agreement with the mechanism via which Lantus® functions (precipitation upon injection due to the increase in pH).

Centrifugation at 4000 rpm is carried out in order to separate the precipitate from the supernatant. Lantus® is then assayed in the supernatant. It results from this that 90% of Lantus® is found in a precipitated form.

Example C12: Precipitation of a Substituted Dextran/Lantus® Composition 0.250 ml of substituted dextran/Lantus® solution prepared in example C3 is added to 0.5 ml of a solution of PBS containing 20 mg/ml of BSA. The PBS/BSA mixture simulates the composition of the subcutaneous medium. A precipitate appears.

Centrifugation at 4000 rpm is carried out in order to separate the precipitate from the supernatant. Lantus® is then assayed in the supernatant. It results from this that 90% of Lantus® is found in a precipitated form. This percentage precipitation of Lantus® is identical to that obtained for the control described in example C11.

Example C13: Precipitation of a Substituted Dextran-Lantus®/Byetta® Composition 0.250 ml of the substituted dextran-Lantus®/Byetta® composition prepared in example C6 is added to 0.5 ml of a solution of PBS containing 20 mg/ml of BSA. The PBS/BSA mixture simulates the composition of the subcutaneous medium. A precipitate appears.

Centrifugation at 4000 rpm is carried out in order to separate the precipitate from the supernatant. Lantus® and Byetta® are then assayed in the supernatant. The percentage precipitation of Lantus® is similar to the control described in example C11.

Example C14: Precipitation of a Substituted Dextran-Lantus®/Victoza® 70/30 Composition 0.250 ml of the substituted dextran-Lantus®/Victoza® composition prepared in example C8 is added to 0.5 ml of a solution of PBS containing 20 mg/ml of BSA (bovine serum albumin). The PBS/BSA mixture simulates the composition of the subcutaneous medium. A precipitate appears.

Centrifugation at 4000 rpm is carried out in order to separate the precipitate from the supernatant. Lantus® and Victoza® are then assayed in the supernatant. The percentage precipitation of Lantus® is similar to the control described in example C11.

Example C15: Precipitation of Various Compositions while Varying the Nature of the Substituted Dextran Other tests under the same conditions as those of examples C13 and C14 were carried out in the presence of other dextrans.

Results with at most 20 mg/ml of substituted dextran and a Lantus®/Byetta® 70/30 composition are collated in table 13 below. It is observed that the solubilization and the precipitation of Lantus® are preserved.

TABLE 13

Results of the solubilization and precipitation tests obtained with at most 20 mg/ml of substituted dextran and a Lantus ®/Byetta ® 70/30 composition

| Polysaccha-ride No. | Solubilization Lantus ®/ Byetta ® 70/30 | Percentage precipitation of Lantus ® |
|---|---|---|
| 1 | Yes | 94 |
| 2 | Yes | 96 |
| 5 | Yes | 88 |
| 7 | Yes | 95 |
| 10 | Yes | Not measured |
| 11 | Yes | 81 |
| 14 | Yes | Not measured |
| 16 | Yes | 96 |
| 26 | Yes | 81 |
| 27 | Yes | 96 |
| 28 | Yes | 96 |
| 29 | Yes | 95 |

Results with at most 20 mg/ml of substituted dextran and various Lantus®/Byetta® compositions are collated in table 14 below. It is observed that the solubilization and the precipitation of Lantus® are preserved.

TABLE 14

Results of the solubilization and precipitation tests obtained with at most 20 mg/ml of substituted dextran and various Lantus ®/Byetta ® compositions

| Polysaccha-ride No. | Ratio Lantus ®/ Byetta ® | Solubilization Lantus ®/ Byetta ® | Percentage precipitation of Lantus ® |
|---|---|---|---|
| 4 | 100/50 | Yes | 95 |
| 4 | 90/10 | Yes | 94 |
| 4 | 70/30 | Yes | 95 |
| 4 | 50/50 | Yes | 90 |
| 4 | 30/70 | Yes | 82 |
| 8 | 100/50 | Yes | 96 |
| 8 | 90/10 | Yes | 94 |
| 8 | 70/30 | Yes | 96 |
| 8 | 50/50 | Yes | 90 |
| 8 | 30/70 | Yes | 81 |

Results with at most 40 mg/ml of substituted dextran and a Lantus®/Victoza® 70/30 composition are collated in table 15 below. It is observed that the solubilization and the precipitation of Lantus® are preserved.

TABLE 15

Results of the solubilization and precipitation tests obtained with at most 40 mg/ml of substituted dextran and a Lantus ®/Victoza ® 70/30 composition

| Polysaccha-ride No. | Solubilization Lantus ®/ Victoza ® 70/30 | Percentage precipitation of Lantus ® |
|---|---|---|
| 1 | Yes | 95 |
| 2 | Yes | 97 |
| 5 | Yes | Not measured |
| 7 | Yes | 97 |
| 10 | Yes | Not measured |
| 11 | Yes | Not measured |
| 14 | Yes | 90 |
| 16 | Yes | 97 |
| 26 | Yes | 74 |
| 27 | Yes | 96 |
| 28 | Yes | 95 |
| 29 | Yes | 94 |

Results with at most 20 mg/ml of substituted dextran and various Lantus®/Victoza® compositions are collated in table 16 below. It is observed that the solubilization and the precipitation of Lantus® are preserved.

TABLE 16

Results of the solubilization and precipitation tests obtained with at most 20 mg/ml of substituted dextran and various Lantus ®/Victoza ® compositions

| Polysaccha-ride No. | Ratio Lantus ®/ Victoza ® | Solubilization Lantus ®/ Victoza ® | Percentage precipitation of Lantus ® |
|---|---|---|---|
| 4 | 90/10 | Yes | 94 |
| 4 | 70/30 | Yes | Not measured |
| 4 | 50/50 | Yes | 90 |
| 4 | 30/70 | Yes | 86 |
| 8 | 100/50 | Yes | 93 |
| 8 | 90/10 | Yes | 95 |
| 8 | 70/30 | Yes | 98 |
| 8 | 50/50 | Yes | 89 |
| 8 | 30/70 | Yes | 85 |

Example C16: Precipitation of a Substituted Dextran-Lantus®/Apidra®/Byetta® 60/20/20 Composition at pH 7

0.250 ml of the substituted dextran-Lantus®/Apidra®/Byetta® composition prepared in example C10 is added to 0.5 ml of a solution of PBS containing 20 mg/ml of BSA. The PBS/BSA mixture simulates the composition of the subcutaneous medium. A precipitate appears.

Centrifugation at 4000 rpm is carried out in order to separate the precipitate from the supernatant. Lantus® is then assayed in the supernatant. The percentage precipitation of Lantus® is similar to the control described in example C11.

II—Hydrophobized Anionic Polymers and Corresponding Compositions

Part A: Synthesis of the Hydrophobized Anionic Polymers

TABLE II-1a list of the hydrophobized anionic polymers exemplified (II-AA1 and II-AB1-II-AB3)
II - Hydrophobized anionic polymers and corresponding compositions
Part A: Synthesis of the hydrophobized anionic polymers

| Hydrophobized anionic polymer No. | II-AA1 | II-AB1 |
|---|---|---|
| Formula | X | V |
| Anionic backbone | (dextran-type structure) | (glycerol-type structure) |
| —$R_5$ (Degree of substitution) | n/a | n/a |
| —R' (Degree of substitution) | (f-[A]-COOH) structure, 1.06 | (f-[A]-COOH) structure, 1.26 |
| or -g-[B]-k-[E]-o-[Hy] | (ethylenediamine-diacyl structure), 0.11 | (cholesterol-leucine structure), 0.04 |

TABLE II-1a-continued list of the hydrophobized anionic polymers exemplified (II-AA1 and II-AB1-II-AB3)
II - Hydrophobized anionic polymers and corresponding compositions
Part A: Synthesis of the hydrophobized anionic polymers

| Hydrophobized anionic polymer No. | II-AB2 | II-AB3 |
|---|---|---|
| Formula | V | V |
| Anionic backbone | [structure with R'] | [structure with R'] |
| —R₅ (Degree of substitution) | n/a | n/a |
| —R' (Degree of substitution) | (f-[A]-COOH) [glycolic acid structure] 1.25 or -g-[B]-k-[E]-o-[Hy] [structure with aspartate diester] 0.05 | (f-[A]-COOH) [glycolic acid structure] 1.00 or -g-[B]-k-[E]-o-[Hy] [structure with ethylenediamine amide] 0.1 |

TABLE II-1b list of the hydrophobized anionic polymers exemplified (II-AB4-II-AB7)

| Hydrophobized anionic polymer No. | II-AB4 | II-AB5 |
|---|---|---|
| Formula | V | V |
| Anionic backbone | [structure with R'] | [structure with R'] |
| —R₅ (Degree of substitution) | n/a | n/a |
| —R' (Degree of substitution) | (f-[A]-COOH) [glycolic acid structure] 1.20 | (f-[A]-COOH) [glycolic acid structure] 1.26 |

TABLE II-1b-continued
list of the hydrophobized anionic polymers exemplified (II-AB4-II-AB7)
| or -g-[B]-k-[E]-o-[Hy] | or -g-[B]-k-[E]-o-[Hy] |
|---|---|
| 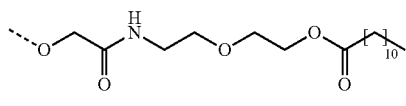 0.1 | 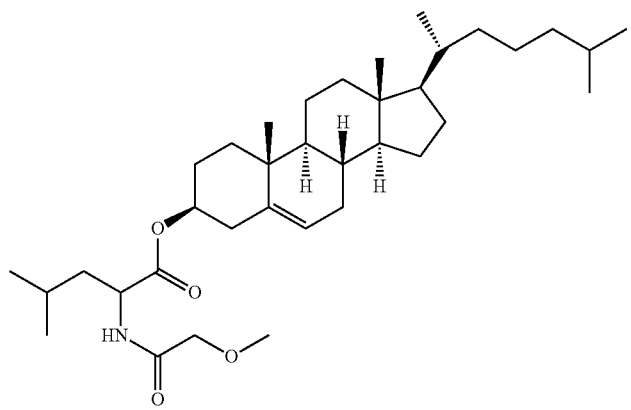 0.04 |
| Hydrophobized anionic polymer No. | II-AB6 | II-AB7 |
|---|---|---|
| Formula | V | V |
| Anionic backbone | 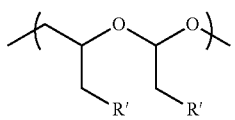 | 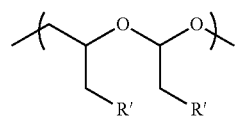 |
| —$R_5$ (Degree of substitution) | n/a | n/a |
| —R' (Degree of substitution) | (f-[A]-COOH) 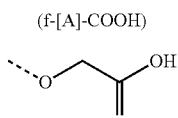 1.20 | (f-[A]-COOH) 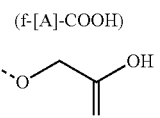 1.26 |
| | or -g-[B]-k-[E]-o-[Hy] 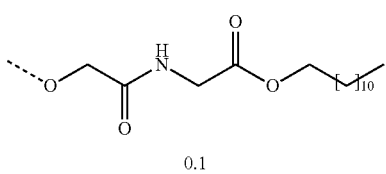 0.1 | or -g-[B]-k-[E]-o-[Hy] 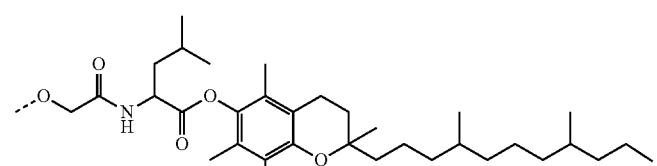 0.04 |

TABLE II-1c list of the hydrophobized anionic polymers exemplified (II-AB8-II-AB10)

| Hydrophobized anionic polymer No. | II-AB8 | II-AB9 |
|---|---|---|
| Formula | V | V |
| Anionic backbone | (polymer structure with R') | (polymer structure with R') |
| —$R_5$ (Degree of substitution) | n/a | n/a |
| —R' (Degree of substitution) | (f-[A]-COOH) — carboxymethyl ether, 1.20 | (f-[A]-COOH) — carboxymethyl ether, 1.25 |
| | or -g-[B]-k-[E]-o-[Hy] — phenylalanine hexyl ester amide, 0.1 | or -g-[B]-k-[E]-o-[Hy] — aspartate dioctyl ester amide, 0.05 |

| Hydrophobized anionic polymer No. | II-AB10 |
|---|---|
| Formula | V |
| Anionic backbone | (polymer structure with R') |
| —$R_5$ (Degree of substitution) | n/a |
| —R' (Degree of substitution) | (f-[A]-COOH) — carboxymethyl ether, 1.10 |
| | or -g-[B]-k-[E]-o-[Hy] — phenylalanine isotridecyl ester amide, 0.20 |

Example II-AA1: Sodium Pullulanmethylcarboxylate Modified with N-(2-aminoethyl)dodecanamide Hydrophobized Anionic Polymer II-AA1

N-(2-Aminoethyl)dodecanamide is obtained according to the process described in U.S. Pat. No. 2,387,201 (Weiner, N; et al.) from the methyl ester of dodecanoic acid (Sigma) and ethylenediamine (Roth).

8 g (i.e. 148 mmol of hydroxyl functions) of pullulan having a weight-average molar mass of approximately 100 kg/mol (Fluka) are dissolved in water. 15 ml of 10 N NaOH (148 mmol NaOH) are added to this solution. The mixture is brought to 35° C., then 23 g (198 mmol) of sodium chloroacetate are added. The temperature of the reaction medium is gradually brought to 60° C. and then maintained at 60° C. for 100 minutes. The reaction medium is diluted with water, neutralized with acetic acid and purified by ultrafiltration on a 5 kD PES membrane against 6 volumes of water. The final solution is assayed by dry extract to determine the polymer concentration, and then assayed by acid/base titration in 50/50 (V/V) water/acetone to determine the degree of substitution with sodium methylcarboxylate.

According to the dry extract: [polymer]=31.5 mg/g

According to the add/base titration: the degree of substitution with sodium methylcarboxylate is 1.17 per monomer unit.

The sodium pullulanmethylcarboxylate solution is passed over a Purolite resin (anionic) to obtain pullulanmethylcarboxylic add, which is then lyophilized for 18 hours.

2 g of pullulanmethylcarboxylic acid (10 mmol of methylcarboxylic acid functions) are dissolved in DMF at 30 g/l and then cooled to 0° C. Once the polymer solution is at 0° C., 1.1 g (11 mmol) of NMM and 1.2 g (11 mmol) of EtOCOCl are then added. After reaction for 10 min, 0.2 g of N-(2-aminoethyl)dodecanamide (0.9 mmol) is introduced and the medium is brought to 30° C. over the course of 90 minutes. An aqueous solution of imidazole at 600 g/l and 40 ml of water are added and the medium is then heated to 50° C. After stirring for 1 h 30 min at 50° C., the solution obtained is ultrafiltered through a 10 kD PES membrane against 0.9% NaCl, 0.01 N sodium hydroxide and water. The solution is lyophilized and analyzed by 1H NMR in D20 to determine the degree of substitution with methylcarboxylate modified with N-(2-aminoethyl)dodecanamide.

According to the 1H NMR: the degree of substitution with methylcarboxylate modified with N-(2-aminoethyl)dodecanamide is 0.11.

Example II-AB1: Polyacetal Methylcarboxylate Modified with Cholesteryl Leucinate Hydrophobized Anionic Polymer II-AB1

Via a process similar to that described in *Biomacromolecules* 2005, 6, 2659-2670, poly(1-hydroxymethylethylene hydroxymethylformal) is synthesized from a dextran having a weight-average molar mass of 5 kg/mol (Pharmacosmos). Via a process similar to that described in example II-AA1, a poly(1-hydroxymethylethylene hydroxymethylformal) functionalized with a degree of substitution with sodium methylcarboxylate of 1.3 per monomer unit is obtained. Via a process similar to that described in example II-AA1, a poly(l-hydroxymethylethylene hydroxymethylformal) sodium methylcarboxylate modified with cholesteryl leucinate, with a degree of substitution with methylcarboxylate modified with cholesteryl leucinate of 0.04, is obtained.

Example II-AB2: Polyacetal Methylcarboxylate Modified with Dilauryl Aspartate Hydrophobized Anionic Polymer II-AB2

Dilauryl aspartate, para-toluenesulfonic acid salt, is prepared from dodecanol and aspartic acid according to the process described in U.S. Pat. No. 4,826,818 (Kenji M., et al.).

Via a process similar to that described in example II-AB1, a poly(1-hydroxymethylethylene hydroxymethylformal) sodium methylcarboxylate modified with dilauryl aspartate, with a degree of substitution with sodium methylcarboxylate of 1.25 and a degree of substitution with methylcarboxylates modified with dilauryl aspartate of 0.05, is obtained.

Example II-AB3: Polyacetal Methylcarboxylate Modified with N-(2-aminoethyl)dodecanamide Hydrophobized Anionic Polymer II-AB3

N-(2-Aminoethyl)dodecanamide is obtained according to the process described in U.S. Pat. No. 2,387,201 (Weiner et al.) from the methyl ester of dodecanoic acid (Sigma) and ethylenediamine (Roth).

Via a process similar to that described in Biomacromolecules 2005, 6, 2659-2670, poly(1-hydroxymethylethylene hydroxymethylformal) is synthesized from a dextran having a weight-average molar mass of 10 kg/mol (Pharmacosmos).

Via a process similar to that described in example II-AB1, a poly(1-hydroxymethylethylene hydroxymethylformal) sodium methylcarboxylate modified with N-(2-aminoethyl) dodecanamide, with a degree of substitution with sodium methylcarboxylate of 1.0 and a degree of substitution with methylcarboxylates modified with N-(2-aminoethyl)dodecanamide of 0.1, is obtained.

Example II-AB4: Polyacetal Methylcarboxylate Modified with 2-(2-aminoethoxy)ethyl dodecanoate Hydrophobized Anionic Polymer II-AB4

2-(2-Aminoethoxy)ethyl dodecanoate, para-toluenesulfonic acid salt, is obtained according to the process described in U.S. Pat. No. 4,826,818 (Kenji M., et al.).

Via a process similar to that described in example II-AB1, a poly(1-hydroxymethylethylene hydroxymethylformal) sodium methylcarboxylate modified with 2-(2-aminoethoxy)ethyl dodecanoate, with a degree of substitution with sodium methylcarboxylate of 1.2 and a degree of substitution with methylcarboxylates modified with 2-(2-aminoethoxy)ethyl dodecanoate of 0.1, is obtained.

Example II-AB5: Polyacetal Methylcarboxylate Modified with Cholesteryl 2-aminoethoxy)carbamate Hydrophobized Anionic Polymer II-AB5

Cholesteryl 2-aminoethoxy)carbamate, hydrochloric acid salt, is prepared according to the process described in application WO2010053140 (Akiyoshi K., et al.).

Via a process similar to that described in example II-AB1, a poly(1-hydroxymethylethylene hydroxymethylformal) sodium methylcarboxylate modified with cholesteryl 2-aminoethoxy)carbamate, with a degree of substitution with sodium methylcarboxylate of 1.26 and a degree of substitution with methylcarboxylates modified with cholesteryl 2-aminoethoxy)carbamate of 0.04, is obtained.

Example II-AB6: Polyacetal Methylcarboxylate Modified with Lauryl Glycinate

Hydrophobized Anionic Polymer II-AB6

Lauryl glycinate, para-toluenesulfonic acid salt, is prepared from dodecanol and glycine according to the process described in U.S. Pat. No. 4,826,818 (Kenji M., et al.).

Via a process similar to that described in example II-AB3, a poly(1-hydroxymethylethylene hydroxymethylformal) sodium methylcarboxylate modified with lauryl glycinate, with a degree of substitution with sodium methylcarboxylate of 1.2 and a degree of substitution with methylcarboxylates modified with lauryl glycinate of 0.1, is obtained.

Example II-AB7: Polyacetal Methylcarboxylate Modified with (±)α-tocopheryl leucinate Hydrophobized Anionic Polymer II-AB7

(±)α-Tocopheryl leucinate, hydrochloric acid salt, is obtained according to the process described in the publication by Takata, J et al., Journal of Pharmaceutical Sciences 1995, 84(1), 96-100.

Via a process similar to that described in example II-AB1, a poly(1-hydroxymethylethylene hydroxymethylformal) sodium methylcarboxylate modified with (±)α-tocopheryl leucinate, with a degree of substitution with sodium methylcarboxylate of 1.26 and a degree of substitution with methylcarboxylates modified with (±)α-tocopheryl leucinate of 0.04, is obtained.

Example II-AB8: Polyacetal Methylcarboxylate Modified with Octanoyl Phenylalaninate Hydrophobized Anionic Polymer II-AB8

Octanoyl phenylalaninate, para-toluenesulfonic acid salt, is prepared from 1-octanol and L-phenylalanine according to the process described in U.S. Pat. No. 4,826,818 (Kenji M., et al.).

Via a process similar to that described in example II-AB3, a poly(1-hydroxymethylethylene hydroxymethylformal) sodium methylcarboxylate modified with octanoyl phenylalaninate, with a degree of substitution with sodium methylcarboxylate of 1.2 and a degree of substitution with methylcarboxylates modified with octanoyl phenylalaninate of 0.1, is obtained.

Example II-AB9: Polyacetal Methylcarboxylate Modified with Didecyl Aspartate Hydrophobized Anionic Polymer II-AB9

Didecyl aspartate, para-toluenesulfonic acid salt, is prepared from dodecanol and aspartic acid according to the process described in U.S. Pat. No. 4,826,818 (Kenji M., et al.).

Via a process similar to that described in example II-AB3, a poly(1-hydroxymethylethylene hydroxymethylformal) sodium methylcarboxylate modified with didecyl aspartate, with a degree of substitution with sodium methylcarboxylate of 1.25 and a degree of substitution with methylcarboxylates modified with didecyl aspartate of 0.05, is obtained.

Example II-AB10: Polyacetal Methylcarboxylate Modified with 3,7-dimethyloctanoyl phenylalaninate Hydrophobized Anionic Polymer II-AB10

3,7-Dimethyloctanoyl phenylalaninate, para-toluenesulfonic acid salt, is prepared from 3,7-dimethyloctan-1-ol and L-phenylalanine according to the process described in U.S. Pat. No. 4,826,818 (Kenji et al.).

Via a process similar to that described in example II-AB1, a poly(1-hydroxymethylethylene hydroxymethylformal) sodium methylcarboxylate modified with 3,7-dimethyloctanoyl phenylalaninate, with a degree of substitution with sodium methylcarboxylate of 1.1 and a degree of substitution with methylcarboxylates modified with 3,7-dimethyloctanoyl phenylalaninate of 0.2, is obtained.

Comparative Example II-AC1: Sodium Dextranmethylcarboxylate Functionalized with Cholesteryl Leucinate Polymer II-AC1

According to the process described in patent application WO 2012/153070, a sodium dextranmethylcarboxylate synthesized from a dextran having a weight-average molar mass of 1 kg/mol (Pharmacosmos) is functionalized with cholesteryl leucinate.

The degree of substitution with sodium methylcarboxylate is 1.60.

The degree of substitution with methylcarboxylates functionalized with cholesteryl leucinate is 0.05.

Part B: Demonstration of the Properties of the Compositions According to the Invention

Example II-B1: 100 IU/Ml Solution of Fast-Acting Insulin Analog (NovoLog®)

This solution is a commercial solution of insulin aspart sold by the company NOVO NORDISK under the name NovoLog® in the United States of America and Novorapid® in Europe. This product is a fast-acting insulin analog.

Example II-B2: 100 IU/ml Solution of Fast-Acting Insulin Analog (Humalog®)

This solution is a commercial solution of insulin lispro sold by the company ELI LILLY under the name Humalog®. This product is a fast-acting insulin analog.

Example II-B3: 100 IU/ml Solution of Fast-Acting Insulin Analog (Apidra®)

This solution is a commercial solution of insulin glulisine sold by the company SANOFI-AVENTIS under the name Apidra®. This product is a fast-acting insulin analog.

Example II-B4: 100 IU/ml Solution of Slow-Acting Insulin Analog (Lantus®)

This solution is a commercial solution of insulin glargine sold by the company SANOFI-AVENTIS under the name Lantus®. This product is a slow-acting insulin analog.

Example II-B5: 100 IU/ml Solution of Human Insulin (ActRapid®)

This solution is a commercial solution of human insulin from NOVO NORDISK sold under the name ActRapid®. This product is a human insulin.

Example II-B6: Solubilization of Insulin Glargine at 100 IU/ml and at pH 7 Using a Hydrophobized Anionic Polymer A weight of at most 120 mg of a lyophilizate of hydrophobized anionic polymer chosen from those described in table 1 is accurately weighed out. The lyophilizate is taken up with 2 ml of the insulin glargine solution of example II-B4 in order to obtain a solution of which the hydrophobized anionic polymer concentration is at most 60 mg/ml. After mechanical stirring on rollers at ambient temperature, the solution becomes clear. The pH of this solution is approximately 6.3. The pH is adjusted to 7 with a 0.1 N sodium hydroxide solution. This clear solution is filtered through a membrane (0.22 µm) and is then placed at +4° C.

The solubilization test according to the protocol above was carried out with various hydrophobized anionic polymers. These solutions are referenced in table 2.

TABLE II-2

Solutions according to example II-B6 with the hydrophobized anionic polymers

| Solution example II-B6 | Hydrophobized anionic polymer | $C_{hydrophobized\ anionic\ polymer}$ (mg/ml) | $C_{insulin\ glargine}$ (IU/ml) |
| --- | --- | --- | --- |
| II-B6(a) | II-AA1 | 60 | 100 |
| II-B6(b) | II-AB1 | 10 | 100 |
| II-B6(c) | II-AB2 | 10 | 100 |
| II-B6(d) | II-AB3 | 10 | 100 |
| II-B6(e) | II-AB4 | 10 | 100 |
| II-B6(f) | II-AB5 | 10 | 100 |
| II-B6(g) | II-AB6 | 10 | 100 |
| II-B6(h) | II-AB7 | 10 | 100 |
| II-B6(i) | II-AB8 | 10 | 100 |
| II-B6(j) | II-AB9 | 10 | 100 |
| II-B6(k) | II-AB10 | 10 | 100 |

Example II-B7: Preparation of a Hydrophobized Anionic Polymer II-AB1/Insulin Glargine/Insulin Glulisine Composition with a 75/25 Insulin Glargine/Insulin Glulisine Ratio at pH 7

0.25 ml of the insulin glulisine solution of example II-B3 is added to 0.75 ml of the solution of hydrophobized anionic polymer II-AB1/insulin glargine prepared according to the protocol described in example II-B6(b), so as to form 1 ml of a composition at pH 7. The composition is clear, attesting to the good solubility of the insulin glargine and the insulin glulisine under these formulation conditions. This clear solution is filtered through a 0.22 µm filter and then placed at +4° C.

Example II-B8: Preparation of a Hydrophobized Anionic Polymer II-AB1/Insulin Glargine/Insulin Lispro Composition with a 75/25 Insulin Glargine/Insulin Lispro Ratio at pH 7

0.25 ml of the insulin lispro solution of example B2 is added to 0.75 ml of the solution of anionic polymer II-AB1/insulin glargine prepared according to the protocol described in example II-B6(b), so as to form 1 ml of a composition at pH 7. The composition is clear, attesting to the good solubility of the insulin glargine and of the insulin lispro under these formulation conditions. This clear solution is filtered through a 0.22 µm filter and then placed at +4° C.

Example II-B9: Preparation of a Hydrophobized Anionic Polymer II-AB1/Insulin Glargine/Insulin Aspart Composition with a 75/25 Insulin Glargine/Insulin Aspart Ratio at pH 7

0.25 ml of the insulin aspart solution of example II-B1 is added to 0.75 ml of the solution of anionic polymer II-AB1/insulin glargine prepared in example II-B6(b), so as to form 1 ml of a composition at pH 7. The composition is clear, attesting to the good solubility of the insulin glargine and of the insulin aspart under these formulation conditions. This clear solution is filtered through a 0.22 µm filter and then placed at +4° C.

Example II-B10: Preparation of a Hydrophobized Anionic Polymer II-AB1/Insulin Glargine/Human Insulin Composition with a 75/25 Insulin Glargine/Human Insulin Ratio at pH 7

0.25 ml of the human insulin solution of example II-B5 is added to 0.75 ml of the solution of hydrophobized anionic polymer II-AB1/insulin glargine prepared in example II-B6(b), so as to form 1 ml of a composition at pH 7. The composition is clear, attesting to the good solubility of the insulin glargine and of the human insulin under these formulation conditions. This clear solution is filtered through a 0.22 µm filter and then placed at +4° C.

Example II-B11: Preparation of a Hydrophobized Anionic Polymer II-AB1/Insulin Glargine/Insulin Lispro Composition with a 60/40 Insulin Glargine/Insulin Lispro Ratio at pH 7

0.4 ml of the insulin lispro solution of example II-B2 is added to 0.6 ml of the solution of hydrophobized anionic polymer II-AB1/insulin glargine prepared in example II-B6(b), so as to form 1 ml of a composition at pH 7. The composition is clear, attesting to the good solubility of the insulin glargine and of the insulin lispro under these formulation conditions. This clear solution is filtered through a 0.22 µm filter and then placed at +4° C.

Example II-B12: Preparation of a Hydrophobized Anionic Polymer II-AB1/Insulin Glargine/Insulin Lispro Composition with a 40/60 Insulin Glargine/Insulin Lispro Ratio at pH 7

0.6 ml of the insulin lispro solution of example II-B2 is added to 0.4 ml of the solution of anionic polymer II-AB1/insulin glargine prepared in example II-B6(b), so as to form 1 ml of a composition at pH 7. The composition is clear, attesting to the good solubility of the insulin glargine and of the insulin lispro under these formulation conditions. This clear solution is filtered through a 0.22 µm filter and then placed at +4° C.

Example II-B13: Insulin Glargine Precipitation 1 ml of the insulin glargine solution of example II-B4 is added to 2 ml of a solution of PBS (phosphate buffered saline) containing 20 mg/ml of BSA (bovine serum albumin). The PBS/BSA mixture simulates the composition of the subcutaneous medium. A precipitate appears, which is in good agreement with the mechanism via which insulin glargine works (precipitation upon injection due to increased pH).

Centrifugation at 4000 rpm is carried out in order to separate the precipitate from the supernatant. The insulin glargine is then assayed in the supernatant by reverse-phase liquid chromatography (RP-HPLC). The result is that the insulin glargine is predominantly in a precipitated form.

Example II-B14: Precipitation of a Hydrophobized Anionic Polymer II-AA1/Insulin Glargine Composition 1 ml of hydrophobized anionic polymer II-AA1/insulin glargine solution prepared in example II-B6(a) is added to 2 ml of a solution of PBS containing 20 mg/ml of BSA. The PBS/BSA mixture simulates the composition of the subcutaneous medium. A precipitate appears.

Centrifugation at 4000 rpm is carried out in order to separate the precipitate from the supernatant. The insulin glargine is then assayed in the supernatant by RP-HPLC. The result is that the insulin glargine is predominantly in a precipitated form.

Solubilization and precipitation tests identical to those described in examples II-B6 and II-B14 were carried out with other hydrophobized anionic polymers with a concentration of at most 60 mg/ml for an insulin glargine concentration of 100 IU/ml. The result is that, for all the compositions II-B6(b) to II-B6(k), the insulin glargine is predominantly in a precipitated form after the addition of 1 ml of the composition to 2 ml of a solution of PBS containing 20 mg/ml of BSA. The results are summarized in table 4.

TABLE II-4

Tests for solubilization and precipitation of a hydrophobized anionic polymer/insulin glargine composition

| Hydrophobized anionic polymer | Insulin glargine solubilization | Insulin glargine precipitation |
| --- | --- | --- |
| II-AA1 | Yes | Yes |
| II-AB1 | Yes | Yes |
| II-AB2 | Yes | Yes |
| II-AB3 | Yes | Yes |
| II-AB4 | Yes | Yes |
| II-AB5 | Yes | Yes |
| II-AB6 | Yes | Yes |
| II-AB7 | Yes | Yes |
| II-AB8 | Yes | Yes |
| II-AB9 | Yes | Yes |
| II-AB10 | Yes | Yes |

Example II-B15: Precipitation of a Hydrophobized Anionic Polymer II-AB1/Insulin Glargine/Insulin Lispro Composition with a 75/25 Insulin Glargine/Insulin Lispro Ratio at pH 7

1 ml of the hydrophobized anionic polymer II-AB1/insulin glargine/insulin lispro 75/25 composition prepared according to the protocol of example II-B8 is added to 2 ml of a solution of PBS containing 20 mg/ml of BSA. The PBS/BSA mixture simulates the composition of the subcutaneous medium. A precipitate appears.

Centrifugation at 4000 rpm is carried out in order to separate the precipitate from the supernatant. The insulin glargine is then assayed in the supernatant by RP-HPLC. The result is that the insulin glargine is predominantly in a precipitated form.

Example II-B16: Precipitation of Various Compositions while Varying the Nature of the Hydrophobized Anionic Polymer Other insulin glargine precipitation tests under the same conditions as those of example II-B15 were carried out in the presence of other hydrophobized anionic polymers.

The results are collated in the following table 5, and it is observed that the solubilization and also the precipitation of the insulin glargine are preserved.

TABLE II-5

Tests for solubilization and precipitation of a hydrophobized anionic polymer/insulin glargine/insulin lispro 75/25 composition at pH 7

| Hydrophobized anionic polymer | Solubilization of insulin glargine/ insulin lispro 75/25 | Insulin glargine precipitation |
| --- | --- | --- |
| II-AA1 | Yes | Yes |
| II-AB1 | Yes | Yes |
| II-AB2 | Yes | Yes |
| II-AB3 | Yes | Yes |
| II-AB4 | Yes | Yes |
| II-AB5 | Yes | Yes |
| II-AB6 | Yes | Yes |
| II-AB7 | Yes | Yes |
| II-AB8 | Yes | Yes |
| II-AB9 | Yes | Yes |
| II-AB10 | Yes | Yes |

Example II-B17: Precipitation of Various Compositions while Varying the Nature of the Prandial Insulin Compositions are prepared by mixing 0.75 ml of the hydrophobized anionic polymer II-AB1/insulin glargine solution prepared according to the protocol of example II-B6(b) with 0.25 ml of a prandial insulin, so as to form 1 ml of hydrophobized anionic polymer II-AB1/insulin glargine/prandial insulin composition (containing 7.5 mg/ml of hydrophobized anionic polymer II-AB1, 75 IU/ml of insulin glargine and 25 IU/ml of prandial insulin).

This composition is added to 2 ml of PBS containing 20 mg/ml of BSA. The PBS/BSA mixture simulates the composition of the subcutaneous medium. A precipitate appears. Centrifugation at 4000 rpm is carried out in order to separate the precipitate from the supernatant. The insulin glargine is then assayed in the supernatant by RP-HPLC. The result is that the insulin glargine is predominantly in a precipitated form. In the presence of the 4 prandial insulins tested, the insulin glargine precipitates from the PBS/BSA mixture. The results are collated in table

TABLE II-6

Tests for solubilization and precipitation of a hydrophobized anionic polymer II-AB1/insulin glargine/prandial insulin 75/25 composition

| Nature of the prandial insulin | Solubilization of insulin glargine/ prandial insulin 75/25 | Insulin glargine precipitation |
| --- | --- | --- |
| Insulin glulisine (Apidra ®) | Yes | Yes |
| Insulin aspart (NovoLog ®) | Yes | Yes |

TABLE II-6-continued

Tests for solubilization and precipitation of a hydrophobized anionic polymer II-AB1/insulin glargine/prandial insulin 75/25 composition

| Nature of the prandial insulin | Solubilization of insulin glargine/ prandial insulin 75/25 | Insulin glargine precipitation |
|---|---|---|
| Insulin lispro (Humalog ®) | Yes | Yes |
| Human insulin (ActRapid ®) | Yes | Yes |

Example II-B18: Preparation of a Concentrated Solution of Slow-Acting Insulin Analog (Insulin Glargine)

A commercial solution of insulin glargine sold by the company SANOFI-AVENTIS under the name Lantus® is concentrated by ultrafiltration on a 3 kDa regenerated cellulose membrane (Amicon® Ultra-15 sold by the company Millipore). At the end of this ultrafiltration step, the insulin glargine concentration is assayed in the retentate by RP-HPLC. The final concentration of insulin glargine is then adjusted by adding commercial insulin glargine solution at 100 IU/ml so as to obtain the desired final concentration. This process makes it possible to obtain concentrated solutions of insulin glargine, denoted $C_{insulin\ glargine}$ at various concentrations greater than 100 IU/ml, such as $C_{insulin\ glargine}$=200, 250, 300 and 333 IU/ml. The concentrated solutions are filtered through a 0.22 μm filter and then stored at +4° C.

Example II-B19: Dialysis of a Commercial Solution of Fast-Acting Insulin Analog (Insulin Lispro)

A commercial solution of insulin lispro (example II-B2) sold by the company ELI LILLY under the name Humalog® is dialyzed by ultrafiltration on a 3 kDa regenerated cellulose membrane (Amicon® Ultra-15 sold by the company Millipore). The dialysis is carried out in a 1 mM phosphate buffer at pH 7. At the end of this dialysis step, the concentration $C_{insulin\ lispro\ dialyzed}$ in the retentate is determined by RP-HPLC. The dialyzed solution is stored in a freezer at −80° C.

Example II-B20: Lyophilization of a Solution of Fast-Acting Insulin Analog (Insulin Lispro) in its Commercial Form A volume $V_{Humalog}$ of a solution of fast-acting insulin lispro (example II-B2) at a concentration of 100 IU/ml in its commercial form is placed in a Lyogard® tray sterilized beforehand in an autoclave. The Lyogard® tray is placed in a freezer at −80° C. for approximately 1 h and then lyophilization with the parameters of temperature 20° C. and pressure 0.31 mbar is carried out.

The resulting sterile lyophilizate is stored at ambient temperature.

Example II-B21: Lyophilzation of a Commercial Solution of Fast-Acting Insulin Analog (Insulin Lispro) which has been Dialyzed A volume $V_{Humalog\ dialyzed}$ of a solution of fast-acting insulin lispro obtained according to example II-B19 at a concentration of $C_{insulin\ lispro\ dialyzed}$ is placed in a Lyogard® tray sterilized beforehand in an autoclave. The Lyogard® tray is placed in a freezer at −80° C. for approximately 1 h and then lyophilization with the parameters of temperature 20° C. and pressure 0.31 mbar is carried out.

The resulting sterile lyophilizate is stored at ambient temperature.

Example II-B22: Preparation of a Hydrophobized Anionic Polymer/Insulin Glargine Composition at pH 7, According to a Process Using Concentrated Insulin Glargine in Liquid Form (in Solution) and a Hydrophobized Anionic Polymer in Solid Form (Lyophilized)

A weight $w_{hydrophobized\ anionic\ poly}$ of hydrophobized anionic polymer is accurately weighed out. This lyophilizate is taken up with a volume $V_{insulin\ glargine}$ of a concentrated solution of insulin glargine prepared according to example II-B18 so as to obtain a composition having a hydrophobized anionic polymer concentration $C_{hydrophobized\ anionic\ poly}$ (mg/ml)=$w_{hydrophobized\ anionic\ poly}/V_{insulin\ glargin}$ and an insulin glargine concentration $C_{insulin\ glargine}$ (IU/ml). The solution is opalescent. The pH of this solution is approximately 6.3. The pH is adjusted to 7 by adding concentrated NaOH and then the solution is placed statically in an incubator at 37° C. for approximately 1 hour until complete solubilization is obtained. A volume $V_{hydrophobized\ anionic\ poly/insulin\ glargine}$ of this visually clear solution is placed at +4° C.

Example II-B23: Preparation of a Hydrophobized Anionic Polymer/Insulin Glargine Composition at pH 7, According to a Process Using Insulin Glargine in Liquid Form (in Solution) and a Hydrophobized Anionic Polymer in Liquid Form (in Solution)

Concentrated solutions of m-cresol, glycerol and Tween® 20 are added to a stock solution of hydrophobized anionic polymer at pH 7 which has a concentration Cstock hydrophobized anionic polymer, so as to obtain a solution of hydrophobized anionic polymer having a concentration Cstock hydrophobized anionic polymer/excipients (mg/ml) in the presence of these excipients at contents equivalent to those described in the commercial solution Lantus® in a 10 ml bottle. In a sterile pot, a volume VLantus of a commercial solution of slow-acting insulin glargine sold under the name Lantus® at a concentration of 100 IU/ml is added to a volume Vstock hydrophobized anionic polymer/excipients of a solution of hydrophobized anionic polymer at the concentration $C_{stock\ hydrophobized\ anionic\ polymer/excipients}$ (mg/ml). A cloudiness appears. The pH is adjusted to pH 7 by adding concentrated NaOH and the solution is placed statically in an incubator at 37° C. for approximately 1 hour until complete solubilization is obtained. This visually clear solution is placed at +4° C.

Example II-B24: Preparation of a Concentrated Hydrophobized Anionic Polymer/Insulin Glargine Composition at pH=7, According to a Process for Concentrating a Dilute Composition A dilute hydrophobized anionic polymer/insulin glargine composition at pH 7 described in example II-B23 is concentrated by ultrafiltration on a 3 kDa regenerated cellulose membrane (Amicon® Ultra-15 sold by the company Millipore). At the end of this ultrafiltration step, the retentate is clear and the insulin glargine concentration in the composition is determined by RP-HPLC. If necessary, the insulin glargine concentration in the composition is then adjusted to the desired value by dilution in a solution of excipients m-cresol/glycerol/Tween® 20 having, for each entity, a concentration equivalent to that described in the commercial solution Lantus® (in a 10 ml bottle). This solution at pH 7, which is visually clear, and which has an insulin glargine concentration $C_{insulin\ glargine}$ (IU/ml) and a hydrophobized anionic polymer concentration $C_{hydrophobized\ anionic\ polymer}$ (mg/ml), is placed at +4° C.

Example II-B25: Preparation of a Hydrophobized Anionic Polymer/Insulin Glargine/Insulin Lispro Composition at pH 7, from a Lyophilizate of a Fast-Acting Insulin Lispro in its Commercial Form (Humalog®)

A volume $V_{hydrophobized\ anionic\ polymer/insulin\ glargine}$ of hydrophobized anionic polymer/insulin glargine solution at pH 7 having an insulin glargine concentration $C_{insulin\ glargine}$ (IU/ml) and a hydrophobized anionic polymer concentration $C_{hydrophobized\ anionic\ polymer}$ (mg/ml) prepared according to example II-B22 is added to a lyophilizate of insulin lispro obtained by lyophilization of a volume $V_{insulin\ lispro}$ of which the preparation is described in example II-B20, such that the ratio $V_{hydrophobized\ anionic\ polymer/insulin\ glargine}/V_{insulin\ lispro} = 100/C_{insulin\ lispro}$ is the concentration of insulin lispro (IU/ml) targeted in the composition. The solution is clear. The zinc content of the formulation is adjusted to the desired concentration $C_{zinc}$ (µM) by adding a concentrated solution of zinc chloride. The final pH is adjusted to 7 by adding concentrated NaOH or HCl.

The formulation is clear, attesting to the good solubility of the insulin glargine and of the insulin lispro under these formulation conditions. This solution is filtered through a 0.22 µm filter and placed at +4° C.

Example II-B26: Preparation of a Hydrophobized Anionic Polymer/Insulin Glargine/Insulin Lispro Composition at pH 7, from a Lyophilizate of a Fast-Acting Insulin Lispro Obtained by Dialysis of a Commercial Solution (Humalog®)

A volume $V_{hydrophobized\ anionic\ polymer/insulin\ glargine}$ of hydrophobized anionic polymer/insulin glargine solution, pH 7, having an insulin glargine concentration $C_{insulin\ glargine}$ (IU/ml) and a hydrophobized anionic polymer concentration $C_{hydrophobized\ anionic\ polymer}$ (mg/ml) prepared according to example II-B22 is added to a lyophilizate of insulin lispro obtained by lyophilization of a volume $V_{insulin\ lispro\ dialyzed}$ of which the preparation is described in example II-B21, such that the ratio $V_{hydrophobized\ anionic\ polymer/insulin\ glargine}/V_{insulin\ lispro\ dialyzed} = C_{insulin\ lispro\ dialyzed}/C_{insulin\ lispro}$ where $C_{insulin\ lispro\ dialyzed}$ is the concentration of insulin lispro (IU/ml) obtained at the end of the dialysis of the commercial solution, the step described in example II-B19, and $C_{insulin\ lispro}$ is the concentration of insulin lispro (IU/ml) targeted in the composition. The solution is clear. The zinc content of the formulation is adjusted to the desired concentration $C_{zinc}$ (µM) by adding a concentrated solution of zinc chloride. The final pH is adjusted to 7 by adding concentrated NaOH or HCl.

The formulation is clear, attesting to the good solubility of the insulins glargine and lispro under these formulation conditions. This solution is filtered through a 0.22 µm filter and placed at +4° C.

Example II-B27: Preparation of a Hydrophobized Anionic Polymer II-AB1/Insulin Glargine/Insulin Lispro Composition at pH 7 Having an Insulin Glargine Concentration of 200 IU/ml and an Insulin Lispro Concentration of 66 IU/ml (Percentage Proportion of Insulin: Insulin Glargine/Insulin Lispro 75/25)

A concentrated insulin glargine solution at 200 IU/ml is prepared according to example II-B18. A hydrophobized anionic polymer II-AB1 (15 mg/ml)/insulin glargine 200 IU/ml composition, pH 7, is prepared from a hydrophobized anionic polymer II-AB1 and according to the preparation method described in example II-B22. This hydrophobized anionic polymer II-AB1/insulin glargine 200 IU/ml composition is added to a lyophilizate of insulin lispro obtained by lyophilization of the solution of fast-acting analog derived from the dialysis of a commercial solution, according to the preparation method described in example II-B26. The solution is clear. The zinc content of the formulation is adjusted to the desired concentration by adding a concentrated solution of zinc chloride. The final pH is adjusted to 7 by adding concentrated NaOH or HCl.

The formulation is clear, attesting to the good solubility of the insulins glargine and lispro under these formulation conditions. This solution is filtered through a 0.22 µm filter and placed at +4° C.

Example II-B28: Preparation of a Hydrophobized Anionic Polymer II-AB1/Insulin Glargine/Insulin Lispro Composition at pH 7 Having an Insulin Glargine Concentration of 300 IU/ml and an Insulin Lispro Concentration of 100 IU/ml (Percentage Proportion of Insulin: Insulin Glargine/Insulin Lispro 75/25)

A concentrated insulin glargine solution at 300 IU/ml is prepared according to example II-B18. A hydrophobized anionic polymer II-AB1 (23 mg/ml)/insulin glargine 300 IU/ml composition, pH 7, is prepared from the hydrophobized anionic polymer II-AB1 and according to the preparation method described in example II-B22. This hydrophobized anionic polymer II-AB1/insulin glargine 300 IU/ml composition is added to a lyophilizate of insulin lispro obtained by lyophilization of the solution of fast-acting analog derived from the dialysis of a commercial solution, according to the preparation method described in example II-B26. The solution is clear. The zinc content of the formulation is adjusted to the desired concentration by adding a concentrated solution of zinc chloride. The final pH is adjusted to 7 by adding concentrated NaOH or HCl.

The formulation is clear, attesting to the good solubility of the insulins glargine and lispro under these formulation conditions. This solution is filtered through a 0.22 µm filter and placed at +4° C.

Hydrophobized anionic polymer/insulin glargine/insulin lispro 300/100 compositions at pH 7 were also prepared with other hydrophobized anionic polymers according to a preparation method identical to that described in example II-B29 with a hydrophobized anionic polymer concentration of 30 mg/ml. These formulations are clear, attesting to the good solubility of the insulins glargine and lispro under these formulation conditions. These compositions result in the examples described in table II-7.

TABLE II-7

| Example | Hydrophobized anionic polymer | $C_{hydrophobized\ anionic\ polymer}$ (mg/ml) | $C_{insulin\ glargine}$ (IU/ml) | $C_{insulin\ lispro}$ (IU/ml) | $C_{insulin\ glargine}/C_{insulin\ lispro}$ (%/%) |
|---|---|---|---|---|---|
| II-B29 | II-AB2 | 30 | 300 | 100 | 75/25 |
| II-B30 | II-AB3 | 30 | 300 | 100 | 75/25 |
| II-B31 | II-AB4 | 30 | 300 | 100 | 75/25 |
| II-B32 | II-AB5 | 30 | 300 | 100 | 75/25 |
| II-B33 | II-AB6 | 30 | 300 | 100 | 75/25 |
| II-B34 | II-AB7 | 30 | 300 | 100 | 75/25 |
| II-B35 | II-AB8 | 30 | 300 | 100 | 75/25 |
| II-B36 | II-AB9 | 30 | 300 | 100 | 75/25 |
| II-B37 | II-AB10 | 30 | 300 | 100 | 75/25 |

Example II-B38: Preparation of a Hydrophobized Anionic Polymer II-AB2/Insulin Glargine/Insulin Lispro Composition at pH 7 Having an Insulin Glargine Concentration of 200 XU/ml and an Insulin Lispro Concentration of 66 IU/ml (Percentage Proportion of Insulin: Insulin Glargine/Insulin Lispro 75/25)

A hydrophobized anionic polymer II-AB2 (20 mg/ml)/insulin glargine 200 IU/ml composition, pH 7, is prepared from a hydrophobized anionic polymer II-AB2 and according to the preparation methods described in examples II-B23 and II-B24. This hydrophobized anionic polymer II-AB2/insulin glargine 200 IU/ml composition is added to a lyophilizate of insulin lispro obtained by lyophilization of the solution of fast-acting analog derived from the dialysis of a commercial solution, according to the preparation method described in example II-B26. The solution is clear. The zinc content of the formulation is adjusted to the desired concentration by adding a concentrated solution of zinc chloride. The final pH is adjusted to 7 by adding concentrated NaOH or HCl.

The formulation is clear, attesting to the good solubility of the insulins glargine and lispro under these formulation conditions. This solution is filtered through a 0.22 μm filter and placed at +4° C.

Hydrophobized anionic polymer/insulin glargine/insulin lispro 200/66 compositions at pH 7 were also prepared with other hydrophobized anionic polymers according to a preparation method identical to that described in example II-B38 with a hydrophobized anionic polymer concentration of 20 mg/ml. These formulations are clear, attesting to the good solubility of the insulins glargine and lispro under these formulation conditions. These compositions result in the examples described in table II-8.

Example II-B47: Preparation of a Hydrophobized Anionic Polymer II-AB1/Insulin Glargine/Insulin Lispro Composition at pH 7 Having an Insulin Glargine Concentration of 250 IU/ml and an Insulin Lispro Concentration of 150 IU/ml (Percentage Proportion of Insulin: Insulin Glargine/Insulin Lispro 63/37)

A hydrophobized anionic polymer II-AB1 (19 mg/ml)/insulin glargine 250 IU/ml composition, pH 7, is prepared from a hydrophobized anionic polymer II-AB1 and according to the preparation methods described in example II-B22. This hydrophobized anionic polymer II-AB1/insulin glargine 200 IU/ml composition is added to a lyophilizate of insulin lispro obtained by lyophilization of the solution of fast-acting analog derived from the dialysis of a commercial solution, according to the preparation method described in example II-B26. The solution is clear. The zinc content of the formulation is adjusted to the desired concentration by adding a concentrated solution of zinc chloride. The final pH is adjusted to 7 by adding concentrated NaOH or HCl.

The formulation is clear, attesting to the good solubility of the insulins glargine and lispro under these formulation conditions. This solution is filtered through a 0.22 μm filter and placed at +4° C.

Hydrophobized anionic polymer/insulin glargine/insulin lispro 250/150 compositions at pH 7 were also prepared with other hydrophobized anionic polymers according to a preparation method identical to that described in example II-B47 with a hydrophobized anionic polymer concentration of 25 mg/ml. These formulations are clear, attesting to the good solubility of the insulins glargine and lispro under these formulation conditions. These compositions result in the examples described in table II-9.

TABLE II-8

| Example | Hydrophobized anionic polymer | $C_{hydrophobized\ anionic\ polymer}$ (mg/ml) | $C_{insulin\ glargine}$ (IU/ml) | $C_{insulin\ lispro}$ (IU/ml) | $C_{insulin\ glargine}/C_{insulin\ lispro}$ (%/%) |
|---|---|---|---|---|---|
| II-B39 | II-AB3 | 20 | 200 | 66 | 75/25 |
| II-B40 | II-AB4 | 20 | 200 | 66 | 75/25 |
| II-B41 | II-AB5 | 20 | 200 | 66 | 75/25 |
| II-B42 | II-AB6 | 20 | 200 | 66 | 75/25 |
| II-B43 | II-AB6 | 20 | 200 | 66 | 75/25 |
| II-B44 | II-AB8 | 20 | 200 | 66 | 75/25 |
| II-B45 | II-AB9 | 20 | 200 | 66 | 75/25 |
| II-B46 | II-AB10 | 20 | 200 | 66 | 75/25 |

TABLE II-9

| Example | Hydrophobized anionic polymer | $C_{hydrophobized\ anionic\ polymer}$ (mg/ml) | $C_{insulin\ glargine}$ (IU/ml) | $C_{insulin\ lispro}$ (IU/ml) | $C_{insulin\ glargine}/C_{insulin\ lispro}$ (%/%) |
|---|---|---|---|---|---|
| II-B48 | II-AB2 | 25 | 250 | 150 | 63/37 |
| II-B49 | II-AB3 | 25 | 250 | 150 | 63/37 |
| II-B50 | II-AB4 | 25 | 250 | 150 | 63/37 |
| II-B51 | II-AB5 | 25 | 250 | 150 | 63/37 |
| II-B52 | II-AB6 | 25 | 250 | 150 | 63/37 |
| II-B53 | II-AB7 | 25 | 250 | 150 | 63/37 |
| II-B54 | II-AB8 | 25 | 250 | 150 | 63/37 |
| II-B55 | II-AB9 | 25 | 250 | 150 | 63/37 |
| II-B56 | II-AB10 | 25 | 250 | 150 | 63/37 |

Example II-B57: Preparation of a Hydrophobized Anionic Polymer II-AB1/Insulin Glargine/Insulin Lispro Composition at pH 7 Having an Insulin Glargine Concentration of 300 IU/ml and an Insulin Lispro Concentration of 100 IU/ml (Percentage Proportion of Insulin: Insulin Glargine/Insulin Lispro 75/25)

A hydrophobized anionic polymer II-AB1 (13 mg/ml)/insulin glargine 300 IU/ml composition, pH 7, is prepared from a hydrophobized anionic polymer II-AB1 and according to the preparation methods described in examples II-B23 and II-B24. This hydrophobized anionic polymer II-AB1/insulin glargine 300 IU/ml composition is added to a lyophilizate of insulin lispro obtained by lyophilization of the solution of fast-acting analog derived from the dialysis of a commercial solution, according to the preparation method described in example II-B26. The solution is clear. The zinc content of the formulation is adjusted to the desired concentration by adding a concentrated solution of zinc chloride. The final pH is adjusted to 7 by adding concentrated NaOH or HCl.

The formulation is clear, attesting to the good solubility of the insulins glargine and lispro under these formulation conditions. This solution is filtered through a 0.22 μm filter and placed at +4° C.

Example II-B58: Precipitation of Various Hydrophobized Anionic Polymer/Insulin Glargine/Insulin Lispro Compositions at pH 7 Having Various Insulin Glargine and Insulin Lispro Concentrations 1 ml of hydrophobized anionic polymer/insulin glargine/insulin lispro composition prepared in examples II-B27 to II-B57 is added to 2 ml of a solution of PBS containing 20 mg/ml of BSA. The PBS/BSA mixture simulates the composition of the subcutaneous medium. A precipitate appears. Centrifugation at 4000 rpm is carried out in order to separate the precipitate from the supernatant. The insulin glargine is then assayed in the supernatant by RP-HPLC. The result is that the insulin glargine is predominantly in a precipitated form.

The solubilization and precipitation results are summarized in table II-10.

TABLE II-10

Solubilization and precipitation test for various hydrophobized anionic polymer/insulin glargine/insulin lispro compositions at pH 7 having various insulin glargine and insulin lispro concentrations

| Examples | Solubilization insulin glargine and insulin lispro at pH 7 | Insulin glargine precipitation |
|---|---|---|
| II-B27 | YES | YES |
| II-B28 | YES | YES |
| II-B29 | YES | YES |
| II-B30 | YES | YES |
| II-B31 | YES | YES |
| II-B32 | YES | YES |
| II-B33 | YES | YES |
| II-B34 | YES | YES |
| II-B35 | YES | YES |
| II-B36 | YES | YES |
| II-B37 | YES | YES |
| II-B38 | YES | YES |
| II-B39 | YES | YES |
| II-B40 | YES | YES |
| II-B41 | YES | YES |
| II-B42 | YES | YES |
| II-B43 | YES | YES |
| II-B44 | YES | YES |
| II-B45 | YES | YES |
| II-B46 | YES | YES |
| II-B47 | YES | YES |
| II-B48 | YES | YES |
| II-B49 | YES | YES |
| II-B50 | YES | YES |
| II-B51 | YES | YES |
| II-B52 | YES | YES |
| II-B53 | YES | YES |
| II-B54 | YES | YES |
| II-B55 | YES | YES |
| II-B56 | YES | YES |
| II-B57 | YES | YES |

Example II-B59: Solubilization of Insulin Glargine at 1 mg/ml and at pH 7 Using the Hydrophobized Anionic Polymer II-AB1 or II-AC1 at the Concentration of 10 mg/ml 10 mg of a hydrophobized anionic polymer II-AB1 or of II-AC1 are accurately weighed out. This lyophilizate is taken up with 1 ml of a solution of insulin glargine at 1 mg/ml, obtained by dilution of the commercial solution of example II-B4. This mixture results in the obtaining of a solution of which the hydrophobized anionic polymer concentration is equal to 10 mg/ml and the insulin glargine concentration is equal to 1 mg/ml. The pH is adjusted to 7 with a 0.1 N sodium hydroxide solution. The solution is clear. This solution is filtered through a (0.22 μm) membrane and then placed at +4° C.

Example II-B60: Solubilization of BMPi-7 at 1 mg/ml and at pH 7 Using the Hydrophobized Anionic Polymer II-AB1 or II-AC1 at the Concentration of 10 Mg/ml Bone morphogenetic protein 7 (BMP-7) is soluble at acidic pH and has a very low solubility limit at pH 7, of about a few micrograms/mi.

10 mg of the hydrophobized anionic polymer II-AB1 or of II-AC1 are accurately weighed out. This lyophilizate is taken up with 1 ml of a solution of BMP-7 at 1 mg/ml and at acidic pH, for example in a 10 mM lactate buffer at pH 3. This mixture results in the obtaining of a solution of which the hydrophobized anionic polymer II-AB1 concentration is equal to 10 mg/ml and the BMP-7 concentration is equal to 1 mg/ml. After mixing, the final pH is adjusted to 7 by adding a 0.1 N sodium hydroxide solution. The solution is clear. This solution is filtered through a (0.22 µm) membrane and then placed at +4° C.

Example II-B61: Precipitation of a Hydrophobized Anionic Polymer/Insulin Glargine Composition 1 ml of hydrophobized anionic polymer/insulin glargine solution prepared in example II-B59 is added to 2 ml of a solution of PBS containing 20 mg/ml of BSA. The PBS/BSA mixture simulates the composition of the subcutaneous medium. A precipitate appears.

Centrifugation at 4000 rpm is carried out in order to separate the precipitate from the supernatant. The insulin glargine is then assayed in the supernatant by RP-HPLC. The result is that the insulin glargine is predominantly in a precipitated form. The results are summarized in table II-11.

Example II-B62: Precipitation of a Hydrophobized Anionic Polymer/BMP-7 Composition 1 ml of hydrophobized anionic polymer/BMP-7 solution prepared in example II-B60 is added to 2 ml of a solution of PBS containing 20 mg/ml of BSA. The PBS/BSA mixture simulates the composition of the subcutaneous medium. The solution is clear, no precipitate is observed. The results are summarized in table II-11 below.

TABLE 11

Tests for solubilization and precipitation of a composition of hydrophobized anionic polymer II-AB1 or of II-AC1 with insulin glargine or with BMP-7

| Polymer 10 mg/ml | Protein 1 mg/ml | Protein solubilization | Protein precipitation |
|---|---|---|---|
| II-AC1 | BMP-7 | Yes | No |
| II-AB1 | | Yes | No |
| II-AC1 | glargine | Yes | Yes |
| II-AB1 | | Yes | Yes |

These results show that the behavior of BMP-7 is different than that of insulin glargine, in particular under the conditions simulating subcutaneous medium. Indeed, under these conditions, the compositions comprising insulin glargine result in the precipitation of the insulin glargine, whereas, with the compositions comprising BMP-7, the latter remains soluble.

C Pharmacodynamics

II-C1. Protocol for Measuring the Pharmacodynamics of the Insulin Solutions A preclinical study was carried out on pigs with a view to evaluating a composition according to the invention:

Insulin glargine/insulin lispro (75/25), formulated with the hydrophobized anionic polymer II-AB1 (13 mg/ml) described in example II-B57.

The hypoglycemic effects of these compositions were compared with those obtained after simultaneous injections of Lantus® (pH 4) and of a prandial insulin Humalog® in the same proportions (75/25) and at the same total dose.

Ten domestic pigs weighing approximately 50 kg, previously catheterized at the level of the jugular, are deprived of food for 2.5 hours before the beginning of the experiment. In the hour preceding the injection of insulin, three blood samples are taken in order to determine the basal level of glucose.

The injection of insulin at a dose of 0.3 IU/kg is carried out by subcutaneous injection in the neck, under the animal's ear, using the Novopen® insulin pen fitted with a 31 G needle.

Blood samples are then taken after 10, 20, 30, 40 and 50 minutes and 1, 1.5, 2, 3, 4, 5, 6, 7, 8, 9, 10, 11, 12, 13, 14, 15 and 16 hours. After taking each sample, the catheter is rinsed with a dilute heparin solution.

A drop of blood is taken to determine the blood glucose level by means of a glucometer.

Figure 13:
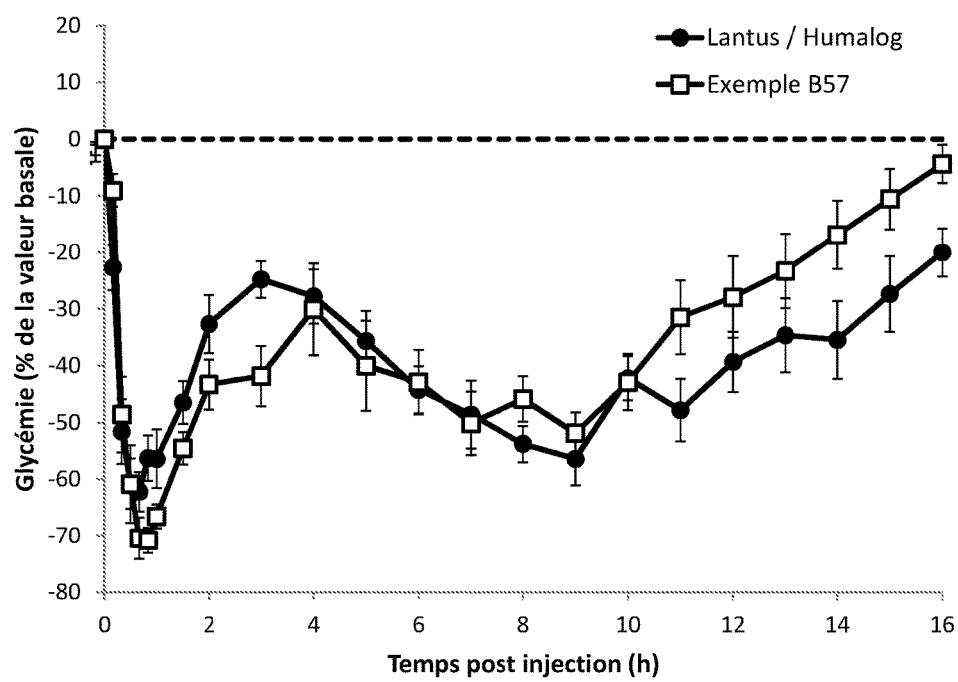
FIG. 13: Curves of means of blood glucose level+/− standard deviation of the mean for the simultaneous administrations of Humalog® (100 IU/ml, 0.075 IU/kg) and Lantus® (100 IU/ml, 0.225 IU/kg) in comparison with the administration of a formulation according to the invention described in example B57 (400 IU/ml, 0.3 IU/kg).

The curve of mean glucose pharmacodynamics, expressed in percentages of the basal level, is represented in FIG. 13.

FIG. 1: Curves of means of blood glucose level 1 standard deviation of the mean for the simultaneous administrations of Humalog® (100 IU/ml, 0.075 IU/kg) and Lantus® (100 IU/ml, 0.225 IU/kg) in comparison with the administration of a formulation according to the invention described in example II-B57 (400 IU/ml, 0.3 IU/kg).

II-C2. Pharmacodynamics Results for the Solution of Insulin of Example II-B57

The pharmacodynamics results obtained with the sequential administrations of Humalog® and Lantus® in comparison with the formulation described in example II-B57 are presented in FIG. 13. The hypoglycemic activity of the formulation described in example II-B57 is two-phase. The first phase, which is rapid, is characterized by a marked decrease in blood glucose level during the first 30 minutes (similar to that induced by the double injection of Lantus®/Humalog®), indicating that the presence of the hydrophobized anionic polymer II-AB1 does not disrupt the fast-acting nature of Humalog®. After 30 minutes, the blood glucose level increases again up to 3 hours, before a second phase characterized by a hypoglycemic activity which is less marked and sustained until 16 hours post-injection. This second phase appears to be similar for the two formulations, indicating that the basal effect of glargine is indeed preserved in the formulation according to the invention, described in example II-B57.

The invention claimed is:

1. A composition in the form of an injectable aqueous solution, the pH of which is between 6.6 and 7.8, comprising a mixture of at least:
   a) a basal insulin, the isoelectric point pI of which is between 5.8 and 8.5; and
   b) a hydrophobized anionic polymer bearing carboxylate charges f-[A]-COOH and hydrophobic radicals -g-[B]-(k-[D])$_p$, having a backbone of formula II-V:

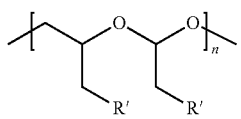

Formula II-V in which, n being the degree of polymerization, of between 3 and 1000, and R' is chosen from the group consisting of the radicals:
—OH;
—O-Alk, Alk being a $C_1$ to $C_3$ alkyl chain;
-(f-[A]-COOH) as the carboxylate charges, wherein
  in at least one of the monomer units of the backbone at least one of the R' of Formula II-V is -(f-[A]-COOH),
  in at least one of the monomer units of the backbone at least one of the R' of Formula II-V is -g-[B]-(k-[D])$_p$,
-[A]- is an at least a divalent radical or moiety,
-[B]- is an at least a divalent radical or moiety, and
-(f-[A]-COOH) is chosen from the group consisting of the following radicals:

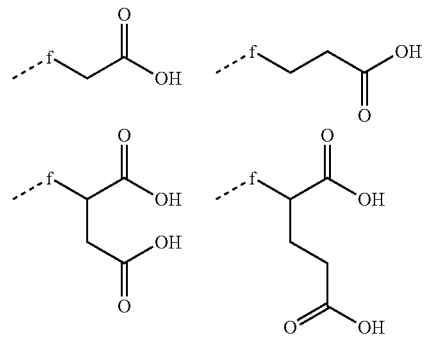

or the salts thereof with alkali metal cations chosen from the group consisting of $Na^+$ and $K^+$, f being chosen from the group consisting of ether, ester, carbamate and carbonate functions; and -g-[B]-(k-[D])$_p$ as the hydrophobic radicals, in which the radical -g-[B]-k-[D] is chosen from the group consisting of the following radicals, wherein g, k and -[D] have the meanings given below:

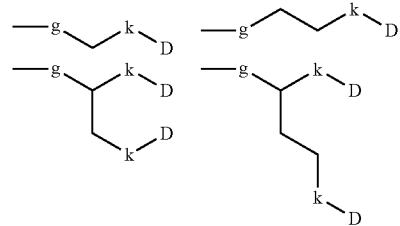

g resulting from the reaction between a carboxyl or alcohol or amine function of the precursor of -g-[B]-(k-)$_p$ and a function of the backbone, and is chosen from the group consisting of ether, amine, ester, carbamate or carbonate functions, p is a positive integer equal to 1 or 2;

-[D] is a radical -[Hy] or -[E]-(o-[Hy])$_t$, wherein when -[D] is a radical -[Hy], k resulting from the reaction between a carboxyl or alcohol or amine function of the precursor of -g-[B]-(k-)$_p$ and an alcohol or acid function of the precursor of -[D] is chosen from the group consisting of ester, amide or carbamate functions;

wherein when -[D] is a radical -[E]-(o-[Hy])$_t$,
  -[E]- is an alkyl group that comprises from 2 to 9 carbon atoms;
  k resulting from the reaction between a carboxyl, amine or alcohol function of the precursor of -k-[E]-(o)$_t$ and an alcohol, carboxyl or amine function of the polymer and is a function chosen from the group consisting of ester, amide, carbonate and carbamate functions;
  o resulting from the reaction between a carboxyl, amine or alcohol function of the precursor of -k-[E]-(o)$_t$ and an alcohol or acid function of the precursor of -[Hy] is a function chosen from the group consisting of ester, amide, urea (carbamide), carbonate and carbamate functions;
  t is a positive integer equal to 1 or 2;
-[Hy] is a $C_8$ to $C_{30}$ linear or cyclic alkyl group or a $C_8$ to $C_{30}$ alkylaryl or arylalkyl, optionally substituted with one or more $C_1$ to $C_3$ alkyl groups, the radical -[Hy] being issued from a hydrophobic compound chosen among (a) a branched or unbranched, unsaturated and/or saturated, hydrophobic alcohol comprising from 8 to 30 carbons free of heteroatoms apart from the alcohol function, (b) a sterol free of heteroatoms apart from the alcohol function, (c) a tocopherol, (d) a menthol free of heteroatoms apart from the alcohol function or (e) a fatty acid chosen from the group consisting of the acids consisting of a branched or unbranched, unsaturated or saturated, alkyl chain comprising from 8 to 30 carbons free of heteroatoms apart from the carboxylic acid function;

and -[A]-, -[B]- and -[E]- are identical or different,
and k and o are identical or different;
and, if -[B]- is a trivalent radical, then -[D] is a radical -[Hy],
and the degree of substitution with the carboxylate charges is greater than or equal to 1.0,
and the degree of substitution with the hydrophobic radicals is less than or equal to 0.5 and greater than 0, and when -g-[B]-(k-[D])$_p$ comprises one Hy chain and Hy is a $C_8$ to $C_{15}$ alkyl, then the product of the degree of substitution with hydrophobic radicals and the average degree of polymerization (n) is greater than or equal to 2, when -g-[B]-(k-[D])$_p$ comprises one Hy chain and Hy is a $C_{16}$ to $C_{20}$ alkyl, then the product of the degree of substitution with hydrophobic radicals and the average degree of polymerization (n) is greater than or equal to 1, when -g-[B]-(k-[D])$_p$ comprises one Hy Chain and Hy is in a tocopherol or a sterol, then the product of the degree of substitution with hydrophobic radicals and the average degree of polymerization (n) is greater than or equal to 0.25, when -g-[B]-(k-[D])$_p$ comprises two Hy chains and Hy is a $C_8$ to $C_9$ alkyl, then the product of the degree of substitution with hydrophobic radicals and the average degree of polymerization (n) is greater than or equal to 2, when -g-[B]-(k-[D])$_p$ comprises two Hy chains and Hy is a C$_{10}$ to C$_{16}$ alkyl, then the product of the degree of substitution with hydrophobic radicals and the average degree of polymerization (n) is greater than or equal to 0.2.

2. The composition according to claim 1, wherein the basal insulin, the isoelectric point of which is between 5.8 and 8.5, is insulin glargine.

3. The composition according to claim 1, which comprises between 40 and 500 IU/ml of basal insulin, the isoelectric point of which is between 5.8 and 8.5.

4. The composition according to claim 1, wherein the concentration of hydrophobized anionic polymer is at most 100 mg/ml.

5. The composition according to claim 1, which also comprises a prandial insulin.

6. The composition according to claim 1, which comprises in total between 40 and 800 IU/ml of insulin wherein the insulin is a combination of prandial insulin and basal insulin, the isoelectric point of the basal insulin being between 5.8 and 8.5.

7. The composition according to claim 6, wherein the proportions between the basal insulin, the isoelectric point of which is between 5.8 and 8.5, and the prandial insulin are, as a percentage (IU basis), 25/75, 30/70, 40/60, 50/50, 60/40, 70/30, 75/25, 80/20, or 90/10 for formulations comprising from 40 to 800 IU/ml.

8. A single-dose formulation at a pH of between 6.6 and 7.8, which comprises composition according to claim 1, and a prandial insulin.

9. A composition in the form of an injectable aqueous solution, the pH of which is between 6.6 and 7.8, comprising a mixture of at least:
a) a basal insulin, the isoelectric point pI of which is between 5.8 and 8.5; and
b) a hydrophobized anionic polymer bearing carboxylate charges and hydrophobic radicals, of formula II-V:

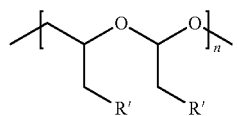

Formula II-V in which
-n being the degree of polymerization, of between 3 and 1000, and
—R' is chosen from the group consisting of the radicals:
—OH;
—O-Alk, Alk being a C$_1$ to C$_3$ alkyl chain;

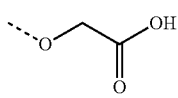

as the carboxylate charges, wherein a degree of substitution of the units with the carboxylate charges is from 1 to 2, and

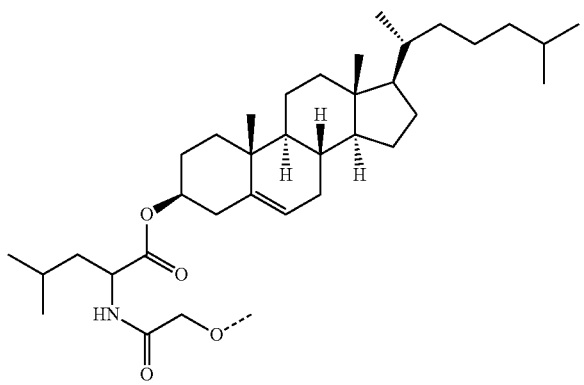

as the hydrophobic radicals, wherein a degree of substitution of the units with the hydrophobic radicals is from greater than 0 to 0.5 or less and the product of the degree of substitution with hydrophobic radicals and average degree of polymerization (n) is greater than or equal to 0.25.

10. The composition according to claim 9, wherein the degree of substitution of the units with the carboxylate charges is 1.26 and the degree of substitution of the units with the hydrophobic radicals is 0.04.

* * * * *